US012663426B2

(12) United States Patent
Krishnan et al.

(10) Patent No.: US 12,663,426 B2
(45) Date of Patent: Jun. 23, 2026

(54) METHOD AND COMPOSITION FOR MEASUREMENT OF NITRIC OXIDE

(71) Applicant: The University of Chicago, Chicago, IL (US)

(72) Inventors: Yamuna Krishnan, Chicago, IL (US); Aneesh T. Veetil, Chicago, IL (US); Maulik S. Jani, Chicago, IL (US)

(73) Assignee: The University of Chicago, Chicago, IL (US)

( * ) Notice: Subject to any disclaimer, the term of this patent is extended or adjusted under 35 U.S.C. 154(b) by 981 days.

(21) Appl. No.: 17/784,481

(22) PCT Filed: Dec. 11, 2020

(86) PCT No.: PCT/US2020/064544
§ 371 (c)(1),
(2) Date: Jun. 10, 2022

(87) PCT Pub. No.: WO2021/119448
PCT Pub. Date: Jun. 17, 2021

(65) Prior Publication Data

US 2023/0055931 A1 Feb. 23, 2023

Related U.S. Application Data

(60) Provisional application No. 62/946,720, filed on Dec. 11, 2019.

(51) Int. Cl.
*G01N 33/00* (2006.01)
*C12N 15/115* (2010.01)
(Continued)

(52) U.S. Cl.
CPC ........... *G01N 33/84* (2013.01); *C12N 15/115* (2013.01); *G01N 33/582* (2013.01);
(Continued)

(58) Field of Classification Search
CPC ...................................................... G01N 33/84
(Continued)

(56) References Cited

U.S. PATENT DOCUMENTS 11,136,618 B2 10/2021 Krishnan et al.
11,898,195 B2 2/2024 Krishnan et al.
(Continued)

FOREIGN PATENT DOCUMENTS

WO 2015159122 A1 10/2015
WO 2016187284 A1 11/2016
(Continued)

OTHER PUBLICATIONS

Awad et al., "Autoxidation of NO in Aqueous Solution", Int. J. Chem. Kinet., 1993, vol. 25, pp. 375-381.
(Continued)

*Primary Examiner* — Lyle Alexander
*Assistant Examiner* — Emily R. Berkeley
(74) *Attorney, Agent, or Firm* — McDonnell Boehnen Hulbert & Berghoff LLP

(57) ABSTRACT

A method for determining nitric oxide concentration in biological samples. The method includes for determining nitric oxide concentration in a sample including: (i) providing a nucleic acid complex comprising a first single-stranded nucleic acid molecule comprising a fluorophore crosslinked to the first strand, the fluorophore comprising diaminorhodamine-4-methylamine (DAR-4M) conjugated, to dibenzocyclooctyne-polyethylene glycol (DBCO-PEGn) linker, wherein n equals 4-12 and a second single-stranded nucleic acid molecule that is partially or fully complementary to the first single-stranded molecule, wherein the nucleic acid complex further comprises a first label and a targeting moiety conjugated to the first single-stranded nucleic acid molecule or the second single-stranded nucleic acid mol- (Continued)

ecule, the first label is capable of producing a signal, wherein the intensity of the signal is dependent at least on concentration of the nucleic acid complex in the sample; (ii) contacting the sample with the nucleic acid complex; (iii) measuring the intensity of the signal: and (iii) determining the nitric oxide concentration from the measured signal. Compositions for determining nitric oxide concentrations in biological samples are also included.

17 Claims, 57 Drawing Sheets

Specification includes a Sequence Listing.

(51) Int. Cl.
*G01N 33/58* (2006.01)
*G01N 33/84* (2006.01)

(52) U.S. Cl.
CPC .. *C12N 2310/16* (2013.01); *C12N 2310/3515* (2013.01); *C12N 2310/3517* (2013.01); *C12N 2310/531* (2013.01)

(58) Field of Classification Search
USPC .......................................................... 436/116
See application file for complete search history.

(56) References Cited

U.S. PATENT DOCUMENTS

| | | | |
|---|---|---|---|
| 2021/0096129 A1 | 4/2021 | Krishnan et al. |
| 2022/0011325 A1 | 1/2022 | Krishnan et al. |
| 2023/0055931 A1 | 2/2023 | Krishnan et al. |
| 2023/0324370 A1 | 10/2023 | Krishnan et al. |
| 2024/0000949 A1 | 1/2024 | Becker et al. |

FOREIGN PATENT DOCUMENTS

| | | |
|---|---|---|
| WO | 2018/191561 A1 | 10/2018 |
| WO | 2020/117701 A1 | 6/2020 |
| WO | 2021/119448 A1 | 6/2021 |
| WO | 2021/194613 A1 | 9/2021 |
| WO | 2022/051724 A1 | 3/2022 |

OTHER PUBLICATIONS

Bredt et al., "Nitric Oxide: A Physiologic Messenger Molecule", Annu. Rev. Biochem., 1994, vol. 63, pp. 175-195.
Brudal et al., "Establishment of Three Francisella Infections in Zebrafish Embryos at Different Temperatures", Infect. Immun., 2014, vol. 82(6), pp. 2180-2194.
Egensperger et al., "J. Fate of DNA from Retinal Cells Dying During Development: Uptake by Microglia and Macroglia (Müller cells)", Dev. Brain Res., 1996, vol. 97, pp. 1-8.
Fulton et al., "Post-Translational Control of Endothelial Nitric Oxide Synthase: Why Isn't Calcium/Calmodulin Enough?", J. Pharmacol. Exp. Ther., 2001, vol. 299(3), pp. 818-824.
Giustarini et al., Nitrite and Nitrate Measurement by Griess Reagent in Human Plasma: Evaluation of Interferences and Standardization. Chapter 23 in Methods in Enzymology, 2008, vol. 440, pp. 361-380.
Hess et al. "Protein S-Nitrosylation: Purview and Parameters", Nat. Rev. Mol. Cell Biol., 2005, vol. 6, pp. 150-166.
Ishibe et al., "Comparative Analysis of the Production of Nitric Oxide (NO) and Tumor Necrosis Factor-Alpha (TNF-alpha) from Macrophages Exposed to High Virulent and Low Virulent Strains of Edwardsiella Tarda", Fish & Shellfish Immunol., 2009, vol. 27, pp. 386-389.
Kojima et al., "Bioimaging of Nitric Oxide with Fluorescent Indicators Based on the Rhodamine Chromophore", Anal. Chem., 2001, vol. 73, pp. 1967-1973.
Kojima et al., "Detection and Imaging of Nitric Oxide with Novel Fluorescent Indicators: Diaminofluoresceins", Anal. Chem., 1998, vol. 70, pp. 2446-2453.
Lewis et al., "Kinetics of the Reaction of Nitric Oxide with Oxygen in Aqueous Solutions", Chem. Res. Toxicol., 1994, vol. 7, pp. 568-574.
Lim et al., "Visualization of Nitric Oxide in Living Cells by a Copper-Based Fluorescent Probe", Nat. Chem. Biol. 2(7), 2006, pp. 375-380.
Maragos, et al., "Complexes of •NO with Nucleophiles as Agents for the Controlled Biological Release of Nitric Oxide. Vasorelaxant Effects." J. Med. Chem. 1991, 34, 3242-3247.
Mancuso et al., "Bacterial Recognition by TLR7 in the Lysosomes of Conventional Dendritic Cells", Nature Immunology, 2009, vol. 10(6), pp. 587-594.
Martin et al., "Endothelial Nitric Oxide Synthase: Correlation with Histologic Grade, Lymph Node Status and Estrogen Receptor Expression in Human Breast Cancer", Tumor. Biol., 2000, vol. 21, pp. 90-97.
McQuade et al., "Fluorescent Probes to Investigate Nitric Oxide and Other Reactive Nitrogen Species in Biology (truncated form: fluorescent probes of reactive nitrogen species)", Curr. Opin. Chem. Biol., 2010, vol. 14, pp. 43-49.
Modi et al., "Recombinant Antibody Mediated Delivery of Organelle-Specific DNA pH Sensors Along Endocytic Pathways", Nanoscale, 2014, vol. 6, pp. 1144-1152.
Pisano et al., "Lysosomotropic Agents III1. Synthesis of N-Retinyl Morpholine", Synth. Commun., 1981, vol. 11(5), pp. 375-378.
Ramamurthi et al., "Measurement and Modeling of Nitric Oxide Release Rates for Nitric Oxide Donors", Chem. Res. Toxicol., 1997, vol. 10, pp. 408-413.
Tschugguel et al., "Expression of Inducible Nitric Oxide Synthase in Human Breast Cancer Depends on Tumor Grade", Breast Cancer Res. Treat., 1999, vol. 56, pp. 145-151.
Underhill et al., "Phagocytosis of Microbes: Complexity in Action", Annu. Rev. Immunol., 2002, vol. 20, pp. 825-852.
Yao et al., "Base-Promoted Reactions of Bridged Ketones and 1,3- and 1,4-Haloalkyl Azides: Competitive Alkylation Vs Azidation Reactions of Ketone Enolates", J. Org. Chem., 2004, vol. 69, pp. 1720-1722.
Ye et al., "Detection of Nitric Oxide in Single Cells", Analyst, 2008, vol. 133(4), pp. 423-433.
Yu et al., "A Lysosome-Targetable and Two-Photon Fluorescent Probe for Monitoring Endogenous and Exogenous Nitric Oxide in Living Cells", J. Am. Chem. Soc., 2012, vol. 134, pp. 17486-17489.
Eroglu, Emrah, et al., "Development of novel FP-based probes for live-cell imaging of nitric oxide dynamics", Nature Communications, Feb. 4, 2016, vol. 1, No. 1, pp. 1-11.
Cruz, Diana et al., "DNA-based sensor against nitrite oxide radical: Evaluation of total antioxidant capacity in beverages," Journal of Electroanalytical Chemistry, Dec. 30, 2015, vol. 763, pp. 110-115.
Thekkan, Shareefa et al., "A DNA-based fluorescent reporter maps HOCI production in the maturing phagosome", Nature Chemical Biology, Dec. 10, 2019, vol. 15, No. 12, pp. 1165-1172.
Jani, Maulik S. et al., "A DNA-based fluorescent probe maps NOS 3 activity with subcellular spatial resolution, Nature Chemical Biology", Mar. 9, 2020, vol. 16, No. 6, pp. 660-666.
Veetil, Aneesh T. et al., "DNA-based fluorescent probes of NOS 2 activity in live brains", Proceedings of the National Academy of Sciences, Jun. 17, 2020, vol. 117, No. 26, pp. 14694-14702.
International Search Report and Written Opinion issued in International Application No. PCT/US2020/064544 dated Apr. 9, 2021.
Li et al., "Sequence Specific Detection of Bacterial 23S Ribosomal RNA by TLR13", eLife, 2012, vol. 1, pp. 1-14.
Li et al., "Microglial Activation by Uptake of fDNA Via a Scavenger Receptor", J. Neuroimmunol., 2004, vol. 147, pp. 50-55.
Li et al., "Pattern Recognition Receptors in Zebrafish Provide Functional and Evolutionary Insight into Innate Immune Signaling Pathways", Cellular & Molecular Immunology, 2016, vol. 14, pp. 80-89.
Lim et al., "Tumour Maintenance is Mediated By eNOS", Nature, 2008, vol. 452, No. 7187, pp. 646-649.

(56) References Cited

OTHER PUBLICATIONS

Lundberg et al., "The Nitrate-Nitrite-Nitric Oxide Pathway in Physiology and Therapeutics", Nature Review Drug Discovery, 2008, vol. 7, pp. 156-167.
Lytton et al., "Thapsigargin Inhibits the Sarcoplasmic or Endoplasmic Reticulum Ca-ATPase Family of Calcium Pumps", The Journal of Biological Chemistry, 1991, vol. 266, No. 26, pp. 17067-17071.
Madigan et al., "A Macrophage Response to Mycobacterium Leprae Phenolic Glycolipid Initiates Nerve Damage in Leprosy", Cell, 2017, vol. 170, pp. 973-985.
Matsuo et al., "Teleost TLR22 Recognizes RNA Duplex to Induce IFN and Protect Cells from Birnaviruses", The Journal of Immunology, 2008, vol. 181, pp. 3474-3485.
Mazaheri et al., "Distinct Roles for BAI1 and TIM-4 in the Engulfment of Dying Neurons by Microglia", Nature Communications, 2014, vol. 5, 4046, pp. 1-11.
Meijer et al., "Host-Pathogen Interactions Made Transparent with the Zebrafish Model", Current Drug Targets, 2011, vol. 12, pp. 1000-1017.
Miller et al., "Mycobacteria Inhibit Nitric Oxide Synthase Recruitment to Phagosomes During Macrophage Infection", Infection & Immunity, 2004, vol. 72, No. 5, pp. 2872-2878.
Modi et al., "A DNA Nanomachine That Maps Spatial and Temporal pH Changes Inside Living Cells", Nature Nanotechnology, 2009, vol. 4, pp. 325-330.
Mogensen, Trine H., "Pathogen Recognition and Inflammatory Signaling in Innate Immune Defenses", Clinical Microbiology Reviews, 2009, vol. 22, No. 2, pp. 240-273.
Namin et al., "Kinetic Analysis of DAF-FM Activation by NO: Toward Calibration of a NO-Sensitive Fluorescent Dye", Nitric Oxide, 2013, vol. 28, pp. 39-46.
Narayanaswamy et al., "A pH-Correctable, DNA-Based Fluorescent Reporter for Organellar Calcium", Nat. Methods, 2019, vol. 16, No. 1, pp. 95-102.
Nishiya et al., TLR3 and TLR7 are Targeted to the Same Intracellular Compartments by Distinct Regulatory Elements, The Journal of Biological Chemistry, 2005, vol. 280, No. 44, pp. 37107-37117.
Oldenburg et al., "TLR13 Recognizes Bacterial 23S rRNA Devoid of Erythromycin Resistance-Forming Modification", Science, 2012, vol. 337, pp. 1111-1115.
Pacelli et al., "Nitric Oxide Potentiates Hydrogen Peroxide-Induced Killing of *Escherichia coli*", The Journal of Experimental Medicine, 1995, vol. 182, pp. 1469-1479.
Peri et al., "Live Imaging of Neuronal Degradation by Microglia Reveals a Role for v0-ATPase a1 in Phagosomal Fusion in vivo", Cell, 2008, vol. 133, pp. 916-927.
Renshaw et al., "A Model 450 Million Years in the Making: Zebrafish and Vertebrate Immunity", Disease Models & Mechanisms, 2012, vol. 5, pp. 38-47.
Rodríguez et al., "Immune Response of Zebrafish (*Danio rerio*) Against a Newly Isolated Bacterial Pathogen Aeromonas Hydrophila", Fish & Shellfish Immunology, 2008, vol. 25, pp. 239-249.
Schindelin et al., "Fiji: An Open-Source Platform for Biological-Image Analysis", Nat. Methods, 2013, vol. 9, pp. 676-682.
Sessa et al., "The Golgi Association of Endothelial Nitric Oxide Synthase is Necessary for the Efficient Synthesis of Nitric Oxide", The Journal of Biological Chemistry, 1995, vol. 270, vol. 30, pp. 17641-17644.
Sierra et al., "Microglia Shape Adult Hippocampal Neurogenesis Through Apoptosis-Coupled Phagocytosis", Cell Stem Cell, 2010, vol. 7, pp. 483-495.
Skupien et al., "CD44 Regulates Dendrite Morphogenesis Through Src Tyrosine Kinase-Dependent Positioning of the Golgi", Journal of Cell Science, 2014, vol. 127, pp. 5038-5051.
Sowa et al., "Trafficking of Endothelial Nitric-Oxide Synthase in Living Cells—Quantitative Evidence Supporting the Role of Palmitoylation as a Kinetic Trapping Mechanism Limiting Membrane Diffusion", The Journal of Biologicaly Chemistry, 1999, vol. 274, No. 32, pp. 22524-22531.
Stuart et al., "Phagocytosis: Elegant Complexity", Immunity, 2005, vol. 22, pp. 539-550.
Surana et al., "An Autonomous DNA Nanomachine Maps Spatiotemporal pH Changes in a Multicellular Living Organism", Nature Communications, 2011, vol. 2, No. 340, pp. 1-7.
Takeuchi et al., "Pattern Recognition Receptors and Inflammation", Cell, 2010, vol. 140, pp. 805-820.
Thekkan et al., "A DNA-Based Fluorescent Reporter Maps HOCI Production in the Maturing Phagosome", Nat. Chem. Biol., 2019, vol. 15, No. 12, pp. 1165-1172.
Thomsen et al., "Nitric Oxide Synthase Activity in Human Breast Cancer", British Journal of Cancer, 1995, vol. 72, pp. 41-44.
To et al., "Endosomal NOX2 Oxidase Exacerbates Virus Pathogenicity and is a Target for Antiviral Therapy", Nature Communications, 2017, vol. 8, No. 69, pp. 1-17.
Utaisincharoen et al., "CpG ODN Activates NO and iNOS Production in Mouse Macrophage Cell Line (RAW 264.7)", Clin. Exp. Immunol., 2002, vol. 128, pp. 467-473.
Vahora et al., "The Potential Role of Nitric Oxide in Halting Cancer Progression Through Chemoprevention", Journal of Cancer Prevention, 2016, vol. 21, No. 1, pp. 1-12.
Veetil et al., "Cell-Targetable DNA Nanocapsules for Spatiotemporal Release of Caged Bioactive Small Molecules", Nature Nanotechnology, 2017, vol. 12, pp. 1183-1189.
Veetil et al., "Chemical Control Over Membrane-Initiated Steroid Signaling with a DNA Nanocapsule", PNAS, 2018, vol. 115, No. 38, pp. 9432-9437.
West et al., "Recognition and Signaling by Toll-Like Receptors", Annu. Rev. Cell Dev. Biol., 2006, vol. 22, pp. 409-437.
Wind et al., "Comparative Pharmacology of Chemically Distinct NADPH Oxidase Inhibitors", British Journal of Pharmacology, 2010, vol. 161, pp. 885-898.
Wink et al., "Nitric Oxide and Redox Mechanisms in the Immune Response", Journal of Leukocyte Biology, 2011, vol. 89, pp. 873-891.
Xu et al., "The Role of Nitric Oxide in Cancer", Cell Research, 2002, vol. 12, No. 5-6, pp. 311-320.
Yang et al., "eNOS Uncoupling and Endothelial Dysfunction in Aged Vessels", Am. J. Physiol. Heart Circ. Physiol., 2009, vol. 297, pp. H1829-H1836.
Anrather et al., "NF-κB Regulates Phagocytic NADPH Oxidase by Inducing the Expression of gp91phox.", The Journal of Biological Chemistry, 2006, vol. 281, No. 9, pp. 5657-5667.
Berlato et al. "Involvement of Suppressor of Cytokine Signaling-3 as a Mediator of the Inhibitory Effects of IL-10 on Lipopolysaccharide-Induced Macrophage Activation", The Journal of Immunology, 2002, vol. 168, pp. 6404-6411.
Blake et al. "SU6656, a Selective src Family Kinase Inhibitor, Used to Probe Growth Factor Signaling", Molecular and Cellular Biology, 2000, vol. 20, No. 3, pp. 9018-9027.
Brandes et al., "Direct Detection of Reactive Oxygen Species Ex Vivo", Kidney International, 2005, vol. 67, pp. 1662-1664.
Cambier et al., "Mycobacteria Manipulate Macrophage Recruitment Through Coordinated Use of Membrane Lipids", Nature, 2014, vol. 505(7482), pp. 218-222.
Chakraborty et al., "Nucleic Acid-Based Nanodevices in Biological Imaging," Annu. Rev. Biochem., 2016, vol. 85, pp. 349-373.
Chakraborty et al. "High Lumenal Chloride in the Lysosome is Critical for Lysosome Function", eLife, Jun. 2017, e28862, pp. 1-21.
Choudhari et al., "Nitric Oxide and Cancer: A Review", World Journal of Surgical Oncology, 2013, vol. 11, No. 118, pp. 1-11.
Dalpke et al., "Immunostimulatory CpG-DNA activates murine microglia", The Journal of Immunology, 2002, vol. 168, pp. 4854-4863.
Davis et al., "Mechanism of Inducible Nitric Oxide Synthase Exclusion from Mycobacterial Phagosomes", PLoS Pathogens, 2007, vol. 3, No. 12, pp. 1887-1894.
Debacq-Chainiaux et al., "Protocols to Detect Senescence-Associated Beta-Galactosidase (SA-βgal) Activity, A Biomarker of Senescent Cells In Culture and In Vivo", Nature Protocols, 2009, vol. 4, No. 12, pp. 1798-1806.

(56) References Cited

OTHER PUBLICATIONS

Diebold et al., "Innate Antiviral Responses by Means of TLR7-Mediated Recognition of Single-Stranded RNA", Science, 2004, vol. 303, pp. 1529-1531.
Duarte et al., "Reduced Fluoresceinamine as a Fluorescent Sensor for Nitric Oxide", Sensors, 2010, vol. 10, pp. 1661-1669.
Dupré-Crochet et al., "ROS Production in Phagocytes: Why, When, and Where?", Journal of Leukocyte Biology, 2013, vol. 94, pp. 657-670.\.
Ellefsen et al., "Dynamic Ca2+ Imaging with a Simplified Lattice Light-Sheet Microscope: A Sideways View of Subcellular Ca2+ Puffs", Cell Calcium, 2018, vol. 71, pp. 34-44.
Eroglu et al., "Development of Novel FP-Based Probes for Live-Cell Imaging of Nitric Oxide Dynamics", Nature Communiation, 2016, vol. 7, 10623, pp. 1-11.
Farber-Katz et al., "DNA Damage Triggers Golgi Dispersal Via DNA-PK and GOLPH3", Cell, 2014, vol. 156, pp. 413-427.
Ferreira et al., "Phototoxic Aptamers Selectively Enter and Kill Epithelial Cancer Cells", Nucleic Acids Research, 2009, vol. 37, No. 3, pp. 866-876.
Fukumura et al., "The Role of Nitric Oxide in Tumour Progression", Nature Reviews Cancer, 2006, vol. 6, pp. 521-534.
Fulton et al., "Localization of Endothelial Nitric-Oxide Synthase Phosphorylated on Serine 1179 and Nitric Oxide in Golgi and Plasma Membrane Defines the Existence of Two Pools of Active Enzyme", The Journal of Biological Chemistry, 2002, vol. 277, No. 6, pp. 4277-4284.
Fulton et al., "Regulation of Endothelium-Derived Nitric Oxide Production by the Protein Kinase Akt", Nature, 1999, vol. 399, pp. 597-601.
Fulton et al., "Targeting of Endothelial Nitric-Oxide Synthase to the Cytoplasmic Face of the Golgi Complex or Plasma Membrane Regulates Akt—Versus Calcium-Dependent Mechanisms for Nitric Oxide Release", The Journal of Biological Chemistry, 2004, vol. 279, No. 29, pp. 30349-30357.
Gao et al., "Cutting Edge: Bacterial DNA and LPS Act in Synergy in Inducing Nitric Oxide Production in RAW 264.7 Macrophages", The Journal of Immunology, 1999, vol. 163, No. 8, pp. 4095-4099.
García-Cardeña et al., "Dynamic Activation of Endothelial Nitric Oxide Synthase by Hsp90", Nature, 1998, vol. 392, pp. 821-824.
Garvey et al., "1400W is a Slow, Tight Binding, and Highly Selective Inhibitor of Inducible Nitric-Oxide Synthase In Vitro and In Vivo", The Journal of Biological Chemistry, 1997, vol. 272, No. 8, pp. 4959-4963.
Goldstein et al., "Reactions of PTIO and Carboxy-PTIO with *NO, *NO2, and O2-* ", The Journal of Biological Chemistry, 2003, vol. 278, No. 51, pp. 50949-50955.
Gregory et al., "Reactive Nitrogen Intermediates Suppress the Primary Immunologic Response to Listeria", J. Immunol., 1993, vol. 150, No. 7, pp. 2901-2909.
Iliev et al., "Neuronal Injury Mediated Via Stimulation of Microglial Toll-Like Receptor-9 (TLR9)", The FASEB Journal, vol. 18, 2003, pp. 412-414.
Jani et al., "Precision Immunomodulation with Synthetic Nucleic Acid Technologies", Nature Review Materials, 2009, vol. 4, pp. 451-458.
Jensen et al., "Sensing of RNA Viruses: A Review of Innate Immune Receptors Involved in Recognizing RNA Virus Invasion", Journal of Virology, 2012, vol. 86, pp. 2900-2910.
Jiang et al., "Real-Time Electrical Detection of Nitric Oxide in Biological Systems with Sub-Nanomolar Sensitivity", Nature Communications, 2013, vol. 4, 2225, pp. 1-7.
Jin, Zheng-Gen, "Where is Endothelial Nitric Oxide Synthase More Critical: Plasma Membrane or Golgi?", Arterioscler. Thomb. Vasc. Biol., 2006, vol. 26, pp. 959-961.
Kaplan et al., "Effect of Nitric Oxide on Staphylococcal Killing and Interactive Effect with Superoxide", Infection and Immunity, 1996, vol. 64, No. 1, pp. 69-76.
Kettle et al., Mechanism of Inactivation of Myeloperoxidase by 4-Aminobenzoic Acid Hydrazide:, Biochem. J., 1997, vol. 321, (Pt 2), pp. 503-508.
Lahdenranta et al., "Endothelial Nitric Oxide Synthase Mediates Lymphangiogenesis and Lymphatic Metastasis", Cancer Res., 2009, vol. 69, No. 7, pp. 2801-2808.
Lee et al., "Trafficking of Endosomal Toll-Like Receptors", Trends Cell Biol., 2014, vol. 24, No. 6, pp. 360-369.
Lee et al., "Dependence of Golgi Apparatus Integrity on Nitric Oxide in Vascular Cells: Implications in Pulmonary Arterial Hypertension", Am. J. Physiol. Heart Circ. Physiol., 2011, No. 300, pp. H1141-H1158.
Lee et al., "Impaired Wound Healing and Angiogenesis in eNOS-Deficient Mice", Am. J. Physiol., 1999, vol. 277, pp. H1600-H1608.
Leung et al., "DNA Nanomachine Chemically Resolves Lysosomes in Live Cells", Nat. Nanotechnol., 2019, vol. 14, No. 2, pp. 176-183.
Yeh et al., "Toll-Like Receptor 9 and 21 Have Different Ligand Recognition Profiles and Cooperatively Mediate Activity of CpG-oligodeoxynucleotides in Zebrafish", PNAS, 2013, vol. 110, No. 51, pp. 20711-20716.
Ying et al., "An Emerging Role for Endothelial Nitric Oxide Synthase in Chronic Inflammation and Cancer", Cancer Res., 2007, vol. 67, pp. 1407-1410.
You et al., "DNA Probe for Monitoring Dynamic and Transient Molecular Encounters on Live Cell Membranes", Nat. Nanotechnol., 2017, vol. 12, No. 5, pp. 453-459.
Zhang et al., "Structural Analysis Reveals that Toll-like Receptor 7 Is a Dual Receptor for Guanosine and Single-Stranded RNA", Immunity, 2016, vol. 45, pp. 737-748.
Zhang et al, "Functional Relevance of Golgi- and Plasma Membrane-Localized Endothelial NO Synthase in Reconstituted Endothelial Cells", Arterioscler. Throm. Basc. Biol., 2006, vol. 26, pp. 1015-1021.
U.S. Appl. No. 18/433,029, filed Feb. 5, 2024.
U.S. Appl. No. 18/667,104, filed May 17, 2024.

c f d c f a)

b)

b)

c)

d)

e)

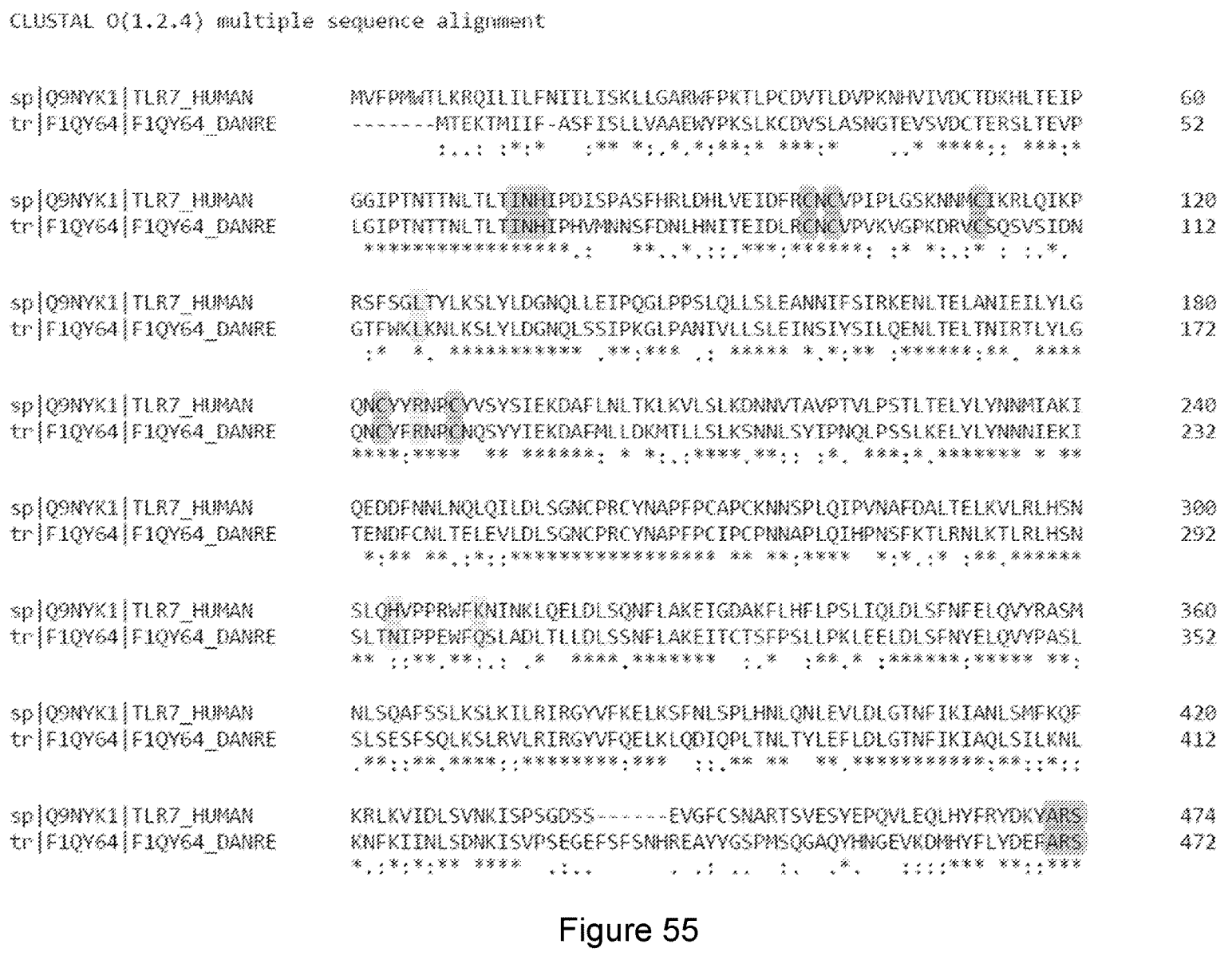

```
CLUSTAL O(1.2.4) multiple sequence alignment

sp|Q9NYK1|TLR7_HUMAN      MVFPMWTLKRQILILFNIILISKLLGARWFPKTLPCDVTLDVPKNHVIVDCTDKHLTEIP   60
tr|F1QY64|F1QY64_DANRE    -------MTEKTMIIF-ASFISLLVAAEWYPKSLKCDVSLASNGTEVSVDCTERSLTEVP   52
                                 :..: :*:*   :** *:.*.*:**:* ***:*    ..* ****:: ***:*

sp|Q9NYK1|TLR7_HUMAN      GGIPTNTTNLTLTINHIPDISPASFHRLDHLVEIDFRCNCVPIPLGSKNNMCIKRLQIKP   120
tr|F1QY64|F1QY64_DANRE    LGIPTNTTNLTLTINHIPHVMNNSFDNLHNITEIDLRCNCVPVKVGPKDRVCSQSVSIDN   112
                           *****************.:   **..*.::.***:******: :* *:.:* : :.*.

sp|Q9NYK1|TLR7_HUMAN      RSFSGLTYLKSLYLDGNQLLEIPQGLPPSLQLLSLEANNIFSIRKENLTELANIEILYLG   180
tr|F1QY64|F1QY64_DANRE    GTFWKLKNLKSLYLDGNQLSSIPKGLPANIVLLSLEINSIYSILQENLTELTNIRTLYLG   172
                           :*  *. *********** .**:*** .: ***** *.*:** :******:**. ****

sp|Q9NYK1|TLR7_HUMAN      QNCYYRNPCYVSYSIEKDAFLNLTKLKVLSLKDNNVTAVPTVLPSTLTELYLYNNMIAKI   240
tr|F1QY64|F1QY64_DANRE    QNCYFRNPCNQSYYIEKDAFMLLDKMTLLSLKSNNLSYIPNQLPSSLKELYLYNNNIEKI   232
                          ****:****  ** ******: * *:.:****.**:: :*. ***:*.******* * **

sp|Q9NYK1|TLR7_HUMAN      QEDDFNNLNQLQILDLSGNCPRCYNAPFPCAPCKNNSPLQIPVNAFDALTELKVLRLHSN   300
tr|F1QY64|F1QY64_DANRE    TENDFCNLTELEVLDLSGNCPRCYNAPFPCIPCPNNAPLQIHPNSFKTLRNLKTLRLHSN   292
                           *:** **.:*::***************** ** **:****  *:*.:* :**.******

sp|Q9NYK1|TLR7_HUMAN      SLQHVPPRWFKNINKLQELDLSQNFLAKEIGDAKFLHFLPSLIQLDLSFNFELQVYRASM   360
tr|F1QY64|F1QY64_DANRE    SLTNIPPEWFQSLADLTLLDLSSNFLAKEITCTSFPSLLPKLEELDLSFNYELQVYPASL   352
                          ** ::**.**::: .*  ****.*******  :.*  :**.* :******:***** **:

sp|Q9NYK1|TLR7_HUMAN      NLSQAFSSLKSLKILRIRGYVFKELKSFNLSPLHNLQNLEVLDLGTNFIKIANLSMFKQF   420
tr|F1QY64|F1QY64_DANRE    SLSESFSQLKSLRVLRIRGYVFQELKLQDIQPLTNLTYLEFLDLGTNFIKIAQLSILKNL   412
                          .**::**.****::*********:***   ::.** **  **.***********:**::*::

sp|Q9NYK1|TLR7_HUMAN      KRLKVIDLSVNKISPSGDSS------EVGFCSNARTSVESYEPQVLEQLHYFRYDKYARS   474
tr|F1QY64|F1QY64_DANRE    KNFKIINLSDNKISVPSEGEFSFSNHREAYYGSPMSQGAQYHNGEVKDMHYFLYDEFARS   472
                          *.:*:*:** ****  .:..      . .: ..  :.  .*.    ::::*** **::***
```

Figure 55

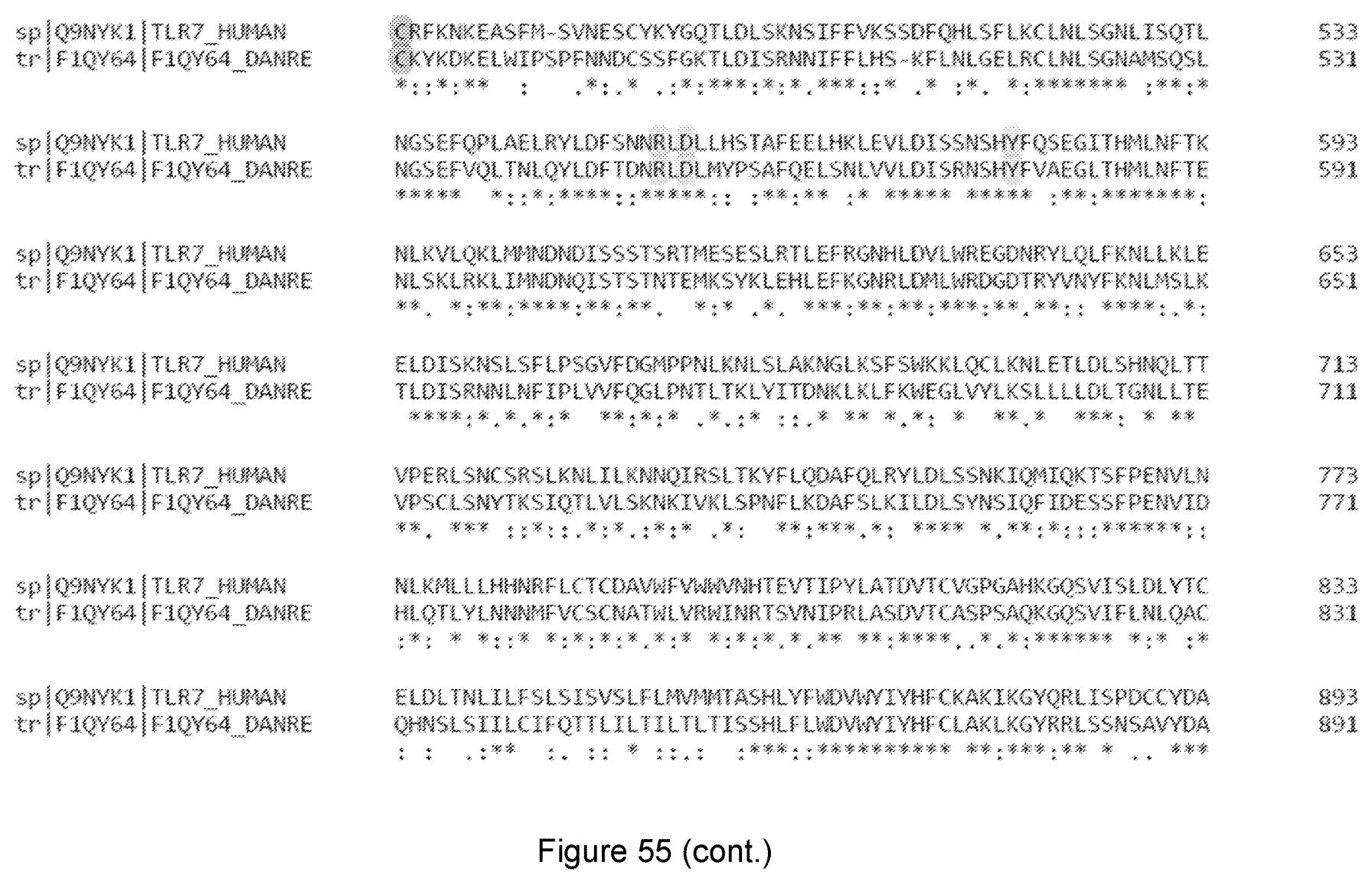

```
sp|Q9NYK1|TLR7_HUMAN      CRFKNKEASFM-SVNESCYKYGQTLDLSKNSIFFVKSSDFQHLSFLKCLNLSGNLISQTL     533
tr|F1QY64|F1QY64_DANRE    CKYKDKELWIPSPFNNDCSSFGKTLDISRNNIFFLHS-KFLNLGELRCLNLSGNAMSQSL     531
                          *::*:**  :    .*:.* .:*:***:*:*.***::* .* :*. *:******* :**:*

sp|Q9NYK1|TLR7_HUMAN      NGSEFQPLAELRYLDFSNNRLDLLHSTAFEELHKLEVLDISSNSHYFQSEGITHMLNFTK     593
tr|F1QY64|F1QY64_DANRE    NGSEFVQLTNLQYLDFTDNRLDLMYPSAFQELSNLVVLDISRNSHYFVAEGLTHMLNFTE     591
                          *****  *::*:****::*****:: :**:** :* ***** ***** :**:*******:

sp|Q9NYK1|TLR7_HUMAN      NLKVLQKLMMNDNDISSSTSRTMESESLRTLEFRGNHLDVLWREGDNRYLQLFKNLLKLE     653
tr|F1QY64|F1QY64_DANRE    NLSKLRKLIMNDNQISTSTNTEMKSYKLEHLEFKGNRLDMLWRDGDTRYVNYFKNLMSLK     651
                          **. *:**:****:**:**.  *:* .*. ***:**:**:***:**.**:: ****:.*:

sp|Q9NYK1|TLR7_HUMAN      ELDISKNSLSFLPSGVFDGMPPNLKNLSLAKNGLKSFSWKKLQCLKNLETLDLSHNQLTT     713
tr|F1QY64|F1QY64_DANRE    TLDISRNNLNFIPLVVFQGLPNTLTKLYITDNKLKLFKWEGLVYLKSLLLLDLTGNLLTE     711
                           ****:*.*.*:*  **:*:* .*.:* ::.* ** *.*: *  **.*  ***: * **

sp|Q9NYK1|TLR7_HUMAN      VPERLSNCSRSLKNLILKNNQIRSLTKYFLQDAFQLRYLDLSSNKIQMIQKTSFPENVLN     773
tr|F1QY64|F1QY64_DANRE    VPSCLSNYTKSIQTLVLSKNKIVKLSPNFLKDAFSLKILDLSYNSIQFIDESSFPENVID     771
                          **. *** ::*::.*:*.:*:* .*:  **:***.*: **** *.**:*:::******::

sp|Q9NYK1|TLR7_HUMAN      NLKMLLLHHNRFLCTCDAVWFVWWVNHTEVTIPYLATDVTCVGPGAHKGQSVISLDLYTC     833
tr|F1QY64|F1QY64_DANRE    HLQTLYLNNNMFVCSCNATWLVRWINRTSVNIPRLASDVTCASPSAQKGQSVIFLNLQAC     831
                          :*: * *::* *:*:*:*.*:* *:*.**.*.** **:****..*.*:****** *:* :*

sp|Q9NYK1|TLR7_HUMAN      ELDLTNLILFSLSISVSLFLMVMMTASHLYFWDVWYIYHFCKAKIKGYQRLISPDCCYDA     893
tr|F1QY64|F1QY64_DANRE    QHNSLSIILCIFQTTLILTILTLTISSHLFLWDVWYIYHFCLAKLKGYRRLSSNSAVYDA     891
                          : :  .:**  :. :: * ::.:  :***::********** **:***:** *  .. ***
```

Figure 55 (cont.)

SEQUENCE LISTING

<160> NUMBER OF SEQ ID NOS: 53

<210> SEQ ID NO 1
<211> LENGTH: 24
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5' AzideN

<400> SEQUENCE: 1
atcaacactg cacaccagac agca 24

<210> SEQ ID NO 2
<211> LENGTH: 24
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5' Alexa488
<220> FEATURE:
<221> NAME/KEY: misc_feature
<222> LOCATION: (24)..(24)
<223> OTHER INFORMATION: 3' CholTEG

<400> SEQUENCE: 2
tgctgtctgg tgtgcagtgt tgat 24

<210> SEQ ID NO 3
<211> LENGTH: 51
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (31)..(32)
<223> OTHER INFORMATION: Alexa647

<400> SEQUENCE: 3
ggctatagca catgggtaaa acgactttgc tgtctggtgt gcagtgttga t 51

<210> SEQ ID NO 4
<211> LENGTH: 24
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5' DAR-PEG10

<400> SEQUENCE: 4
atcaacactg cacaccagac agca 24

<210> SEQ ID NO 5
<211> LENGTH: 24
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature

```
<222> LOCATION: (1)..(1)
<223> OTHER INFORMATION: 5' ATTO647N

<400> SEQUENCE: 5

tgctgtctgg tgtgcagtgt tgat                                              24


<210> SEQ ID NO 6
<211> LENGTH: 46
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5' ATTO647N

<400> SEQUENCE: 6

tgctgtctgg tgtgcagtgt tgattttcca tgacgttcct gacgtt                      46


<210> SEQ ID NO 7
<211> LENGTH: 46
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5' ATTO647N

<400> SEQUENCE: 7

tgctgtctgg tgtgcagtgt tgattttcca tgagcttcct gacctt                      46


<210> SEQ ID NO 8
<211> LENGTH: 48
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5' ATTO647N

<400> SEQUENCE: 8

tgctgtctgg tgtgcagtgt tgattttcgt cgttgtcgtt ttgtcgtt                    48


<210> SEQ ID NO 9
<211> LENGTH: 47
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5' ATTO647N

<400> SEQUENCE: 9

tgctgtctgg tgtgcagtgt tgattttgct gctgtgcttt tgtgctt                     47


<210> SEQ ID NO 10
<211> LENGTH: 47
<212> TYPE: DNA
<213> ORGANISM: Artificial Sequence
<220> FEATURE:
<223> OTHER INFORMATION: Synthetic oligonucleotide
<220> FEATURE:
```

```
<221> NAME/KEY: misc_feature
<222> LOCATION: (1)..(1)
<223> OTHER INFORMATION: 5' ATTO647N

<400> SEQUENCE: 10

tgctgtctgg tgtgcagtgt tgattttgga cggaaaagac cccgugg                   47


<210> SEQ ID NO 11
<211> LENGTH: 46
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5' ATTO647N

<400> SEQUENCE: 11

tgctgtctgg tgtgcagtgt tgattttgga cgggaagacc ccgugg                    46


<210> SEQ ID NO 12
<211> LENGTH: 24
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5' SH
<220> FEATURE:
<221> NAME/KEY: misc_feature
<222> LOCATION: (24)..(24)
<223> OTHER INFORMATION: 3' pHlicker-SH

<400> SEQUENCE: 12

atcaacactg cacaccagac agca                                            24


<210> SEQ ID NO 13
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 13

tttccatgac gttcctgacg tt                                              22


<210> SEQ ID NO 14
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 14

tttccatgag cttcctgacc tt                                              22


<210> SEQ ID NO 15
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 15

tttcgtcgtt gtcgttttgt cgtt                                            24
```

<210> SEQ ID NO 16
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 16
tttgctgctg tgcttttgtg ctt 23

<210> SEQ ID NO 17
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 17
tttggacgga aaagaccccg ugg 23

<210> SEQ ID NO 18
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 18
tttggacggg aagaccccgu gg 22

<210> SEQ ID NO 19
<211> LENGTH: 72
<212> TYPE: RNA
<213> ORGANISM: Artificial Sequence
<220> FEATURE:
<223> OTHER INFORMATION: Synthetic oligonucleotide

<400> SEQUENCE: 19
ccccagaaag gcaucccugg cguucaagau uugggucggc uguagcucca gguuuagucc 60
ggacaauagg gg 72

<210> SEQ ID NO 20
<211> LENGTH: 1045
<212> TYPE: PRT
<213> ORGANISM: Danio rerio

<400> SEQUENCE: 20

```
Met Thr Glu Lys Thr Met Ile Ile Phe Ala Ser Phe Ile Ser Leu Leu
1               5                   10                  15

Val Ala Ala Glu Trp Tyr Pro Lys Ser Leu Lys Cys Asp Val Ser Leu
            20                  25                  30

Ala Ser Asn Gly Thr Glu Val Ser Val Asp Cys Thr Glu Arg Ser Leu
        35                  40                  45

Thr Glu Val Pro Leu Gly Ile Pro Thr Asn Thr Thr Asn Leu Thr Leu
    50                  55                  60

Thr Ile Asn His Ile Pro His Val Met Asn Asn Ser Phe Asp Asn Leu
65                  70                  75                  80

His Asn Ile Thr Glu Ile Asp Leu Arg Cys Asn Cys Val Pro Val Lys
                85                  90                  95

Val Gly Pro Lys Asp Arg Val Cys Ser Gln Ser Val Ser Ile Asp Asn
            100                 105                 110
```

-continued

```
Gly Thr Phe Trp Lys Leu Lys Asn Leu Lys Ser Leu Tyr Leu Asp Gly
        115                 120                 125

Asn Gln Leu Ser Ser Ile Pro Lys Gly Leu Pro Ala Asn Ile Val Leu
    130                 135                 140

Leu Ser Leu Glu Ile Asn Ser Ile Tyr Ser Ile Leu Gln Glu Asn Leu
145                 150                 155                 160

Thr Glu Leu Thr Asn Ile Arg Thr Leu Tyr Leu Gly Gln Asn Cys Tyr
                165                 170                 175

Phe Arg Asn Pro Cys Asn Gln Ser Tyr Tyr Ile Glu Lys Asp Ala Phe
            180                 185                 190

Met Leu Leu Asp Lys Met Thr Leu Leu Ser Leu Lys Ser Asn Asn Leu
        195                 200                 205

Ser Tyr Ile Pro Asn Gln Leu Pro Ser Ser Leu Lys Glu Leu Tyr Leu
    210                 215                 220

Tyr Asn Asn Asn Ile Glu Lys Ile Thr Glu Asn Asp Phe Cys Asn Leu
225                 230                 235                 240

Thr Glu Leu Glu Val Leu Asp Leu Ser Gly Asn Cys Pro Arg Cys Tyr
                245                 250                 255

Asn Ala Pro Phe Pro Cys Ile Pro Cys Pro Asn Asn Ala Pro Leu Gln
            260                 265                 270

Ile His Pro Asn Ser Phe Lys Thr Leu Arg Asn Leu Lys Thr Leu Arg
        275                 280                 285

Leu His Ser Asn Ser Leu Thr Asn Ile Pro Pro Glu Trp Phe Gln Ser
    290                 295                 300

Leu Ala Asp Leu Thr Leu Leu Asp Leu Ser Ser Asn Phe Leu Ala Lys
305                 310                 315                 320

Glu Ile Thr Cys Thr Ser Phe Pro Ser Leu Leu Pro Lys Leu Glu Glu
                325                 330                 335

Leu Asp Leu Ser Phe Asn Tyr Glu Leu Gln Val Tyr Pro Ala Ser Leu
            340                 345                 350

Ser Leu Ser Glu Ser Phe Ser Gln Leu Lys Ser Leu Arg Val Leu Arg
        355                 360                 365

Ile Arg Gly Tyr Val Phe Gln Glu Leu Lys Leu Gln Asp Ile Gln Pro
    370                 375                 380

Leu Thr Asn Leu Thr Tyr Leu Glu Phe Leu Asp Leu Gly Thr Asn Phe
385                 390                 395                 400

Ile Lys Ile Ala Gln Leu Ser Ile Leu Lys Asn Leu Lys Asn Phe Lys
                405                 410                 415

Ile Ile Asn Leu Ser Asp Asn Lys Ile Ser Val Pro Ser Glu Gly Glu
            420                 425                 430

Phe Ser Phe Ser Asn His Arg Glu Ala Tyr Tyr Gly Ser Pro Met Ser
        435                 440                 445

Gln Gly Ala Gln Tyr His Asn Gly Glu Val Lys Asp Met His Tyr Phe
    450                 455                 460

Leu Tyr Asp Glu Phe Ala Arg Ser Cys Lys Tyr Lys Asp Lys Glu Leu
465                 470                 475                 480

Trp Ile Pro Ser Pro Phe Asn Asn Asp Cys Ser Ser Phe Gly Lys Thr
                485                 490                 495

Leu Asp Ile Ser Arg Asn Asn Ile Phe Phe Leu His Ser Lys Phe Leu
            500                 505                 510

Asn Leu Gly Glu Leu Arg Cys Leu Asn Leu Ser Gly Asn Ala Met Ser
        515                 520                 525
```

-continued

```
Gln Ser Leu Asn Gly Ser Glu Phe Val Gln Leu Thr Asn Leu Gln Tyr
    530                 535                 540

Leu Asp Phe Thr Asp Asn Arg Leu Asp Leu Met Tyr Pro Ser Ala Phe
545                 550                 555                 560

Gln Glu Leu Ser Asn Leu Val Val Leu Asp Ile Ser Arg Asn Ser His
                565                 570                 575

Tyr Phe Val Ala Glu Gly Leu Thr His Met Leu Asn Phe Thr Glu Asn
            580                 585                 590

Leu Ser Lys Leu Arg Lys Leu Ile Met Asn Asp Asn Gln Ile Ser Thr
        595                 600                 605

Ser Thr Asn Thr Glu Met Lys Ser Tyr Lys Leu Glu His Leu Glu Phe
    610                 615                 620

Lys Gly Asn Arg Leu Asp Met Leu Trp Arg Asp Gly Asp Thr Arg Tyr
625                 630                 635                 640

Val Asn Tyr Phe Lys Asn Leu Met Ser Leu Lys Thr Leu Asp Ile Ser
                645                 650                 655

Arg Asn Asn Leu Asn Phe Ile Pro Leu Val Val Phe Gln Gly Leu Pro
            660                 665                 670

Asn Thr Leu Thr Lys Leu Tyr Ile Thr Asp Asn Lys Leu Lys Leu Phe
        675                 680                 685

Lys Trp Glu Gly Leu Val Tyr Leu Lys Ser Leu Leu Leu Leu Asp Leu
    690                 695                 700

Thr Gly Asn Leu Leu Thr Glu Val Pro Ser Cys Leu Ser Asn Tyr Thr
705                 710                 715                 720

Lys Ser Ile Gln Thr Leu Val Leu Ser Lys Asn Lys Ile Val Lys Leu
                725                 730                 735

Ser Pro Asn Phe Leu Lys Asp Ala Phe Ser Leu Lys Ile Leu Asp Leu
            740                 745                 750

Ser Tyr Asn Ser Ile Gln Phe Ile Asp Glu Ser Ser Phe Pro Glu Asn
        755                 760                 765

Val Ile Asp His Leu Gln Thr Leu Tyr Leu Asn Asn Asn Met Phe Val
    770                 775                 780

Cys Ser Cys Asn Ala Thr Trp Leu Val Arg Trp Ile Asn Arg Thr Ser
785                 790                 795                 800

Val Asn Ile Pro Arg Leu Ala Ser Asp Val Thr Cys Ala Ser Pro Ser
                805                 810                 815

Ala Gln Lys Gly Gln Ser Val Ile Phe Leu Asn Leu Gln Ala Cys Gln
            820                 825                 830

His Asn Ser Leu Ser Ile Ile Leu Cys Ile Phe Gln Thr Thr Leu Ile
        835                 840                 845

Leu Thr Ile Leu Thr Leu Thr Ile Ser Ser His Leu Phe Leu Trp Asp
    850                 855                 860

Val Trp Tyr Ile Tyr His Phe Cys Leu Ala Lys Leu Lys Gly Tyr Arg
865                 870                 875                 880

Arg Leu Ser Ser Asn Ser Ala Val Tyr Asp Ala Phe Val Ile Tyr Asp
                885                 890                 895

Thr Thr Asp Pro Ala Val Gln Glu Trp Val Met Gln Glu Leu Arg Val
            900                 905                 910

His Leu Glu Asp Lys Gly Asp Pro Arg Met Asn Leu Cys Leu Glu Glu
        915                 920                 925

Arg Asp Trp Val Pro Gly Cys Pro Leu Ile Glu Asn Leu Ser Gln Ser
    930                 935                 940

Ile Gln Leu Ser Gln Arg Thr Val Phe Ile Leu Thr Glu Arg Tyr Ile
```

-continued

```
945                 950                 955                 960

Arg Ser Gly Ser Phe Arg Thr Ala Phe Tyr Leu Ala His Gln Arg Leu
                965                 970                 975

Met Asp Glu Arg Asn Asp Val Ile Val Leu Ile Phe Leu Glu Arg Met
            980                 985                 990

Pro Cys His Ser Lys Tyr Leu Arg  Leu Arg Lys Arg Leu  Tyr Lys Lys
        995                 1000                1005

Ser Val  Leu Glu Trp Pro Arg  Asn Pro Gln Ala Gln  Arg Tyr Phe
    1010                 1015                 1020

Trp Phe  Ser Leu Arg Ser Leu  Met Ala Thr Glu Ser  Gln Tyr Asn
    1025                 1030                 1035

Thr Leu  Phe Gln Glu Thr Leu
    1040                 1045


<210> SEQ ID NO 21
<211> LENGTH: 1049
<212> TYPE: PRT
<213> ORGANISM: Homo sapiens

<400> SEQUENCE: 21

Met Val Phe Pro Met Trp Thr Leu Lys Arg Gln Ile Leu Ile Leu Phe
1               5                   10                  15

Asn Ile Ile Leu Ile Ser Lys Leu Leu Gly Ala Arg Trp Phe Pro Lys
            20                  25                  30

Thr Leu Pro Cys Asp Val Thr Leu Asp Val Pro Lys Asn His Val Ile
        35                  40                  45

Val Asp Cys Thr Asp Lys His Leu Thr Glu Ile Pro Gly Gly Ile Pro
    50                  55                  60

Thr Asn Thr Thr Asn Leu Thr Leu Thr Ile Asn His Ile Pro Asp Ile
65                  70                  75                  80

Ser Pro Ala Ser Phe His Arg Leu Asp His Leu Val Glu Ile Asp Phe
                85                  90                  95

Arg Cys Asn Cys Val Pro Ile Pro Leu Gly Ser Lys Asn Asn Met Cys
            100                 105                 110

Ile Lys Arg Leu Gln Ile Lys Pro Arg Ser Phe Ser Gly Leu Thr Tyr
        115                 120                 125

Leu Lys Ser Leu Tyr Leu Asp Gly Asn Gln Leu Leu Glu Ile Pro Gln
    130                 135                 140

Gly Leu Pro Pro Ser Leu Gln Leu Leu Ser Leu Glu Ala Asn Asn Ile
145                 150                 155                 160

Phe Ser Ile Arg Lys Glu Asn Leu Thr Glu Leu Ala Asn Ile Glu Ile
                165                 170                 175

Leu Tyr Leu Gly Gln Asn Cys Tyr Tyr Arg Asn Pro Cys Tyr Val Ser
            180                 185                 190

Tyr Ser Ile Glu Lys Asp Ala Phe Leu Asn Leu Thr Lys Leu Lys Val
        195                 200                 205

Leu Ser Leu Lys Asp Asn Asn Val Thr Ala Val Pro Thr Val Leu Pro
    210                 215                 220

Ser Thr Leu Thr Glu Leu Tyr Leu Tyr Asn Asn Met Ile Ala Lys Ile
225                 230                 235                 240

Gln Glu Asp Asp Phe Asn Asn Leu Asn Gln Leu Gln Ile Leu Asp Leu
                245                 250                 255

Ser Gly Asn Cys Pro Arg Cys Tyr Asn Ala Pro Phe Pro Cys Ala Pro
            260                 265                 270
```

-continued

```
Cys Lys Asn Asn Ser Pro Leu Gln Ile Pro Val Asn Ala Phe Asp Ala
        275                 280                 285

Leu Thr Glu Leu Lys Val Leu Arg Leu His Ser Asn Ser Leu Gln His
    290                 295                 300

Val Pro Pro Arg Trp Phe Lys Asn Ile Asn Lys Leu Gln Glu Leu Asp
305                 310                 315                 320

Leu Ser Gln Asn Phe Leu Ala Lys Glu Ile Gly Asp Ala Lys Phe Leu
                325                 330                 335

His Phe Leu Pro Ser Leu Ile Gln Leu Asp Leu Ser Phe Asn Phe Glu
            340                 345                 350

Leu Gln Val Tyr Arg Ala Ser Met Asn Leu Ser Gln Ala Phe Ser Ser
        355                 360                 365

Leu Lys Ser Leu Lys Ile Leu Arg Ile Arg Gly Tyr Val Phe Lys Glu
    370                 375                 380

Leu Lys Ser Phe Asn Leu Ser Pro Leu His Asn Leu Gln Asn Leu Glu
385                 390                 395                 400

Val Leu Asp Leu Gly Thr Asn Phe Ile Lys Ile Ala Asn Leu Ser Met
                405                 410                 415

Phe Lys Gln Phe Lys Arg Leu Lys Val Ile Asp Leu Ser Val Asn Lys
            420                 425                 430

Ile Ser Pro Ser Gly Asp Ser Ser Glu Val Gly Phe Cys Ser Asn Ala
        435                 440                 445

Arg Thr Ser Val Glu Ser Tyr Glu Pro Gln Val Leu Glu Gln Leu His
    450                 455                 460

Tyr Phe Arg Tyr Asp Lys Tyr Ala Arg Ser Cys Arg Phe Lys Asn Lys
465                 470                 475                 480

Glu Ala Ser Phe Met Ser Val Asn Glu Ser Cys Tyr Lys Tyr Gly Gln
                485                 490                 495

Thr Leu Asp Leu Ser Lys Asn Ser Ile Phe Phe Val Lys Ser Ser Asp
            500                 505                 510

Phe Gln His Leu Ser Phe Leu Lys Cys Leu Asn Leu Ser Gly Asn Leu
        515                 520                 525

Ile Ser Gln Thr Leu Asn Gly Ser Glu Phe Gln Pro Leu Ala Glu Leu
    530                 535                 540

Arg Tyr Leu Asp Phe Ser Asn Asn Arg Leu Asp Leu Leu His Ser Thr
545                 550                 555                 560

Ala Phe Glu Glu Leu His Lys Leu Glu Val Leu Asp Ile Ser Ser Asn
                565                 570                 575

Ser His Tyr Phe Gln Ser Glu Gly Ile Thr His Met Leu Asn Phe Thr
            580                 585                 590

Lys Asn Leu Lys Val Leu Gln Lys Leu Met Met Asn Asp Asn Asp Ile
        595                 600                 605

Ser Ser Ser Thr Ser Arg Thr Met Glu Ser Glu Ser Leu Arg Thr Leu
    610                 615                 620

Glu Phe Arg Gly Asn His Leu Asp Val Leu Trp Arg Glu Gly Asp Asn
625                 630                 635                 640

Arg Tyr Leu Gln Leu Phe Lys Asn Leu Leu Lys Leu Glu Glu Leu Asp
                645                 650                 655

Ile Ser Lys Asn Ser Leu Ser Phe Leu Pro Ser Gly Val Phe Asp Gly
            660                 665                 670

Met Pro Pro Asn Leu Lys Asn Leu Ser Leu Ala Lys Asn Gly Leu Lys
        675                 680                 685

Ser Phe Ser Trp Lys Lys Leu Gln Cys Leu Lys Asn Leu Glu Thr Leu
```

```
    690                 695                 700

Asp Leu Ser His Asn Gln Leu Thr Thr Val Pro Glu Arg Leu Ser Asn
705                 710                 715                 720

Cys Ser Arg Ser Leu Lys Asn Leu Ile Leu Lys Asn Asn Gln Ile Arg
                725                 730                 735

Ser Leu Thr Lys Tyr Phe Leu Gln Asp Ala Phe Gln Leu Arg Tyr Leu
            740                 745                 750

Asp Leu Ser Ser Asn Lys Ile Gln Met Ile Gln Lys Thr Ser Phe Pro
        755                 760                 765

Glu Asn Val Leu Asn Asn Leu Lys Met Leu Leu Leu His His Asn Arg
    770                 775                 780

Phe Leu Cys Thr Cys Asp Ala Val Trp Phe Val Trp Trp Val Asn His
785                 790                 795                 800

Thr Glu Val Thr Ile Pro Tyr Leu Ala Thr Asp Val Thr Cys Val Gly
                805                 810                 815

Pro Gly Ala His Lys Gly Gln Ser Val Ile Ser Leu Asp Leu Tyr Thr
            820                 825                 830

Cys Glu Leu Asp Leu Thr Asn Leu Ile Leu Phe Ser Leu Ser Ile Ser
        835                 840                 845

Val Ser Leu Phe Leu Met Val Met Met Thr Ala Ser His Leu Tyr Phe
    850                 855                 860

Trp Asp Val Trp Tyr Ile Tyr His Phe Cys Lys Ala Lys Ile Lys Gly
865                 870                 875                 880

Tyr Gln Arg Leu Ile Ser Pro Asp Cys Cys Tyr Asp Ala Phe Ile Val
                885                 890                 895

Tyr Asp Thr Lys Asp Pro Ala Val Thr Glu Trp Val Leu Ala Glu Leu
            900                 905                 910

Val Ala Lys Leu Glu Asp Pro Arg Glu Lys His Phe Asn Leu Cys Leu
        915                 920                 925

Glu Glu Arg Asp Trp Leu Pro Gly Gln Pro Val Leu Glu Asn Leu Ser
    930                 935                 940

Gln Ser Ile Gln Leu Ser Lys Lys Thr Val Phe Val Met Thr Asp Lys
945                 950                 955                 960

Tyr Ala Lys Thr Glu Asn Phe Lys Ile Ala Phe Tyr Leu Ser His Gln
                965                 970                 975

Arg Leu Met Asp Glu Lys Val Asp Val Ile Ile Leu Ile Phe Leu Glu
            980                 985                 990

Lys Pro Phe Gln Lys Ser Lys Phe  Leu Gln Leu Arg Lys  Arg Leu Cys
        995                 1000                1005

Gly Ser  Ser Val Leu Glu Trp  Pro Thr Asn Pro Gln  Ala His Pro
    1010                1015                1020

Tyr Phe  Trp Gln Cys Leu Lys  Asn Ala Leu Ala Thr  Asp Asn His
    1025                1030                1035

Val Ala  Tyr Ser Gln Val Phe  Lys Glu Thr Val
    1040                1045
```

<210> SEQ ID NO 22
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 22
agcggctccc aggcccacga 20

<210> SEQ ID NO 23
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 23
acctgcagtc ccgggca 17

<210> SEQ ID NO 24
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 24
cctcgccttt gccgatcc 18

<210> SEQ ID NO 25
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 25
gagtccatca cgatcccagt 20

<210> SEQ ID NO 26
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 26
tcattagatc catattttcc ttcct 25

<210> SEQ ID NO 27
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 27
tcatggtctt ctcagtcatc tgaaa 25

<210> SEQ ID NO 28
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 28
tcaaggacac cattggtcca aacat 25

<210> SEQ ID NO 29
<211> LENGTH: 25
<212> TYPE: DNA
<213> ORGANISM: Artificial Sequence
<220> FEATURE:

<223> OTHER INFORMATION: Synthetic oligonucleotide

<400> SEQUENCE: 29
agtaccagcg gaacaagcat tttca 25

<210> SEQ ID NO 30
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 30
gctttctctt gatttccttt tcatt 25

<210> SEQ ID NO 31
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 31
acagtttaaa agtaccttag ccgct 25

<210> SEQ ID NO 32
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 32
ggtacacttc cagggatgga ga 22

<210> SEQ ID NO 33
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 33
ttctagttga ccttgtttgt agag 24

<210> SEQ ID NO 34
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 34
ctctgtattt tccaaaccac tctg 24

<210> SEQ ID NO 35
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 35
cctgatcaca gagtctcctg aaag 24

```
<210> SEQ ID NO 36
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 36

ggggaagatg gcgct                                                    15


<210> SEQ ID NO 37
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 37

ccagaagagc ggctgcactc                                               20


<210> SEQ ID NO 38
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 38

tttaggtcaa ggggtggatt ac                                            22


<210> SEQ ID NO 39
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 39

ctactatgtc ggctgattgt tctc                                          24


<210> SEQ ID NO 40
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 40

ggagaacagt ggcgtcgctt ac                                            22


<210> SEQ ID NO 41
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 41

gttcttttgc actgtttgga tcag                                          24


<210> SEQ ID NO 42
<211> LENGTH: 24
<212> TYPE: DNA
<213> ORGANISM: Artificial Sequence
<220> FEATURE:
<223> OTHER INFORMATION: Synthetic oligonucleotide
```

<400> SEQUENCE: 42
gtttgcagca gtattttggt catc 24

<210> SEQ ID NO 43
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 43
gttctctgat ttatggctgt ctttg 25

<210> SEQ ID NO 44
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 44
cgagcaggag atgggaacc 19

<210> SEQ ID NO 45
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 45
caacggaaac gctcattgc 19

<210> SEQ ID NO 46
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 46
acggaaagac ccc 13

<210> SEQ ID NO 47
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 47 aaagacccc 9

<210> SEQ ID NO 48
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 48 aaagacccc 9

<210> SEQ ID NO 49
<211> LENGTH: 9

-continued

```
<212> TYPE: DNA
<213> ORGANISM: Artificial Sequence
<220> FEATURE:
<223> OTHER INFORMATION: Synthetic oligonucleotide

<400> SEQUENCE: 49

aaagacccc                                                              9


<210> SEQ ID NO 50
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 50

acggaaagac ccc                                                        13


<210> SEQ ID NO 51
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 51

acggaaagac ccc                                                        13


<210> SEQ ID NO 52
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 52

acggaaagac ccc                                                        13


<210> SEQ ID NO 53
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 53

acggaaagac ccc                                                        13
```

METHOD AND COMPOSITION FOR MEASUREMENT OF NITRIC OXIDE

CROSS-REVERENCE TO RELATED APPLICATIONS

This application is a section 371 national phase of PCT/US2020/064544, filed Dec. 11, 2020, which claims the benefit of priority of U.S. Provisional Patent Application No. 62/946,720, filed Dec. 11, 2019, both which are hereby incorporated by reference in its entirety.

SEQUENCE LISTING

A computer readable form of the Sequence Listing is filed with this application by electronic submission and is incorporated into this application by reference in its entirety. The sequence listing submitted herewith is contained in the file created Dec. 9, 2020, entitled "19-2367-WO_Sequence-Listing_ST25.txt" and 29 kilobytes in size.

FIELD OF DISCLOSURE

This disclosure relates to a method and composition for determining nitric oxide concentrations in biological samples. More particularly, this disclosure relates to methods capable of mapping nitric oxide synthase activity with subcellular spatial resolution and mapping, nitric oxide in living tissue using nucleic acid complexes.

BACKGROUND OF DISCLOSURE

Nitric oxide synthase (NOS) catalyzes the synthesis of NO, an essential precursor for the S-nitrosylation of proteins. S-nitrosylation is a post-translational modification with pivotal roles in cell signaling (Hess, D. T., Matsumoto A., Kim, S.-O., Marshall, H. E. & Stamler, J. S. Protein S-nitrosylation: purview and parameters. *Nat. Rev. Mol. Cell Biol.* 6, 150-166 (2005)). Unlike most second messengers, NO cannot be stored and released as it is charge neutral, highly diffusible and reactive. Therefore, activation of all NO synthase isoforms is stringently controlled both spatially and temporally, the dysregulation of which leads to diverse diseases (Bredt, D. S. &. Snyder, S. H. Nitric oxide: a physiologic messenger molecule. *Annu. Rev. Biochem.* 63, 175-195 (1994)). In particular, dysregulation of NOS3 is strongly implicated in cancer (Lim, K.-H., Ancrile, B. B., Kashatus, D. F. & Counter, C. M. Tumour maintenance is mediated by eNOS. *Nature* 452, 646-649 (2008); Xu, W., Liu, L. Z., Loizidou, M., Ahmed, M. & Charles, I. G. The role of nitric oxide in cancer. *Cell Res.* 12, 311-320 (2002)) It affects cell proliferation, apoptosis, angiogenesis, metastasis and the immune response (Fukumura, D., Kashiwagi S. & Jain, R. K. The role of nitric oxide in tumour progression. Nat. Rev. Cancer 6, 521-534 (2006); Landenranta, J. et al. Endothelial nitric oxide synthase mediates lymphangiogenesis and lymphatic metastasis. *Cancer Res.* 69, 2801-2808 (2009): Ying, L. & Hofseth, L. J. An emerging role for endothelial nitric oxide synthase in chronic inflammation and cancer. *Cancer Res.* 67, 1407-1410 (2007)). NOS3 upregulation correlates with histological tumor grade and invasiveness (Thomsen, L. L. et al. Nitric oxide synthase activity in human breast cancer. *Br. J. Cancer* 72, 41-44 (1995); Tschugguel, W. et al. Expression of inducible nitric oxide synthase in human breast cancer depends on tumor grade. *Breast Cancer Res. Treat.* 56, 145-151 (1999): Martin, J. H., Begum, S., Alalami, O., Harrison, A. & Scott, K. W. Endothelial nitric oxide synthase: correlation with histologic grade, lymph node status and estrogen receptor expression in human breast cancer. *Tumour Biol.* 21, 90-97 (2000)). Importantly, the amount, duration and location of NO generated due to NOS3 activity can lead to different physiological outcomes (Fukumura, D., Kashiwagi, S. & Jain, R. K. The role of nitric oxide in tumour progression. *Nat. Rev. Cancer* 6,521-534 (2006); Choudhari, S. K., Chaudhary, M., Bagde, S., Gadbail, A. R. & Joshi V. Nitric oxide and cancer: a review. *World J Surg Oncol* 11, 118 (2013)). For example, high NO levels are also anti-tumorigenic, inducing tumor cell cytotoxicity and sensitization of tumor cells to radiation treatment (Fukumura, D., Kashiwagi., S. & Jain, R. K. The role of nitric oxide in tumour progression. *Nat. Rev. Cancer* 6,521-534 (2006)). The mechanisms that toggle these opposing effects arising from abnormal NO levels are still unknown.

Spatial control over NO production in living systems is generally achieved by constraining the various NO synthase isoforms to specific sub-cellular locations. For example, NOS3 is localized in two distinct regions of the cell, one at the plasma membrane and the other at trans-Golgi network (TGN) (Sowa, G. et al. Trafficking of endothelial nitric-oxide synthase in living cells. Quantitative evidence supporting the role of palmitoylation as a kinetic trapping mechanism limiting membrane diffusion. *J. Biol. Chem.* 274, 22524-22531 (1999); Sessa, W. C. et al. The Golgi association of endothelial nitric oxide synthase is necessary for the efficient synthesis of nitric oxide. *J Biol. Chem.* 270, 17641-17644 (1995)). The presence, activity and importance of NOS3 at the plasma membrane and the TGN are critical in physiology and disease, yet it has proved highly challenging to resolve the contribution of either population in any context (Zhang, Q. et al. Functional relevance of Golgi- and plasma membrane-localized endothelial NO synthase in reconstituted endothelial cells. *Arterioscler. Thromb. Vasc. Biol.* 26, 1015-1021 (2006); Jin, Z.-G. Where is endothelial nitric oxide synthase more critical: plasma membrane or Golgi? *Arterioscler. Thromb. Vasc. Biol.* 26, 959-961 (2006)). Thus, a method to sub-cellularly map reactive nitrogen species (RNS) produced due to NOS3 activity would enable one to precisely pinpoint the aberrant NOS3 sub-population.

In addition to its important role to x-nitrosylation of proteins. NO production also plays an role in the mechanism by which innate immune cells destroy pathogens. Innate immune cells destroy pathogens by ingesting and trapping them within a transient, sub-cellular organelle called the phagosome (Hess, D. T., Matsumoto, A., Kim, S.-O., Marshall, H. E. & Stamler, J. S. Protein S-nitrosylation: purview and parameters. *Nat. Rev. Mol. Cell Biol.* 6, 150-166 (2005); Bredt, D. S. & Snyder. S. H. Nitric oxide: a physiologic messenger molecule. *Annu. Rev. Biochem.* 63, 175-195 (1994)). The phagosome rapidly develops into a lethal hotspot of noxious chemicals such as reactive oxygen species (ROS) and nitric oxide (NO) that are produced by the enzymes. In mammals, ROS is produced by reduced nicotinamide-adenine dinucleotide phosphate (NADPH) oxidase (NOX), while NO can be produced by three different isoforms of NO synthases (NOS): neuronal NOS (nNOS or NOS1), inducible NOS (NOS2 or NOS2), and endothelial NOS (eNOS or NOS3) (Lim. K.-H., Ancrile, B. B., Kashatus, D. F. & Counter, C. M. Tumour maintenance is mediated by eNOS. *Nature* 452, 646-649 (2008); Xu, W., Liu, L. Z., Loizidou, M., Ahmed. M. & Charles, I. G. The role of nitric oxide in cancer. Cell Res. 12, 311-320 (2002)). NOS1 and NOS3 are constitutively active. NOS1 is preferentially expressed in neurons and plays an important role in synaptic plasticity. NOS3 is expressed in endothelial cells where its activity is critical for vasodilation. NOS2 is majorly expressed in immune cells and is pivotal to neutralizing microbes within host phagosomes. Due to their differential susceptibilities to ROS and NO, different microbes are neutralized to different extents in the phagosome (Xu, W., Liu, L. Z., Loizidou M., Ahmed, M. & Charles, I. G. The role of nitric oxide in cancer. *Cell Res.* 12, 311-320 (2002)).

Innate immune cells target pathogens for destruction by recognizing them through an array of endosome-resident or plasma membrane-resident receptors called pattern recognition receptors (PRRs) such as Toll-like receptors (TLRs), RIG-like receptors (RLRs) or NOD-like receptors (NLRB) (Fukumura, D, Kashiwagi, S. & Jain, R. K. The role of nitric oxide in tumour progression. *Nat. Rev. Cancer* 6, 521-534 (2006)). PRRs recognize conserved structural motifs of molecules present in the pathogen termed pathogen-associated molecular patterns (PAMPs) (Landenranta, J. et al. Endothelial nitric oxide synthase mediates lymphangiogenesis and lymphatic metastasis. *Cancer Res.* 69, 2801-2808 (2009)). For example, TLR-4, TLR-3 and TLR-9 detect bacterial lipopolysaccharide (LPS), viral RNA (dsRNA) and bacterial DNA (CpG DNA) respectively (Ying, L. &. Hofseth, L. J. An emerging role for endothelial nitric oxide synthase in chronic inflammation and cancer. *Cancer Res.* 67, 1407-1410 (2007)). When a TLR receptor recognizes its cognate PAMP, it initiates the TLR signaling cascade to activate NOS2 at the phagosome. When macrophages are challenged with imunogens such as *Mycobacterium smegmatic* or CpG-containing sequences, there is an initials burst of NO within the first hour. This is followed by a second phase of NO production that lasts for hours over transcriptional time scales due to NOS2 expression induced by the transcription factor NF-κB as a result of TLR stimulation. The ability to directly map the initial burst of phagosomal NO in vivo could provide a new avenue to identify mechanisms that are operational at the early stages of pathogen infection. Mice express 13 different TLRs whose cognate ligands have been identified, of which 10 have human homologs. In contrast, cognate ligands are known for only 7 of the 20 TLRs in zebrafish (Thomsen, L. L. et al. Nitric oxide synthase activity in human breast cancer. *Br. J. Cancer* 72, 41-44 (1995)). Recognition between a TLR and its cognate PAMP initiates the TLR signaling cascade, where the transcription factor NF-κB induces NOS2 expression, leading to NO production in the phagosome (Tschugguel, W. et al. Expression of inducible nitric oxide synthase in human breast cancer depends on tumor grade. *Breast Cancer Res. Treat.* 56, 145-151 (1999): Martin, J. H., Begum, S., Alalami, O., Harrison, A. & Scott, K. W. Endothelial nitric oxide synthase: correlation with histologic grade, lymph node status and estrogen receptor expression in human breast cancer. *Tumour Biol.* 21, 90-97 (2000)).

Different pathogens are differently susceptible to the various reactive species produced within the phagosome. *E. coli* is most effectively cleared by the simultaneous production of NO and ROS, *S. aureus* needs a burst of ROS followed by NO while for *L. monocytogenes* ROS is ineffective yet NO is lethal (Choudhari S. K., Chaudhary M., Bagde, S., Gadbail, A. R. & Joshi V. Nitric oxide and cancer: a review. *World J Surg Oncol* 11, 118 (201); Sowa, G. et al. Trafficking of endothelial nitric-oxide synthase in living cells. Quantitative evidence supporting the role of palmitoylation as a kinetic trapping mechanism limiting membrane diffusion. *J. Biol. Chem.* 274, 22524-22531 (1999): Sessa, W. C. et al. The Golgi association of endothelial nitric oxide synthase is necessary for the efficient synthesis of nitric oxide. *J. Biol. Chen.* 270, 17641-17644 (1995)). Phagosomal NO either directly kills the pathogen, and/or blocks a pathway the pathogen uses to evade the host immune response. For example, *M. tuberculosis* survives the phagosome by preventing the recruitment of NOS2 to the phagosome given its high susceptibility to NO (Zhang, Q. et al. Functional relevance of Golgi- and plasma membrane-localized endothelial NO synthase in reconstituted endothelial cells. *Arterioscler. Thromb. Vasc. Biol.* 26, 1015-1021 (2006): Jin, Z.-G. Where is endothelial nitric oxide synthase more critical: plasma membrane of Golgi? *Arterioscler. Thromb. Vasc. Biol.* 26, 959-961 (2006)). One such way is by masking selected PAMPs from PRRs by using surface lipids (Modi, S. et al. A DNA nanomachine that maps spatial and temporal pH changes inside living cells. *Nat. Nanotechnol.* 4, 325-330 (2009)). Thus, the ability to directly map phagosomal NO in viva could provide new approaches to identify mechanisms are operational at the early stages of pathogen infection.

NO that is produced due to PAMP-PRR recognition is spontaneously oxidized to nitrite ($NO_2^-$) that is then converted to nitrous acid (HONO) and detected by the Griess assay (Surana, S., Bhat, J. M., Koushika S. P. & Krishnan, Y. An autonomous DNA nanomachine maps spatiotemporal pH changes in a multicellular living organism. *Nat. Commun.* 2, 340 (2011)). Currently the Griess assay detects NO in the extracellular milieu and does not provide single-cell level information. Excellent small molecule detection chemistries are available for NO but the reacted probe molecules diffuse rapidly obscuring spatial information (Chakraborty K., Leung, K. & Krishnan, Y. High lumenal chloride in the lysosome is critical for lysosome function. *Elife* 6, e28862 (2017); Narayanaswamy, N. et al. A pH-correctable, DNA-based fluorescent reporter for organellar calcium. *Nat. Methods* 16, 95-102 (2019)). Although such probes can be targeted to the lysosome using protonatable morpholine derivatives, it is impossible to verify whether the probe molecules localize before or after reacting with NO (Leung, K., Chakraborty, K., Saminathan, A. & Krishnan, Y. A DNA nanomachine chemically resolves lysosomes in live cells. *Nat. Nanotechnol.* 14, 176-183 (2019)). Additionally, both NOS2 activity and morpholine-based targeting are highly dependent on organelle pH. Thus it is impossible to distinguish between NO production efficiency and probe targeting efficiency (Thekkan, S. et. al. A DNA-based fluorescent reporter maps HOCl production in the maturing phagosome. *Nat. Chem. Biol.* 151165-1172 (2019)). Current protein-based NO reporters lack the specificity and sensitivity of small molecules probes, are pH sensitive and need to be supplemented with large amounts of iron for their function, thus precluding their utility in live animal imaging (Kojima, H. et. al. Bioimaging of nitric oxide with fluorescent indicators based on the rhodamine chromophore. *Anal. Chem.* 73, 1967-1973 (2001)).

SUMMARY OF DISCLOSURE

Novel nucleic acid complexes of the disclosure can efficiently and accurately determine NOS activity and NO levels in cells at specific subcellular locations.

In one aspect, a method for determining nitric oxide concentration in a sample is provided. The method comprises: providing a nucleic acid complex comprising: (i) a first single-stranded nucleic acid molecule comprising a fluorophore crosslinked to the first strand, the fluorophore comprising diaminorhodamine-4-methylamine (DAR-4M)

conjugated to dibenzocyclooctyne-polyethylene glycol ($DBCO-PEG_n$) linker, wherein n equals 4-12; and a second single-stranded nucleic acid molecule that is partially or fully complementary to the first single-stranded molecule, wherein the nucleic acid complex further comprises a first label and a targeting moiety conjugated to the first single-stranded nucleic acid molecule or the second single-stranded nucleic acid molecule, the first label is capable of producing a signal, wherein the intensity of the signal is dependent at least on concentration of the nucleic acid complex in the sample; (ii) contacting the sample with the nucleic acid complex; (iii) measuring the intensity of the signal; and (iv) determining the nitric oxide concentration from the measured signal.

In one embodiment, the determining can be in plasma membrane, trans Golgi network, phagosome, macrophage or microglia.

In another embodiment, the first label is a normalizing fluorophore which is insensitive to NO. Representative examples of the first label include Alexa488 or Alexa647. In some embodiments, the first label is crosslinked to the second strand. In other embodiments, the targeting moiety or targeting label is crosslinked to the second strand. Representative examples of the targeting moiety comprises a cholesterol moiety, a DNA aptamer, oligodeoxynucleotide phosphorothioate, or oligoribonucleotide phosphorothioate. In further embodiments, the first label and the targeting label are crosslinked to the second strand.

In one embodiment, the first label is Alexa488 and the targeting label is a cholesterol moiety. In another embodiment, the first label is Alexa647 and the targeting label is a DNA aptamer.

In some embodiments, the first and/or second single-stranded nucleic acid molecule is less than 200 nucleotides; or less than 100 nucleotides; or less than 50, 45, 40, 35, 30, 25 or 20 nucleotides.

In another aspect of the invention, a nucleic acid complex complex is provided. The nucleic acid complex comprises: (i) a first single-stranded nucleic acid molecule comprising a fluorophore crosslinked to the first strand, where the fluorophore, the fluorophore comprising diaminorhodamine-4-methylamine (DAR-4M) conjugated to dibenzocyclooctyne-polyethylene glycol ($DBCO-PEG_n$) linker, wherein n equals 4-12; and (ii) a second single-stranded nucleic acid molecule that is partially or fully complementary to the first single-stranded molecule, wherein the nucleic acid complex further comprises a first label and a targeting moiety conjugated to the first single-stranded nucleic acid molecule or the second single-stranded nucleic acid molecule, the first label is capable of producing a signal, wherein the intensity of the signal is at least dependent on concentration of the nucleic acid complex in the sample. The fluorophore crosslinked to the first strand is generally a target (NO) sensitive molecule.

In one embodiment, the first label is a normalizing fluorophore. Representative examples of the first label include Alexa488 or Alexa647. In some embodiments, the first label is crosslinked to the second strand. In other embodiments, the targeting moiety is crosslinked to the second strand. Representative examples of the targeting, moiety comprises a cholesterol moiety, a DNA aptamer, oligodeoxynucleotide phosphorothioate, or oligoribonucleotide phosphorothioate. In further embodiments, the first label and the targeting label are crosslinked to the second strand. The normalizing fluorophore is generally a target insensitive fluorophore. In embodiments, the ratio of the NO sensitive fluorophore to the normalizing fluorophore is 1:1.

In one embodiment, the first label is Alexa488 and the targeting label is a cholesterol moiety. In another embodiment, the first label is Alexa647 and the targeting label is a DNA aptamer.

In one embodiment, the first strand has the following sequence:

```
                                        (SEQ ID NO: 01)
5'-/5AzideN/ATC AAC ACT GCA CAC CAG ACA GCA-3'
```

The second strand has the following sequence:

```
                                        (SEQ ID NO: 02)
5'-/Alexa488N/TGC TGT CTG GTG TGC AGT GTT GAT/
3-CholTEG/-3'
or
                                        (SEQ ID NO: 03)
5'-GGC TAT AGC ACA TGG GTA AAA CGA CTT TGC T/
Alexa647/G TCT GGT GTG CAG TGT TGA T-3'.
```

In another embodiment, the first label is ATTO647N and the targeting moiety is ODP or ORP. In other embodiments, the first strand has the following sequence:

```
                                        (SEQ ID NO: 04)
5'-/DAR-PEG10/ATC AAC ACT GCA CAC CAG ACA GCA-3'.
```

The second strand has the following sequence:

```
(S2-strand)
                                        (SEQ ID NO: 05)
5'-/ATTO647N/TGC TGT CTG GTG TGC AGT GTT GAT-3';
(NOckout1826CpG)
                                        (SEQ ID NO: 06)
5'-/ATTO647N/TGC TGT CTG GTG TGC AGT GTT GAT
tttccatgacgttcctgacgtt-3';
(NOckout1826GC)
                                        (SEQ ID NO: 07)
5'-/ATTO647N/TGC TGT CTG GTG TGC AGT GTT GAT
tttccatgagcttcctgacctt-3';
(NOckout2007CpG)
                                        (SEQ ID NO: 08)
5'-/ATTO647N/TGC TGT CTG GTG TGC AGT GTT GAT
tttcgtcgttgtcgttttgtcgtt-3';
(NOckout2007GC)
                                        (SEQ ID NO: 09)
5'-/ATTO647N/TGC TGT CTG GTG TGC AGT GTT GAT
tttgctgctgtgcttttgtgctt-3';
(NOckoutRNA)
                                        (SEQ ID NO: 10)
5'-/ATTO647N/TGC TGT CTG GTG TGC AGT GTT GAT
tttggacggaaaagaccccgugg-3';
(NOckoutRNA)
                                        (SEQ ID NO: 11)
5'-/ATTO647N/TGC TGT CTG GTG TGC AGT GTT GAT
tttggacgggaagaccccgugg-3';
or
```

-continued (pHlicker-SH)

(SEQ ID NO: 12)

5'-HS-ATC AAC ACT GCA CAC CAG ACA GCA-3'.

Figure 14:
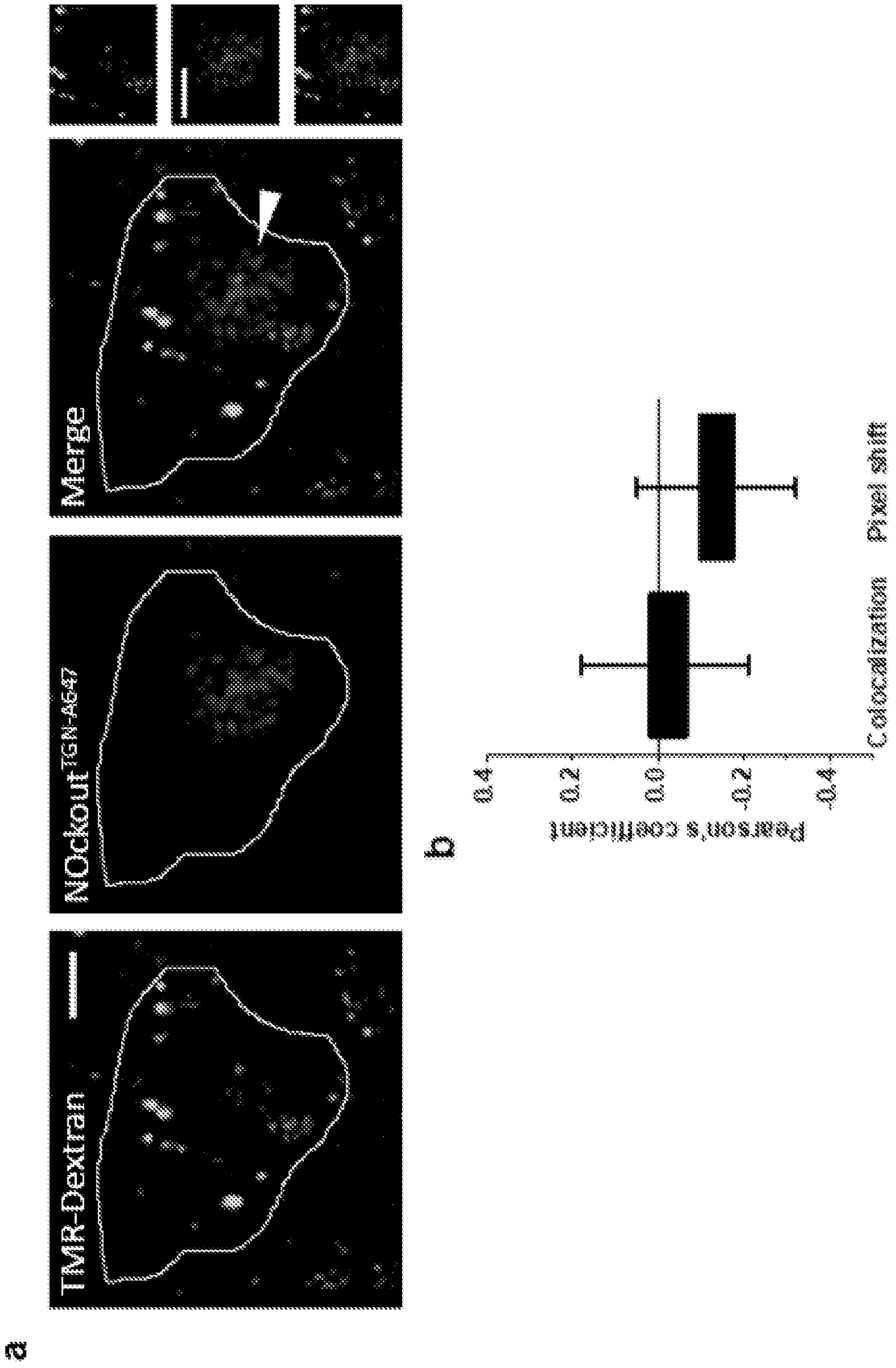

FIG. 14. Anti-colocalization of NOckout$^{TGN}$ with pan endosomal marker TMR-Dextran. (a) Representative images of T-47D cells where all endosomes are labeled with a steady state pulse of TMR-Dextran (green) and then labeled with NOckout$^{TGN\text{-}A647}$ (red) (b) Pearson's correlation coefficient reveals that NOckout$^{TGN}$ does not localize in endosomes. Scale bar: 10 μm. Error bars represent S.E.M. from two independent experiments.

Figure 15:
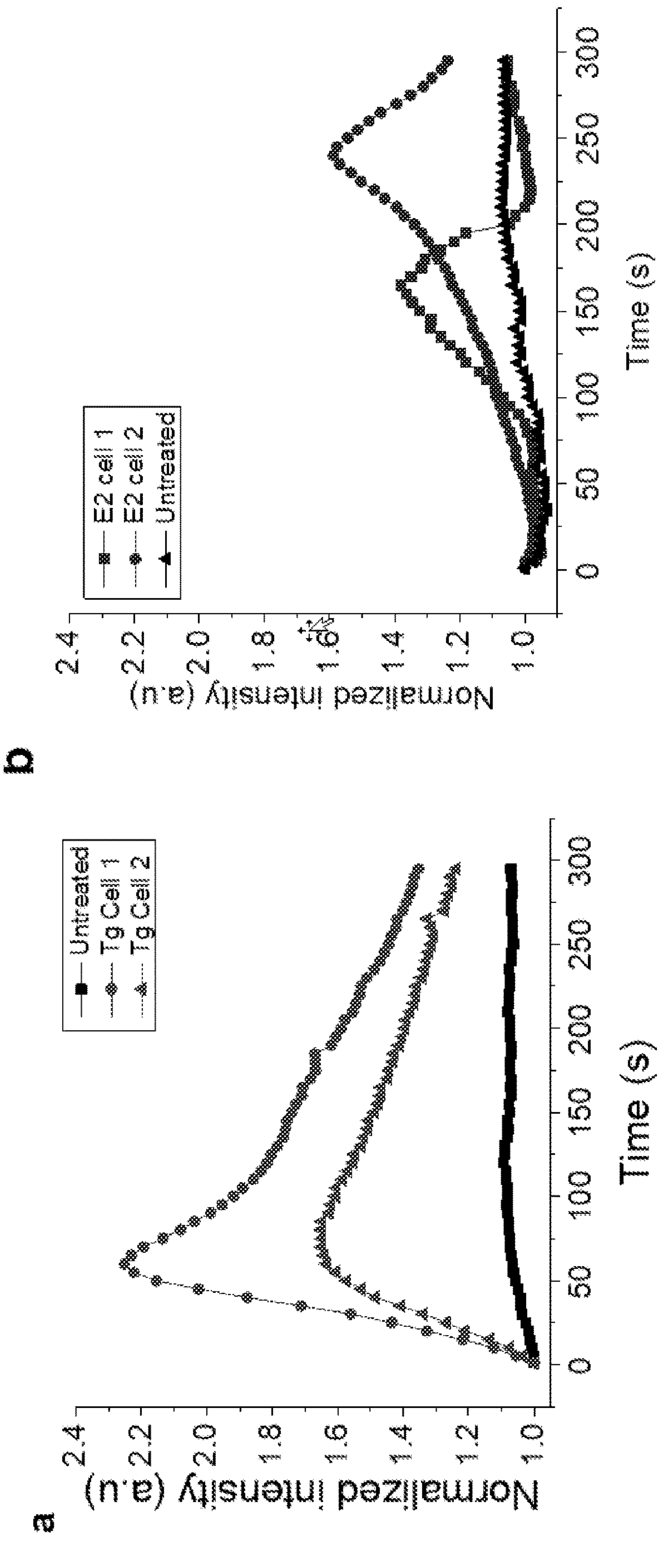

FIG. 15: Intracellular calcium imaging followed by agonist treatment in T-47D cells. (a) Representative traces of cytosolic $Ca^{2+}$ elevation given by DAF-2DA, a cytoplasmic calcium indicator ($\lambda_{ex}$=488 nm). Cells were treated with Thapsigargin (Tg, 100 nM, Red traces) or vehicle alone (Black). (b) Representative traces of cytosolic $Ca^{2+}$ elevation upon treating cells with 17-β-Estradiol ($E_2$, 300 nM).

Figure 16:
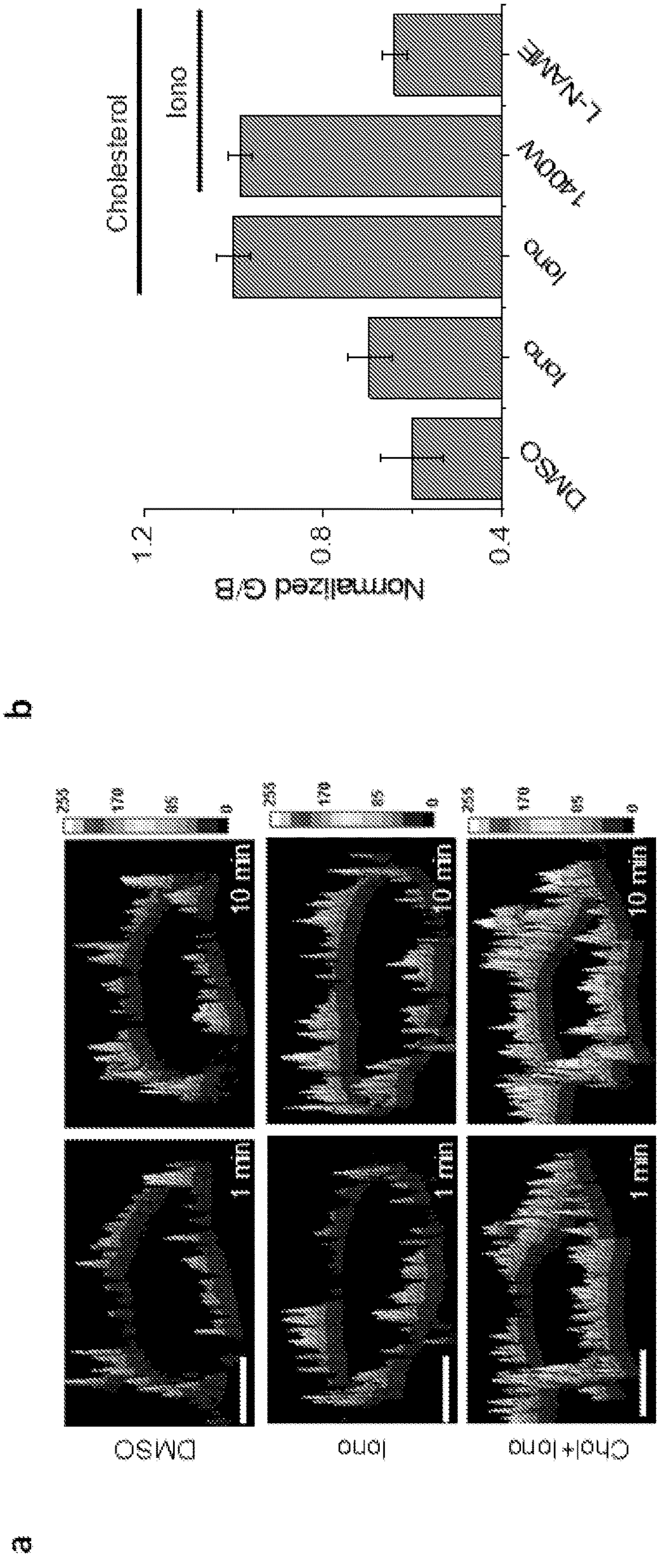

FIG. 16: NOckout probes measure activity of NOS3. (a) Surface plots showing NOckout$^{PM}$ labeled T-47D cells treated with DMSO, Ionomycin (Iono) or cholesterol+Ionomycin (Chol+Iono). (b) NOckout$^{PM}$ signal from T-47D cell is represented as the ratio of DAR intensity to that of A488 (G/B)) at 10 min post treatment of T-47D cells with DMSO. ionomycin (1 μM) or ionomycin in combination with cholesterol (500 μM) with or without 1400 W or L-NAME. Ratios are calculated for n=20 cells.

Figure 17:
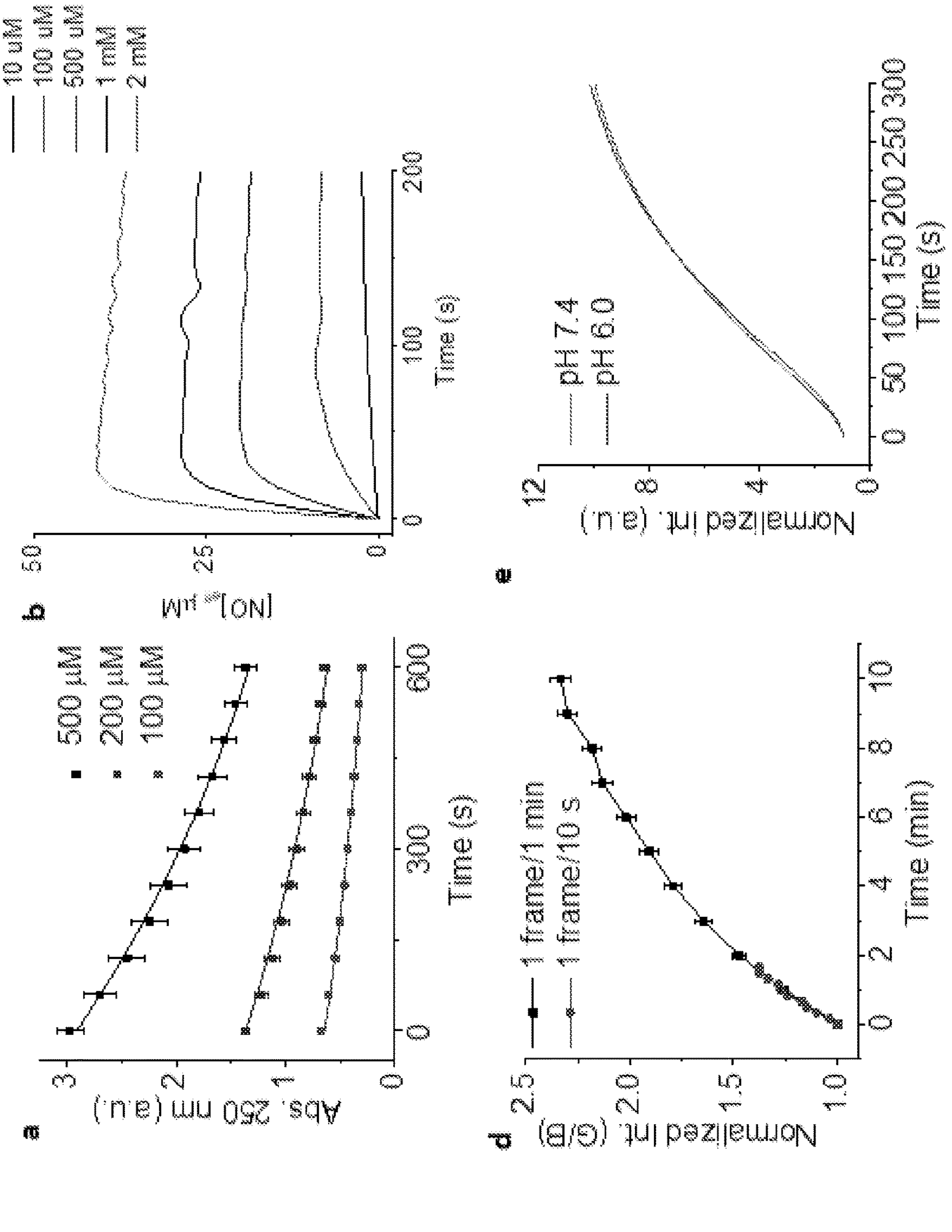
Figure 17:
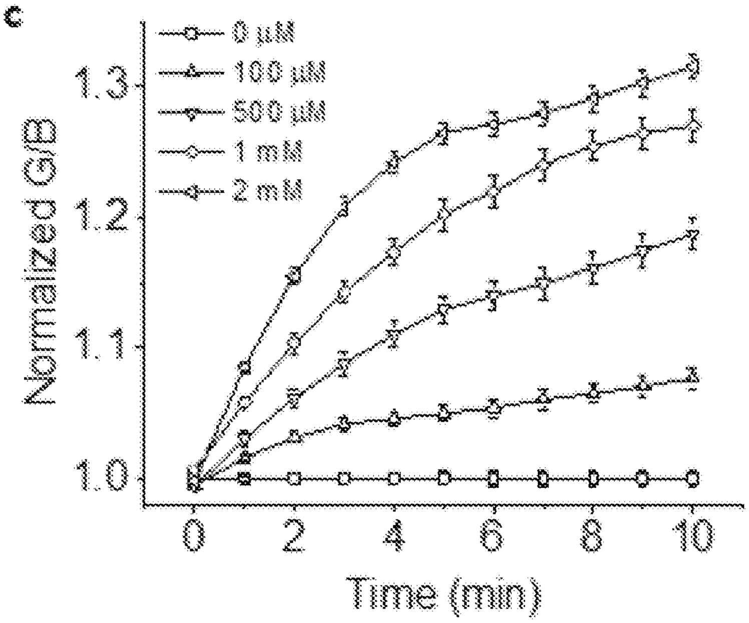
Figure 17:
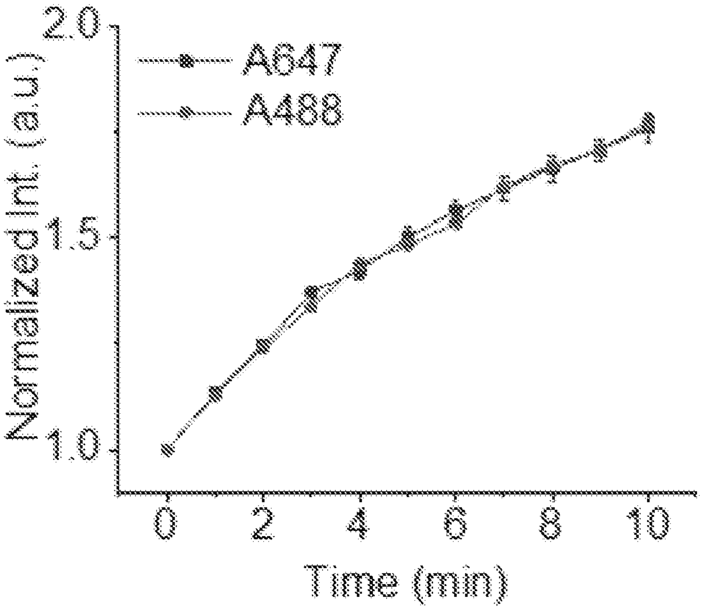

FIG. 17: Quantification of NO using NOckout probes. (a) in-vitro decomposition kinetics of DEA-NONOate observed by UV absorption at 250 nm. (b) Rate of $[NO]_{eff}$ production at indicated DEA-NONOate concentrations as predicted by equation 1 (c) In-cellulo kinetic traces showing G/B signal from NOckout$^{PM}$ containing cells upon treatment with indicated concentrations of DEA-NONOate (d) NOckout$^{PM}$ treated cells were treated with 500 mM of DEA-NONOate and were imaged in DAR (G) and A488 (B) channel either every 1 min (1 frame/1 min, black trace) or every 10 seconds (1 frame/10 s, red trace). (e) in-vitro DAR reaction kinetics upon addition of 500 μM of DEA-NONOate at pH 6.0 (red trace, 200 mM phosphate buffer) and at pH 7.4 (green trace, 200 nM phosphate buffer). (f) in-cellulo kinetics comparison of NOckout$^{PM}$ containing either A647 as normalizing dye (red curve) or A488 as normalizing the (green curve) upon addition of 500 μM of DEA-NONOate.

Figure 18:
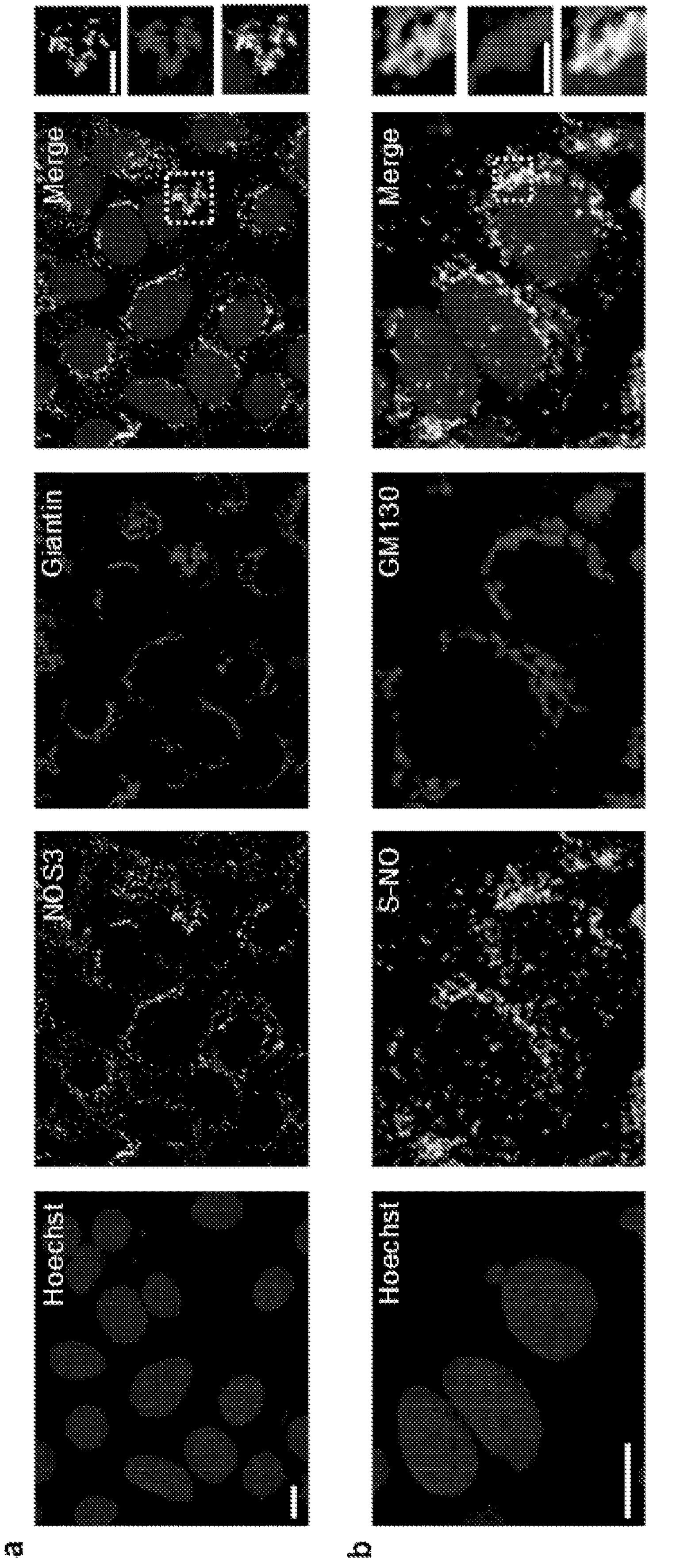

FIG. 18: Golgi is a hotspot for S-nitrosylation station in breast cancer cells. (a) Co-localization of NOS3 (green) with the Golgi marker protein Giantin (red) in MCF-7 cells. (b) Confocal images of T-47D cells immunostained with anti S-NO antibody (green) and anti GM-130, a Golgi marker (red). Insets shows merged images in higher magnification for a) and b). Scale bar: 10 μm. Inset scale bars: 10 μm.

Figure 19:
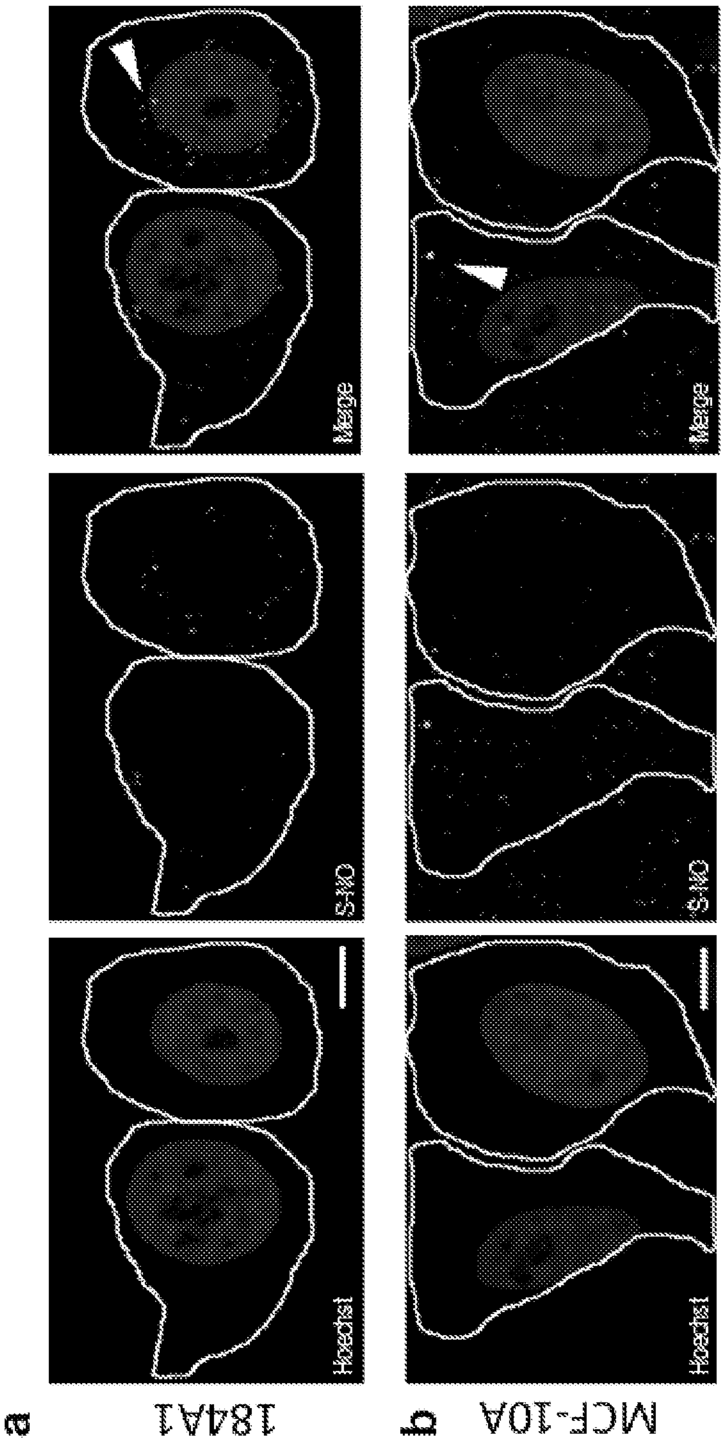

FIG. 19: Normal breast epithelial cell lines lack the robust Golgi S-nitrosylation seen in breast cancer cells. Immunostaining with anti-S-nitrosocysteine (green) in normal human breast cell lines (a) 184A1 and (b) MCF-10A. Hoechst (blue) is used to stain nuclei. Scale bar=10 μm.

Figure 20:
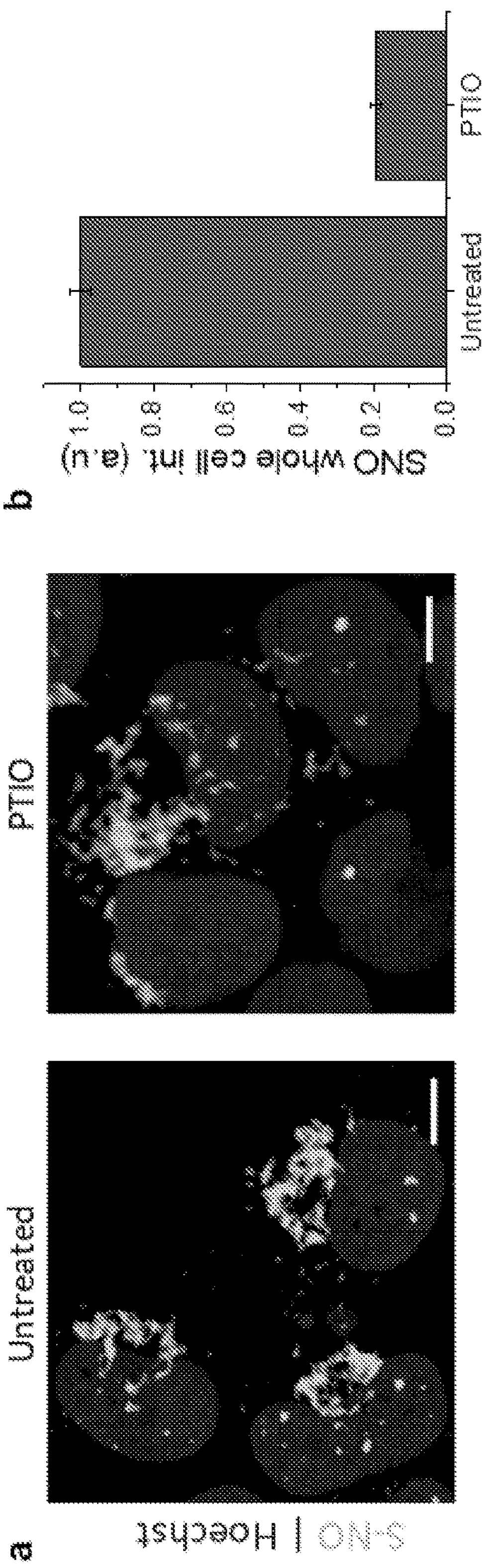

FIG. 20: NO scavenger PTIO reduces extent of S-nitrosylation. (a) Representative images of anti-S-nitrosocysteine immunostaining of T-47D cells treated with or without 200 μM PTIO for 48 h. (b) Quantification of whole cell S-nitrosylation intensity. n=150 cells, Scale bar: 10 μm. Error bars represent S.E.M. from three independent experiments.

Figure 21:
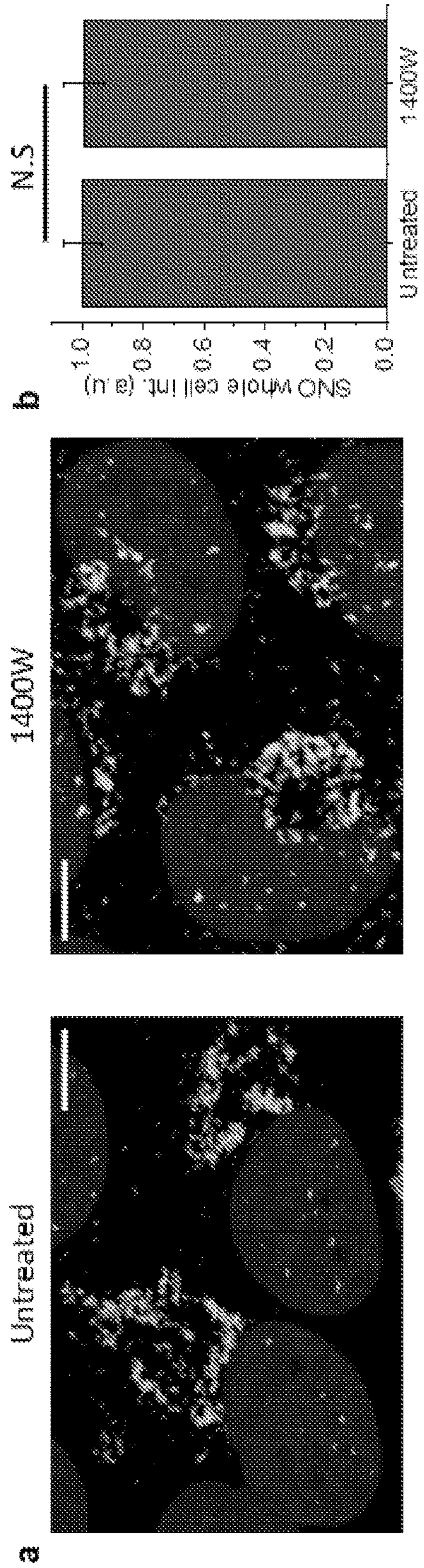

FIG. 21: NOS2 is not responsible for Golgi S-nitrosylation. (a) T-47D cells cultured in presence or absence of NOS2 inhibitor 1400 W (10 μM) for 48 h and immunostained with anti-S-nitrosocysteine (green). (b) Whole cell intensity in S-nitrosocysteine channel (A488 channel). Error bars are S.E.M from three independent experiments, n=200 cells. Significance as given by two tailed students T test. N.S=non-significant. Scale bar=10 μm. Hoechst is used to stain nuclei.

Figure 22:
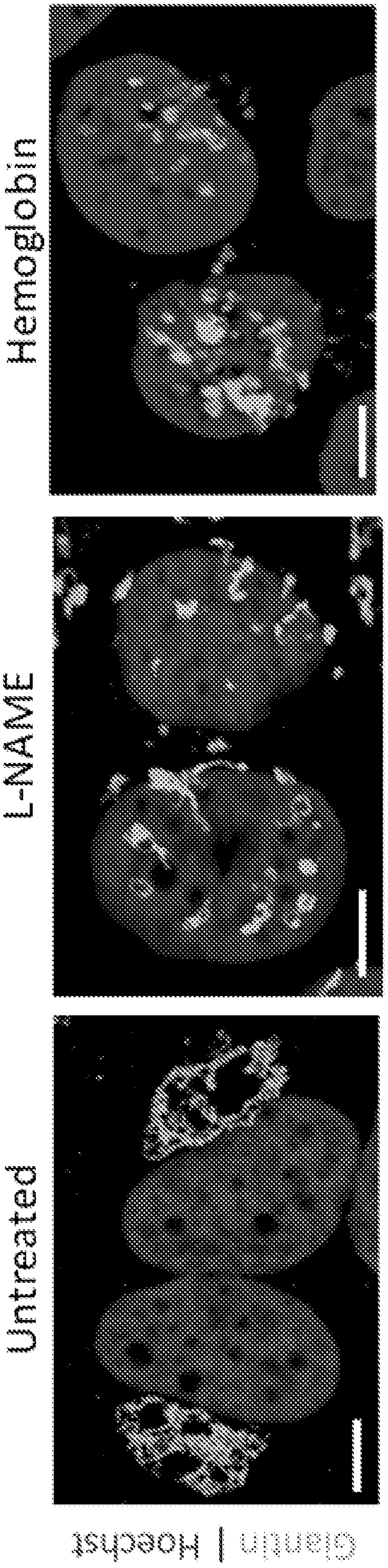

FIG. 22: NO scavenging causes Golgi fragmentation in T-47D cells. Giantin (green) immunostaining of untreated cells, Methylene blue (20 μM) or Hemoglobin (20 μM) treated cells. Hoechst is used to stain nuclei. Scale bar: 10 μm.

Figure 23:
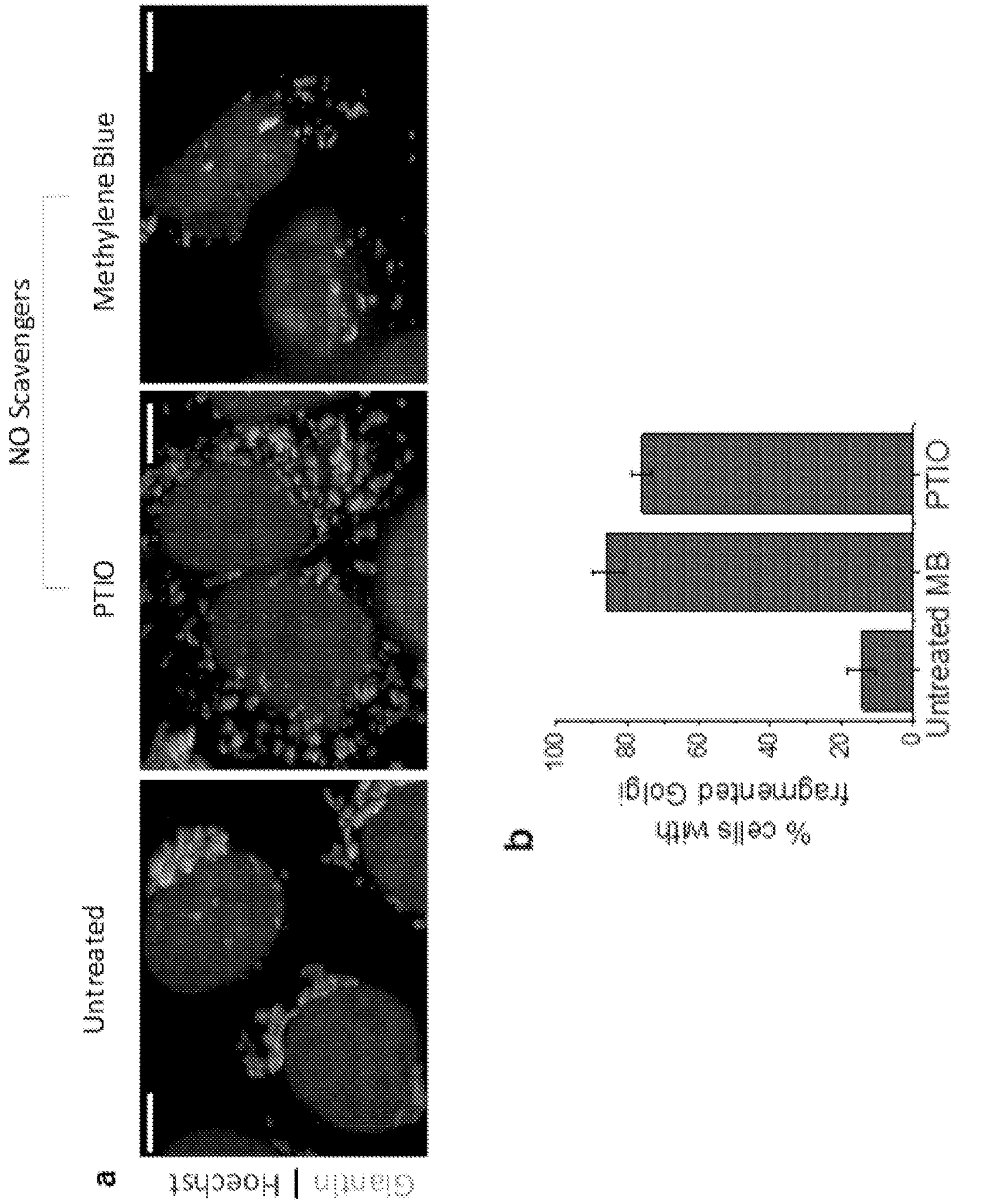

FIG. 23: NO scavenging causes Golgi fragmentation in MCF-7 cells. (a) Giantin (green) immunostaining of untreated cells, PTIO (100 μM) or Methylene blue treated cells (20 μM). Hoechst is used to stain nuclei. (b) Quantification of fragmentation. Error bars represent S.E.M. from three independent experiment; n=150 cells. Scale bar: 10 μm.

Figure 24:
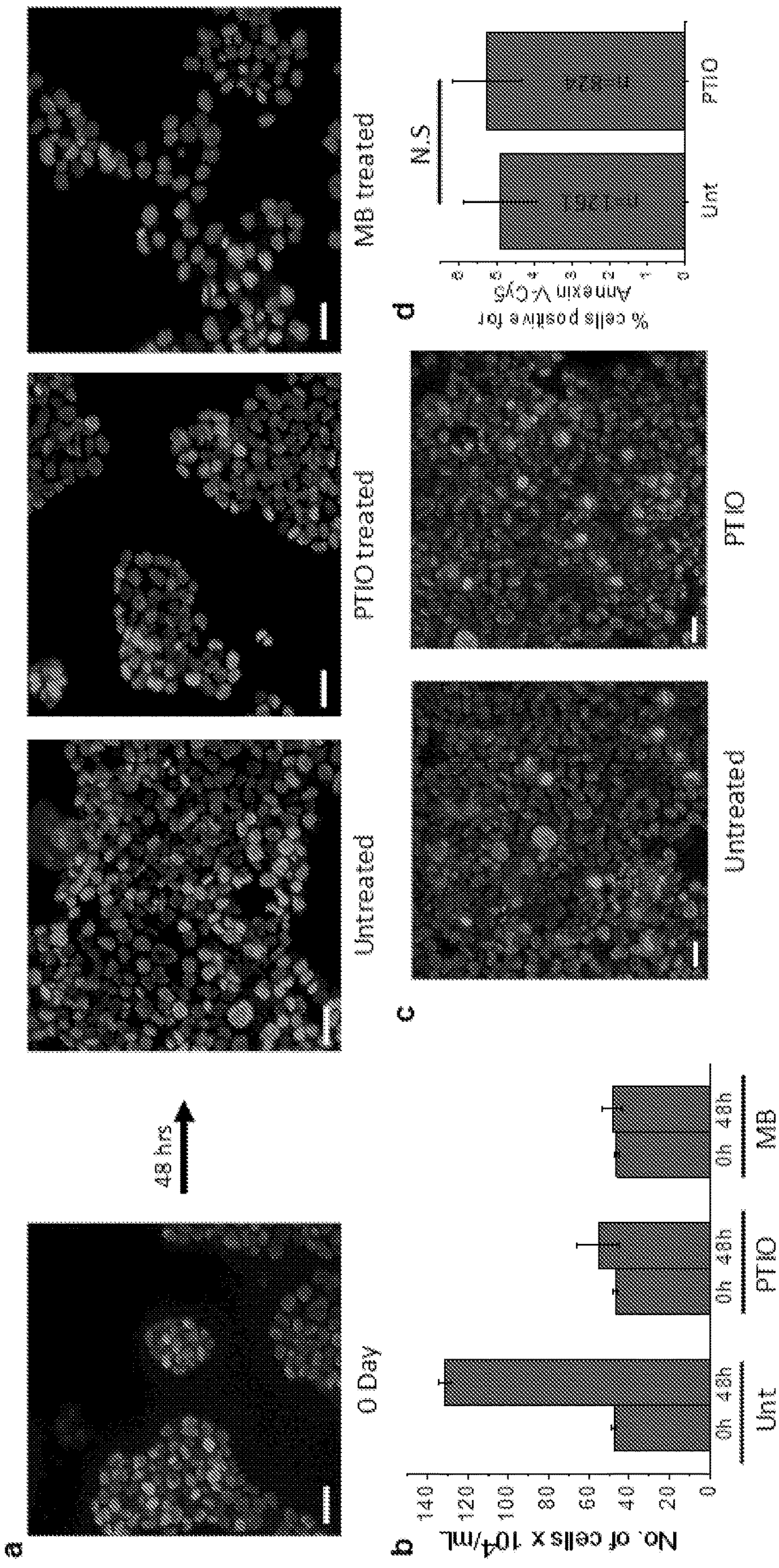

FIG. 24: NO Scavenging causes growth retardation in T-47D cells. (a) T-47D cells are untreated, treated with PTIO (200 μM) or Methylene blue (MB, 20 μM) for 48 h. (b) Number of cells after 48 h treatment with PTIO or MB compared to untreated. (c) PTIO treated cells stained with apoptotic cell marker Annexin V-Cy5 (Biovision 1013-200). (d) Quantification of cells in (c). Error bars are S.E.M from three independent experiments. Significance from two tailed students T test. N.S=non-significant. Scale bar=50 μm. Hoechst (blue, $\lambda_{ex}$=405 nm) was used as nuclear stain.

Figure 25:
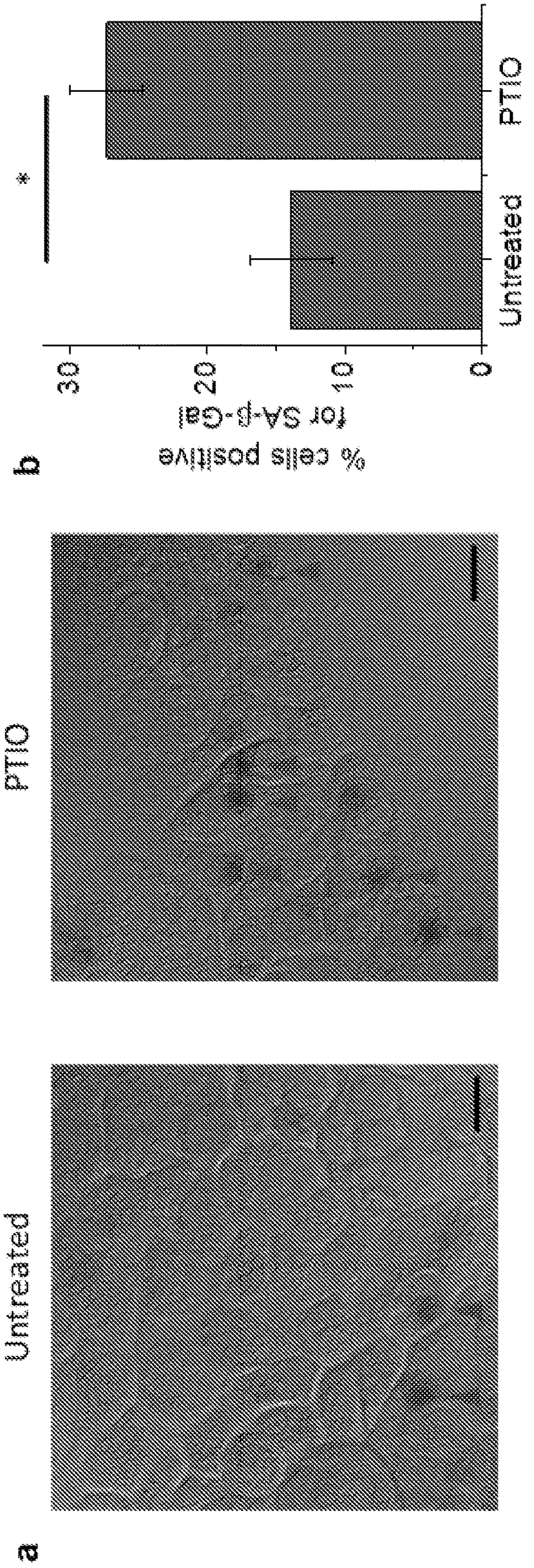

FIG. 25: NO scavenging causes cell senescence in T-47D cells. (a) Cells grown in the presence or absence of PTIO (200 μM), stained for senescence associated with □-galactosidase (SA-b-Gal) activity. (b) Percentage of cells positive for SA-β-Gal activity for untreated and PTIO treated cells. Error bars are S.E.M from three independent experiments and n=200 cells. Significance as given by two tailed students T test. *$p<0.05$, Scale bar=10 μm.

Figure 26:
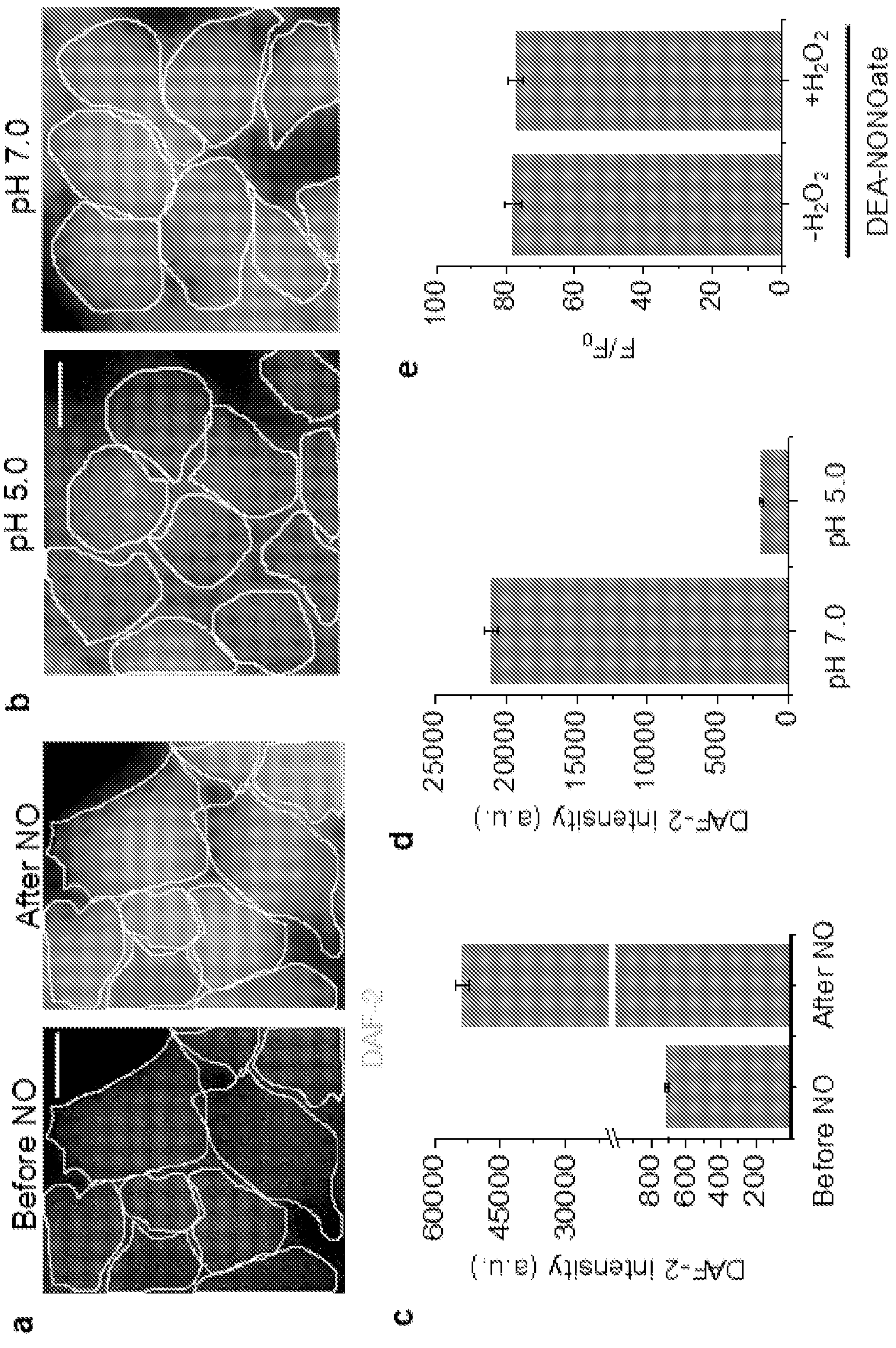

FIG. 26: NO measurements using small molecule DAF-2DA. (a) Representative images of HEK cells loaded with DAF-2DA (10 μM) before addition of NO donor DEA-NONOate (Before NO) or 10 minutes after the addition of DEA-NONOate (500 μM, after NO), Scale bar=10 μm. (h) Representative images showing HEK cells loaded with DAF-2DA and treated with DEA-NONOate were clamped at pH 5.0 or at pH 7.0. (c) and (d) are graphical representation where y-axis denotes whole cell DAF-2 intensities for experiments (a) and (b) respectively, where n=20 cells. (e) Bar graph showing fold changes in DAF-2 intensities of cells either pre-treated with $H_2O_2$ or pre-treated with $H_2O$ (—$H_2O_2$) upon addition of DEA-NONOate (500 μM) Error bars are S.E.M from three independent experiments.

Figure 27:
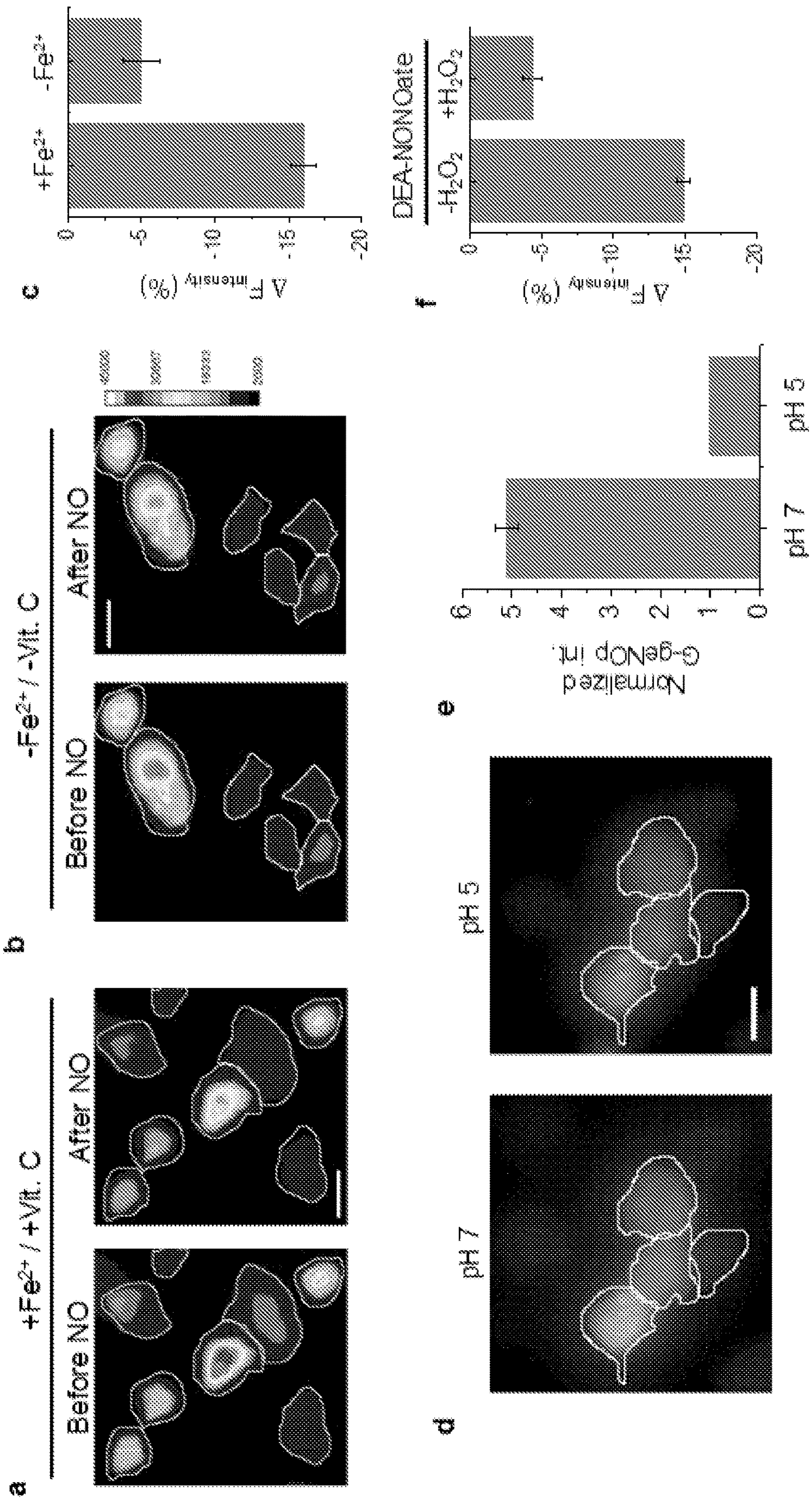

FIG. 27: NO measurements using genetically encodable NO probe (G-geNOp). Representative pseudo-color images of HEK cells expressing cytoplasmic G-geNOp, where cells were treated with either $Fe^{2+}$ and Vit. C (a) or in the absence of them (b), before and after the addition of NO donor DEA-NONOate, Scale bar=10 μm. (c) Bar graph showing delta fluorescence signal in percentage for (a) and (b), where n=20 cells. (d) HEK cells expressing cytoplasmic G-geNOp were pH clamped either at pH 5.0 or at pH 7.0 using UB4 buffer. (e) Whole cells G-geNOp intensities from (d), n=20 cells and Scale bar=10 μm. (f) Bar graph showing delta fluorescence signal in percentage of cells expressing G-geNOp which were either pre-treated with $H_2O_2$ or pre-treated with $H_2O$ (—$H_2O_2$) upon addition of DEA-NONOate (500 μM). Error bars are S.E.M from three independent experiments.

Figure 28:
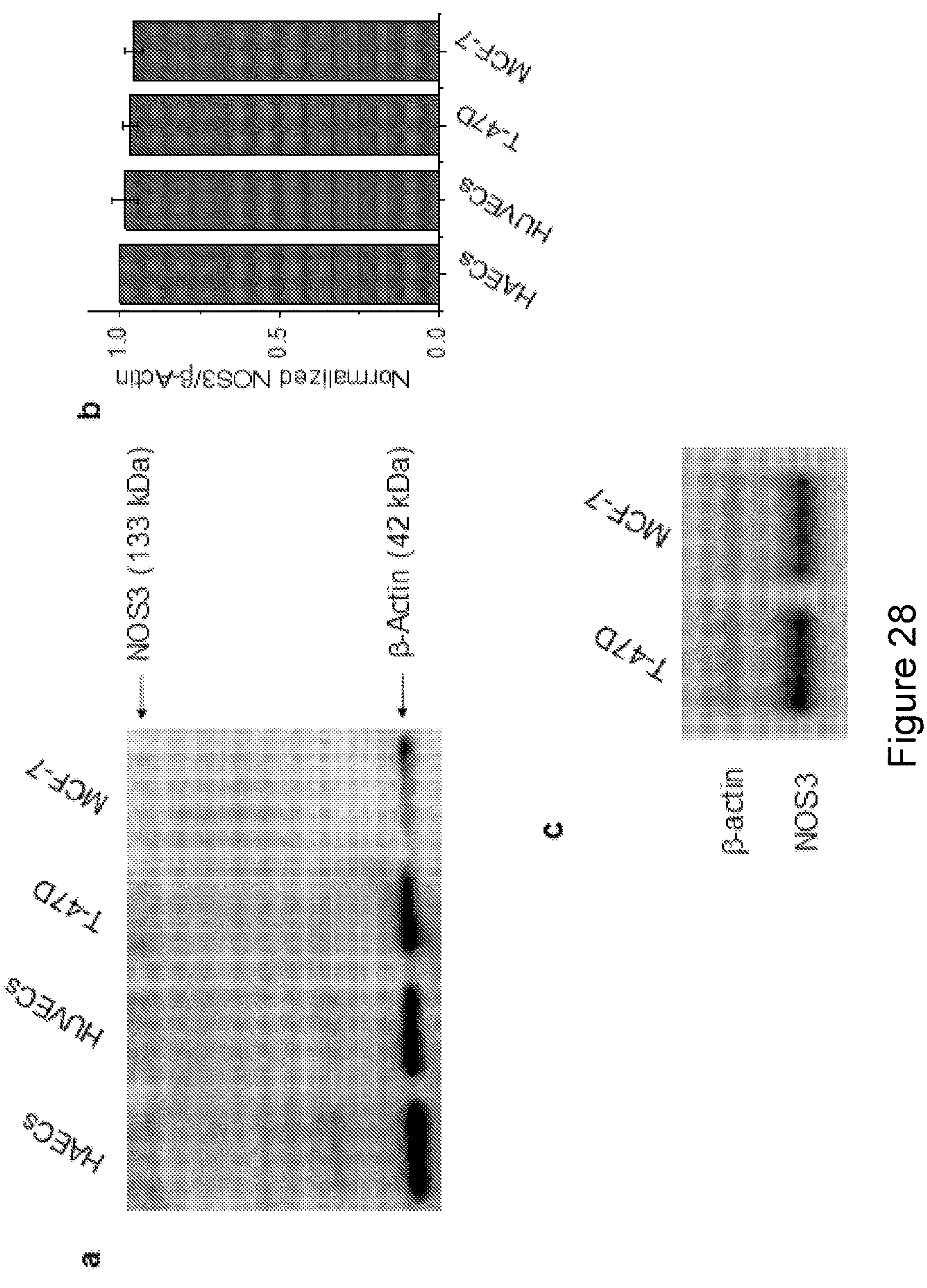

FIG. 28: T47D cells and MCF-7 cells express NOS3. (a) Whole cell lysates of Human aortic endothelial cells (HAECs), Human umbilical vein endothelial cells (HUVECs), T-47D and MCF-7 cells were immunoblotted with primary rabbit anti-NOS3 and Mouse anti-actin antibody followed by respective secondary antibodies conjugated with HRP. (a) is a representative image of three independent experiments (b) Bar graph showing normalized NOS3/β-Actin for each lane from (a). (c) RT-PCR results showing expression of NOS3 RNA in both T-47D and MCF-7 cells, β-actin was used as loading control.

Figure 29:
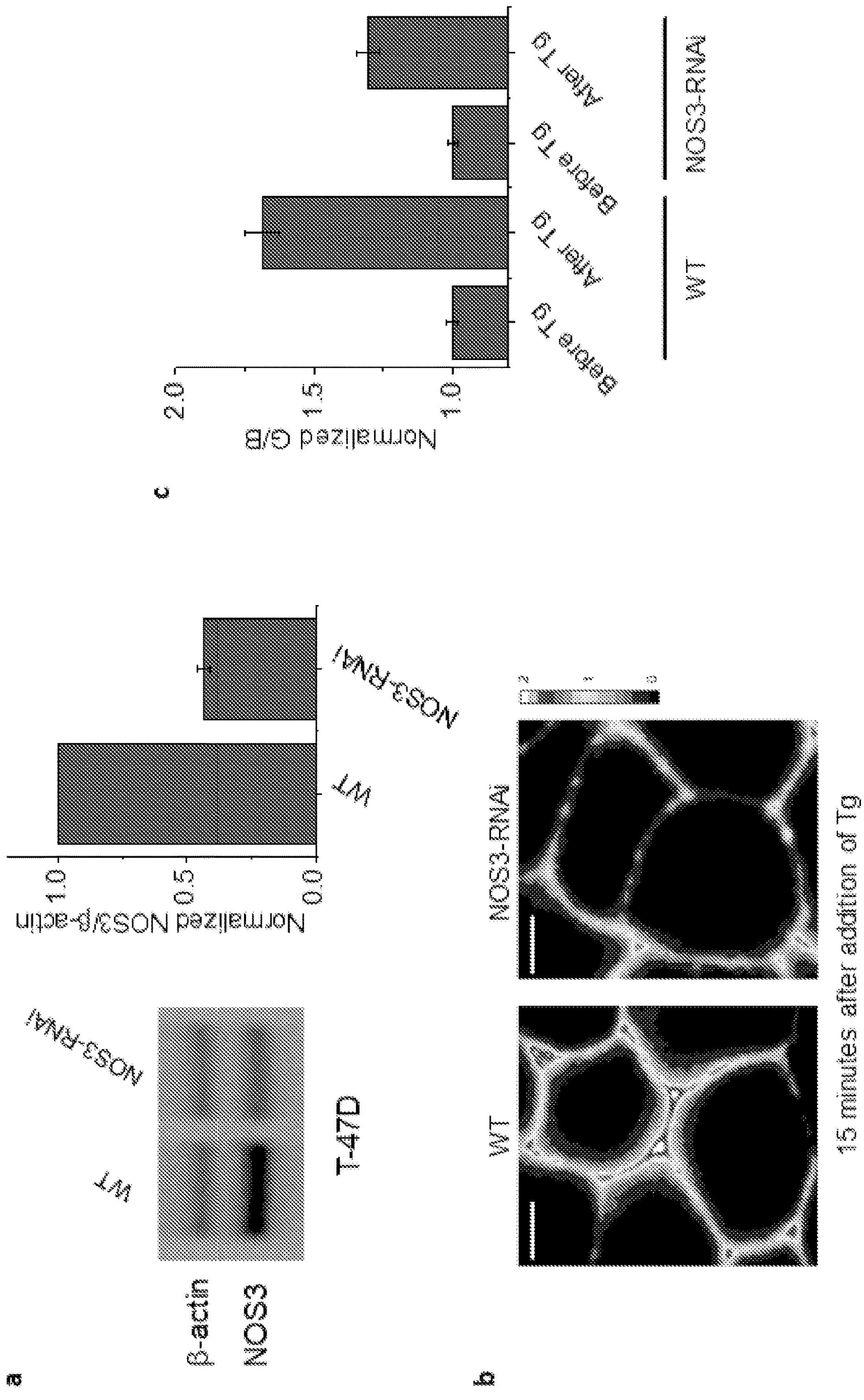

FIG. 29: NOS3 knockdown decreases activity measured by NOckoutPM (a) Agarose gel showing RT-PCR product of T-47D cells not treated with RNAi (WT) or treated with NOS3-RNAi and its quantification. (b) NO production by NOS3 upon treatment with thapsigargin (Tg) as monitored by NOCkoutPM. (c) Quantification of activity of NOS3 monitored by NOckoutPM before and after thapsigargin treatment. Number of cells n=20, Scale bar=10 μm.

Figure 30:
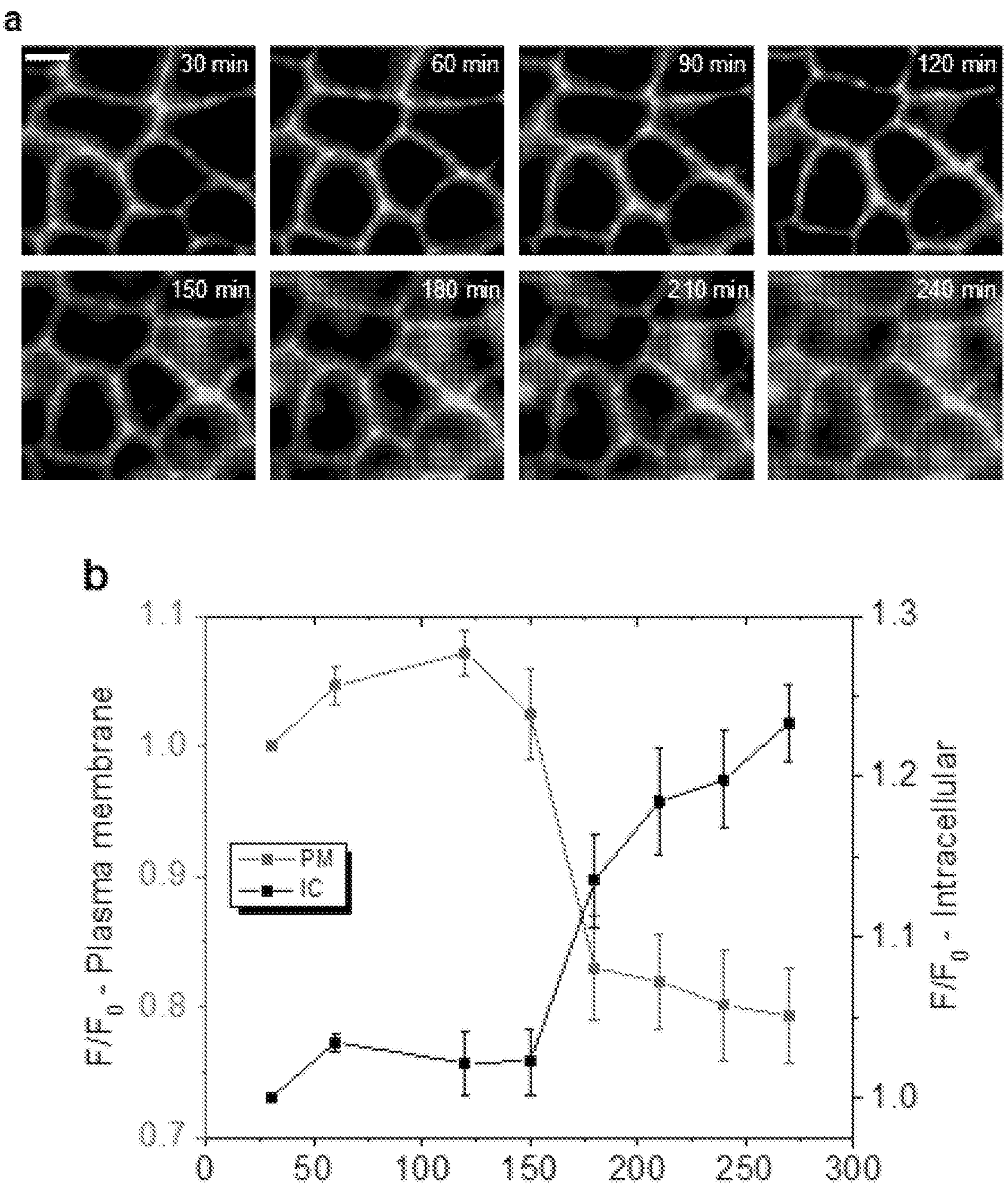

FIG. 30: Localization of $NOckout^{PM}$ on plasma membrane (a) T-47D cells were pulsed with 500 nM NOckoutPM-A488 and subsequently imaged every 30 minutes in HBSS buffer, Scale bar=10 μm. (b) Quantification of $NOckout^{PM}$-A488 intensities for each time point at the plasma membrane (PM) and intracellular space (IC), n=8 cells.

Figure 31:
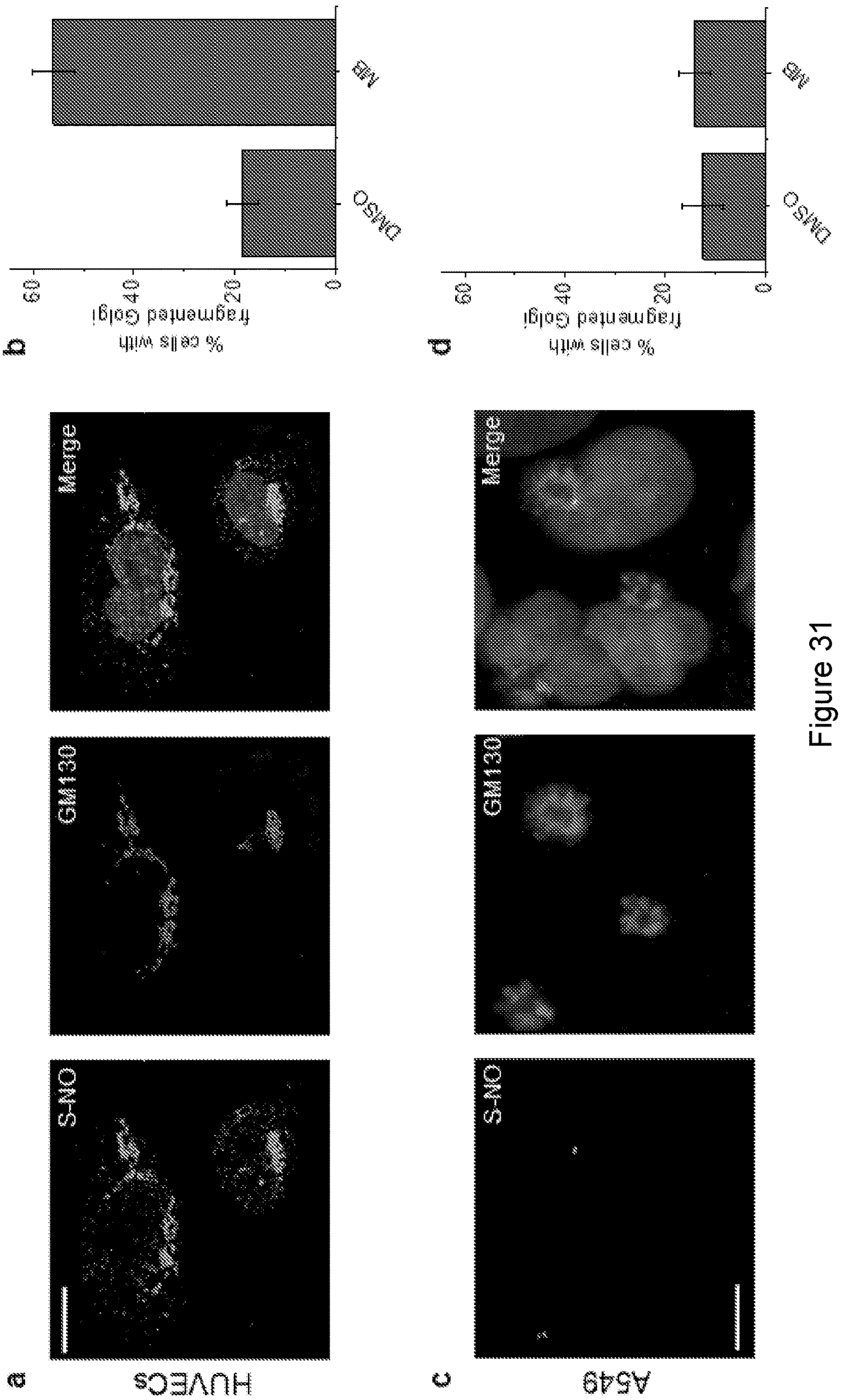

FIG. 31: (a) and (c) Confocal images showing extensive endogenous S-Nitrosylation (green) on the Golgi apparatus as shown by colocalization with Golgi marker protein GM-130 (red). (b) and (d) Bar graph showing quantification of Golgi fragmentation induced upon addition of NO scavenger methylene blue (MB) in HUVECs and A549 respectively.

Figure 32:
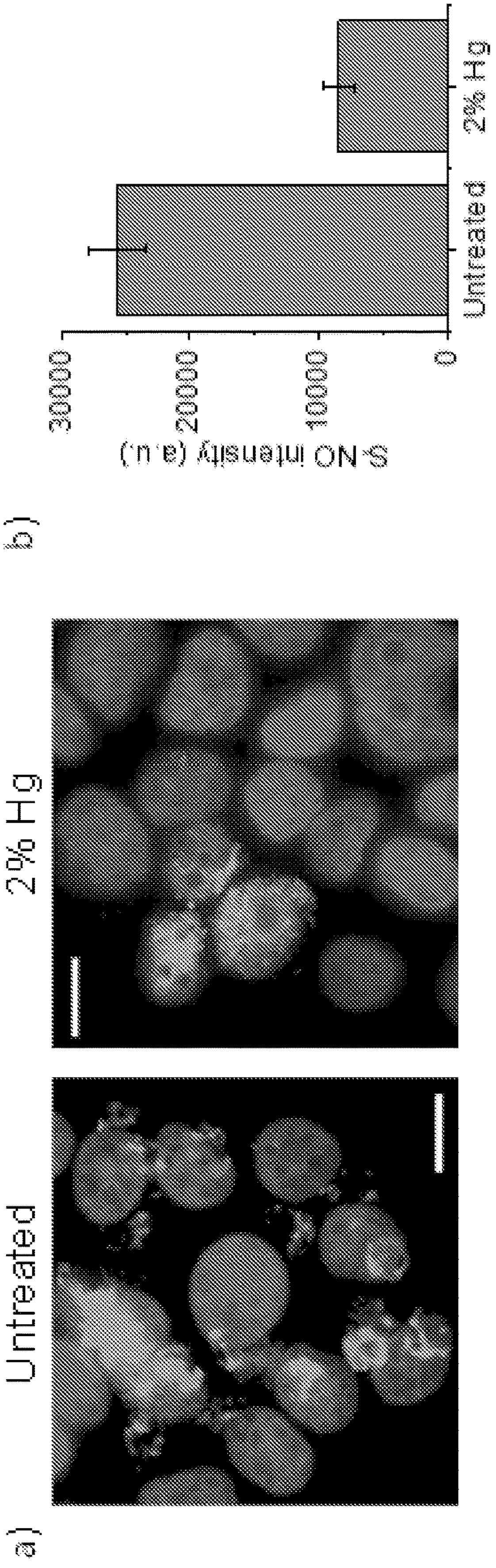

FIG. 32: $HgCl_2$ treatment abolishes αS-NO signal. (a) Inununofluorescence of T-47D cells using anti-SNO antibody treated without (untreated) or with $HgCl_2$, (2% Hg) (b) Quantification of the data from n=25 cells. Nuclei are stained with Hoechst, error bars correspond to the standard error of the mean.

Figure 33:
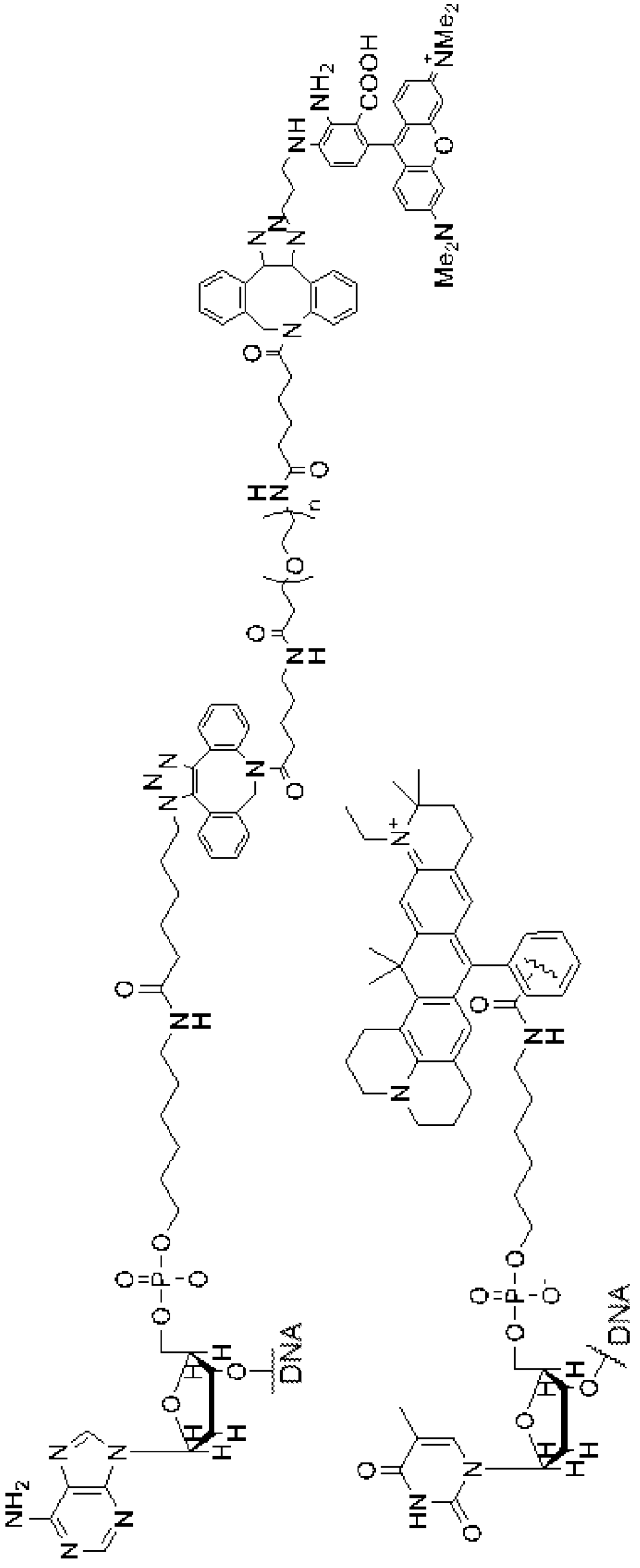

FIG. 33: (a) Chemical structure of DAR, linked to the ssDNA (24-mer) to its 5'-end using a long polyethylene glycol linker. (b) Chemical structure of ATTO647N fluorophore (normalizing the linked to the 5'-end of fully complementary ssDNA (24-mer).

Figure 34:
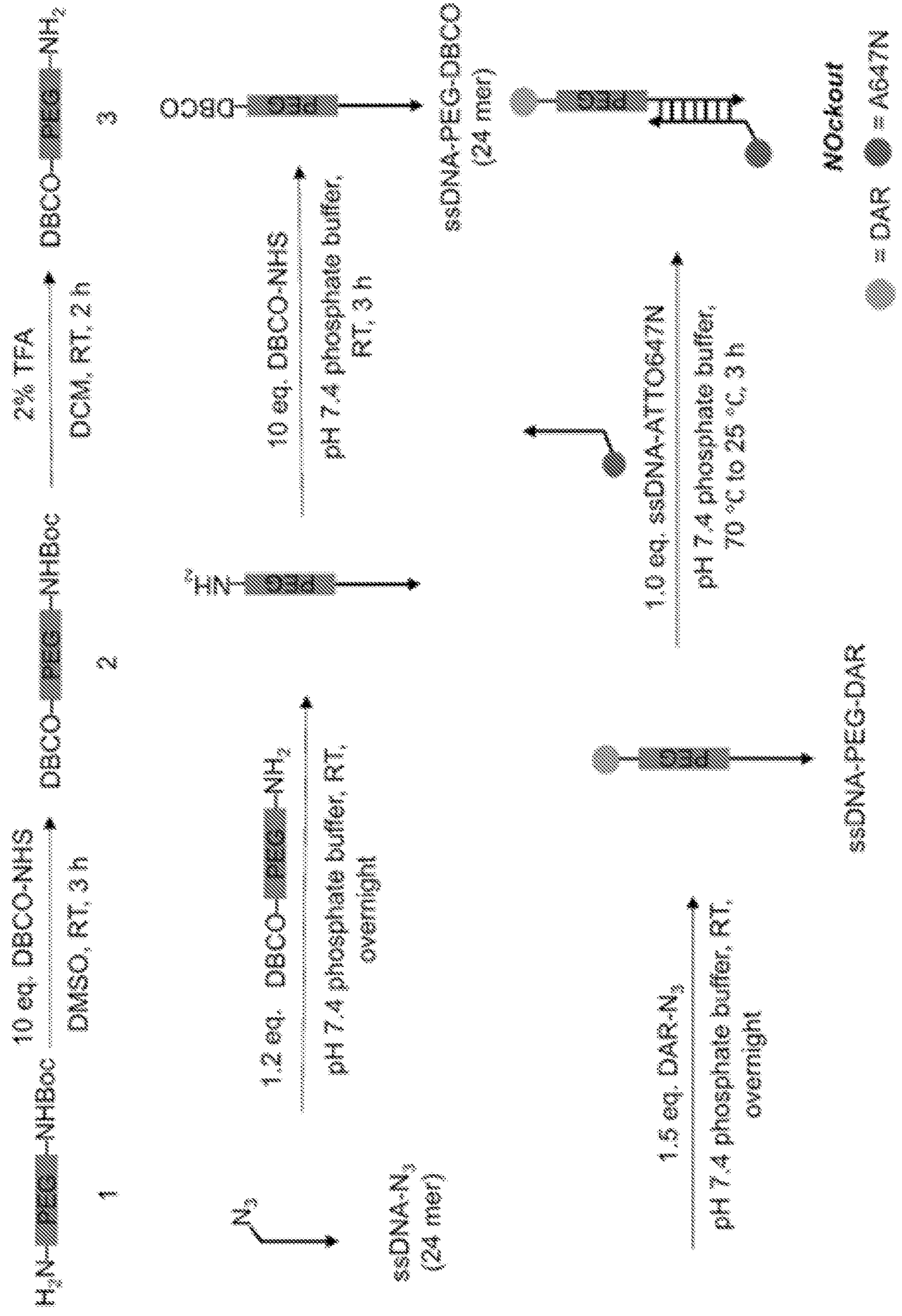

FIG. 34: Bio-conjugation steps employed in the synthesis of NOckout probe. A 10 kDa bifunctional PEG linker was employed to chemically link DAR-fluorophore to the ssDNA to obtain ssDNA-PEG-DAR, which was then annealed to an ssDNA-ATTO647N strand to assemble NOckout. Green circle represents DAR-fluorophore and red-circle represents ATTO647N, the normalizing fluorophore.

Figure 35:
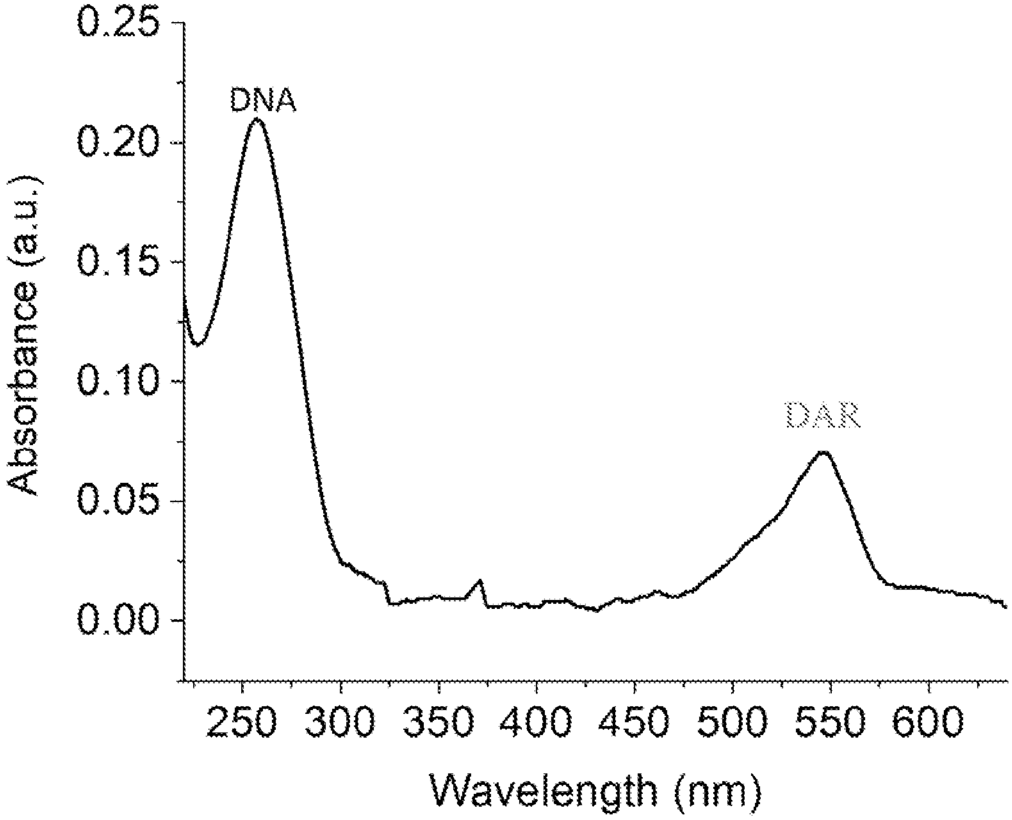

FIG. 35: UV-Vis absorption spectrum of ssDNA-PEG-DAR (0.8 μM, in 100 mM phosphate buffer, pH 7.2 at 25° C.) showing a 1:1 labeling of NO-sensing fluorophore (DAR) to the 24-mer ssDNA-strand.

Figure 36:
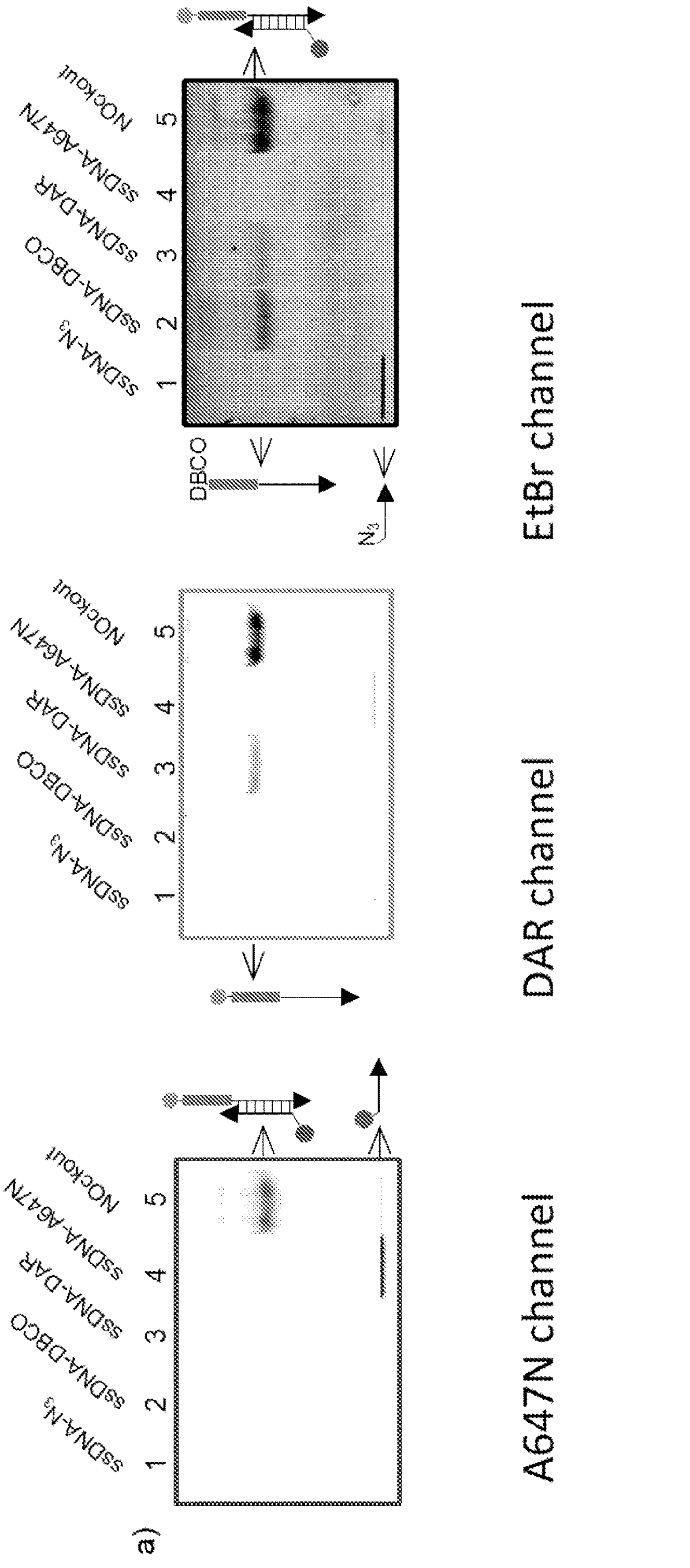
Figure 36:
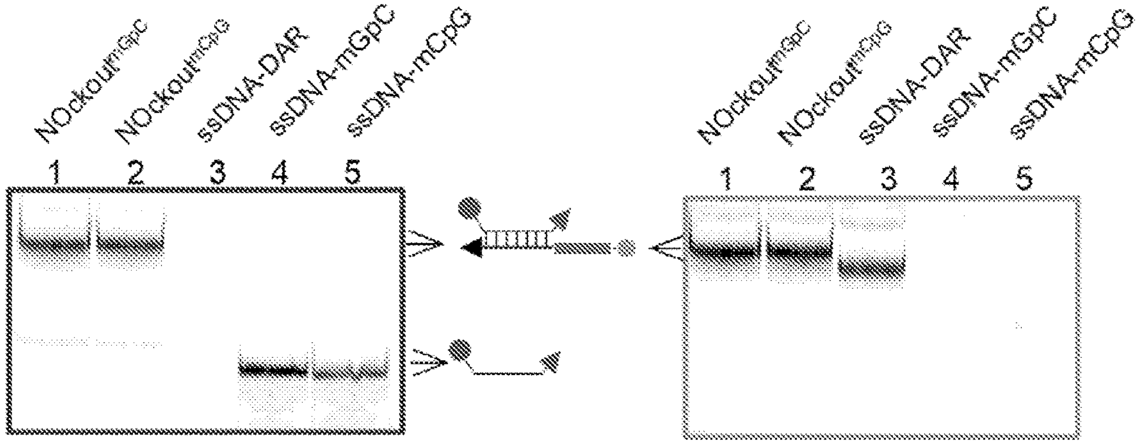
Figure 36:
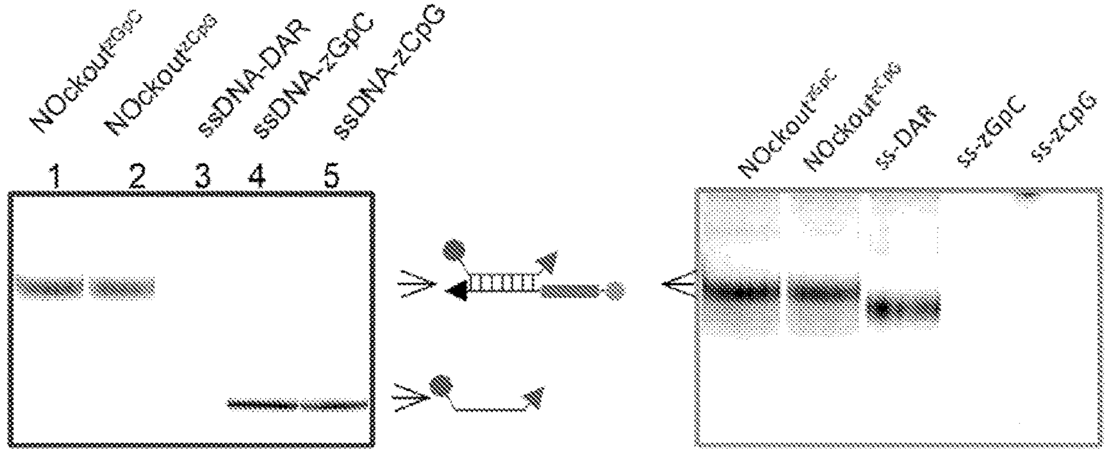
Figure 36:
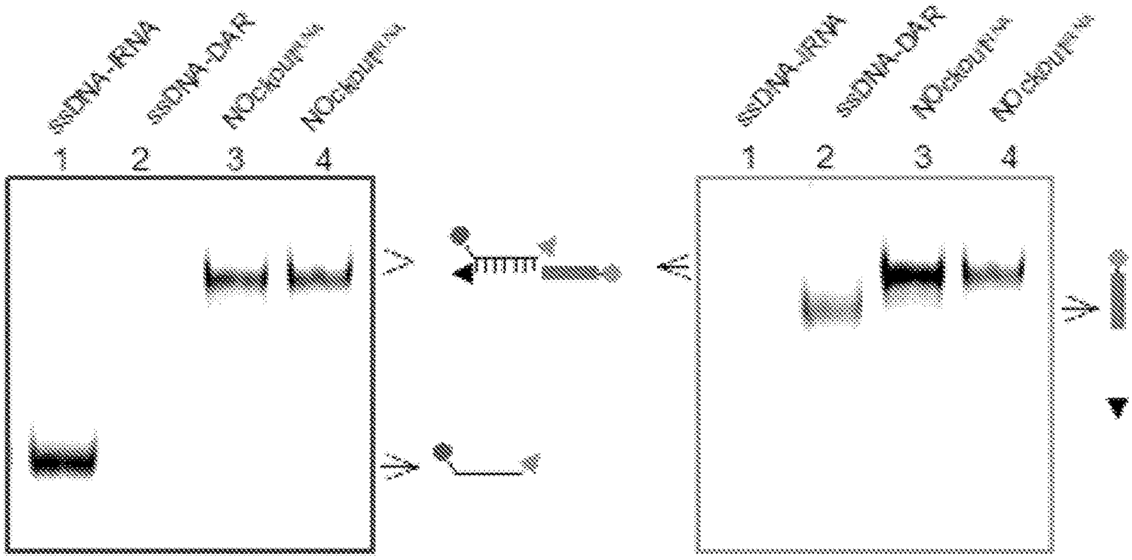
Figure 36:
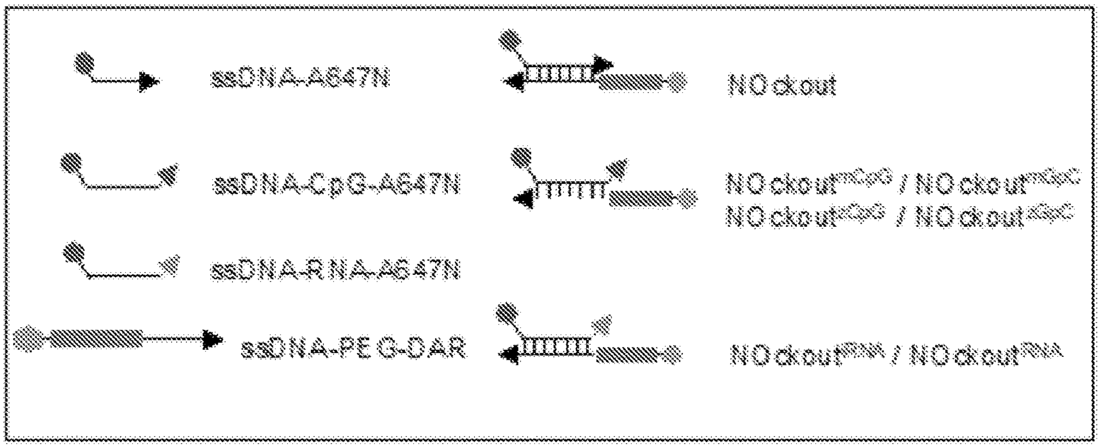

FIG. 36: Characterization of NOckout probes using gel electrophoresis. (a) Gel mobility shift observed for NOckout in a 15% native polyacrylamide gel excited in the A647N (red box), DAR (green box) and EtBr channels (black box). Panels (b), (c) and (d) shows mobility of $NOckout^{mCpG}$, $NOckout^{zCpG}$ and $NOckout^{iRNA}$ respectively in 15% PAGE. (e) Cartoons representing all the DNA and RNA conjugates used in the gel shift assay.

Figure 37:
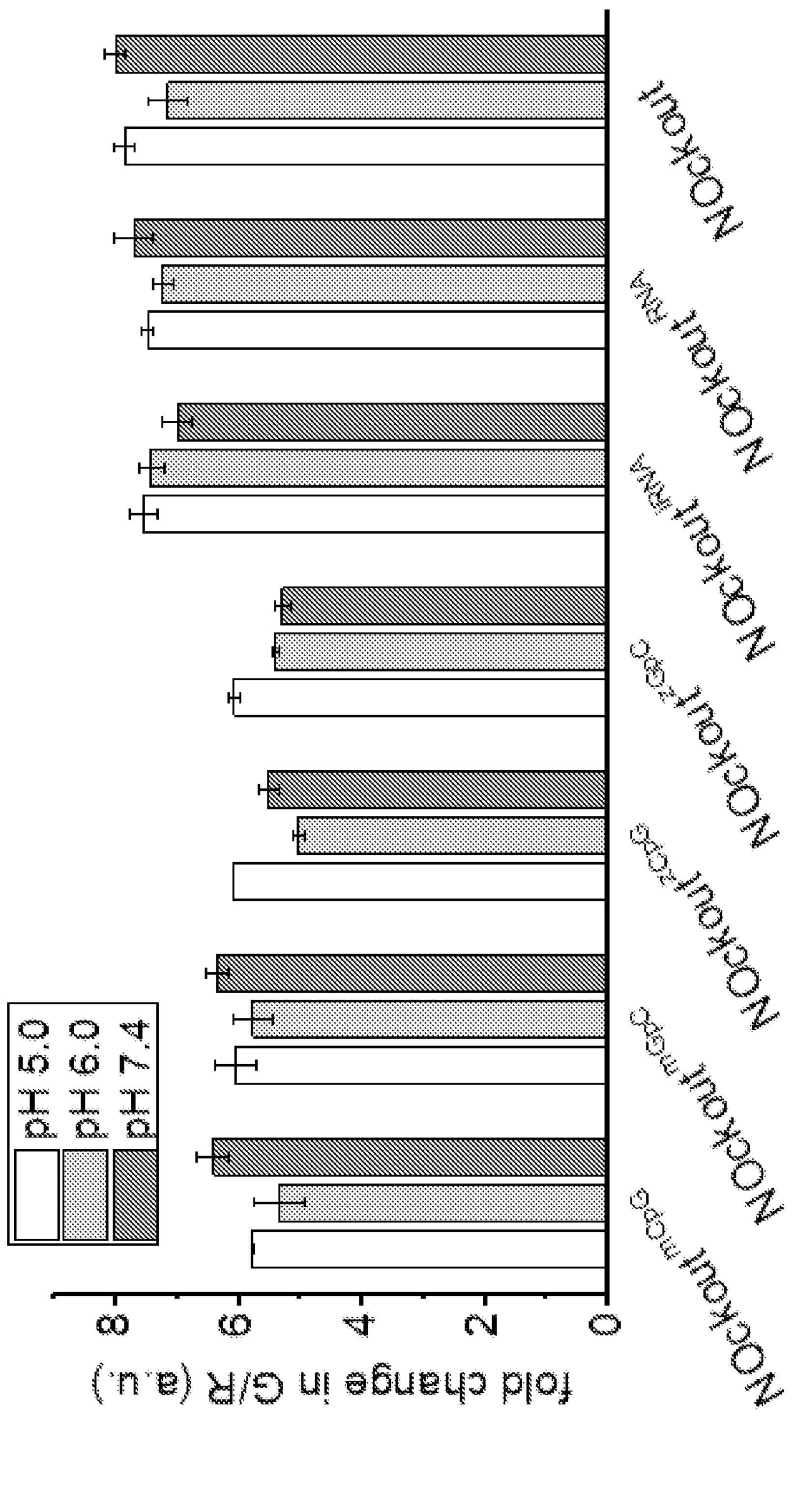

FIG. 37: Effect of pH on fold change of NOckout probes. A647N (R) and DAR (G) fluorophores were excited sequentially at 650 nm and 550 nm respectively and the emission maxima at 660 nm (A647N) and 575 nm (DAR) was computed to obtain the G/R ratio for all the NOckout probes. Fold change was represented as the G/R ratio.

Figure 38:
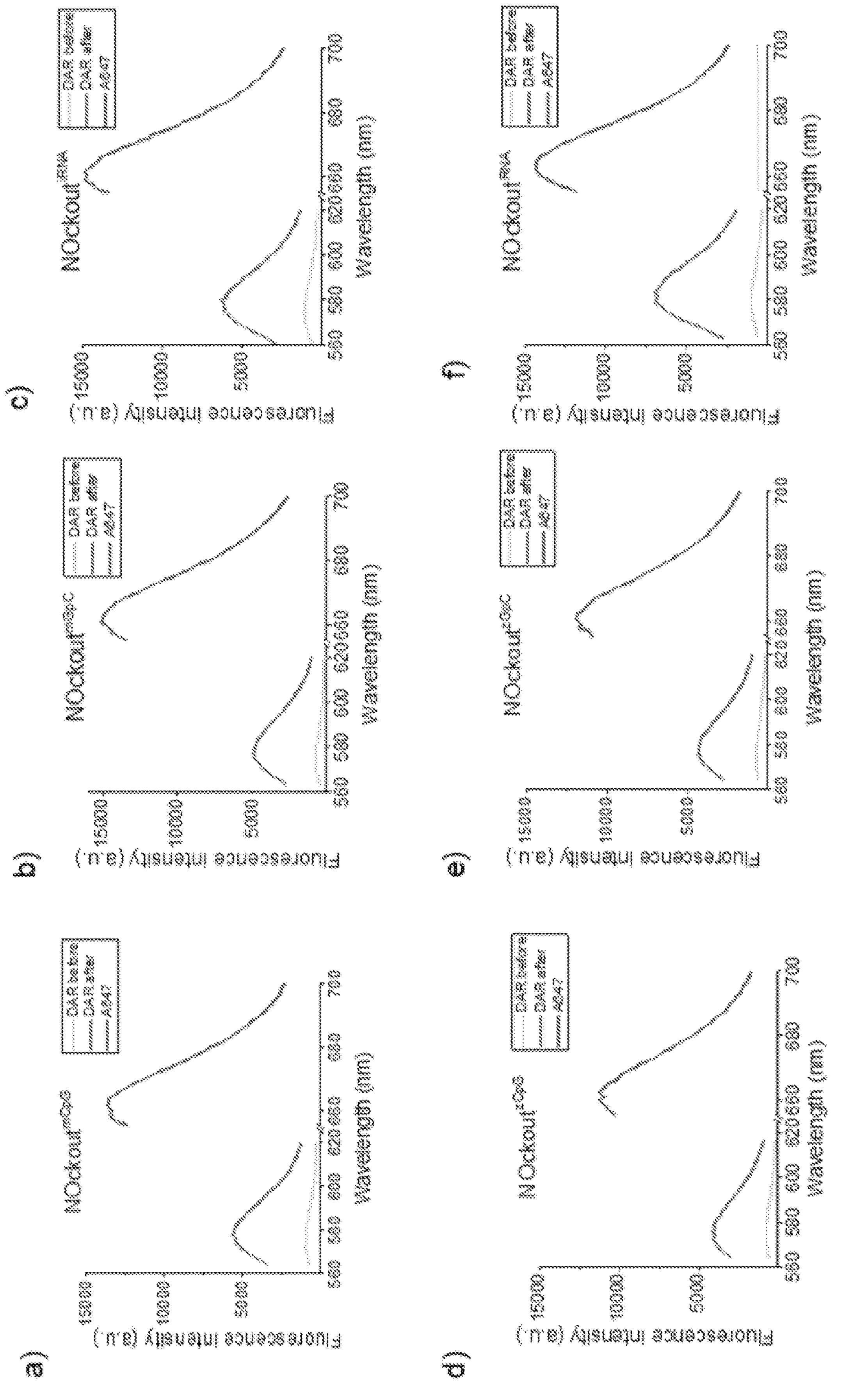

FIG. 38: Fluorescence emission spectra of $NOckout^{fn}$ probes (200 nM) excited in the DAR ($\lambda_{ex}$=550 nm) and A647N ($\lambda_{ex}$=650 nm) channels (slit width=2 nm each). Light green spectra indicate DAR emission before the addition of NO donor (30 μM) in 50 mM of pH 6.0 phosphate buffer and the dark green spectra represents completely NO reacted DAR at t=3 minutes. Red curves indicate the emission of A647N that is insensitive to the addition of NO.

Figure 39:
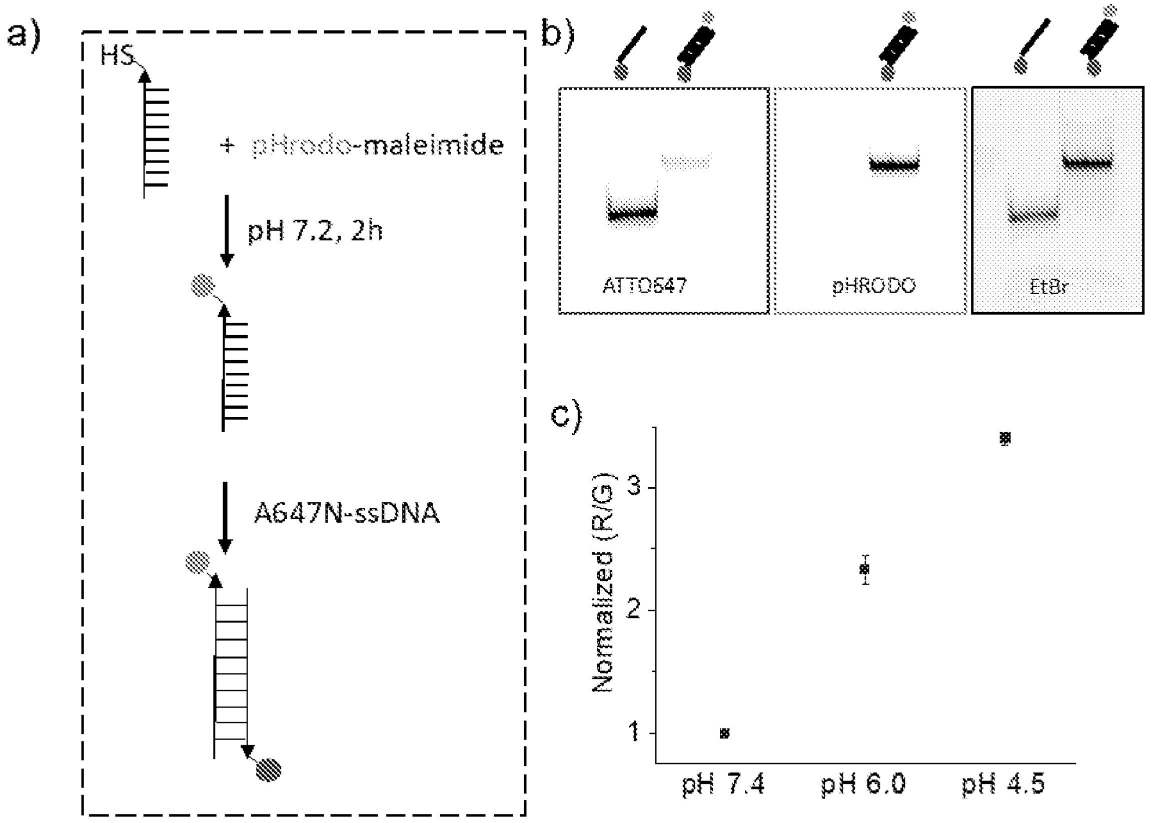

FIG. 39: Assembly, characterization and pH sensitivity of pHlickr. (a) Scheme showing the assembly of pHlickr from a 24-mer thiol (-SH) labeled ssDNA (see SI table1) that is conjugated to pHrodo-maleimide. ssDNA conjugated to the pHrodo fluorophore was annealed with fully complementary A647N labeled ssDNA (24-mer) to obtain pHlickr. (b) 15% PAGE showing the quantitative assembly of pHlickr and (c) pH sensing property of pHlickr (200 nM) incubated in respective buffers (see methods) and fluorescence spectra was recorded in the pHrodo (Green, G) and A647N channels (Red, R) by exciting at 560 nm and 650 nm respectively. G/R ratio at different pH was calculated and plotted.

Figure 40:
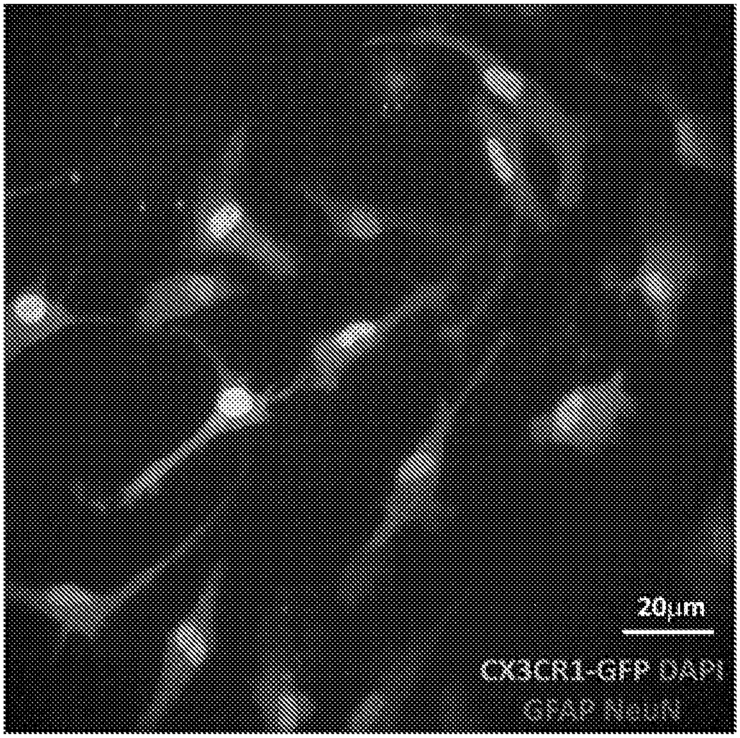

FIG. 40: Purity of microglial culture. Immunohistochemistry performed on mixed glial culture after the purification process. Astrocytes (red, GFAP maker) and neurons (magenta, NeuN marker) were absent in the culture containing predominantly microglia (green, GFP).

Figure 41:
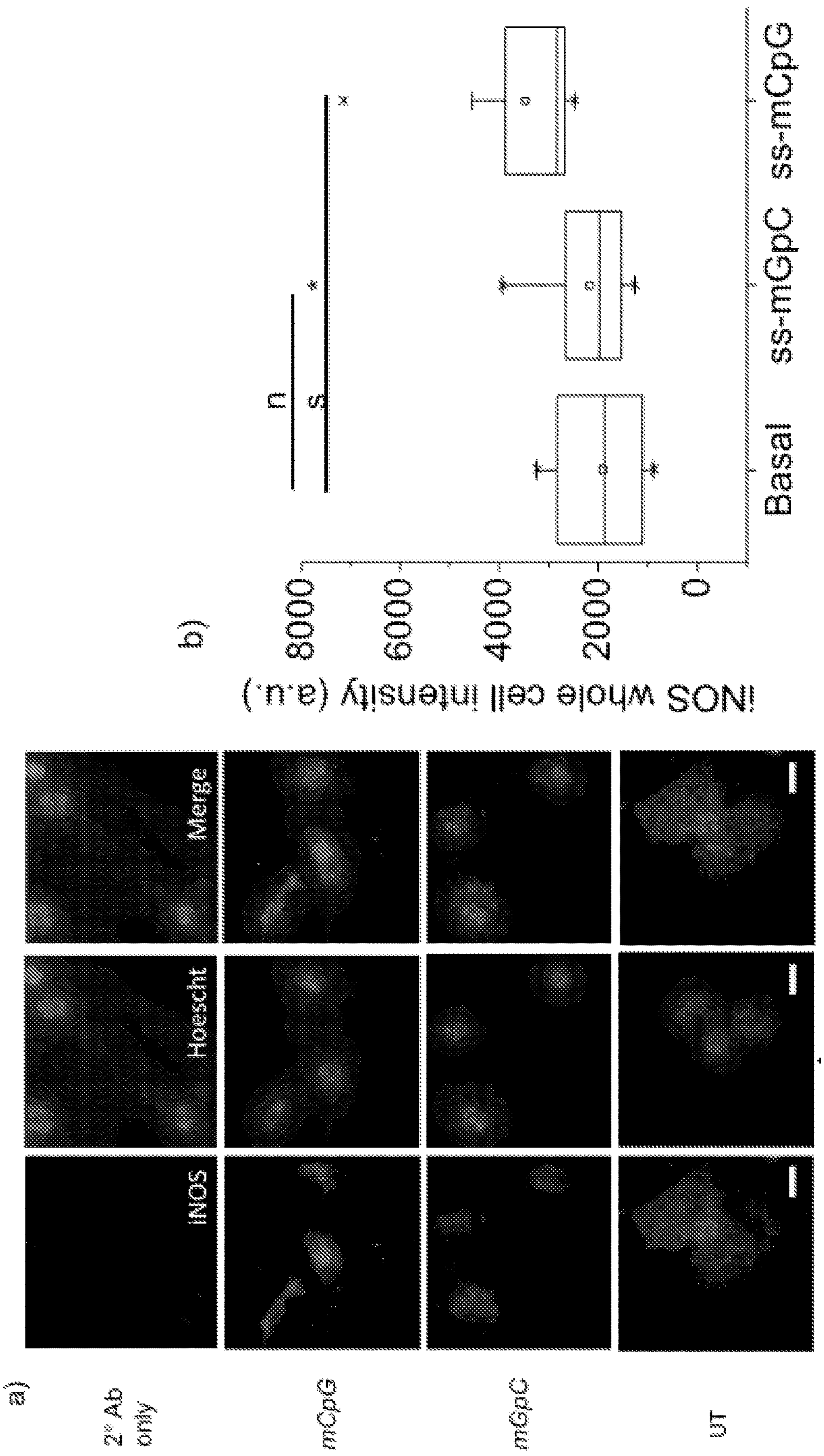

FIG. 41: NOS2 (iNOS) expression in murine primary microglia 2 weeks in culture. (a) Cell were treated with either 1 μM $NOckout^{mCpG}$ or 1 μM $NOckout^{mGpC}$ for 3 h before fixing it with 2.5% paraformaldehyde and subsequently incubated with NOS2 antibody (1:30 dilution). A488 (Green) labeled goat anti-rabbit antibody was used for fluorescence detection. (b) Quantification of the whole cell fluorescence intensity observed from the mCpG and mGpC treated cells compared to that of the untreated cells (n=12 cells). Scale=10 μm.

Figure 42:
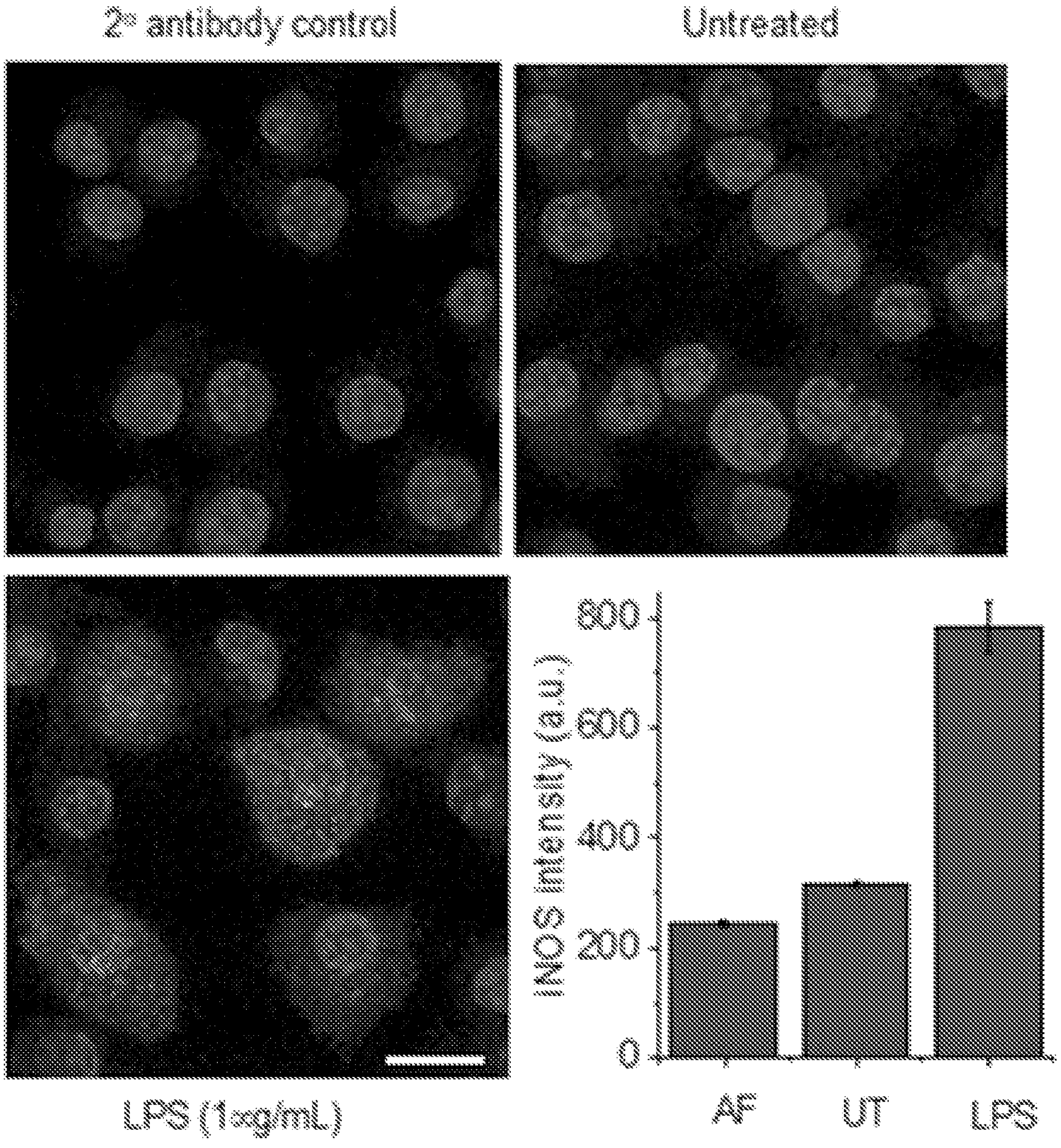

FIG. 42: NOS2 (iNOS) expression in J774A.1 cells. (a) Immunostaining control for J774A.1 cells with secondary antibody only (b) NOS2 Immunostaining (λex=488 nm, green) of untreated J774A.1 cells (c) NOS2 Immunostaining of J774A.1 cells treated with 1 μg/mL of LPS for 12 hours. (d) Quantification of whole cell NOS2 (green channel) intensities. n=75 cells and error bars represent S.E.M from two independent experiments. Hoechst (λex=405 nm, blue) was used as nuclear stain, Scale=10 μm.

Figure 43:
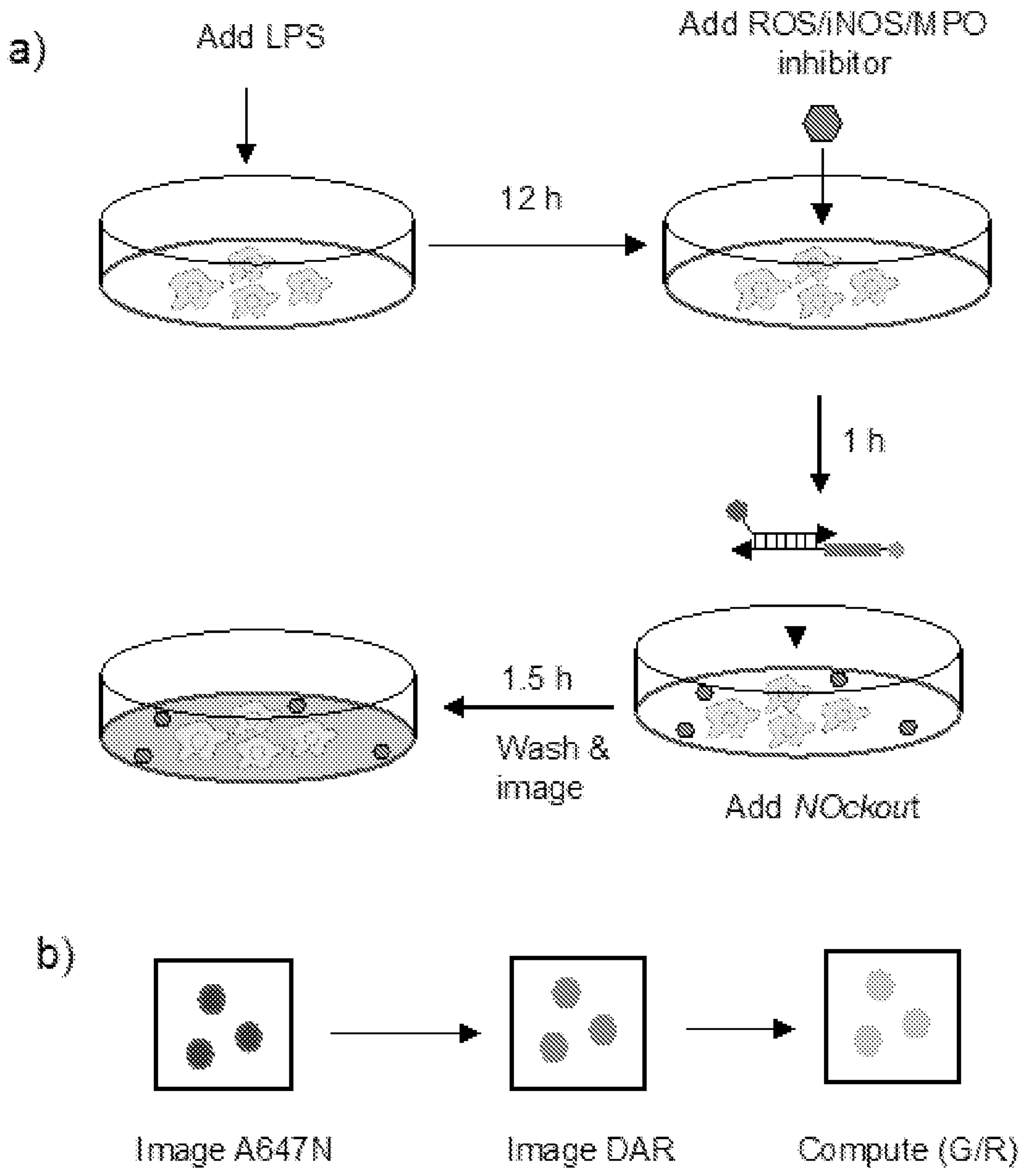

FIG. 43: (a) Cartoon representing the sequence of in cellulo specificity experiment performed in J774A.1 cells with NOckout sensor. (b) Fluorescence images from cells were acquired simultaneously in the A647N (red) and DAR (green) channels to compute endosomal G/R ratio (yellow) that represents NO production in those compartments.

Figure 44:
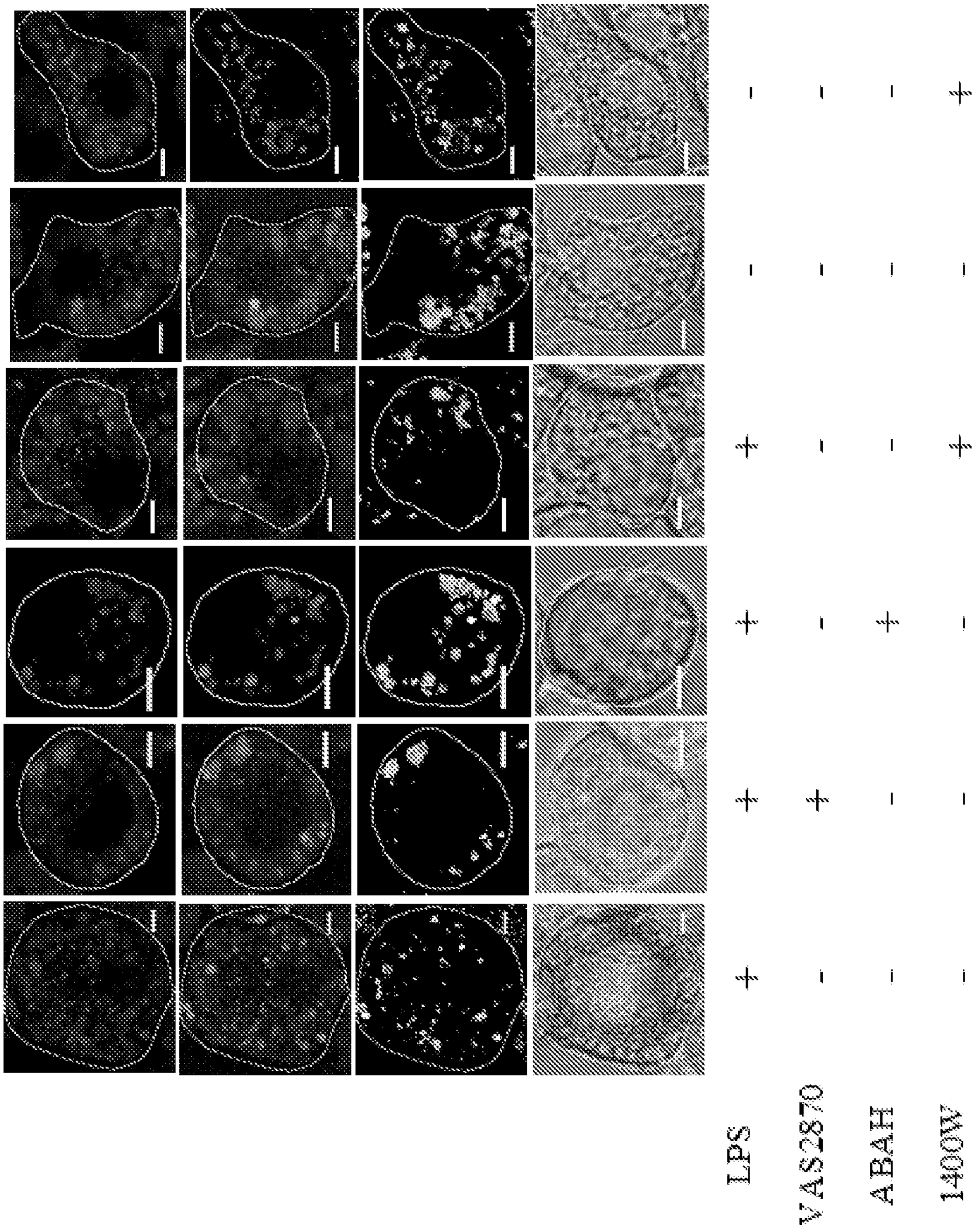

FIG. 44: In cellulo specificity of NOckout towards NO in J774 cells. Pharmacological inhibition of NOX using VAS2870 and MPO using ABAH did not reduce NO signal whereas treatment with 1400 W (NOS2) inhibitor significantly reduced NO signal. Red represents signal from A647N and green represents DAR signal. Ratio images in heatmap represents endosomal G/R values. Scale=10 μm.

Figure 45:
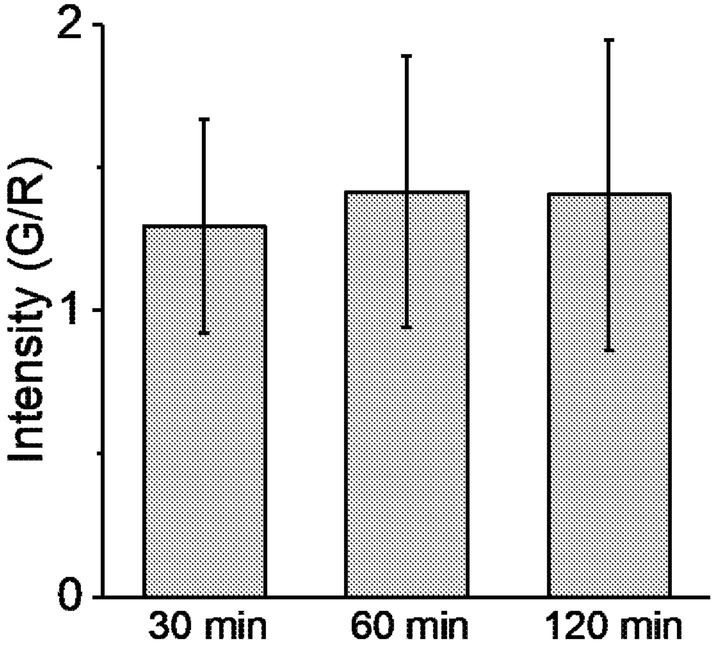

FIG. 45: In cellulo stability of NOckout in J774A.1 cells. NOckout pulsed cells were incubated at 37° C. at different time intervals and images were acquired in DAR (G) and A647N (R) channels and the ratio was plotted as whole cell intensity (GR).

Figure 46:
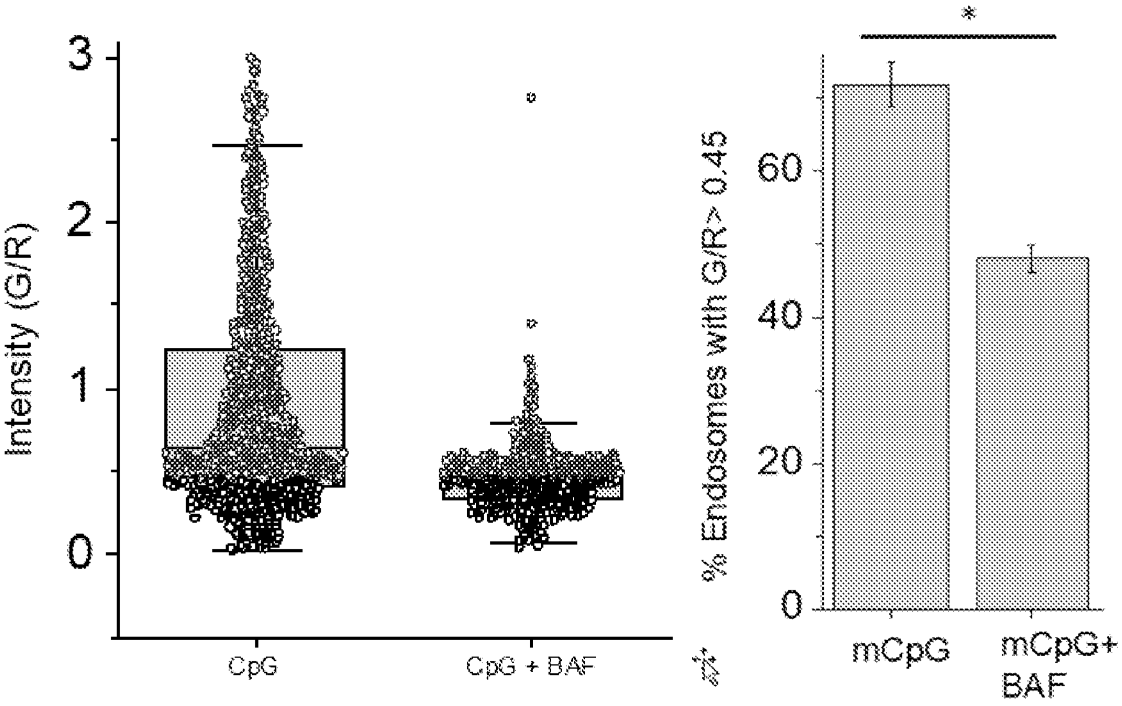

FIG. 46: Bafilomycin A1 treatment perturbs NO production in endosomes it microglia. (a) Endosomes (n=600) from primary microglial cells pulsed with $NOckout^{mCpG}$ (500 nM) showing low (black) and high (red) NO signals represented as G/R ratio. (b) Percentage of endosomes showing high G/R value decreased upon Bafilomycin A1 treatment.

Endosomes showing G/R value>0.45 is considered as high NO containing endosomes. G/R value>0.45 represents the mean of Bafilomycin A1 treated sample. $p=0.03$ for $n=2$ independent trials. Error bar represents standard error of mean (S.E.M) for n=20 cells.

Figure 47:
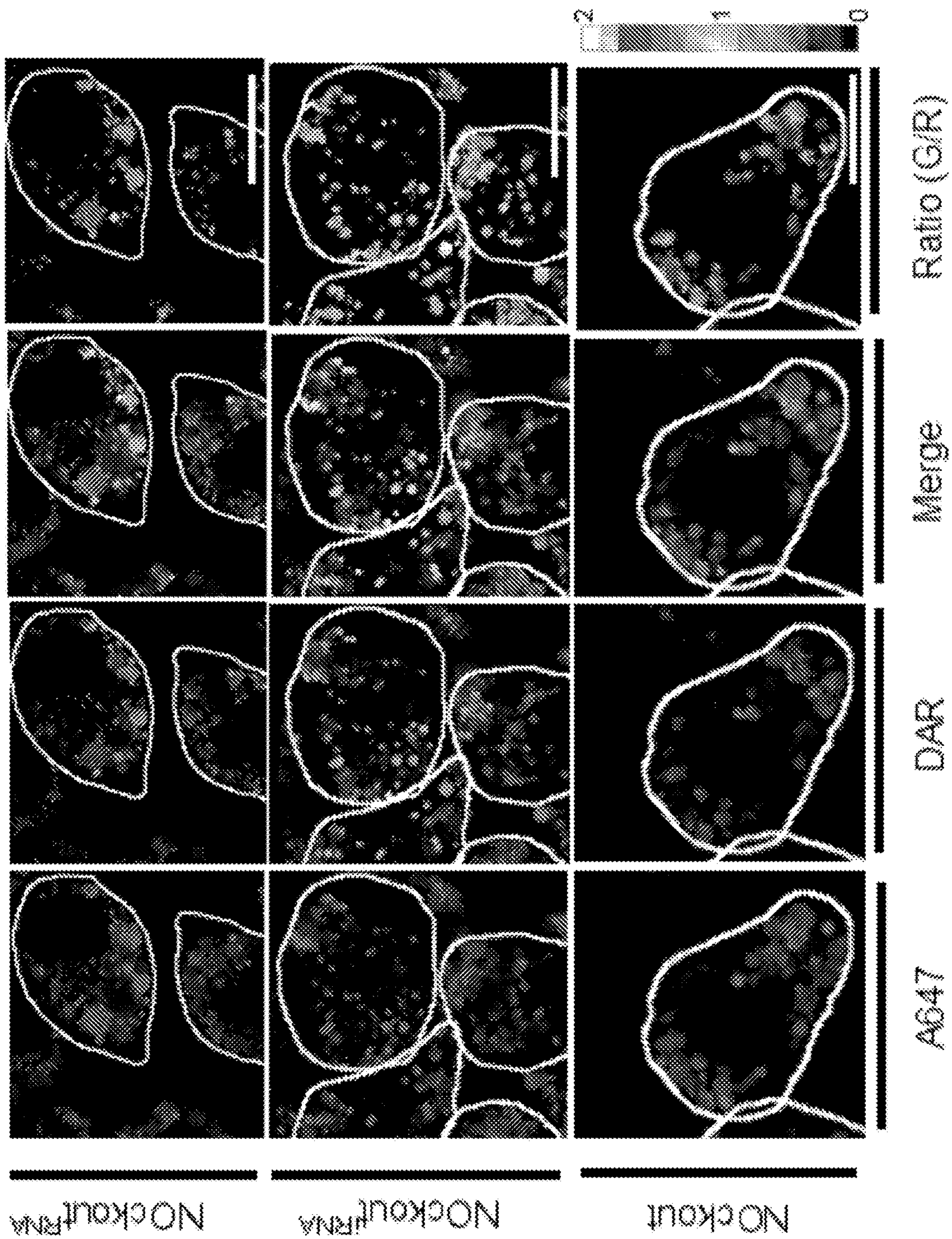

FIG. 47: Representative images of NOckout$^{RNA}$ and NOckout$^{iRNA}$ (500 nM each) pulsed samples from J774A.1 cells. Red represents fluorescent signal from A647N and green represents DAR signal. Ratio images in heatmap represents endosomal G/R values. Scale=10 μm.

Figure 48:
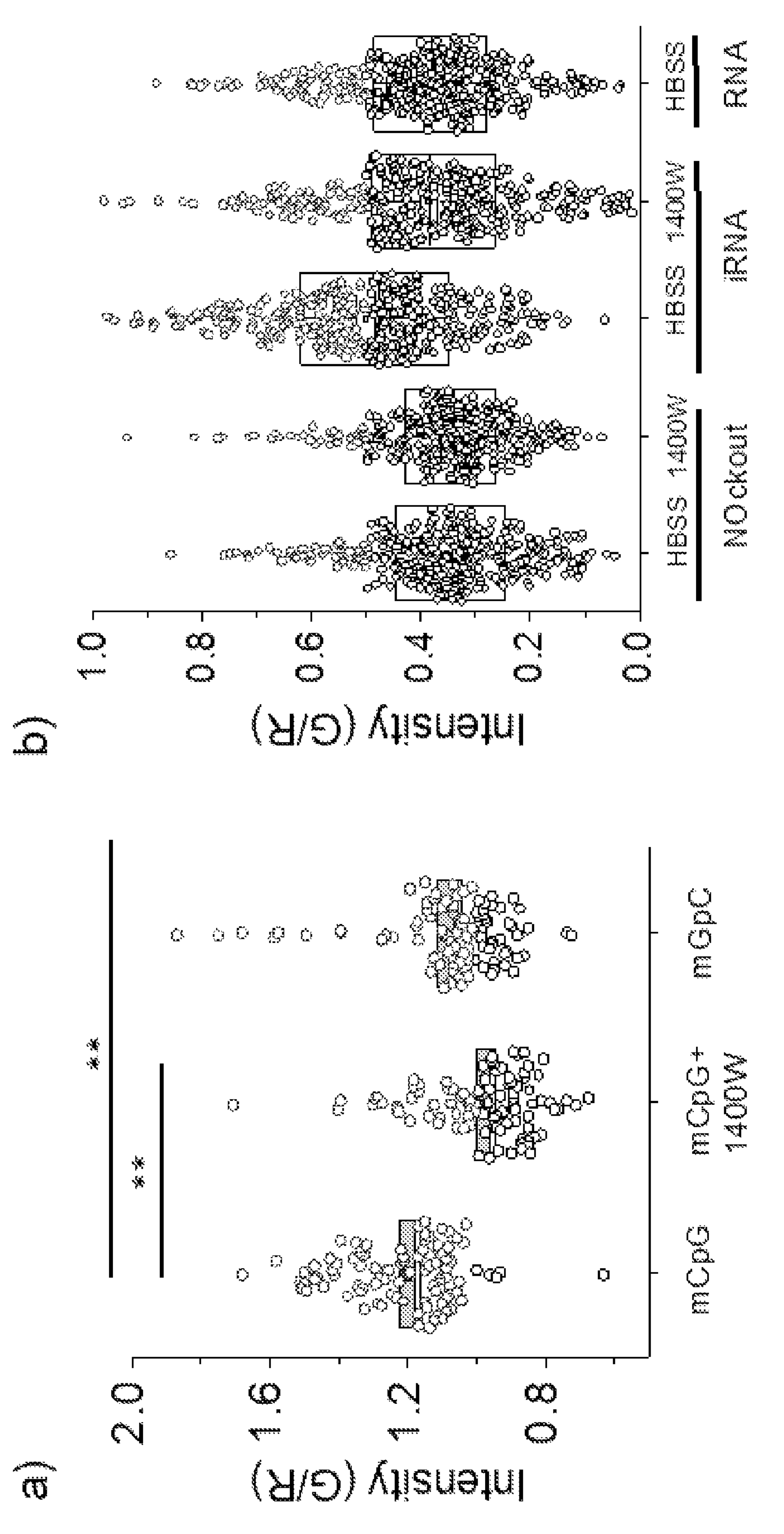

FIG. 48: (a) Absolute G/R values observed for individual endosomes from mCpG or mGpC (500 nM each) treated primary microglia. Red circles represent endosomes with G/R value above a threshold of 1 (for n=100 endosomes from n=50 cells in each samples). (b) Absolute G/R values observed for individual endosomes from iRNA or RNA (500 nM each) treated J774A.1 cells. Red circles represent endosomes with G/R value above a threshold of 0.5 (for n=250 endosomes from n=50 cells in each samples). All experiments were performed in duplicates. **$p<0.005$ for $n=2$ trials.

Figure 49:
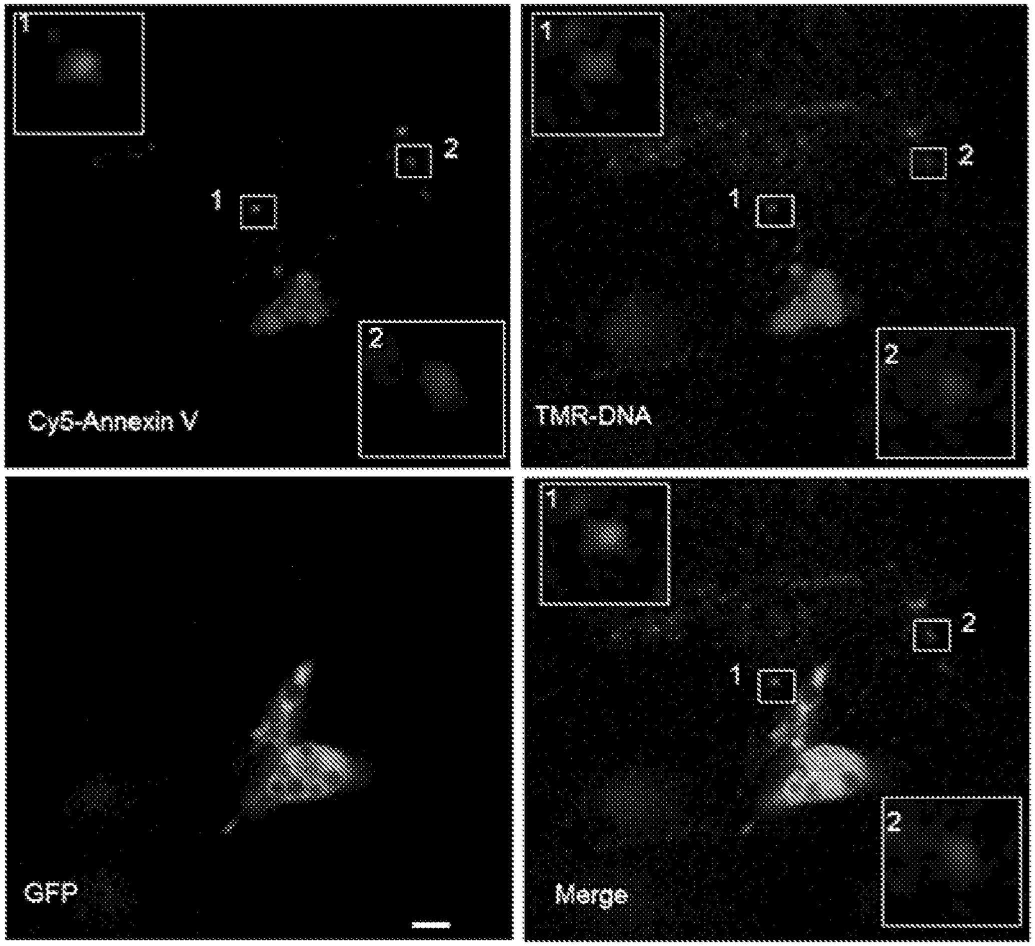

FIG. 49: Microinjected dsDNA$^{TMR}$ (24-mer) (blue) co-localizes with apoptotic body (red) prior to its uptake by the microglial cells (green). Inset shows zoomed images of the co-localized puncta. Scale=10 μM.

Figure 50:
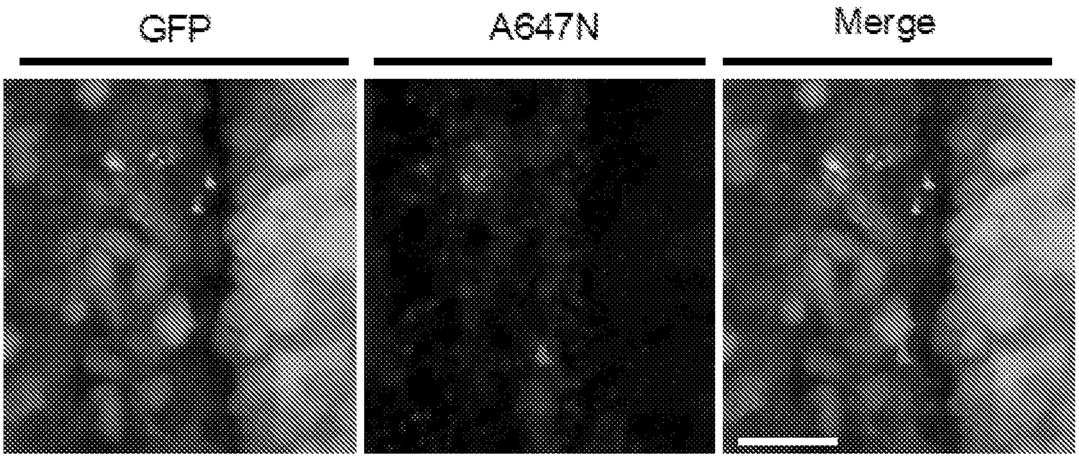

FIG. 50: Neurons do not uptake dsDNA$^{A647}$ (24-mer) injected in the brain. Images of 3 dpf old (Tg(Huc:Kaede)) fish injected with dsDNA$^{A647}$ (10 μM, 20 nL) recorded in the optic tectum area. Green represents Kaede emission from all the neurons (520 nm) and red represents fluorescence emission from dsDNA$^{A647N}$. Merged image indicates anti-colocalization of dsDNA with the neurons. Scale=30 μm.

Figure 4:
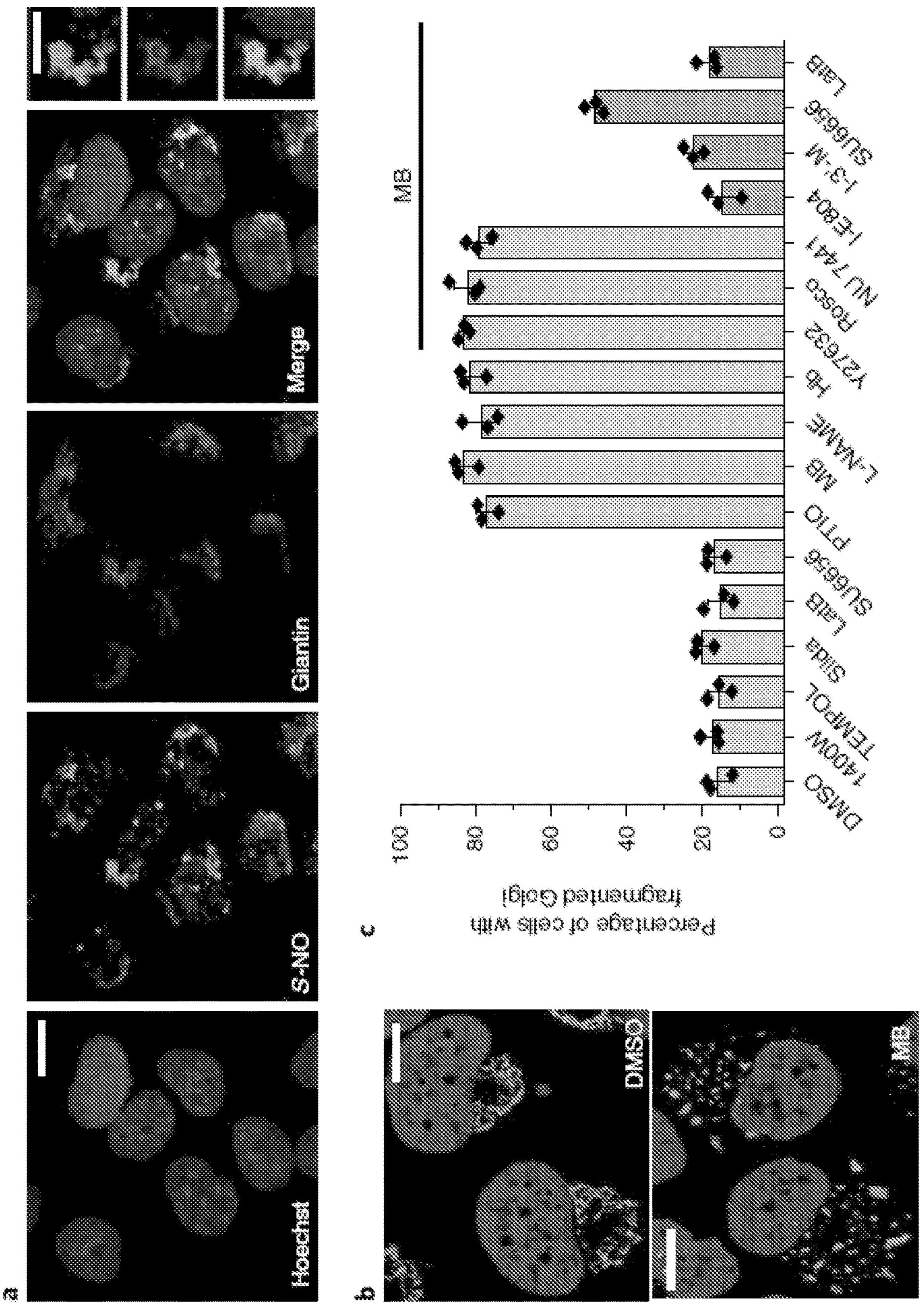
FIG. 4. Golgi apparatus is a primary S-Nitrosylation station in breast cancer cells (a) Confocal images showing extensive endogenous S-Nitrosylation (green) in the Golgi apparatus of T-47D cells, shown by colocalization with Golgi marker protein GM-130 (red). Inset shows merged images in higher magnification. Representative images are shown from total of three independent experiments. (b) Pharmacological scavenging of NO in T-47D cells using methylene blue (MB) leads to Golgi fragmentation. Fragmented Golgi is observed as a highly vesicular structure (green, Giantin) in a MB treated cells compared to that of the control (DMSO). Representative images are shown from total of three independent experiments. (c) Quantification of percentage of cells with fragmented Golgi upon treatment with indicated small molecules. Hoechst was used as nuclear stain (blue), Scale bar=10 μm, error bars represent standard error of mean (s.e.m) from three independent experiments. (d) Proposed model depicting mechanism responsible for NO scavenging mediated Golgi fragmentation. NOS3 activity can S-nitrosylate cSrc increasing its activity. Active cSrc can reduce polymerization of actin filaments, resulting in less tensile pull force and hence intact Golgi. In the case where NOS3 is blocked, cSrc activity is lower which allows for actin polymerization, increased tensile pull force and eventual Golgi fragmentation.
Figure 4:
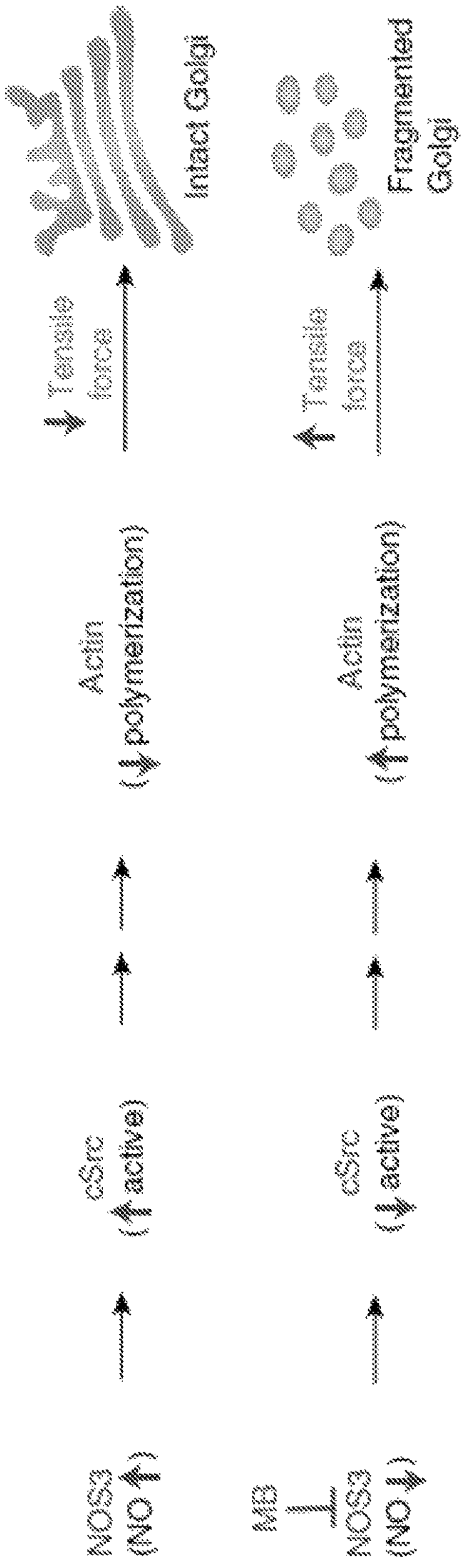
Figure 51:
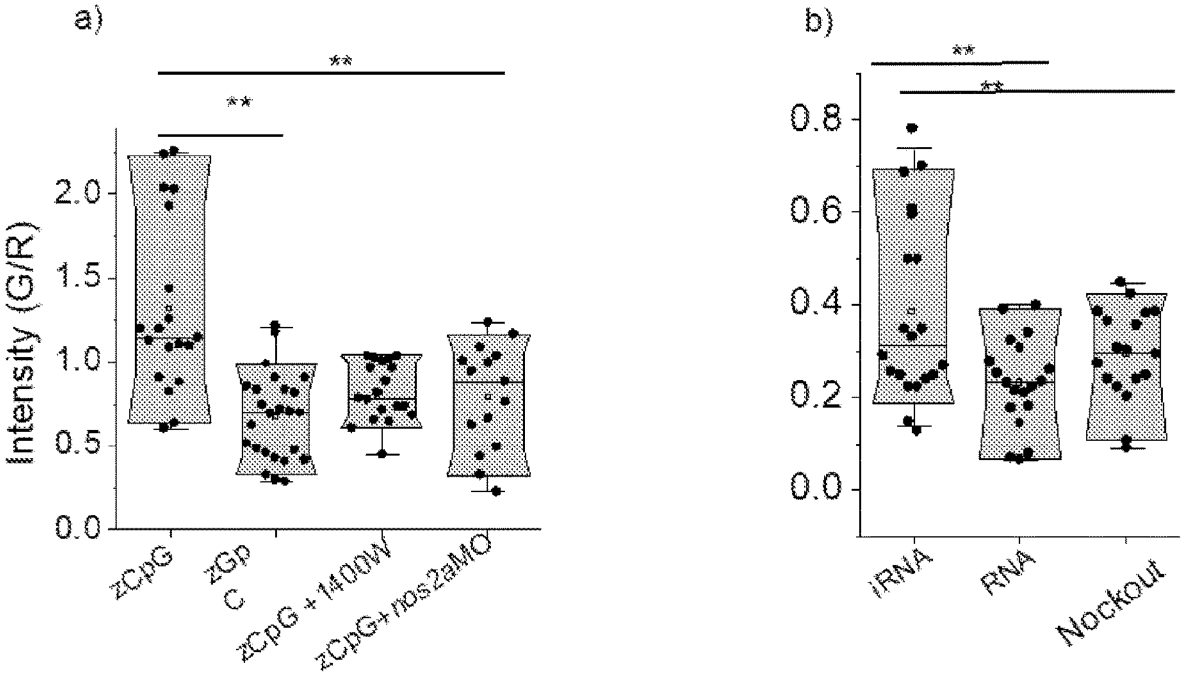

FIG. 51: (a) Raw data representing FIG. 4*d* and (b) Raw data representing FIG. 4*f*. $p<0.05$ for $n=2$ independent trials. Error bar represents standard error of mean (S.E.M) for n=8 fish in each treatment.

Figure 52:
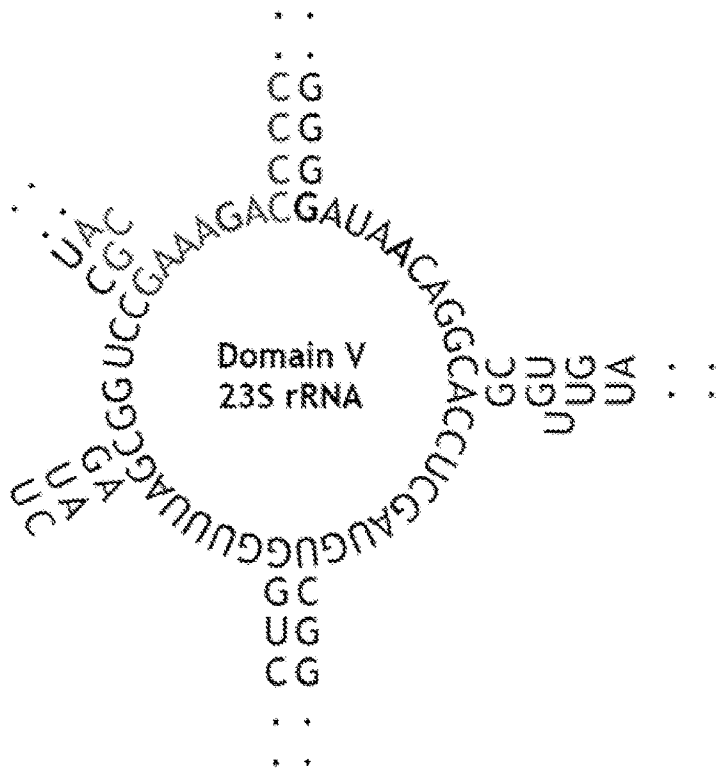

FIG. 52: Structure of the rRNA ribozyme (domain V; SEQ ID NO:19) hosting the conserved immunogenic 13nt RNA sequence highlighted in red.

Figure 53:
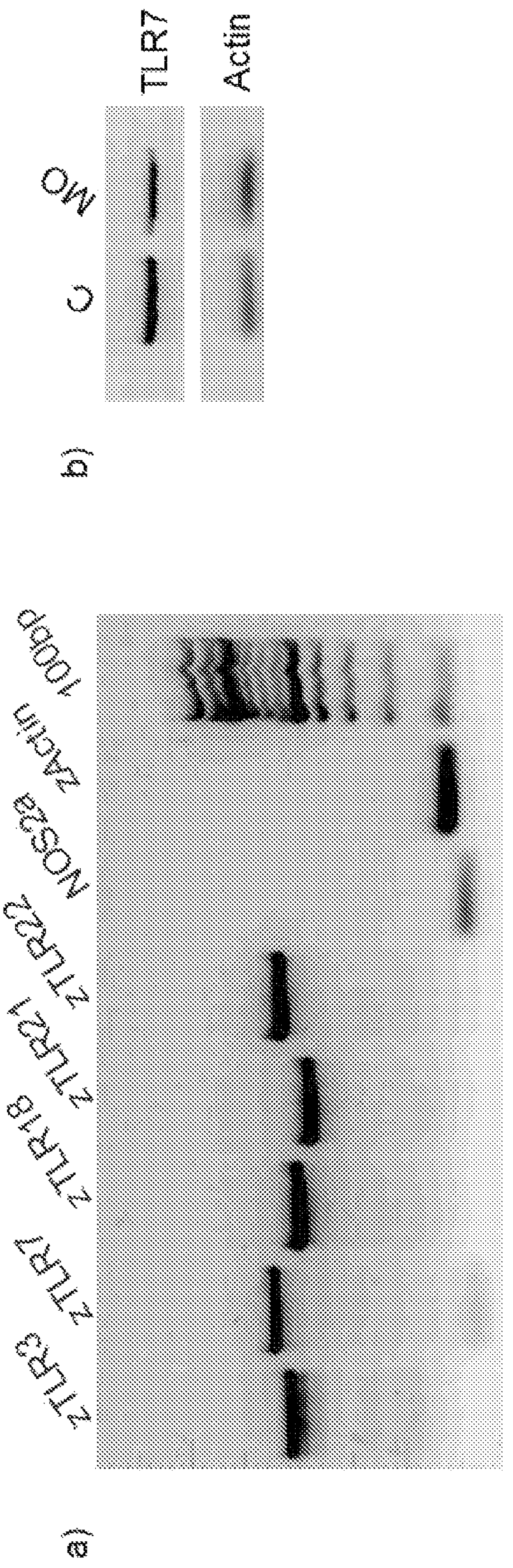

FIG. 53: (a) RT-PCR detection of mRNAs of zebrafish TLR (zTLR) receptors in 3 dpf old larval zebrafish. (b) Validation of morpholino knockdown of zTLR7 in 3 dpf old fish. Actin mRNA is used as the loading control.

Figure 54:
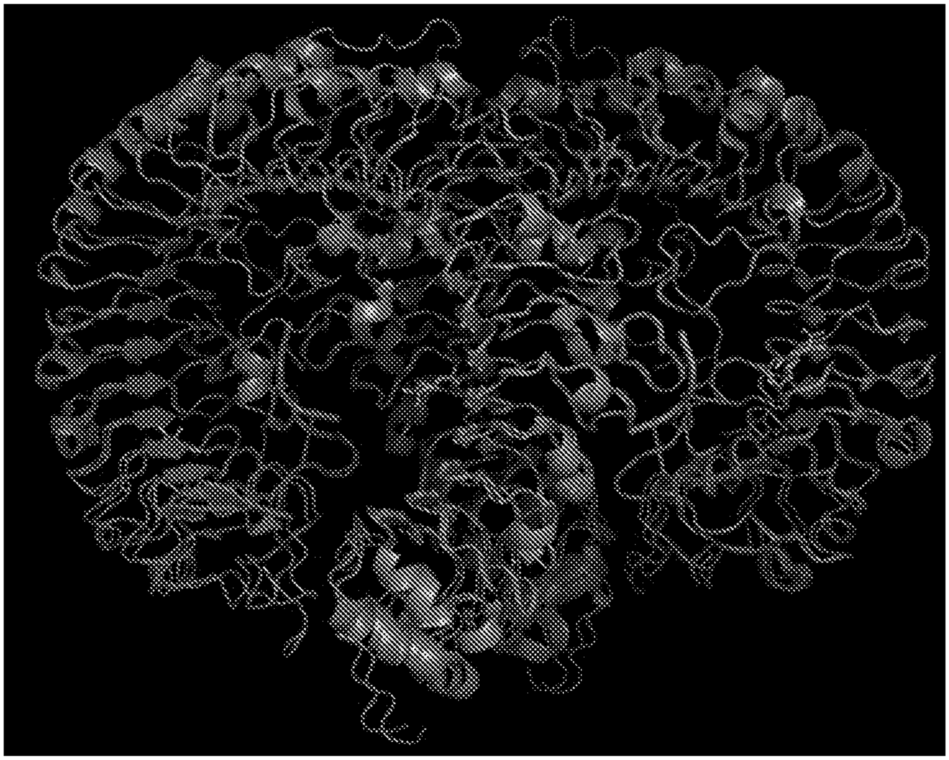

FIG. 54: (a) Predicted zTLR7 (magenta) structure superimposed with the known crystal structure of ssRNA (orange) bound Rhesus macaque TLR7(cyan) (PDB:5GMF).

FIG. 55: Clustal Omega multiple sequence alignment showing the similarity between zTLR7 (Uniprot ID: F1QY64; (SEQ ID NO:20)) and human TLR7 (Uniprot ID: Q9NYK1; (SEQ ID NO:21)) amino acid sequences. Highlighted residues in blue are critical for ssRNA binding and in yellow are residues important in NF-κB activation in HEK293T cells. Residues important in both ssRNA binding and NF-κB activation are either conserved or show conservative mutations in the zebrafish counterpart.

DETAILED DESCRIPTION OF THE DISCLOSURE

Before the disclosed methods and materials are described, it is to be understood that the aspects described herein are not limited to specific embodiments, and as such can, of course, vary. It is also to be understood that the terminology used herein is for the purpose of describing particular aspects only and, unless specifically defined herein, is not intended to be limiting. In view of the present disclosure, the methods described herein can be configured by the person of ordinary skill in the art to meet the desired need.

Nitric oxide synthase 3 (NOS3) produces the gasotransmitter, nitric oxide (NO) that drives critical cellular signaling pathways by S-nitrosylating target proteins. Endogenous NOS3 resides at two distinct sub-cellular locations—the plasma membrane and the trans Golgi network. However, NO generation arising from the activities of both these pools of NOS3 and its relative contribution to physiology or disease is not yet resolvable. A fluorescent DNA-based probe technology, NOckout, is described to quantitatively map the activities of endogenous NOS3 at both sub-cellular locations in live cells. It was found that although NOS3 at the Golgi is ten-fold less active than at the plasma membrane, its activity is essential for the structural integrity of the Golgi. The newfound ability to spatially map NOS3 activity provides a platform to discover selective regulators of the distinct pools of NOS3.

Here, a novel DNA-based fluorescent probe technology is disclosed which can quantitatively map NOS3 activity in real time while providing subcellular spatial resolution. DNA-based fluorescent probes are a fairly recent development that combine the sensitivity and photophysical advantages of small molecule probes with the stable localization provided by proteins. They have been successfully deployed to quantitatively map second messengers such as pH, chloride and calcium with sub-cellular resolution in living systems. The 1:1 stoichiometry of DNA hybridization facilitates the integration of these multiple functions with stoichiometric precision onto a single probe. Thus, the DNA-based fluorescent probes for NO, denoted NOckout include (i) an NO sensitive fluorophore possessing the specificity and sensitivity of small molecule probes (ii) an internal reference dye for ratiometric quantitation and (iii) a targeting function that stably localizes the reporter at either the plasma membrane or the Golgi.

In this disclosure, the NOckout probes were found to be useful for quantitating NOS3 activity simultaneously at the two relevant sub-cellular locations: the plasma membrane and the TGN. This was achieved using two spectrally different NOckout probes, one localized at the plasma membrane (NOckout$^{PM}$ or 1) and the other localized at the TGN (NOckout$^{TGN}$ or 2). It was found that when NOS3 is activated, NO production due to enzymatic activity at the plasma membrane was ~7-fold higher than at the TGN. It was also found that the high activity of the NOS3 fraction at the plasma membrane was due to this population being selectively phosphorylated at S1177. Interestingly, low activity of NOS3 at the TGN is critical for Golgi integrity. This is because, despite the low NOS3 activity at the TGN, the Golgi is highly enriched fin S-Nitrosylated proteins. Reducing S-nitrosylation at the TGN by inhibiting NOS3 led to fragmentation of the Golgi and subsequent cell senescence in breast cancer cells through a Src kinase mediated pathway. This reveals that the Golgi apparatus in breast cancer cells is a hotspot for S-Nitrosylation and is critical for the structural integrity of this organelle.

The NOckout probes combines the advantages of small molecule probes, with the stable spatial localization afforded by proteins. The DNA scaffold can be molecularly programmed to display a well-defined nucleic acid-based PAMP, simultaneously display NO detection chemistry, as well as a reference fluorophore, which can be used for ratiometric imaging since the latter is insensitive to ROS, NO, pH and other ions. All three functionalities can be integrated in a well-defined stoichiometry onto a single assembly by hybridizing complementary DNA strands, each bearing one of the functionalities. Thus the resultant assembly is a DNA duplex that is recognized in the living brain as fragmented self-DNA, packaged into apoptotic bodies, which are then ingested by microglia resident in the brain and targeted to their phagosomes.

When specific PAMPs are displayed on NOckout probes, it was found that they triggered NOS2 activation by binding a cognate endosomal TLR in macrophages in cell culture as well as microglia in live zebrafish brains. The modular nature of DNA-based assemblies allows us to create a series of NOckout probes, each displaying a different nucleic-acid based PAMP, but having identical NO detection characteristics. This was achieved by simply replacing the PAMP-bearing DNA strand in a given NOckout variant with another DNA/RNA sequence bearing a different PAMP. Using this plug and play strategy, assay of phagosomal NO production due to NOS2 activation as a result of engaging a specific TLR through the PAMP on the NOckout probe can be performed. Using these “trigger and detect” NOckout probes it was found that single stranded RNA (ssRNA) of microbial origin can act as PAMPs in zebrafish. This reveals that zebrafish have the capacity to detect ssRNAs derived from pathogenic sources as PAMPs to induce phagosomal NO production.

The oligonucleotides and nucleic acid molecules in the compositions and methods described herein may include one or more labels. Nucleic acid molecules can be labeled by incorporating moieties detectable by one or more means including, but not limited to, spectroscopic, photochemical, biochemical, immunochemical, or chemical assays. The method of linking or conjugating the label to the nucleotide or oligonucleotide depends on the type of label(s) used and the position of the label on the nucleotide or oligonucleotide.

As used herein, “labels” are chemical or biochemical moieties useful for labeling a nucleic acid. “Labels” include, for example, fluorescent agents, chemiluminescent agents, chromogenic agents, quenching agents, radionucleotides, enzymes, substrates, cofactors, inhibitors, nanoparticles, magnetic particles, and other moieties known in the art. Labels are capable of generating a measurable signal and may be covalently or noncovalently joined to an oligonucleotide or nucleotide. The labels can be conjugated to the nucleic acid molecules directly or indirectly by a variety of techniques. Depending on the precise type of label used, the label can be located at the 5' or 3' end of the oligonucleotide or located internally in the oligonucleotide’s nucleotide sequence. For instance, using commercially available phosphoramidite reagents, one can produce nucleic acid molecules containing functional groups (e.g., thiols or primary amines) at either terminus, for example by coupling of a phosphoramidite dye to the 5' hydroxyl of to 5' base by the formation of a phosphate bond, or internally, via an appropriately protected phophoramidite.

A “normalizing fluorophore” is generally a NO target insensitive fluorophore. Any suitable normalizing fluorophore may be used such as the ones described in WO 2016/187284, which is incorporated by reference in its entirety. Representative examples of suitable normalizing fluorophores as the first label include Alexa488 or Alexa647. In some embodiments, the normalizing fluorophore is cross-linked to the second strand. In embodiments the ratio of the NO sensitive fluorophore to the normalizing fluorophore is 1:1.

In embodiments, the nucleic acid complex further comprises a targeting moiety which targets a specific location or region of the cell such as the plasma membrane, trans golgi network, pahagosome, macrophage and microglia. Representative examples of a targeting moiety include a cholesterol moiety, an oligodeoxynucleotide phosphorothiolate or oligoribonucleotide phosphorothiate. In some embodiments, the targeting moiety is a nucleic acid sequence. In some embodiments, the targeting moiety has a cognate artificial protein receptor. The artificial receptor may be, for example, a single chain variable fragment (scFv), transcription factor, Zn-fingered protein, leucine zipper, or DNA binding immunoglobulin, In some embodiments, the targeting moiety is encoded on the same nucleic acid strand as the first and/or second single-stranded nucleic acid molecule. In some embodiments, the targeting moiety is selected from an aptamer, a duplex domain targeted to an artificial protein receptor, a nucleic acid sequence that binds an anionic-ligand binding receptor, and an endocytic ligand. In some embodiments, the targeting moiety comprises a peptide directly or indirectly conjugated to the nucleic acid molecule. In some embodiments, the targeting moiety peptide comprises one or more of a fusogenic peptide, a membrane-permeabilizing peptide, a sub-cellular localization sequence, or a cell-receptor ligand. In some embodiments, the sub-cellular localization sequence targets the nucleic acid complex to a region of the cell where spatial localization of a targeted protein is present. In some embodiments, the sub-cellular localization sequence targets the nucleic acid complex to a region of the cell selected from the group consisting of: the medial trans Golgi cistemae or trans Golgi network, lysosome, endosome, phagosome, and a specific spatial location on the plasma membrane. In some embodiments, the sub-cellular organelle is one that exchanges membrane directly or indirectly with the plasma membrane.

A “sample” refers to a biological sample selected from a cell, cell extract, cell lysate, tissue, tissue extract, bodily fluid, serum, blood and blood product. In some embodiments, the sample is a live cell. In other embodiments, the sample is a region of the cell such as a cellular membrane or a intracellular organelle.

The nucleic acid complexes as described herein can be readily introduced into a host cell, e.g., a mammalian (optionally human), bacterial, parasite, yeast or insect cell by any method in the art. For example, nucleic acids can be transferred into a host cell by physical, chemical or biological means. It is readily understood that the introduction of the nucleic acid molecules yields a cell in which the intracellular NO may be monitored. Thus, the method can be used to measure intracellular NO in cells cultured in vitro. The nucleic acid complex of the disclosure can also be readily introduced into a whole organism to measure the NO in a cell, organelle or tissue in vivo. For example, nucleic acid complex of the disclosure can be transferred into an organism by physical, chemical or biological means, e.g., direct injection.

In certain embodiments, the methods for introducing nucleic acid complexes of the disclosure may be those disclosed in Chakraborty et al. “Nucleic Acid-Based Nanodevices in Biological imaging,” Annu. Rev. Biochem. 85:349-73 (2016), incorporated in its entirety by reference herein.

Chemical means for introducing a polynucleotide into a host cell include colloidal dispersion systems, such as macromolecule complexes, nanocapsules microspheres, beads, and lipid-based systems including oil-in-water emulsions, micelles, mixed micelles, and liposomes. One colloidal system for use as a delivery vehicle in vitro and in vivo is a liposome (i.e., an artificial membrane vesicle). The preparation and use of such systems is well known in the art.

In some embodiments, the use of lipid formulations is contemplated for the introduction of the nucleic acid complex of the disclosure into host cells in vitro, ex vivo or in vivo). In some embodiments, the nucleic acid complex of the disclosure may be associated with a lipid. The nucleic acid complex of the disclosure associated with a lipid may be encapsulated in the aqueous interior of a liposome, interspersed within the lipid bilayer of a liposome, attached to a liposome via a linking molecule that is associated with both the liposome and the oligonucleotide(s), entrapped in a liposome, complexed with a liposome, dispersed in a solution containing a lipid, mixed with a lipid, combined with a lipid, contained as a suspension in a lipid, contained or complexed with a micelle, or otherwise associated with a lipid. The lipid, lipid/nucleic acid complex compositions are not limited to any particular structure in solution. For example, they may be present in a bilayer structure, as micelles, or with a "collapsed" structure. They may also simply be interspersed in a solution, possibly forming aggregates which are not uniform in either size or shape.

In some embodiments, the one or more nucleic acid complexes of the disclosure are linked to a targeting sequence that directs the nucleic acid complex to a desired cellular compartment.

As used herein,"nucleic acid," "nucleotide sequence," or"nucleic acid sequence" refer to a nucleotide, oligonucleotide, polynucleotide, or any fragment thereof and to naturally occurring or synthetic molecules. The term "peptide nucleic acid" or "IRNA" as used herein generally refers to nucleic acid analogue in which the sugar phosphate backbone of natural nucleic acid has been replaced by a synthetic peptide backbone. The term "RNA equivalent" in reference to a DNA sequence, is composed of the same linear sequence of nucleotides as the reference DNA sequence with the exception that all occurrences of the nitrogenous base thymine are replaced with uracil, and the sugar backbone is composed of ribose instead of deoxyribose. It is understood to be a molecule that has a sequence of bases on a backbone comprised mainly of identical monomer units at defined intervals. The bases are arranged on the backbone in such a way that they can enter into a bond with a nucleic acid having a sequence of bases that are complementary to the bases of the oligonucleotide. The most common oligonucleotides have a backbone of sugar phosphate units. A distinction may be made between oligodeoxyribonucleotides, which do not have a hydroxyl group at the 2' position, and oligoribonucleotides, which have a hydroxyl group in this position. Oligonucleotides also may include derivatives, in which the hydrogen of the hydroxyl group is replaced with organic groups, e.g., an allyl group. An oligonucleotide is a nucleic acid that includes at least two nucleotides.

One nucleic acid sequence may be"complementary" to a second nucleic acid sequence. As used herein, the terms-"complementary" or"complementarity," when used in reference to nucleic acids (i.e., a sequence of nucleotides such as an oligonucleotide or a target nucleic acid), refer to sequences that are related by base-pairing rules. For natural bases, the base pairing rules are those developed by Watson and Crick. As an example, for the sequence "T-G-A", the complementary sequence is "A-C-T." Complementarity can be "partial," in which only some of the bases of the nucleic acids are matched according to the base pairing rules. Alternatively, there can be "complete" or "total" complementarity between the nucleic acids. The degree of complementarity between the nucleic acid strands has effects on the efficiency and strength of hybridization between the nucleic acid strands.

Oligonucleotides as described herein may be capable of forming hydrogen bonds with oligonucleotides having a complementary base sequence. These bases may include the natural bases such as A, G, C, T and U, as well as artificial bases. An oligonucleotide may include nucleotide substitutions. For example, an artificial or modified base may be used in place of a natural base such that the artificial base exhibits a specific interaction that is similar to the natural base.

An oligonucleotide that is complementary to another nucleic acid will "hybridize" to the nucleic acid under suitable conditions (described below). As used herein,"hybridization" or "hybridizing" refers to the process by which an oligonucleotide single strand anneals with a complementary strand through base pairing under defined hybridization conditions. "Specific hybridization" is an indication that two nucleic acid sequences share a high degree of complementarity. Specific hybridization complexes form under permissive annealing conditions and remain hybridized after any subsequent washing steps. "Hybridizing" sequences which bind under conditions of low stringency are those which bind under non-stringent conditions (6×SSC/50% formamide at room temperature) and remain bound when washed under conditions of low stringency (2×SSC, 42° C.), Hybridizing under high stringency refers to the above conditions in which washing is performed at 2×SSC, 65° C. (where SSC is 0.15M NaCl, 0.015M sodium citrate, pH 7.2).

In some embodiments, a kit comprising a nucleic acid complex for quantifying NO is contemplated.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or." It is also contemplated that anything listed using the term "or" may also be specifically excluded.

As used in this specification and claim(s), the words "comprising" and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

EXAMPLES

Certain aspects of the disclosure are illustrated further by the following examples, which are not to be construed as limiting the disclosure in scope or spirit to the specific methods and materials described in them.

Materials and Methods

Part 1 (DNA-Based Fluorescent Probe Mapping of NOS3 Activity with Sub-Cellular Spatial Resolution) (Examples 1-6)

Figure 9:
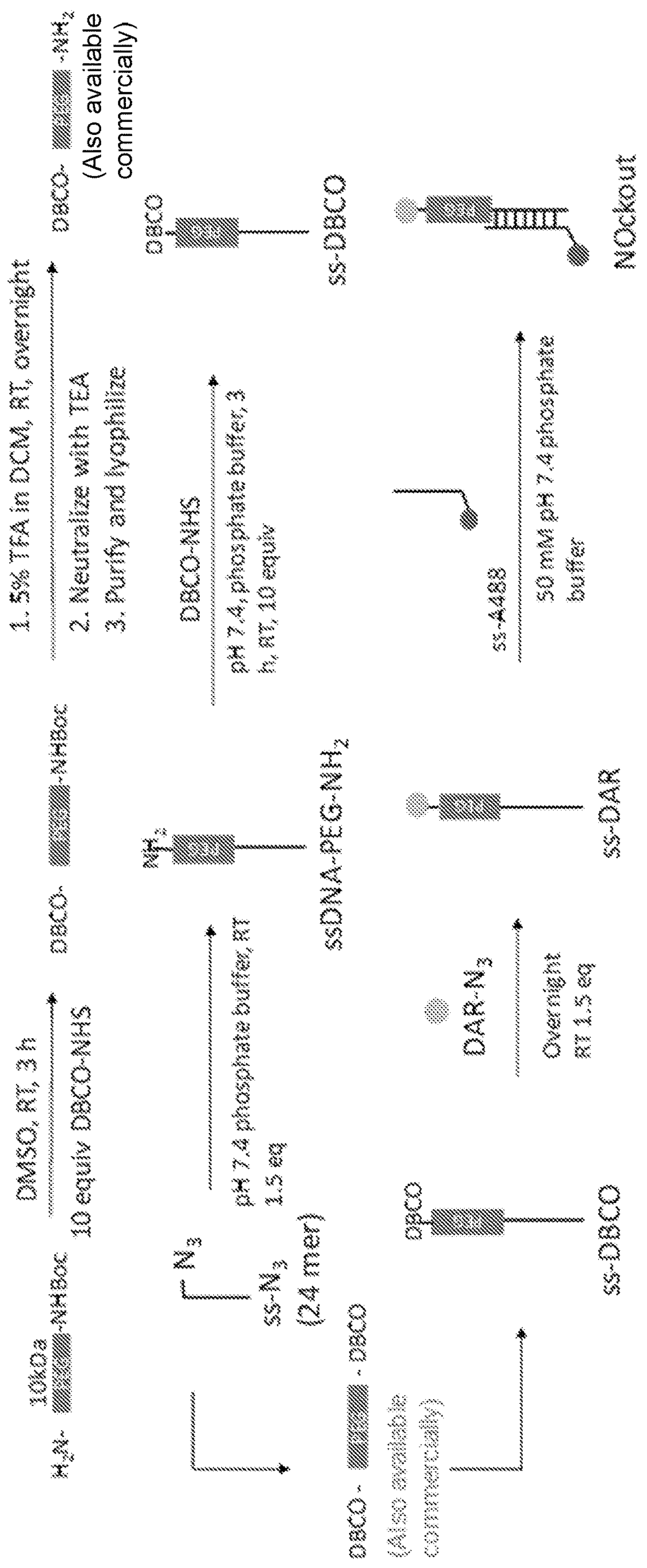
FIG. 9 displays stepwise synthesis of DAR-S1 strand and assembly of NOckout according to an example embodiment.
Figure 9:
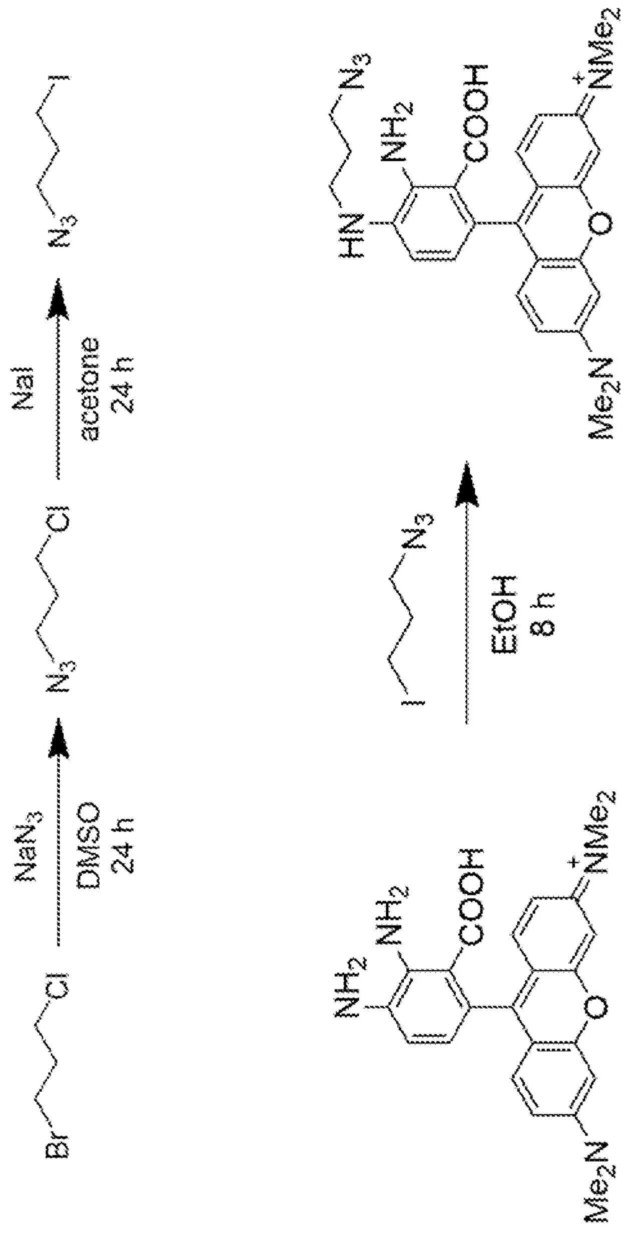

Reagents. All oligonucleotides (Table 1) were purchased from Integrated DNA Technology (IDT, USA). HPLC purified DNA oligonucleotides were used without further purification, whereas fluorescently modified oligonucleotides were precipitated from ethanol prior to further use. DAR was functionalized to Si as shown in FIG. 9. Oligos were quantified using UV-V is spectrophotometry (Shimadzu UV-2700), dissolved in Milli-Q water to prepare a 200 μM stock, aliquoted and stored at −20° C.

TABLE 1

| Name | Sequence |
|---|---|
| S1 | 5'-/5AzideN/ATC AAC ACT GCA CAC CAG ACA GCA-3' (SEQ ID NO: 01). |
| $S2^{PM}$ | 5'-/5Alexa488N/TGC TGT CTG GTG TGC AGT GTT GAT/3-CholTEG/-3' (SEQ ID NO: 02) |
| $S2^{TGN}$ | 5'-GGC TAT AGC ACA TGG GTA AAA CGA CTT TGC T/iAlexa647N/G TCT GGT GTG CAG TGT TGA T-3' (SEQ ID NO: 03) |

1400 W, PTIO, $E_2$, L-NAMF and DEA-NONOate were purchased from Carnan chemicals. All other chemicals were purchased from Sigma Aldrich. Stock solutions of Methylene blue and PTIO were prepared in DMSO (50 mM). Stock solution of $E_2$ was prepared in ethanol (10 mM), DEA-NONOate stocks were prepared in NaOH (10 mM, pH 9), and were all used within a week. For incubations lasting longer than 24 h, the aforementioned agonists or antagonists were replenished to the same concentration in new medium every 24 h. DsiRNA to knockdown NOS3 were purchased from IDT (hs.Ri.NOS3.13.1 and hs.Ri.NOS:3.13.2), NOS3 forward primer: AGC GGC TCC CAG GCC CAC GA (SEQ ID NO:22), reverse primer: CAG ACC TGC AGT CCC GGG CA (SEQ ID NO:23) and β-actin forward primer: CCT CGC CTT TGC CGA TCC (SEQ ID NO:24), reverse: primer: GAG TCC ATC ACG ATC CCA GT (SEQ ID NO:25).

Figure 10:
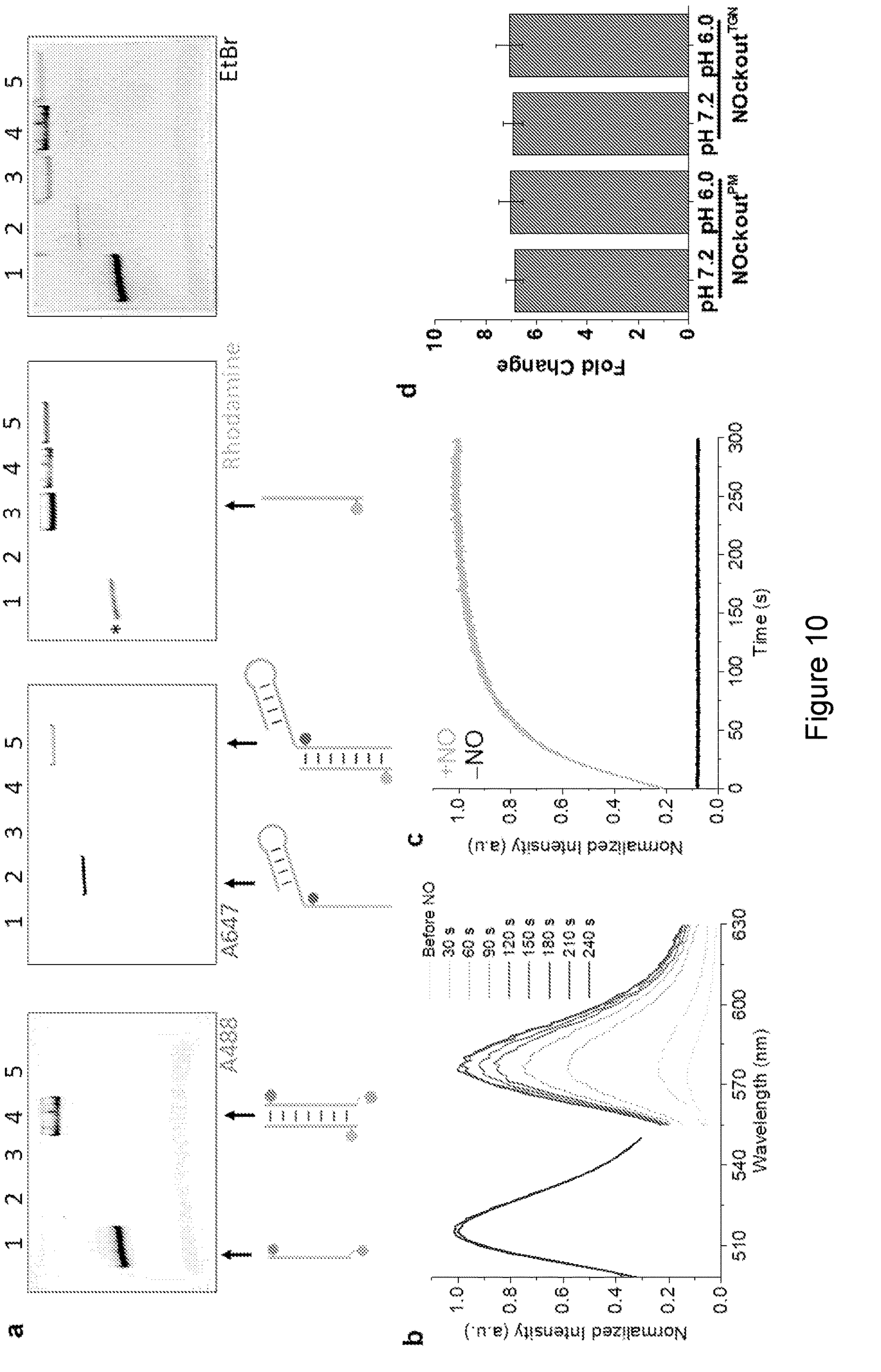
FIG. 10. Characterization of NOckout probes. (a) 15% PAGE showing integrity and purity of NOckout probes. Lane 1: S2$^{PM}$, Lane 2: S2$^{TGN}$, Lane 3: DAR-S1, Lane 4: NOckout$^{PM}$ and Lane 5: NOckout$^{TGN}$. (b) Fluorescence emission spectra of NOckout$^{PM}$ obtained after the addition of NO donor (DEA-NONOate, 50 µM, pH 7.2) and recorded at 30-second intervals for 3.5 minutes. DAR (λex=554 nm) and A488 (λex=488 min) are shown in green and blue, respectively. (c) Representative kinetic traces of DAR (λex=554 nm) upon addition of 50 µM DEA-NONOate (green) or DMSO (black). (4) Fold change in DAR/reference dye intensity ratios of NOckout variants upon treatment with DEA-NONOate at pH 6.0 and pH 7.4 corresponding to the pH of the TGN lumen and extracellular pH respectively. Error bars represent S.E.M. from three independent experiments.

In vitro fluorescence measurement. All fluorescence studies were carried out on a Fluoromax-4 (Horiba Scientific, Japan) spectrophotometer. A 10 μM stock of NOckout sensors was diluted to 100 nM final concentration with 100 mM sodium phosphate buffer, pH 6.0, unless mentioned otherwise. The emission spectra of DAR, A488 and A647 were acquired by exciting the sample at 550 nm, 488 nm and 650 nm respectively (FIG. 10). Emission spectra collection range of DAR, A488 and A647 were 560-620 nm, 495-540 nm and 655-700 nm respectively. DEA NONOate (Cayman, United States) was added to a final concentration of 50 μM. The sample was immediately put back to spectrometer and emission spectra of DAR was acquired every 30 seconds. A488 or A647 spectra were acquired before and 3.5 min after the addition of DEA NONOate. Emission intensity of DAR at either 571 ruin before $NO^-$ addition or 578 nm after NO addition (G) was normalized to the emission intensity of either A488 at 520 nm (B) or that of A647 at 660 nm (R). Fold Change in G/B or G/R ratio was calculated from the ratio of steady state G/B or G/R values after to before $NO^-$ addition. For pH sensitivity, stocks of NOckout sensors were diluted in 100 mM, pH 6.0 sodium phosphate butler or 100 mM, pH 7.4 sodium phosphate buffer prior to the experiment (FIG. 10). Fluorescence spectra were recorded before and 15 min after the addition of DEA NONOate as described above.

Cell culture. T-47D cells and MCF-7 cells were kind gifts from Prof. Geoffrey Greene (The Ben May Department for Cancer Research, The University of Chicago). Normal breast epithelial cells MCF-10A and 184A1 were a kind gift from Prof. Marsha Rosner (The Ben May Department for Cancer Research, The University of Chicago). Cells were grown according to manufacturer's protocol. Briefly, T-47D cells were grown in RPMI-1640 medium (Gibco, Life technologies) supplemented with 100 units/mL of Penicillin, 100 μg/mL of streptomycin (Life technologies), 10% final concentration of heat inactivated fetal bovine serum (Gibco, Life technologies) and 0.2 U/mL human recombinant insulin. MCF-7 cells were grown in DMEM supplemented with 100 units/mL of Penicillin, 100 μg/mL of streptomycin (Life technologies), 10% final concentration of heat inactivated fetal bovine serum (Gibco, Life technologies) and 0.01 mg/mL human recombinant insulin. MCF-10A and 184A1 cells were grown in MEBM+MEGM medium containing 0.005 mg/ML transferrin and 1 ng/mL cholera toxin. Cells were maintained at 37° C. in a humidified chamber at 5% $CO_2$ concentration. All the experiments were performed at early passage number (after receiving, n<17) and at 60% confluency.

Immunofluorescence staining. Cells were cultured on a glass bottom 3.5 cm imaging dish to reach 60% confluency. Cells were treated with NO scavengers (100 μM PTIO, 20 μM Methylene blue, 20 μM hemoglobin) or NOS2 blocker 1400 W (10 μM) or ROS scavenger TEMPOL (2 mM). Treated cells were then washed three times with 1× PBS (pH 7.4) and fixed using, 4% paraformaldehyde at room temperature (RT, 15 min). Subsequently, cells were permeabilized using 0.25% triton X-100 followed by blocking using 3% BSA in 1× PBS. Cells were then incubated with indicated primary antibodies—mouse monoclonal anti-eNOS antibody (SantaCruz Cat #sc-376751), Polyclonal Anti-S-nitrosocysteine antibody (Abeam Cat #ab94930 or Abeam Cat #ab50185), Rabbit polyclonal Anti-Giantin antibody (Abeam Cat #ab24586) or Mouse monoclonal Anti-GM130 antibody (BD Biosciences Cat #610822) in blocking buffer (3% BSA in 1× 4 PBS) for 1 hour at RT. Cells were then washed for 5 min with 1× PBS (3×). Respective secondary antibodies conjugated with either Alexafluor 488 or Alexafluor 647 were added to the cells and incubated for 1 hr at RT. Cells were washed again to remove excess secondary antibody using 1× PBS for 5 min (3×). Hoechst 33342 (5 μM) was added 10 min prior to imaging to stain nuclear DNA. Cells were then imaged on a Leica SP8 laser scanning confocal microscope using excitation wavelengths 405 nm (Hoechst), 488 nm (AlexaFluor 488) and 647 nm (AlexaFluor 647). Images were processed using Fiji and maximum z-projection of 2-3 z-planes are used in representative images.

Figure 1:
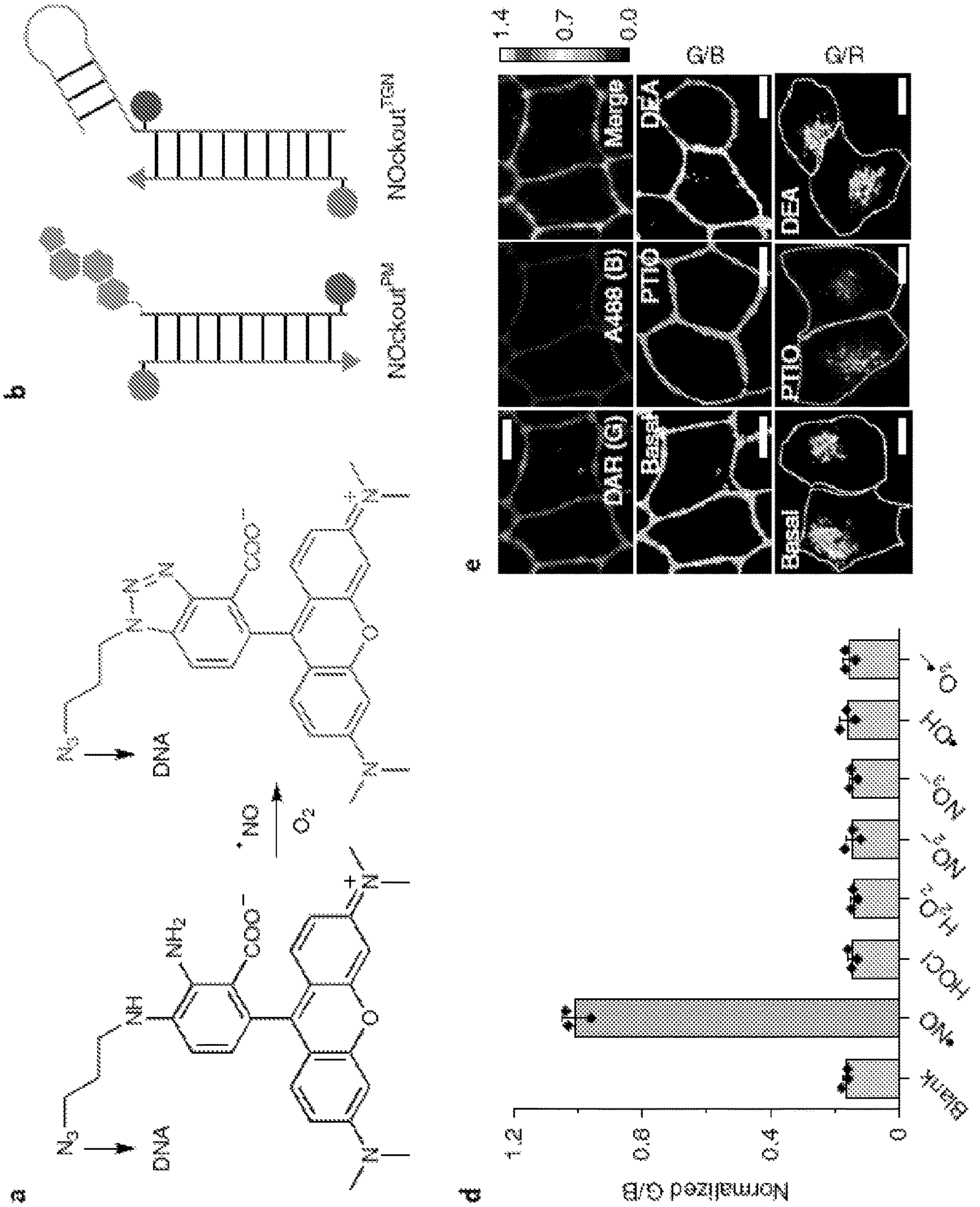
FIG. 1. NOckout reporters measure endogenous NO production at the plasma membrane and Golgi (a) Structure and mechanism by which DAR senses NO (b) Schematic showing design of two NOckout reporters, $NOckout^{PM}$ (plasma membrane targeting) and $NOckout^{TGN}$ (trans-Golgi network targeting). Green and blue circles in $NOckout^{PM}$ represent NO sensing fluorophore (DAR) and normalizing fluorophore (A488), respectively. In the case of $NOckout^{TGN}$, Alexa 647 (red) functions as the normalizing fluorophore. Cholesterol moiety (grey) attached to the the $NOckout^{PM}$ sensor targets it to the cell membrane and MUC1 aptamer (grey hairpin) engineered in $NOckout^{TGN}$ traffics it to the Golgi apparatus. (c) Schematic showing simultaneous targeting of NOckout reporters to the subcellular compartments of cancer cells. $NOckout^{PM}$ (blue cylinder) localizes to the plasma membrane using cholesterol as a bilayer anchor. $NOckout^{TNG}$ (red cylinder) upon binding with MUC1 protein (dark green crescent) traffics it to the trans-Golgi network ((TGV). (d) Sensitivity of $NOckout^{PM}$ towards various reactive oxygen species or towards NO metabolites reported as normalized G/B values, error bars represent standard error of mean (s.e.m) from three independent experiments. (e) $NOckout^{PM}$ and $NOckout^{TGN}$ detects endogenous NO production and modulations brought about by DEA (300 μM, NO donor), PTIO (300 μM, NO scavenger), or in untreated cells (Basal) at the plasma membrane or at the Golgi of T-47D cells. DAR, A488 and A647 channels are shown in green (G), blue (B) and Red (R) respectively, G/B and G/R ratios are shown in pseudo-color. Representative images are shown from total of three independent experiments (f) Bar graphs showing the quantification of normalized G/B ($NOckout^{PM}$) or G/R ($NOckout^{TGN}$) ratios across six treatments (PTIO, DEA-NONOate, L-NAME, basal, ATP and $E_2$), error bars represent standard error of mean (s.e.m) from three independent experiments, n≥35.
Figure 1:
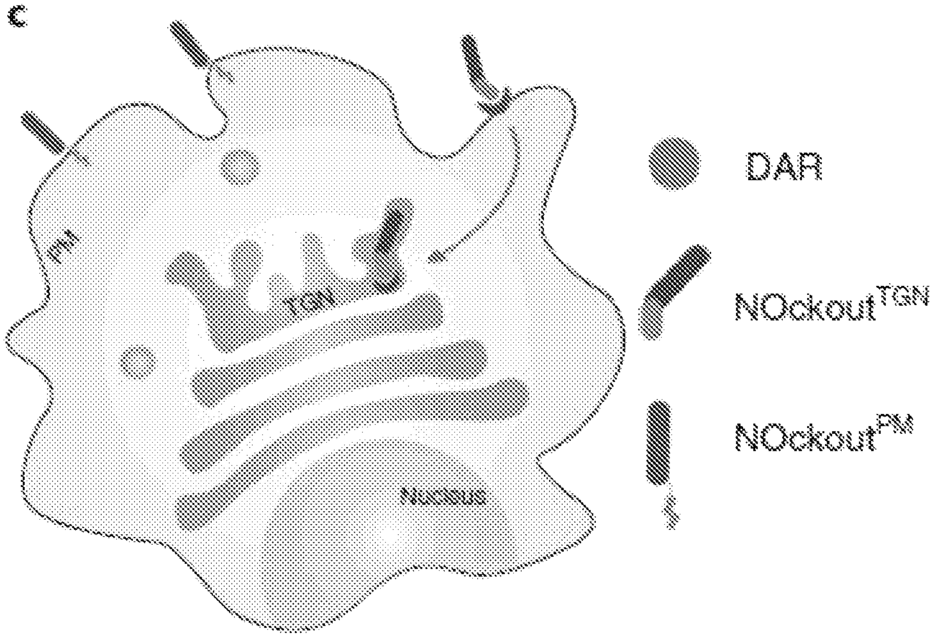
Figure 1:
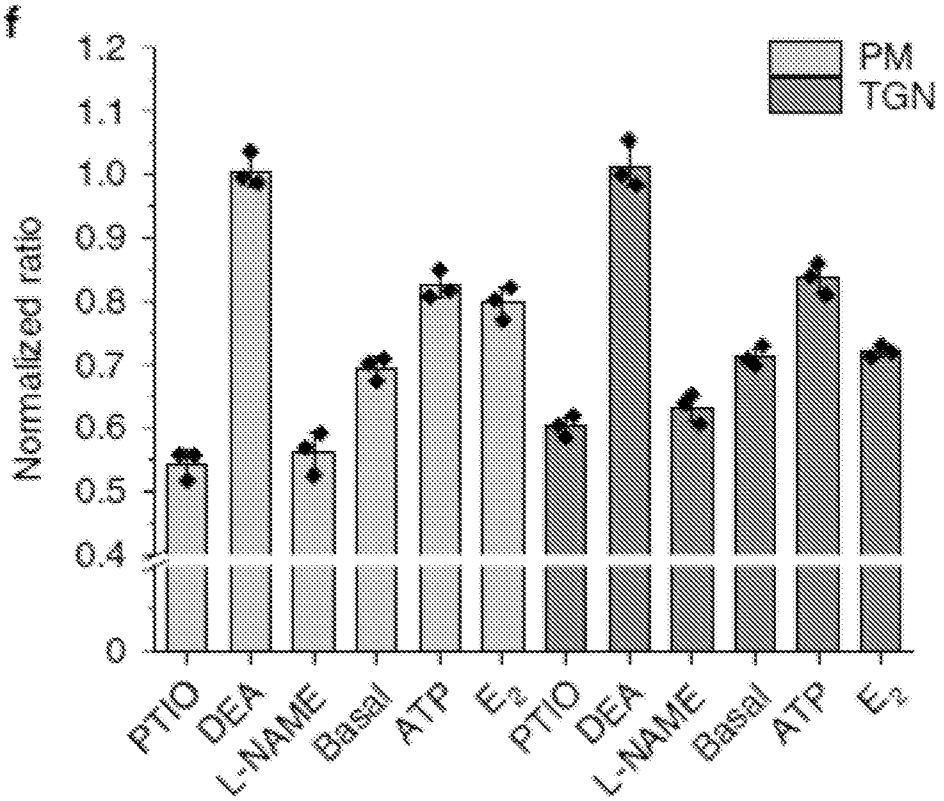

Image acquisition. T-47D cells were maintained as mentioned above in the cell culture section. Cells were washed twice with Hank's balanced salt solution (HBSS) before incubating them with 500 nM $NOckout^{TGN}$ for 30 min or 500 nM $NOckout^{PM}$ for 10 min at 37° C. followed by 3 washes with HBSS solution to remove any unloaded sensors. For steady state imaging (FIG. 1), cells were treated with indicated agonists or antagonists for 1 hr in complete RPMI-1640 medium. Care was taken not to exceed the final concentration of DMSO>1% at any time of the experiment. Additionally, 1% DMSO was used as a negative control in untreated (Basal) cells. Since DEA-NONOate is a cell impermeable NO donor, it was straightforward to add it to the cells and fully turn on NOckout$^{PM}$ at the plasma membrane. For the TGN, the NOckout$^{TGN}$ with DEA-NONOate is incubated in solution to fully turn it on, and then pulse cells with the turned-on NOckoutTGN (500 μM). The cells are then washed and imaged (FIG. 1*f*).

For simultaneous imaging cells were treated with 500 nM NOckout$^{TGN}$ for 30 min where last 10 min cells were co-incubated with 500 nM NOckout$^{PM}$. In order to achieve lowest signal (PTIO, FIG. 1*e-f*) or to achieve bleaching profile (PTIO, FIG. 3*e*) cells were pre-treated with 500 μM PTIO for 15 minutes. Images were captured on a Laser scanning confocal Leica SP8 microscope using 63×, 1.4UV NA objective. Desired excitation and emission wavelengths was achieved using white light laser along with notch filters and acousto-optical tunable filters. A488, DAR and A647 were imaged using the following settings—Alexa488 ($\lambda_{ex}$=488 nm, $\lambda_{em}$=500 nm to 540 nm), DAR ($\lambda_{ex}$=554 nm, $\lambda_{em}$=565 nm to 610 nm) and Alexa647 ($\lambda_{ex}$=647 nm, $\lambda_{em}$=665 nm to 710 nm).

Figure 2:
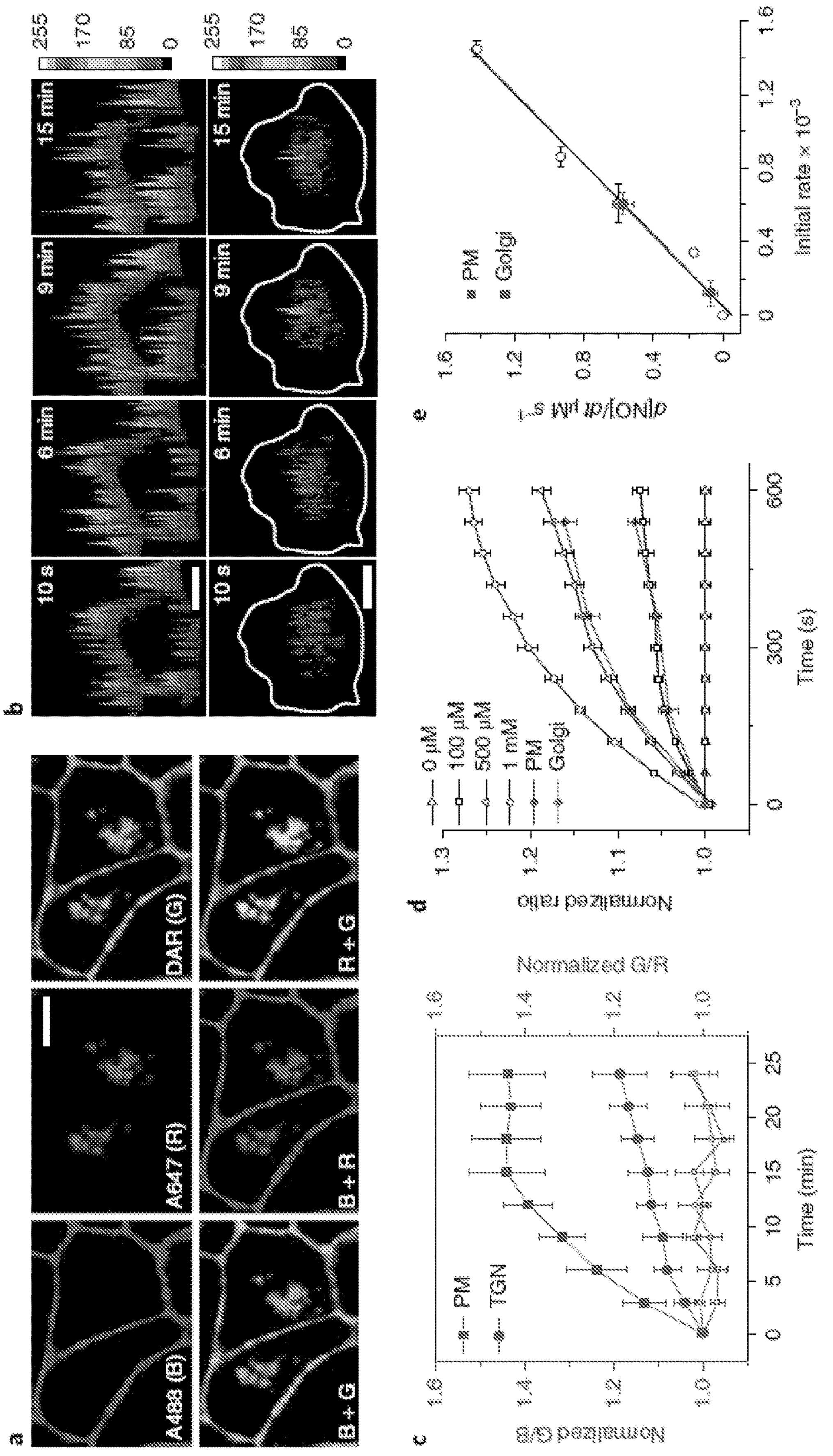
FIG. 2. Simultaneous, quantitative NO imaging from two distinct subcellular locations (a) Simultaneous pulsing of $NOckout^{PM}$ (500 nM) and $NOckout^{TGN}$ (500 nM) on T-47D cells results in robust labeling of both plasma membrane and Golgi apparatus of the same cell. Representative images are shown from total of three independent experiments. (b) $NOckout^{PM}$ and $NOckout^{TGN}$ reports subcellular simultaneous NO dynamics upon stimulation with thapsigargin (1 μM) in T-47D cells. Single confocal plane images were taken every 3 min for 24 min. NO signals are calculated as ratio between DAR to A488 (in the case of $NOckout^{PM}$) and DAR to A647 (in the case of $NOckout^{TGN}$) to represent as surface plots using Fiji. Representative images are shown from total of three independent experiments. (c) Kinetic traces of NO production from two distinct sub-cellular locations in live T-47D cells. Simultaneous NO signals from $NOckout^{PM}$ and $NOckout^{TGN}$ are monitored as a function of time from single cells, post thapsigargin treatment (filled squares and circles) or upon PTIO treatment (empty squares and circles). Average intensities are plotted as ratios of DAR/A488 (G/B, $NOckout^{PM}$) and DAR/A647 (G/R, $NOckout^{TGN}$) for n=10 cells, error bars represent standard error of mean (s.e.m) from three independent experiments. (d) In-cellulo kinetic traces showing G/B signal from $NOckout^{PM}$ containing cells upon treatment with indicated concentrations of DEA-NONOate, overlayed with $NOckout^{PM}$ and $NOckout^{TGN}$ traces from (c) (e) In-vitro (d[NO]/dt) vs. in-cellulo (initial rate×$10^{-3}$) graph overlaid with initial rates for thapsigargin (1 μM) treated plasma membrane (green filled square) and Golgi (red filled square) calculated from (FIG. 17). Error bars represent standard error of mean (s.e.m) from three independent experiments.

Image analysis. Image analysis was performed using Fiji (Schindelin, J. et al. Fiji: an open-source platform for biological-image analysis. *Nat Methods* 9, 676-682 (2012)). Auto-fluorescence was subtracted from images for ratiometric analysis. For representation, images were further processed by smooth and despeckle functions. In order to present G/B or G/R images, a mask for each image was constructed using Otsu thresholding method, and mask-multiplied images were used for division. The ROI plugin in Fiji was used to select either TGN (Alexa647 channel) or PM (Alexa488 channel) and these ROIs were recalled in DAR channel to measure intensity in all three channels. These raw values were used to plot G/B or G/R values in FIGS. 1 and 2.

Surface plots shown in FIG. 2*a* were plotted using Fiji plugin Surface plotter. 2D images of the same cells in G/B and G/R format were processed using the following command—Analyze>Surface plot. Indicated time point images were acquired from Fiji and are shown in FIG. 2*a*.

Golgi fragmentation was quantified with immunofluorescence images of Golgi structural protein Giantin. Merge images of Hoechst and Giantin allowed identification of cell numbers and enumeration of Golgi fragments per cell (≤3 Golgi fragments per cell was considered intact Golgi) (Lee, J. E. et al. Dependence of Golgi apparatus integrity on nitric oxide in vascular cells: implications in pulmonary arterial hypertension. *Am. J. Physiol. Heart Circ. Physiol.* 300, H1141-58 (2011)).

Sub-cellular nitric oxide quantification. DEA NONOate is a pH dependent small molecule NO donor with half-life about 9 min at pH 7.4 at 25° C. (FIG. 16). The mode of NO release from DEA NONOate is described by following equation:

$$\text{DEA NONOate} \leftrightharpoons 2\text{NO*} + \text{DEA} \qquad \text{(Reaction 1)}$$

Each DEA NONOate molecule releases 1.5 molecules of NO effectively. (C. Maragos et al. 1992) On the other hand, lifetime of NO radical in aerobic solution depends on its reaction with $O_2$, which is the first and rate limiting step of various reactive nitrogen species (RNS) generation (see Namin, S. M., Nofallah, S., Joshi, M. S., Kavallieratos, K. & Tsoukias, N. M. Kinetic analysis of DAF-FM activation by NO: toward calibration of a NO-sensitive fluorescent dye. *Nitric Oxide* 28, 39-46 (2013)).

$$2\text{NO*} + O_2 \leftrightharpoons 2NO_2 \qquad \text{(Reaction 2)}$$

From equation 1 and 2, rate of NO generation in DEA NONOate solution can be calculated:

$$\frac{d[\text{NO}]}{dt} = 1.5k_1[\text{NONO}ate] - 4k_2[\text{NO}]^2[O_2] \qquad \text{(Equation 1)}$$

Where $k_1=1.31\times10^{-3}\ s^{-1}$ (calculated from FIG. 16*a*) and $k_2=2.1\times10^6 M^{-1}s^{-1}$ are forward rate constant for equation 1 and 2 respectively. Additionally, DEA-NONOate concentration follows first order decay and can be described with initial DEA-NONOate concentration (indicated by $[\text{NONOate}]_0$).

$$\frac{d[\text{NO}]}{dt} = 1.5k_1e^{-k_1t}[\text{NONO}ate]_0 - 4k_2[\text{NO}]^2[O_2] \qquad \text{(Equation 2)}$$

By solving the differential equation 2 numerically predicted time dependent traces of NO concentration given an initial NONOate concentration (FIG. 16*b*) can be obtained (see Ramamurthi, A. & Lewis, R. S. Measurement and modeling of nitric oxide release rates for nitric oxide donors. *Chem. Res. Toxicol.* 10, 408-413 (1997)).

After characterizing NO releasing profile of DEA NONOate, cellular NO production was compared to NO released from DEA-NONOate. To obtain a calibration curve, NOckout$^{PM}$ labeled T47D cells was treated with a range of DEA NONOate concentrations in 100 mM pH 7.4 phosphate buffer at room temperature. As expected G/B intensity increases over time and the rate of increase is proportional to DEA-NONOate concentration. Then 1 μM thapsigargin was added to get the initial rate of NO production at the plasma membrane.

The following assumptions were made to directly relate rate of increase FIG. 16*b* to FIG. 16*c*: First, G/B is proportional to concentration of turned on triazole form of [DAR, MAR-T]. Second, it is considered that DAR reacts with a reactive intermediate of NO oxidation. ($N_2O_3$ or in Kojima, 2001, $NO_2$ as in Namin 2013) (Kojima, H. et al. Bioimaging of nitric oxide with fluorescent indicators based on the rhodamine chromophore. *Anal. Chem.* 73, 1967-1973 (2001); Namin, S. M., Nofallah, S., Joshi, M. S., Kavallieratos, K. & Tsoukias, N. M. Kinetic analysis of DAF-FM activation by NO: toward calibration of a NO-sensitive fluorescent dye. *Nitric Oxide* 28, 39-46 (2013)). Although the exact reaction mechanism of DAR-T formation is still debatable, this reactive intermediate $NO_x$ will have much lower concentration than NO in solution and pseudo steady state approximation can be applied to this reactive intermediate (Lewis, R. S. & Deer, W. M. Kinetics of the reaction of nitric oxide with oxygen in aqueous solutions. *Chem. Res. Toxicol.* 7, 568-574 (1994)). And this steady state concentration $[NO_x]_s$ will be proportional to [NO] such that:

$$\frac{d[DAR-T]}{dt} \propto \frac{d[\text{NO}]}{dt} \qquad \text{(Equation 3)}$$

Note this only applies to the initial phase of DAR activation where [DAR] can be considered as constant. From the predicted [NO] from DEA-NONOate, the tested concentration of NONOate, the first 30 s [NO] increases with t. The average slope is taken for first 30 s of the predicted [NO] curve as initial d[NO]/dt. In the in-cellulo experiment, an image is taken every minute and the slope is taken of the first minute after NONOate addition as initial rate of G/B increase. As FIG. 16*d* shows that the slope of first minute almost equal to slope of first 30 s. For every $[NONOate]_0$ initial rate of d[NO]/dt from predicted [NO] curve is plotted against initial rate of G/B from in vitro cell experiment, generating a linear fit with $R^2$=0.97, confirming the approximation of equation 3. This is the calibration curve that allows for measurement of NO produced by NOS3.

Figure 3:
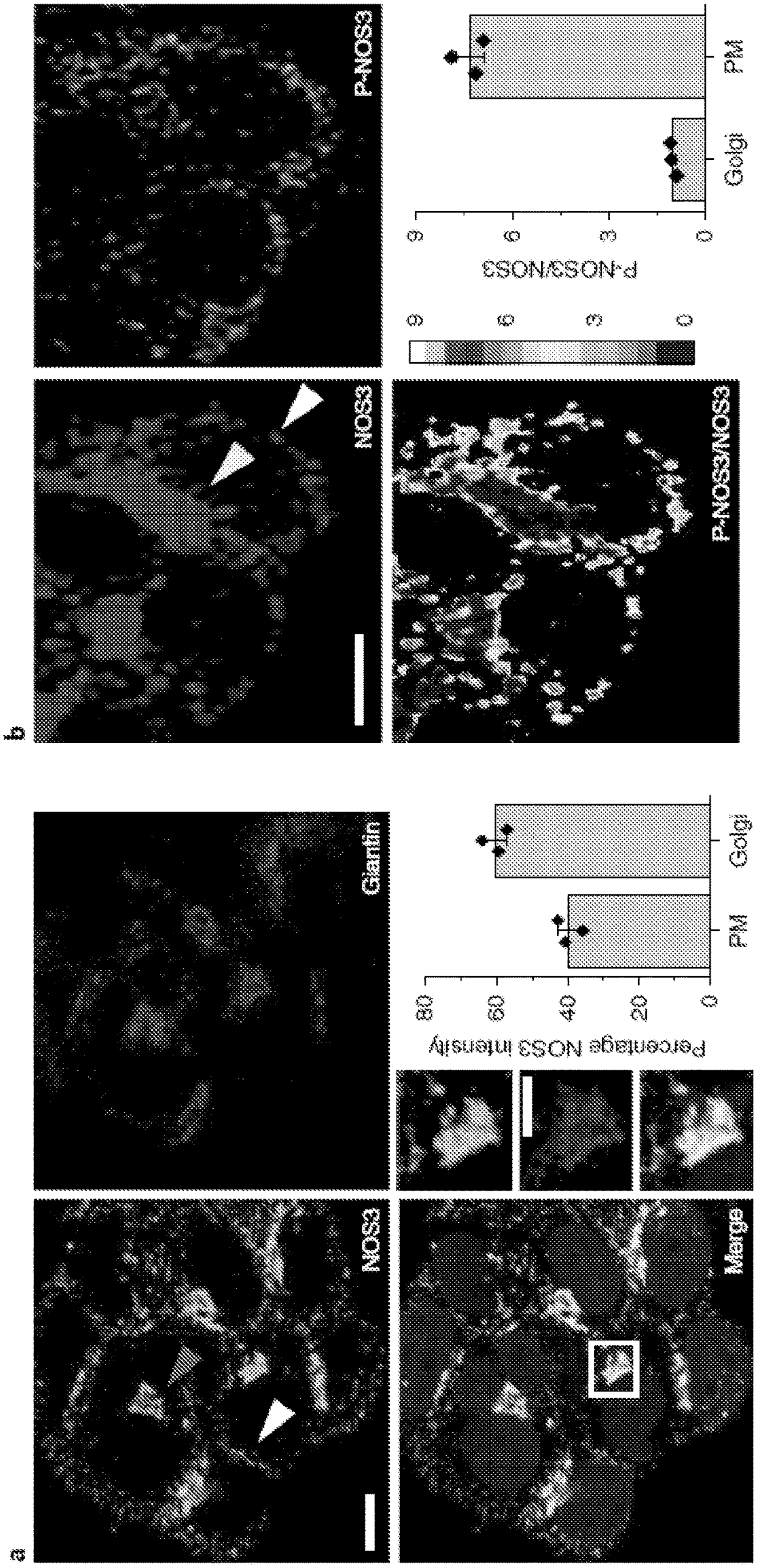
FIG. 3. Phosphorylated NOS3 is enriched at the plasma membrane. (a) Co-localization of NOS3 (green) with the Golgi marker protein Giantin (red) in T-47D cells. Inset shows merged images in higher magnification. White and maroon arrowhead represents NOS3 population at the plasma membrane and at the Golgi, respectively. Also, Bar graphs showing percentage of NOS3 located at PM and at Golgi apparatus in T-47D cells. Error bars represent standard error of mean (s.e.m) from three independent experiments, n=50 cells, Scale bar=10 μm (b) Representative images of T-47D cells immunostained with NOS-3 and P-NOS3 antibodies, pseudo colored P-NOS-3/NOS3 image shows the extent of phosphorylation where white and yellow arrowheads represent NOS3 population at the plasma membrane and at the Golgi respectively, quantification of the same is shown in the bar graph format. Error bars represent standard error of mean (s.e.m) from three independent experiments, n=30 cells. Scale bar=10 μm.
Figure 7:
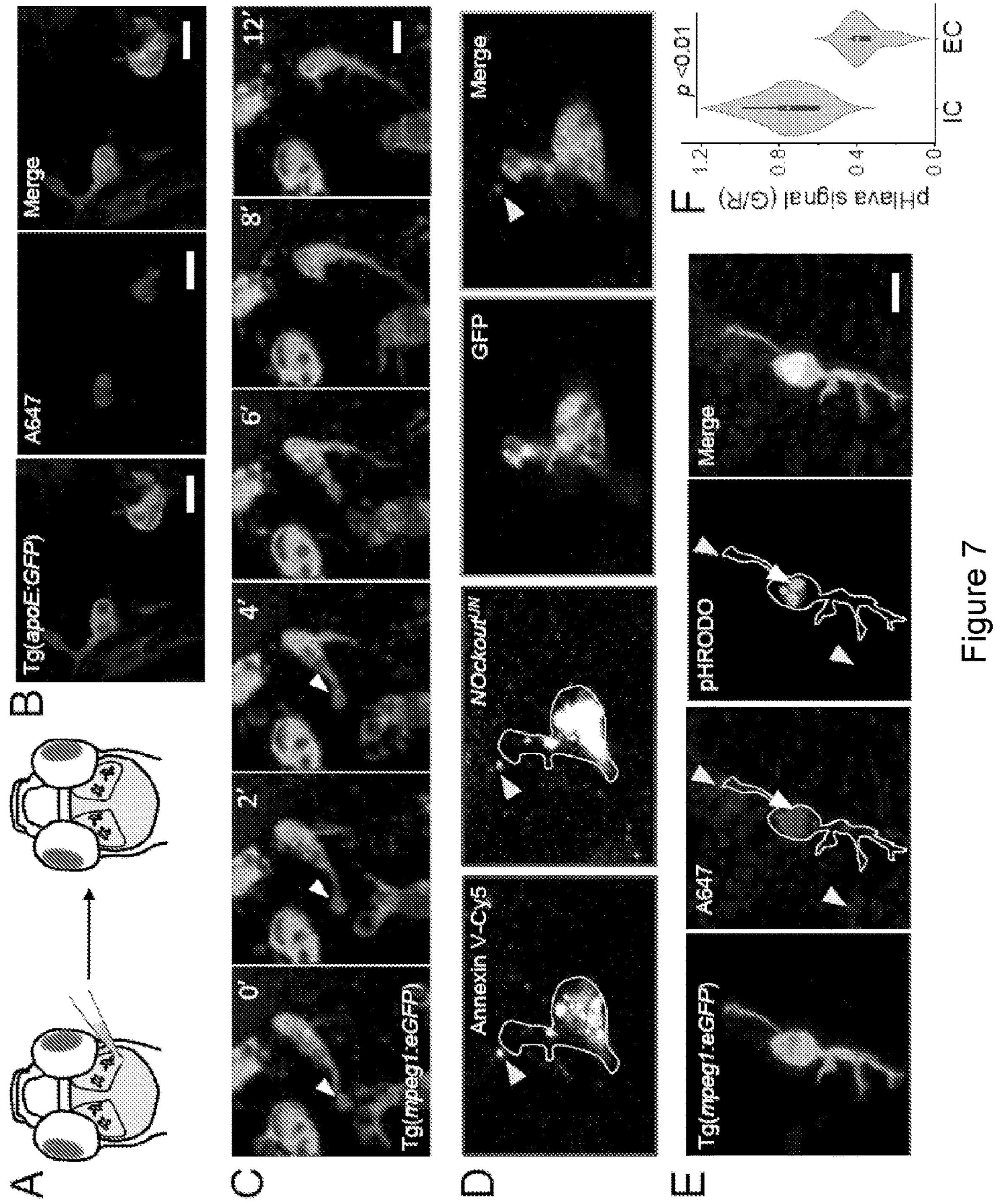
FIG. 7. NOckout$^{UN}$ localizes in phagosomes of zebrafish microglia in vivo: (a) Schematic of the larval transgenic zebrafish brain expressing GFP in microglia (Tg(apoE: GFP)). NOckout$^{UN}$ (0.2 pmoles in HBSS) was microinjected in the optic tectum of 3 dpf old fish. (b) Images acquired 1 h post injection of NOckout$^{UN}$ (0.2 pmoles in HBSS) shows probe localization in phagosomes of microglia Tg(apoE: GFP) fish. (c) Time-lapse images (0-12 min) shows NOckout$^{UN}$ uptake by microglia. Fusion of newly formed phagosomes with existing phagosomes are also observed (white arrowhead). (d) Colocalization of NOckout$^{UN}$ with apoptotic body marker AnnexinV-Cy5 prior to phagocytosis by microglia (yellow arrowhead). (e) Representative images of pHlava injected in Tg(mpeg1:eGFP) fish shows strong signal in phagosomes (white arrowhead) in the pHrodo channel ($\lambda_{em}$=570 nm), while extracellular puncta show no signal indicating high and low acidities respectively. (f) pHlava signal from the phagosomes (IC) and the extracellular milieu (EC) are plotted as the ratio of pHrodo to A647 channel intensities (n=16 phagosomes from n=8 fish). All experiments were performed in triplicate. Scale bar: 10 µm. P values are obtained using Kruskal-Wallis statistical test.

Using the calibration curve, the initial G/B rates from thapsigargin treated cells is plugged in and the plasma membrane NO production was measured to be 576±61 nM/s (FIG. 3*e*). In order to measure NO production at the Golgi and to compare it to the plasms membrane two important control experiments were performed: (i) Prove that the DAR reaction kinetics to form fluorescent DAR-T is pH independent: Since $NOckout^{PM}$ and $NOckout^{TGN}$ sees pH units of 7.4 and 6 respectively, the kinetics of DAR reactivity was checked using pH insensitive NO donor S-Nitroso-N-acetyl-DL-penicillamine (SNAP, 1 mM) (Roy, 1994) (FIG. 7*e*). It was found that the DAR shows same reaction kinetics in the pH range tested and (ii) Prove that photo-physical properties of the normalizing dye (A647 for $NOckout^{PM}$ and A488 $NOckout^{TGN}$) doesn't alter ratiometric signal of NOckout devices. To do this, $NOckout^{PM}$ with either A488 as normalizing dye or A647 as normalizing dye were created and measured their kinetics on the plasma membrane of T-47D cells upon treatment with 500 μM of DEA NONOate. It was found that the signal increase for $NOckout^{PM\text{-}A488}$ or $NOckout^{PM\text{-}A647}$ is the same and did not not change upon changing., the normalizing fluorophore (FIG. 16*f*). After ruling out these two factors, the initial rate from Golgi ($NOckout^{PM}$ containing T-47D cells treated with 1 μM thapsigargin) was plugged in and it was found that the NO production was 74±41 nM/s.

In vitro specificity of NOckout. Fluorescence measurements in vitro were performed as mentioned above. Aqueous solution of DEA NONOate (Cayman, United States) was added to a final concentration of 50 μM. Aqueous $H_2O_2$ solution was used as $H_2O_2$ donor and concentration of $H_2O_2$ was quantified using ε=43.6 $M^{-1}$ $cm^{-1}$ at 240 nm. Xanthine/Xanthine oxidase was used for superoxide generation, which was quantified using Cytochrome C reduction (Brandes, R. P. & Janiszewski, M. Direct detection of reactive oxygen species ex vivo. *Kidney Int.* 67, 1662-1664 (2005)). Fenton chemistry was used for the generation of hydroxyl radical (*OH) (Duarte, A. J. & da Silva, J. C. G. E. Reduced fluoresceinamine as a fluorescent sensor for nitric oxide. *Sensors* (*Basel*) 10, 1661-1669 (2010)). Aqueous solutions of $NO_2^-$ and $NO_3^-$ were prepared from their respective sodium salts.

ROS/RNS generators were added to 100 nM of NOckout in pH 6.0 100 mM sodium phosphate buffer, to a final concentration of 100 μM each of $H_2O_2$, ·OH, $O_2^{\cdot-}$, $NO_2^-$ and $NO_3^-$. 10 μM NaOCl was added to generate 10 μM HOCl. Samples were incubated for 15 minutes at 37° C. and fluorescence spectra were recorded in A488 and DAR channels. Fold change of G/B in each case was normalized to that of NOckout with DEA NONOate.

Intracellular Calcium Imaging. T-47D cells were maintained as described above. Fluo-4, AM was purchased from Invitrogen (ThermoFisher, #F-14201) and 1 mM stock solutions were made in dry DMSO. For efficient intracellular loading of the probe, cells were washed three times with HBSS (pH 7.4), followed by incubation with 10 μM Fluo-4, AM in HBSS for 40 minutes. Subsequently, cells were washed with HBSS 3 times and treated with Thapsigargin (100 mM) or 17-β-Estradiol (300 nM) (FIG. 14) in HBSS. Time-lapse fluorescence imaging was done on Olympus IX81 wide-field microscope using 40× oil objective. FITC/GFP filter cube with 450-490 nm excitation filter and 515-586 nm emission filter were used for acquiring images. Images were recorded for 300 s with 5 s of time delay between frames. Kinetic analysis was performed on SlideBook software.

Apoptosis detection assay. Cells were treated with either DMSO or NO scavenger PTIO for 48 hours before staining for apoptotic cells with Annexin V-Cy5 (Biovision 1013-200) as per manufacturer's protocol. Briefly, T-47D cells cultured under indicated treatments were washed twice with HBSS before incubating them with 1× Annexin V binding buffer for 5 minutes. 1 of Annexin V-Cy5 was added on to the cells and imaging dishes were incubated for 5 minutes in dark. Cells were trashed three times with HBSS before image acquisition.

Cell senescence assay. Cells were treated with either DMSO or NO scavenger PTIO (200 μM) for 48 hours were stained for senescence associated β-galactosidase (SA-b-Gal) activity (see Debacq-Chainiaux, F., Erusalimsky, J. D., Campisi, J. & Toussaint, O. Protocols to detect senescence-associated beta-galactosidase (SA-betagal) activity, a biomarker of senescent cells in culture and in vivo. *Nat. Protoc.* 4, 1798-1806 (2009)). Briefly, sub confluent cells were washed twice with HBSS for 30 s per wash. Cells were fixed in 4% para formaldehyde solution for 4 min and washed twice with HBSS. Cells were incubated with staining solution (40 mM citric acid/Na phosphate buffer, 5 nM $K_4[Fe(CN)_6]$ $3H_2O$, 5 mM $K_3[Fe(CN)_6]$, 150 mM sodium chloride, 2 mM magnesium chloride and 1 mg/ml X-gal in distilled water) for 16 hours at 37° C. Cells were washed three times with HBSS before image acquisition.

Part 2 (DNA nanodevices for mapping nitric oxide in the living brain) (Examples 7-11)

Reagents: All functionalized DNA oligonucleotides were purchased from Integrated DNA Technologies (IDT) as a lyophilized powder. Oligonucleotides were dissolved in milli-Q water and quantified using a UV-Vis spectrophotometer (Shimadzu UV-3600, Japan) and subsequently stored in a refrigerator at −20° C. Immunostimulatory ATTO647N labeled DNA and RNA containing phosphorothioate backbone were custom synthesized by IDT. All the chemicals used for the synthesis of DAR-$N_3$ were purchased from Acros Organics (USA) and Sigma (USA). Nitric oxide donor (DEANONOate), NOS2 inhibitor (1400 W), NADPH-oxidase inhibitor (VAS2870), Myeloperoxidase inhibitor (ABAH) and V-ATPase inhibitor (Bafilomycin A1) was purchased from Cayman Chemicals (USA). Diamino polyethylene glycol linker (10 kDa) was purchased from Creative PEGWorks (USA). Annexin V-Cy5 apoptosis kit was purchased from BioVision (Cat No: K103) and pHrodo maleimide was purchased from Thermo Fisher Scientific (Cat. No: P35371). NOS2 antibody was obtained from Novus Biologicals (NB300-605). LAMP1 antibody was obtained from Abeam (ab62562). Morpholino sequences were purchased from Gene Tools (USA). DAR-$N_3$ was synthesized as known in the art.

Image acquisition: Wide field microscopy was carried out on an IX83 inverted microscope (Olympus Corporation of the Americas, Center Valley, PA, USA) using either a 100× or 60×, 1.4 NA, DIC oil immersion objective (PLAPON, Olympus) equipped with an Evolve Delta 512 EMCCD camera (Photometrics, USA). Filter wheel, shutter and CCD camera were controlled using MetaMorph software (Molecular Devices, USA). For NOckout stability assay J774A.1 cells were excited simultaneously in the DAR (546 nm) and A647N (650 nm) channels. Volume images were maximum intensity projected to calculate whole cell intensities from individual channels. Images were background subtracted using intensities from a cell-flee area in respective Channels.

Confocal images from1774A.1 cells and primary microglia were captured with a. Leica TCS SP5 II STED laser scanning confocal microscope (Leica Microsystems, Inc. Buffalo Grove, IL, USA) equipped with a 63×, 1.4 NA, Oil immersion objective. DAR was excited using a diode-pumped solid-state laser with 561 nm wavelength. A647N was excited using a He—Ne laser with 633 nm wavelength. Acousto-Optical Beam Splitter (AOBS) with settings suitable for each fluorophore and recorded using hybrid detectors (HyD).

Zebrafish brain was imaged in the optic tectum using an upright Zeiss LSM-710 confocal microscope equipped with water immersion objectives (20×, or 40×). Zebrafish larvae (3-4 dpf were mounted dorsally in a 1.5% low-melting point agar-bed on a confocal imaging dish (3.5 cm glass bottom). E3-containing 0.003% MS-222 was present in the imaging dish though out the imaging section. For NOckout injected samples, images were acquired simultaneously in GFP, DAR, and A647N channels using excitation wavelengths 488 nm, 560 nm and 645 nm from Argon-ion (488 nm), Helium-Neon (543 nm & 632 nm) laser sources respectively. pHrodo was imaged using the same settings as that of DAR.

Image analysis: A MATLAB based program called Findosome was used to calculate the (G/R) values of individual endosomes from the acquired images. Maximum Z-projected images created using Fiji (NIH) were fed to Findosome to pick endosomal compartments as ROI corresponding to individual endosomes based on the A647 channel intensity. For each ROI, the program calculates fluorescence intensities both in the normalizing channel (A647, R) as well as in the DAR (G) channel. The results were exported as an excel file. From the results, (G/R) value for individual endosomes can be calculated. Phagosomal (G/R) values from the zebrafish microglia are calculated using Fiji software. Images were imported to Fiji and maximum Z-projected images were created. ROI were manually drawn around clearly identifiable phagosomes using the normalizing channel A647 intensity. Fluorescence intensities in A647 and DAR channels were calculated. G/R values are either represented as heat map images using Fiji or as bar graph using Origin software. Intracellular measurements of (G/R) values was performed in GFP colocalized microglia. For (G/R) ratio quantification experiments, only those vesicles that are present in both green (G) and red (R) channels were considered. This was because the cell had ~2 to 5% of vesilves that were highly autofluorescent in the green channel This percentage can be estimated by labeling cells with a dsDNA carrying only an Atto647N label. Autofluorescent vesicles can be identified as puncta in the green channel (in such samples) that do riot show up in the red chapel and typically correspond to <5%. Therefore, the autofluorescent vesicles were identified and removed during our analysis.

Cell culture protocol: J774A.1 cells were cultured in Dulbecco's Modified Eagle's Medium (Gibco, USA, 11960044) with 10% Fetal bovine serum (Gibco, USA, 26140079) containing 100 U/mL penicillin and 100 μg/mL streptomycin and maintained at 37° C. under 5% $CO_2$. For all the experiments cells passage number less than thirty was employed.

Adult microglia isolation protocol: Adult microglia were isolated from 7-week C5BL/6 female mice as described previously with few modifications (Underhill, D. M. & Ozinsky, A. Phagocytosis of microbes: complexity in action. *Annu. Rev. Immunol.* 20, 825-852 (2002); Dupré-Crochet, S., Erard, M. & Nüße, O. ROS production in phagocytes: why, when, and where? *J. Leukoc. Biol.* 94, 657-670 (2013)). Briefly, after perfusion with ice-cold HBBS, brains were dissected and subjected to mechanical digestion by homogenization in HBBS, to prepare single cell suspension. Tissue debris were removed by passing the cell suspension through a 40 μm cell strainer. The brain cell suspension was re-suspended in 37% isotonic Percoll and underlayed with 70% Percoll. This was followed by overlaying of 30% Percoll and HBBS before centrifugation at 600 g for 30 min at 4° C. The top myelin layer was removed and the cells at the interface of 70/30 were collected and washed thrice with HBBS and pelleted at 300 g. The cells were counted and approximately 4000 cells were seeded in 35 mm cell culture dishes in RPMI media without FBS and used for microglial experiment with NOckout sensors.

Neonatal primary microglia isolation: Mouse primary mixed cortical and hippocampal glial culture were isolated and cultured as described previously (Wink, D. A. et al. Nitric oxide and redox mechanisms in the immune response. *J. Leukoc. Biol.* 89, 873-891 (2011)). Briefly, brains from postnatal day 1-2 C57BL/6 mice were isolated. After removing of striatum and meninges, the remaining cortical and hippocampal tissue was mechanically dissociated and enzymatically digested in trypsin (Gibco, USA, 59418C) and DNAse-I (10 mg/mL, Sigma, USA, D5025) in HBSS for 30 minutes at 37° C. 1:1 (v/v) Dulbecco's modified Eagle's medium (DMEM, Gibco, USA, 11965092) with 10% fetal bovine serum (FBS, Gibco USA, 26140079) was added to terminate digestion. Tissue was harvested by centrifugation and plated at a density of $5\times10^5$ cells/mL in T-75 $cm^2$ tissue culture flasks. Media was changed the next day and every 3 days until a cellular monolayer had formed after 2 weeks.

Microglia cells were isolated from mixed glial culture after overnight serum-starvation using mild trypsinization as previously described (Takeuchi, O. & Akira, S. Pattern recognition receptors and inflammation. *Cell* 140, 805-820 (2010). Media was removed from established mixed glial culture. Cell monolayers were washed with Dulbecco's phosphate buffered saline (DPBS, Gibco, USA, 14040133) to remove residual FBS. Trypsin-EDTA (Gibco, USA, 25200056) diluted 1:4 (v/v) in DMEM was added for mid trypsinization for 45 minutes at 37° C. Detached astrocytic cells were removed and adherent microglia was washed with DPBS followed by supplement of DMEM containing 10% FBS. Isolated microglia cultures were sequentially serum-starved from 10% to 5% to 2.5% to 0% FBS concentration via daily media changes. Purity of microglia cultures was assessed before experiments (FIG. 40).

Immunocytochemistry: Primary microglia cells were treated with 1 μM NOckout 1826 CpG/GpC for 3 hours. Cells were then washed three times with 1× PBS (pH 7.4) and fixed using 2.5% paraformaldehyde at room temperature for 15 min. The cells were subsequently washed 3 times with 1× PBS and followed by incubation with 3% bovine serum albumin (BSA) for blocking in PBS (1×) for 1 hour at room temperature. Then the cells were incubated with anti-mouse NOS2 antibody (Novus, NB300-605, 1:30 dilution) in blocking solution (3% BSA in PBS) for 1 hour at room temperature. To remove excess primary antibody cells were washed three times with 1× PBS. Cells were then treated with Alexa Fluor 488 conjugated goat anti-rabbit secondary antibody (Invitrogen, a11008, 1:2000 dilution) for 1 hour followed by three washes with 1× PBS. Cells were incubated with Hoechst 33342 (5 μM) for 10 minutes to stain the nucleus. Cells were imaged on a confocal microscope as described elsewhere. LPS (1 μg/mL) treated J774A.1 cells (for 12 h) were immunostained for NOS2 using a similar protocol as described above for the microglial cells. (FIGS. 41 and 42)

Pharmacological inhibition: Pharmacological inhibition of different enzymes were performed by employing known inhibitors. NOS2 inhibition was achieved using a specific and irreversible inhibitor, 1400 W (10 μM) ($K_1$ value against NOS2 is 7 nM) (Mogensen, T. H. Pathogen recognition and inflammatory signaling in innate immune defenses. *Clin. Microbiol. Rev.* 22. 240-73, Table of Contents (2009)). ROS produced in J774A.1 cells by NADPH-oxidase was inhibited by using a selective inhibitor VAS2870 (10 μM) (West, A. P., Koblansky, A. A. & Ghosh, S. Recognition and signaling by toll-like receptors. *Annu. Rev. Cell Dev. Biol.* 22, 409-437 (2006)). Myeloperoxidase activity to produce HOCl was blocked by using 4-aminobenzoic acid hydrazide (ABAH, 50 μM) (Li, Y., Li, Y., Cao, X., Jin, X. &. Jin, T. Pattern recognition receptors in zebrafish provide functional and evolutionary insight into innate immune signaling pathways. *Cell Mol Immunol* 14, 80-89 (2017)). Vacuolar $H^+$-ATPases (V-ATPases) were blocked by using a selective and reversible inhibitor Bafilomycin $A_1$ (300 nM). Cells were bathed in inhibitors 1 h prior to the addition of NOckout probes during the specificity experiment performed in J774A.1 cells. (FIG. 43).

TNF-α Quantification: To quantify the immunogenicity NOckout probes and the corresponding immunogen alone, ELISA for TNF-α was performed in J774A.1 cells. Briefly, J774A.1 cells cultured in DMEM were incubated with 500 nM NOckout sensors, CpG nucleotides, RNA, or LPS at 37° C. for 2 h. Postincubation 100 μL of extracellular medium from the culture was used to perform TNF-α quantification using ELISA kit (Cayman, catalog number 500850) according to manufacturers instructions. The calibration curve for TNF-α was generated using recombinant. TNF-α as per the vendor's instructions.

In vitro specificity of NOckout to NO: In vitro specificity experiment of NOckout was performed in the presence of $NO^-$ and various ROS ($O_2{*}^-$, $H_2O_2$, HOCl etc.). $NO^-$ was generated from corresponding $NO^-$ donor, DEANONOate (30 μM). $H_2O_2$ (100 μM) was used directly from its aqueous stock solution and it was quantified by using UV-Vis spectroscopy (ε=43.6 $M^{-1}$ $cm^{-1}$ at 240 nm). Xanthine/Xanthine oxidase was used for superoxide generation and it was quantified using Cytochrome C reduction as described earlier (Gao, J. J. et al. Cutting edge: bacterial DNA and LPS act in synergy in inducing, nitric oxide production in RAW 264.7 macrophages. *J. Immunol.* 163. 4095-4099 (1999)). Hydroxyl radical (*OH, 100 μM) was generated using Fenton chemistry of $H_2O_2$. NaOCl (5 uM) used directly as received (Sigma). Aqueous solutions of $NO_2^-$ and $NO_3^-$ (100 μM) were prepared from their respective sodium salts. NOckout (100 nM, pH 6, 50 mM phosphate buffer) was allowed to react with individual ROS and RNS at 37° C. for 15 minutes and fluorescent spectra was recorded by exciting DAR (G) and A647N (R) fluorophores. The sensitivity of NOckout against different reactive species were expressed as G/R value, where a high G/R indicate high reactivity.

In cellulo specificity of NOckout to NO: In cellulo specificity of the NOckout probe towards $NO^-$ was validated in J774A.1 cells. J774A.1. cells were chosen due to the known expression of NOS2, NADPH-oxidase and MPO in those cells and they are also known to produce $NO^{\bullet}$, $O_2^{\bullet-}$ and HOCl respectively (Utaisincharoen, P., Anuntagool, Chaisuriya, P., Pichyangkul, S. & Sirisinha, S. CpG ODN activates NO and NOS2 production in mouse macrophage cell line (RAW 264.7). *Clin. Exp. Immunol.* 128, 467-473 (2002); Pacelli, R. et al. Nitric oxide potentiates hydrogen peroxide-induced killing of *Escherichia coli. J. Exp. Med.* 182, 1469-1479 (1995)). J774A.1 cells were treated with 1 μg/mL LPS for 12 h prior to the addition of NOckout (500 nM in HBSS) either in the presence or in absence of specific inhibitors. LPS addition was employed to induce the expression of NOS2NOX and MPO. This would induce the production of $NO^-$ and ROS in the same cells, thus allowing to probe their reactivity towards NOckout by using a single and a robust assay. Pharmacological inhibitors of NOX (VAS2870, 10 μM), MPO (ABAH, 50 μM) and NOS2 (1400 W, 10 μM) were added to the media 1 hour before the addition of 500 nM of NOckout to J774A.1 cells. After 90 minutes of incubation with the NOckout culture media was removed from the cells and three washes were performed using HBSS to remove extracellular NOckout before proceeding to the fluorescence imaging. Inhibitors were present during all the washing steps and in the imaging solution (HBSS). Cells were imaged in live at room temperature using confocal microscopy as described above (FIG. 44).

In cellulo stability of NOckout: NOckout (500 nM in pH 6 phosphate buffer) was treated with DEANONOate (30 μM) until reaching a maximum G/R value as validated by performing in vitro fluorescence measurements. J774A.1 cells pretreated with LPS (1 μg/mL) for 12 h and untreated J774A.1 cells were incubated with 500 nM of NOckout in HBSS for 30 min. Excess NOckout was washed two times with HBSS solution and subsequently complete DMEM was added to the cells. Followed by this, cells were incubated at 37° C. in a tissue culture incubator for 30 min, 60 min, and 120 min. After the respective incubation period, cells were washed two times with HBSS and subsequently imaged on a wide-field epifluorescence microscope to record fluorescence intensity in DAR (G) and A647N (R) channels. The integrity of the NOckout inside cells can be compromised in endosomes or phagosomes due to the presence of DNAases in those compartments. Potentially, DNAase can degrade dsDNA backbone of NOckout and A647N fluorophore of the NOckout could escape due to this degradation from the endosomal compartments to the cytoplasm. On the contrary, DAR attached to the DNA through a 10 kDa PEG spacer will retain in the endosomes even after DNA degradation due to its polymeric nature. Thus, a dramatic increase in G/R signal would indicate an active DNA degradation process due to the loss of A647N (R) signal. The experiments with NOckout in cells are completed within 2 hours and no degradation of the probes were observed with in this time period (FIG. 45).

Endosomal pH perturbation using Bafilomycin Bafilomycin $A_1$: Bafilomycin $A_1$ (BAF) is a macrolide antibiotic that selectively inhibits the vacuolar type $H^+$-ATPase (V-ATPase) and prevents the acidification of endosomal organelles. It has been known from previous studies that TLR-mediated signaling is dependent on acidification of endosomal/lysosomal compartments (Kaplan, S. S., Lancaster, J. R., Basford, R. E. & Simmons, R. L. Effect of nitric oxide on staphylococcal killing and interactive effect with superoxide. Infect. Immun. 64, 69-76 (1996); Gregory, S.

H., Wing, E. J., Hoffman, R. A. & Simmons, R. L. Reactive nitrogen intermediates suppress the primary immunologic response to Listeria. Immunol. 150, 2901-2909 (1993)). 200 nM of BAF were added one hour prior to and during the addition of NOckout$^{mCpG}$ (500 nM, for 120 min) in primary microglial cells. NOckout$^{mCpG}$ signals in DAR (G) and A647N (R) channels were collected using the image settings described above. The G/R values for individual endosomes were calculated using Findosome, a MATLAB software developed to locate and calculate intensities from endosomes. NOckout$^{mCpG}$ incubated samples showed a high population endosomes with a high G/R value compared to that of the (NOckout$^{mCpG}$+BAF) treated sample (SI FIG. 13). About 70% of endosomes in NOckout$^{mCpG}$ treated sample showed a G/R value≥0.45 compared to only 50% observed in BAF treated sample (SI FIG. 13). This result indicates that a perturbed TLR signaling due to the change ire endosomal acidification leads to an aberrant NO production in those compartments. (FIG. 46)

Zebrafish breeding and maintenance: Zebrafish (*Danio rerio*) were maintained as described (Westerfield, 1995). Zebrafish were kept at 26° C.-27° C. in a 14-hr light and 10-hr dark cycle. Embryos were collected by natural spawning and raised at 28° C. in E3 buffer. To avoid pigmentation, 0.003% 1-phenyl-2-thiourea (PTU) was added at 1 dpf. All the transgenic lines used in this study Tg(mpeg:EGFP), Tg(apoe: EGFP), Tg(HuC:Kaede) have been described previously (Miller, B. H. et al. Mycobacteria inhibit nitric oxide synthase recruitment to phagosomes during macrophage infection. *Infect. Immun.* 72, 2872-2878 (2004); Davis, A. S. et al. Mechanism of inducible nitric oxide synthase exclusion from mycobacterial phagosomes. *PLoS Pathog.* 3, e186 (2007); Cambier, C. J. et al. Mycobacteria manipulate macrophage recruitment through coordinated use of membrane lipids. *Nature* 505, 218-222 (2014)). Tg(apoe:EGFP) fish was a kind gift from Prof. William Talbot laboratory (Stanford). For microinjection of NOckout probes, embryos were obtained from wild type AB, Tg(mpeg: EGFP), Tg(apoe: EGFP), and Tg(HuC:Kaede). Animals were housed in Dr. Melina Hale's fish facility according to the IACUC regulation of University of Chicago (Protocol number: 72468).

Protein homology modelling: The SWISS-MODEL server was used in order to perform zTLR-7 homology modelling (Giustarini, D., Rossi, R., Milzani, A. & Dalle-Donne, I. in *Nitric Oxide, Part F* 440, 361-380 (Elsevier, 2008): Kojima, H. et al. Detection and imaging of nitric oxide with novel fluorescent indicators: diaminofluoresceins. *Anal. Chem.* 70, 2446-2453 (1998)). Fully automated workflow on the UniProt provided zTLR-7 sequence gave us following modelling results.

TABLE 2

| Model # | Template | Description | Query coverage | QMEAN* |
|---|---|---|---|---|
| 1 | 5gmf.1.A | Macaca TLR-7 | 0.77 | −2.23 |
| 2 | 3j0a.1.A | Human TLR-5 | 0.75 | −8.82 |
| 3 | 2a0z.1.A | Human TLR-3 | 0.62 | −6.93 |

*QMEAN is a composite scoring function, which is able to derive both global (i.e. for the entire structure), and local (i.e. per residue) error estimates based on one single model. Scores of −4.0 or below are an indication of models with low quality.

Model #1 shows the QMEAN value of −2.23, which depicts good global and local homology between, sequences as evident from FIG. 30. Other TLRs like TLR-5 and TLR-3, which do give decent query coverage but do not show acceptable QMEAN values in homology modelling. The homology modelling results suggest that zTLR-7 is similar to Macaca TLR-7 structurally and sequence wise (74% similarity, FIGS. 29 and 30).

Microinjection of NOckout and NOckout$^{Fn}$ in the brain of larval zebrafish: About 20-30 nL NOckout or NOckout$^{Fn}$ (20 μM stock solution in HBSS) were injected to the optic tectum area of MS-222 treated 3 dpf zebrafish using a microinjector. Post injection of the probes, fish were allowed to recover from anesthesia by placing them in fresh E3 medium. Subsequently fish were re-anesthetized and embedded in agar for confocal imaging. Coninjection experiments of TMF-labeled NOckout$^{UN}$ and Cy5-annexin V were performed by employing a similar protocol to that used for the NOckout injections. Briefly, dsDNA$^{TMR}$ (20 μM in HBSS) and annexin V-Cy5 (10 μM) were mixed in a microfuge tube by vortexing. About 20 nL of the mixed solution was injected in the optic tectum of 3-dpf-old fish. Injected fish were allowed to recover from anesthesia by placing them in a fresh E3 medium, and the fish were further incubated for 1 h in E3 medium before imaging their brains using a confocal mixroscope (LSM-710) in the TMR and Cy5 hannels. MorpholNOS2 (Gene Tools) were dissolved in HBSS and injected at one cell stage.

Co-injection experiments: Co-injection experiments of dsDNA$^{TMR}$ and Cy-5 annexin V was performed by employing a similar protocol that is used for the NOckout injections. Briefly, dsDNA$^{TMR}$ (20 μM in HBSS) and AnnexinV-Cy5 (10 μM) was mixed in a microfuge tube by vortexing. About 20 nL of the mixed solution was injected in the optic tectum of 3 dpf old fish. Injected fish was allowed to recover from anesthesia by placing them in a fresh E3 medium and the fish was further incubated for 1 hour in E3 medium before imaging its brain using a confocal microscope (LSM-710) in the TMR and Cy5-channels.

Morpholino injections and RT-PCR: MorpholNOS2 were purchased from Gene Tools, Philomath, USA were dissolved in E3 medium and injected at one cell stage as described earlier. 1 pmol of NOS2a morpholino was used as per the previous literature (McQuade, L. E. & Lippard, S. J. Fluorescent probes to investigate nitric oxide and other reactive nitrogen species in biology (truncated form: fluorescent probes of reactive nitrogen species). *Curr. Opin. Chem. Biol.* 14, 43-49 (2010)). Morpholino sequences and primer used for RT-PCR are listed in SI Table 4 and 5 respectively. Total RNAs were extracted from embryos and larvae using TRIzol. reagent (Invitrogen) as per the manufacturer's instructions. cDNAs were then generated using Superscript III reverse. cDNAs were used to generate gene-specific amplicon using primers listed in SI table 5. Reverse transcription was performed at 50° C. for 1 h. PCR conditions were 2 min of initial denaturation at 94° C., 45 cycles of denaturation at 94° C. for 20 s. annealing at 52-58° C. for 45 s and extension at 72 for 1 min, followed by a final extension step at 72° C. for 10 min (Yu, H., Xiao, Y. &. Jin, L. A lysosome-targetable and two-photon fluorescent probe for monitoring endogenous and exogenous nitric oxide in living cells. *J. Am. Chem. Soc.* 134, 17486-17489 (2012)).

TABLE 3

| Morpholino sequences employed | |
|---|---|
| Morpholino Name | Sequence (5'-3') |
| TLR3 | TCATTAGATCCATATTTTCCTTCCT (SEQ ID NO: 26) |
| TLR7 | TCATGGTCTTCTCAGTCATCTGAAA (SEQ ID NO: 27) |
| TLR9 | TCAAGGACACCATTGGTCCAAACAT (SEQ ID NO: 28) |
| TLR18 | AGTACCAGCGGAACAAGCATTTTCA (SEQ ID NO: 29) |
| TLR22 | GCTTTCTCTTGATTTCCTTTTCATT (SEQ ID NO: 30) |
| NOS2a | ACAGTTTAAAAGTACCTTAGCCGCT[19](SEQ ID NO: 31) |

TABLE 4

RT-PCR primer sequences used

| Gene | Forward Primer (5'-3') | Reverse Primer (5'-3') |
|---|---|---|
| zTLR3 | GGTACACTTCCAGG GATGGAGA (SEQ ID NO: 32 | TTCTAGTTGACCTT GTTTGTAGAG (SEQ ID NO: 33 |
| zTLR7 | CTCTGTATTTTCCA AACCACTCTG (SEQ ID NO: 34 | CCTGATCACAGAGT CTCCTGAAAG (SEQ ID NO: 35 |
| zTLR9 | GGGGAAGATGGCGC T TTCAG (SEQ ID NO: 36 | CCA GAA GAG CG GCTG CACTC (SEQ ID NO: 37 |
| zTLR18 | TTTAGGTCAAGGGG TGGATTAC (SEQ ID NO: 38 | CTACTATGTCGGCT GATTGTTCTC (SEQ ID NO: 39 |
| zTLR21 | GGAGAACAG TGGC GTCGCTTAC (SEQ ID NO: 40 | GTTCTT TTG CAC TGTTTGGATCAG (SEQ ID NO: 41 |
| ZTLR22 | GTTTGCAGCAGTAT TTTG GTCATC (SEQ ID NO: 42 | GTTCTCTGATTTAT GGCTGTCTTTG (SEQ ID NO: 43 |
| zActin | CGAGCAGGAGATGG GAACC (SEQ ID NO: 44 | CAACGGAAACGCTC ATTGC (SEQ ID NO: 45 |

Example 1: Preparation of DAR-$N_3$

DAR-4 was synthesized by methods used in Kojima, et al. (Kojima H. at al. Bioimaging of nitric oxide with fluorescent indicators based on the rhodamine chromophore. *Anal. Chew.* 73, 1967-1973 (2001)) and 3-azido-1-iodopropane was synthesized by methods used in Yao, et al. (Yao, L., Smith, B. T. & Aubé, J. Base-promoted reactions of bridged ketones and 1,3- and 1,4-haloalkyl azides: competitive alkylation vs azidation reactions of ketone enolates. *J. Org. Chem.* 69, 1720-1722 (2004)).

Scheme 1: Synthesis of DAR-$N_3$ from DAR-4M

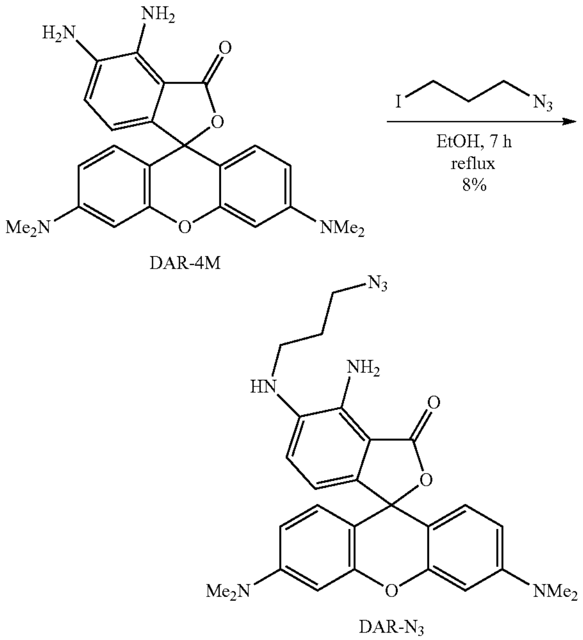

DAR-4M

DAR-$N_3$

Synthesis of 1-azido-3-iodopropane: 1-azido-3-iodopropane (5) was synthesized from 1-bromo-3-chloropropane (3) as described in Yao et al. (*J. Org. Chem.* 2004, 69, 5, 1720-1722). And DAR-4M (6) was synthesized according to Kojima et al. (*Anal. Chem.* 2001, 73, 1967-1973).

(a) Synthesis of DAR-$N_3$: 3-azide-1-iodopropane (50 mg, 0.23 mmol) was added in two equal portions at 2 h and 4 h to a refluxing solution of DAR-4M (28 mg, 0.067 mmol) in dry ethanol (4 mL). Reaction was monitored by TLC and LC-MS every hour. After 7 h, the reaction mixture was cooled to room temperature and solvent was evaporated under vacuum. The product was purified by silica gel chromatography with methanol/dichloromethane (1:9 v/v) to yield DAR-$N_3$(2.7 mg, 8.0%).

DAR-$N_3$: 1H NMR($CDCl_3$, 500 MHz, ppm) δ=1.98 (m, 2H), 2.97 (s, 12H), 3.27 (t, 2H, J=6.5 Hz), 3.52 (t, 2H, J=6.5 Hz), 6.41 (dd, 2H, J=2.5 Hz, 8.5 Hz), 6.43 (d, 1H, J=3.0 Hz), 6.47 (d, 2H, J=2.5 $_{Hz}$), 6.76 (d, 2H, J=4.0 Hz), 6.85 (d, 1H, J=8.0 Hz);

13C NMR ($CDCl_3$, 125 MHz, ppm) δ=33.0, 40.5, 42.2, 49.7, 98.6, 108.5, 108.8, 111.9, 113.3, 118.1, 129.2, 135.7, 135.9, 152.2, 153.2, 171.4

HRMS: predicted 499.2332, observed 499.2631

Example 2: NOckout Sensors Assembly (a) Appending of DBCO group: Mono-protected amine functionalized 10 kDa polyethyleneglycol (3 mg, Creative PEG works) was dissolved in 150 μL of dry DMSO. To achieve basic pH. 2 μL of triethylamine was added. DBCO-NHS ester was added to a final concentration of 20 mM. Reaction was stirred for 3 h at room temperature. The reaction mixture was diluted by a factor of 100 with milli-Q water to make DMSO content less than 1%. Extra DBCO-NHS ester was excluded by centrifugation on Amicon 3 kDa filters. The reaction mixture was continually diluted with milli-Q water and tested for DBCO-NHS ester by taking UV spectra of each Amicon flow through. This purification step was performed until there was no detectable absorbance at 309 nm in the flow through. Purified product was lyophilized and can be stored at −80° C. up to 3 months.

(b) Deprotection of Boc: 5 mg oft was dissolved in 200 μL trifluoroacetic acid/dichloromethane (5:95 v/v). The reaction mixture was stirred overnight at room temperature. The solvent was evaporated using a gentle nitrogen flow until most of the liquid evaporated. 100 μL milli Q water was added, and the solution was neutralized with triethylamine. The product concentration was determined by UV ($\lambda_{ex}$=309 nm). Product was lyophilized and can be stored at −80° C. up to 3 months.

(c) DNA-PEG conjugation: A 24-mer ssDNA with a 5'-azido group (Strand S1, See Table 1 for sequence) was dissolved in 50 mM potassium phosphate buffer, pH 7.4, to a final concentration of 50 μM. Compound 2 was added to a final concentration of 75 μM. The reaction was stirred overnight. Reaction completion was checked by 15% native PAGE gel shift assay. Compound 3 will migrate much slower than 24-mer DNA. Amicon purification was applied as described using 10 kDa MW Amicon tubes and pH 7.4, 100 mM phosphate buffer as exchange buffer. DBCO group was added to terminal primary amine as described above with solvent changed to phosphate buffer.

(d) PEG-DAR conjugation: DARN$_3$ was dissolved in DMSO to make 3 mM stock. Exact concentration was determined by UV ($\lambda_{ex}$=571 nm, ε=7.8×10$^4$ M cm$^{-1}$). DAR-N$_3$ was added to a final concentration of 1.5 equivalence of 4. Reaction was stirred overnight at room temperature and purified with 3 kDa MW Amicon tube and pH 7.4, 100 mM phosphate buffer as exchange buffer. Filtrate from Amicon was tested by UV until no absorbance from DAR-N$_3$ was observed.

(e) Annealing: Above mentioned DAR-S1 and S2$^{PM}$/S2$^{TGN}$ (Table 1) were mixed in equimolar ratios to a final concentration of 10 μM in 20 mM potassium phosphate buffer, pH 7.4 containing 100 mM KCl. Annealing was performed by heating to 90° C. for 5 min, cooling to room temperature over 3 hr at 5° C./15 min and equilibrating at 4° C. overnight.

Formation of Nockout was confirmed by a gel mobility shift assay using 15% native PAGE (ran in 1×TBE buffer, constant 100V at room temperature for 120 min). The gel was imaged using BIO-RAD ChemiDoc MP imaging system (FIG. 10). Alexa488 (referred to as 'B') channel gel images were acquired using Epi-blue filters (excitation 460-490 nm and emission 518-446 nm). DAR channel gel images (referred to as 'G') were acquired using Epi-green filters (520-545 nm excitation and 577-613 nm emission). Alexa647 channel gel images (referred to as 'R') were acquired using Epi-red filters (625-650 nm excitation and 675-725 nm emission). The gel was further stained with EtBr solution for 5 min and imaged in EtBr channel. Due to broad excitation and emission filters in ChemiDoc MP gel imager, there is a bleedthrough of Alexa488 in the Epi-green filter set (asterisk, DAR channel, SI FIG. 1A), as observed in the gel (FIG. 10*a*). Note that these filer sets are used only while imaging the gel for integrity: microscope imaging was done using specific narrow filter sets as mentioned in image acquisition section below.

Example 3: Imaging NOS3 Activity with Sub-Cellular Spatial Resolution

The working principle and characterization of the two NOckout variants NOckout$^{PM}$ and NOckout$^{TGN}$ can be described as follows. Both variants comprise a 24-base pair DNA duplex comprising two strands S1 and S2 bearing three functionalities (FIG. 1*a*, Table 1). The first is an NO sensing dye, based on the diamino rhodamine fluorophore, DAR (FIG. 1*a*), attached to the 5' end of Si (FIG. 1*b*) (Kojima, H. et al. Bioimaging of nitric oxide with fluorescent indicators based on the rhodamine chromophore. *Anal. Chem.* 73, 1967-1973 4 2001)). DAR fluorescence is quenched by intramolecular photoinduced electron transfer (PeT) from the aromatic diamino group (OFF state, FIG. 1*a*). This diamino group reacts stoichiometrically with NO to form the triazole, DAR-T, where PeT is disrupted thereby increasing fluorescence (ON state, $\lambda_{ex}$=550 nm; $\lambda_{em}$=575 nm) (Kojima. H. et al. Detection and imaging of nitric oxide with novel fluorescent indicators: diaminofluoresceins. *Anal. Chem.* 70, 2446-2453 (1998)). DAR-T is photostable, bright (Φ=0.42, & ε=76000 M$^{-1}$ cm$^{-1}$), is pH insensitive hon pH 4-10 and has an NO detection limit of 7 nM (Kojima, H. et al. Bioimaging of nitric oxide with fluorescent indicators based on the rhodamine chromophore. *Anal. Chem.* 73, 1967-1973 (2001)). The second module is an internal reference dye, which is different for each NOckout variant. The reference dye ratiometrically corrects for DAR intensity differences due to varying sensor abundances within the cell that arise from non-uniform probe distribution, probe trafficking and cell to cell heterogeneity. The NOckout variant targeted to the plasma membrane, NOckout$^{PM}$, uses Alexa488 as its reference dye, whereas NOckout$^{TGN}$, uses Alexa647 as its reference dye attached to the 5' end of S2 (FIG. 1*b*). Both Alexa488 and A647 were chosen for their high photostability, brightness and insensitivity to pH, reactive oxygen species (ROS) and reactive nitrogen species (RNS). Since the reference dyes are spectrally distinct, this enables the simultaneous visualization of both NOckout$^{PM}$ and NOckout$^{TGN}$ in dually labeled cells (FIG. 1*b-c*). NOckout$^{PM}$ and NOckout$^{TGN}$ were assembled by annealing equimolar amounts of S1 and S2 strands to yield duplexes bearing a 1:1 ratio of DAR and the reference dye. Their formation and integrity were confirmed using gel electrophoresis that indicated >99% yield (FIG. 10). Both probes report on NO by sequential excitation of DAR and the reference dye and monitoring emission intensities at 575 inn (G for DAR) and 520 nm (B for NOckout$^{PM}$) or 665 nm (R for NOckout$^{TGN}$). The third module comprises a targeting moiety to localize the NOckout probe specifically either at the plasma membrane or the TGN. Thus, NOckout$^{PM}$ was covalently conjugated to a cholesterol moiety such that upon its addition to the extracellular milieu the cholesterol moiety inserts into the outer leaflet of the plasma membrane stably anchoring the probe on the cell surface (FIG. 1*b*, grey) (you, M. et al. DNA probes for monitoring dynamic and transient molecular encounters on live cell membranes. *Nat. Nanotechnol.* 12, 453-459 (2017)). Since NOS3 localizes in cholesterol-rich domains of the plasma membrane, the cholesterol anchor is expected to position NOckout$^{PM}$ proximal to NOS3 but on the opposite face of the plasma membrane (FIG. 1*c*). For targeting to the TGN, NOckout$^{TGN}$ uses a. high affinity DNA aptamer (5-TRG2, $K_d$=18 nM) that binds hypo-glycosylated MUC-1 presented on the plasma membrane of cancer cells[25]. NOckout$^{TGN}$ incorporates the 5-TRG2 sequence at the 5' end of S2 (FIG. 1*b*). Upon addition to the extracellular milieu, NOckout$^{TGN}$ engages hypo-glycosylated MUC-1 at the plasma membrane through the 5-TRG2 domain and labels the lumen of the TGN by retrograde endocytosis (FIG. 1*b-c*) (Ferreira, C. S. M., Cheung, M. C., Missailidis, S., Bisland, S. & Gariépy, J. Phototoxic aptamers selectively enter and kill epithelial cancer cells. *Nucleic Acids Res.* 37, 866-876 (2009)).

The response characteristics of both NOckout probes was studied by monitoring the fluorescence emission spectra as a function of time in the presence of the NO donor DEA-NONOate (50 μM, pH 6.0). DAR fluorescence (G) of NOckout$^{PM}$ increased rapidly, with >80% response in <1 min, while the fluorescence of Alexa488 (B) remained constant (FIG. 10*b-c*). Further, the NO response characteristics of NOckout probes were pH-insensitive from pH 6 to 7.4 (FIG. 10*d*). The fold change in G/B or G/R values before and after reaction with NO was ~6.5 for both NOckout probes (FIG. 10*d*).

Next, the sensitivity of NOckout probes to various reactive oxygen species (ROS) was studied to determine their specificity to NO because, under metabolic stress, NOS3 can get uncoupled to produce ROS (Yang, Y.-M., Huang, A., Kaley, G. & Sun, D. eNOS uncoupling and endothelial dysfunction in aged vessels. *Am. J. Physiol. Heart Circ. Physiol.* 297, H1829-36 (2009)). NADPH oxidase is the major source of ROS in breast cancer cells. The sensor response to other metabolites of NO such as $NO_2^-$ and $NO_3^-$ was also studied (Lundberg, J. O., Weitzberg, E. & Gladwin, M. T. The nitrate-nitrite-nitric oxide pathway in physiology and therapeutics. *Nat. Rev. Drug Discov.* 7, 156-167 (2008)). The G/B ratios of NOckout$^{PM}$ revealed high selectivity towards NO and negligible reactivity to other reactive species consistent with the parent NO sensing molecule DAR (FIG. 1*d*) (Kojima, H. et al. Bioimaging of nitric oxide with fluorescent indicators based on the rhodamine chromophore. *Anal. Chem.* 73, 1967-1973 (2001) Kojima, H. et al. Detection and imaging of nitric oxide with novel fluorescent indicators: diaminofluoresceins. *Anal. Chem.* 70, 2446-2453 (1998)). The high selectivity, favorable percentage signal change, fast response times and pH-insensitivity of NOckout probes make them well placed to simultaneously map NOS3 activities at the plasma membrane (pH 7.4) and the TGN (pH ~6.0).

Figure 11:
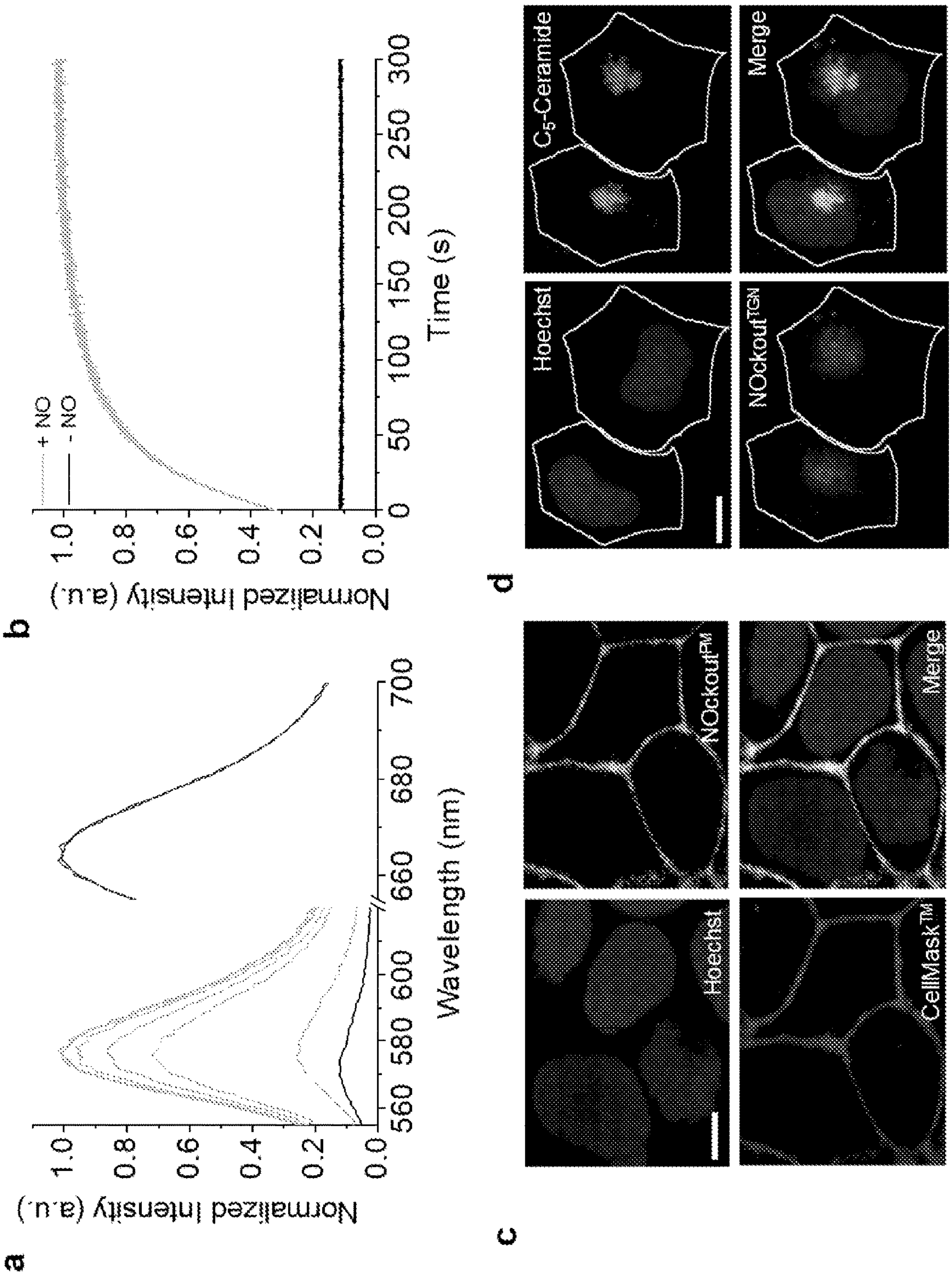
FIG. 11. (a) Fluorescence emission spectra of NOckout$^{TGN}$ obtained after the addition of NO donor (DEA-NONOate, 50 µM, pH 7.2) and recorded at 30-second intervals for 3.5 minutes. DAR ($\lambda_{ex}$=554 nm) and A647 (λex=647 nm) are shown in green and red, respectively. (b) Representative kinetic traces of DAR (λex=554 nm) upon addition of 50 µM DEA-NONOate (green) or DMSO (black). (c) Confocal images showing colocalization of NOckout$^{PM}$ (green) with the PM stain CellMask™ (red, $\lambda_{ex}$=647 nm) in T-47D cells. (d) Confocal images showing co-localization of NOckout$^{TGN}$ (red, $\lambda_{ex}$=647 nm) with trans-Golgi network stain BODIPY™ FL $C_5$-Ceramide (green, $\lambda_{ex}$=488 nm) in T-47D cells. Hoechst (blue, $\lambda_{ex}$=405 nm) was used as nuclear stain.
Figure 12:
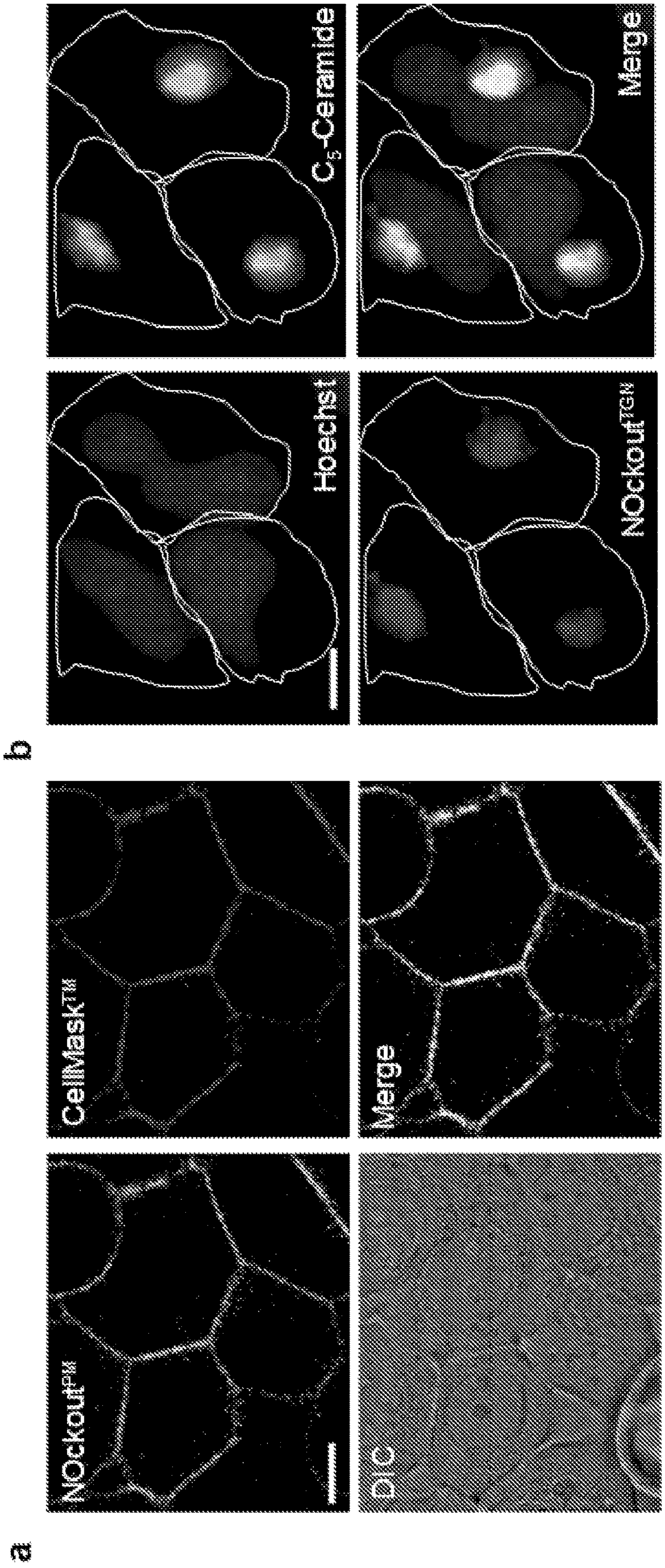
FIG. 12. Targeting of NOckout variants in MCF-7 cells. (a) Confocal images showing colocalization of NOckout$^{PM}$ (green, $\lambda_{ex}$=488 nm) with the plasma membrane stain CellMask™ (red, $\lambda_{ex}$=647 nm) in MCF-7 cells. (b) Confocal images showing co-localization of NOckout$^{TGN}$ (red, $\lambda_{ex}$=647 nm) with trans-Golgi network stain BODIPY™ FL $C_5$-Ceramide (green, $\lambda_{ex}$=488 nm) in MCF-7 cells. Hoechst (blue, $\lambda_{ex}$=405 nm) was used as nuclear stain. Scale bar: 10 µm.
Figure 13:
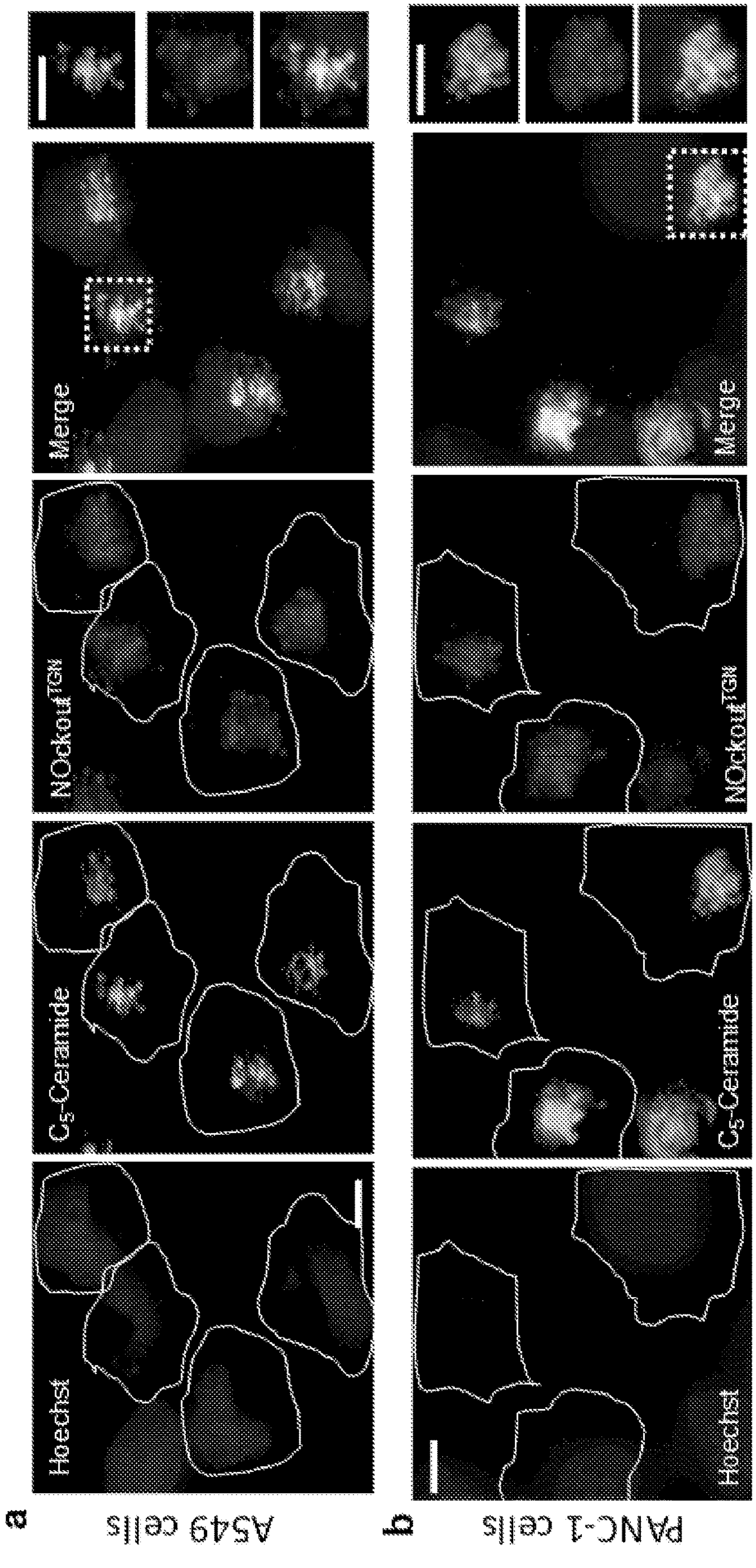
FIG. 13. NOckout$^{TGN}$ is targeted to lung and pancreatic carcinoma cells. Colocalization of NOckout$^{TGN}$ (red) with the trans-Golgi network stain BODIPY™ FL C5-Ceramide (green, $\lambda_{ex}$=488 nm) in (a) A549 lung carcinoma cells A549 and (b) pancreatic tumor cells PANC-1. Hoechst is used to stain nuclei. Scale bar: 10 μm.

Despite ample evidence for NOS3 localization at the plasma membrane as well as the TGN, its relative activity at either location is still unknown (Sowa, G. et al. Trafficking of endothelial nitric-oxide synthase in living cells. Quantitative evidence supporting the role of palmitoylation as a kinetic trapping mechanism limiting membrane diffusion. *J Biol. Chem.* 274, 22524-22531 (1999); Sessa, W. C. et al. The Golgi association of endothelial nitric oxide synthase is necessary for the efficient synthesis of nitric oxide. *J. Biol. Chem.* 270, 17641-17644 (1995); Fulton, D., Gratton, J. P. & Sessa, W. C. Post-translational control of endothelial nitric oxide synthase: why isn't calcium/calmodulin enough? *J. Pharmacol. Exp. Ther.* 299. 818-824 (2001); Fulton, D. et al. Localization of endothelial nitric: oxide synthase phosphorylated serine 1179 and nitric oxide in Golgi and plasma membrane defines the existence of two pools of active enzyme. *J Biol. Chem.* 277, 4277-4284 (2002)). In this disclosure, mapping NOS3 activity at both locations by targeting spectrally distinct NOckout probes to either location was sought. NOckout$^{PM}$ robustly labeled the plasma membrane of T-47D, MCF-7 and diverse cancer cell lines as revealed by co-localization with the plasma membrane marker CellMask™ (FIG. 11*c*). There was no observable endocytosis of cell-membrane anchored NOckout$^{PM}$ up to 2 h post-labeling (FIGS. 12*a* and 30). NOckout$^{TGN}$, on the other hand, was effectively internalized from the extracellular milieu by many cancer cell lines including T-47D cells (FIG. 11*d* and FIGS. 12-13). Colocalization with the TGN-marker BODIPY-$C_5$-ceramide revealed that NOckout$^{TGN}$ was robustly trafficked to the TGN in all of these cells (FIG. 11*d* and FIGS. 12*b*, 13 and 14).

Next, endogenous, basal NOS3 activity was estimated at each of these sub-cellular locations in T-47D cells without explicitly activating NOS3. To do this, the ratiometric NOckout$^{PM}$ response, i.e. the G/B ratio, was first measured under conditions where cells were depleted of NO using the NO scavenger 2-phenyl-4,4,5,5-tetramethylimidazoline-1-oxyl 3-oxide (PTIO, 300 μM) (Goldstein, S., Russo, A. & Samuni, A. Reactions of PTIO and carboxy-PTIO with *NO, *NO2, and O2−*. *J Biol. Chem.* 278, 50949-50955 (2003)). Then, the G/B ratio was measured upon saturating the cell with DEA-NONOate (500 μM) which is expected to completely turn on the NOckout probe. These two extreme cases provide the minimum and maximum G/B signals afforded by NOckout$^{PM}$ in the cell (FIG. 1*e-f*). The G/B values under any subsequent condition are normalized to the maximum G/B signal. Next, basal NOS3 activity at the plasma membrane at steady state was obtained by labeling cells with NOckout$^{PM}$ and obtaining G/B values 1 h post-labeling (FIG. 1*e-f*). A similar approach was used to measure basal NOS3 activity at the TGN using G/R values of NOckout$^{TGN}$(FIG. 1*e-f*). This revealed that the basal NOS3 activity at the plasma membrane and the TGN were comparable (FIG. 1*e-f*). When cells were treated with L-N$^{G}$-Nitroarginine methyl ester (L-NAME, 1 mM) that effectively inhibits all NOS isoforms, G/B and G/R values of NOckout probes reflected those of PTIO-treated cells (FIG. 1*e-f*), whereas 1400 W an NOS2 specific inhibitor has no effect (FIG. 16). This reveals that the change in G/B and G/R signal of the NOckout probes is due to the activity of NOS3 as the contribution of NOS2 activity to the signal is negligible (FIGS. 16, 28 and 29).

Next, NOS3 was pharmacologically activated by two different pathways, both of which are associated with cancer etiology and probed the steady state activity of NOS3 at the plasma membrane and at the TGN. ATP addition activates Akt kinase through P2Y2 receptors which phosphorylates NOS3 thereby increasing its activity (Zhang. Q. et al. Functional relevance of Golgi- and plasma membrane-localized endothelial NO synthase in reconstituted endothelial cells. *Arterioscler. Thromb. Vasc. Biol.* 26, 1015-1021 (2006); Fulton, D. et al. Regulation of endothelium-derived nitric oxide production by the protein kinase Akt. *Nature* 399, 597-601 (1999)). In contrast, 17 β-Estradiol ($E_2$) increases cytosolic $Ca^{2+}$ and activates NOS3 by recruiting calmodulin (FIG. 15) (Veetil, A. T., Jani, M. S. & Krishnan, Y. Chemical control over membrane-initiated steroid signaling with a DNA nanocapsule. *Proc. Natl. Acad. Sci. USA* 115, 9432-9437 (2018)). Interestingly, activating NOS3 by ATP addition revealed significantly higher G/B and G/R ratios of NOckout$^{PM}$ and NOckout$^{TGN}$ respectively compared to basal levels at both locations (FIG. 1*f*). However, $E_2$ selectively activated NOS3 only at the plasma membrane (FIG. 1*f*).

Example 4: Quantitative, Sub-Cellular Imaging of Enzymatic Rate

Given that the NOckout probes could report NOS3 activity at steady state, mapping NOS3 activity in real-time was sought. Cytosolic $Ca^{2+}$ elevation is considered to activate both pools of NOS3 in the cell (Fulton, D. et al. Targeting of endothelial nitric-oxide synthase to the cytoplasmic face of the Golgi complex or plasma membrane regulates Akt-versus calcium-dependent mechanisms for nitric oxide release. *J. Biol. Chem.* 279, 30349-30357 (2004)). Although NOS3 has been suggested to be more active at the plasma membrane, this is based on available $NO_2^-$ and $NO_3^-$, that are by-products of the resultant NO produced, in the extracellular milieu (Zhang, Q. et al. Functional relevance of Golgi- and plasma membrane-localized endothelial NO synthase in reconstituted endothelial cells. *Arterioscler Thromb. Vasc. Biol.* 26, 1015-1021 (2006); Fulton, D. et al. Targeting of endothelial nitric-oxide synthase to the cytoplasmic face of the Golgi complex or plasma membrane regulates Akt-versus calcium-dependent mechanisms for nitric oxide release. *J. Biol. Chem.* 279, 30349-30357 (2004)). In order to be available for measurement in the extracellular milieu, any NO produced at the TGN has to cross a ~5 mM. barrier of cytoplasmic thiols without dismutation. Therefore, the relative activity of both pools of NOS3 is still unclear and can be resolved only by measuring NOS3 activity directly on site.

Therefore, the plasma membrane and the TGN of T-47D cells were simultaneously labeled with $NOckout^{PM}$ and $NOckout^{TGN}$ as described elsewhere (FIG. 2*a*). To image NOS3 activity at both sites simultaneously, dually labeled cells were treated with 1 μM thapsigargin. Thapsigargin elevates cytosolic $Ca^{2+}$ by blocking Sarco/endoplasmic reticulum $Ca^{2+}$-ATPase (SERCA), preventing $Ca^{2+}$ reuptake by the ER which thereby activates NOS3 (Lytton, J., Westlin, M. & Hanley, M. R. Thapsigargin inhibits the sarcoplasmic or endoplasmic reticulum Ca-ATPase family of calcium pumps. *J. Biol. Chem.* 266, 17067-17071 (1991)). Fluorescence images of stimulated, dually labeled cells were acquired in the G, B and R channels as a function of time (FIG. 2*b*). The G/B ratio at the plasma membrane showed a sigmoidal increase with time, while the G/R ratio at the TGN started to increase slowly only alter 3 minutes (FIG. 2*b-c*). G/B and G/R values in PTIO-treated cells stayed fairly constant over the observed timescales, indicating that background bleaching and non-specific probe reactivity were negligible (FIG. 2*c*).

Next, in order to measure the relative activities of NOS3 at the plasma membrane and the TGN, a method was developed to quantify sub-cellular NO generated due to NOS3 activity. The concentration of a reactive species such as NO changes with time, ramping up due to enzymatic activity, reaching a maximum value, $[NO]_{max}$ (Namin S. M., Nofallah, S., Joshi, M. S., Kavallieratos, K. &. Tsoukias, N. M. Kinetic analysis of DAF-FM activation by NO: toward calibration of a NO-sensitive fluorescent dye. *Nitric Oxide* 28, 39-46 (2013)). When enzyme activity stops, NO levels fall due to diffusion, chemical dismutation, or reaction with other biomolecules (FIG. 17*a-b*) (Jiang, S. et al. Real-time electrical detection of nitric oxide in biological systems with sub-nanomolar sensitivity. *Nat. Commun.* 4, 2225 (2013)). As the effective concentration of NO at any time, $[NO]_{eff}$, changes with time, NOS3 activity is best quantified by the rate of NO production. Therefore, the decomposition rate constant ($k_1$ $sec^{-1}$) of DEA-NONOate was first measured from its UV absorbance at 250 nm, to obtain $[NO]_{eff}$ over time in solution for fixed DEA-NONOate concentrations (FIG. 17*a*, Methods) (Ramamurthi, A. & Lewis, R. S. Measurement and modeling of nitric oxide release rates for nitric oxide donors. *Chem. Res. Toxicol.* 10, 408-413 (1997)). Thus, for fixed concentrations of DEA-NONOate and known values of $[NO]_{max}$, the initial rates of NO production (FIG. 17*a-b*) were obtained.

An in-cell calibration protocol was developed to measure the rate of NO production for various concentrations of DEA-NONOate using NOckout probes. A fixed concentration of DEA-NONOate was added to $NOckout^{PM}$ labeled cells and acquired G/B maps as a function of time. The average GB value from ~20 cells yielded sigmoidal curves as a function of time (FIG. 17*c*). From this, the initial rate of G/B increase of $NOckout^{PM}$ at the plasma membrane for each DEA-NONOate concentration could be obtained. The in-cell rates for a range of DEA-NONOate concentrations was plotted against its corresponding in-vitro rate of NO production (FIG. 2*d-e*). This yields a calibration profile for $NOckout^{PM}$ response at different initial rates of NO production. $NOckout^{PM}$ labeled cells was then treated with 1 μM thapsigargin and measured the rate of NO production given by the increasing G/B ratio. Comparing this rate with the $NOckout^{PM}$ calibration curve, it was found that NOS3 produces NO at the rate of 576±61 nM/sec at the plasma membrane (FIG. 2*e*).

$NOckout^{TGN}$ is localized in the lumen of the TGN, which has a pH of 6.5 (Modi, S., Halder, S., Nizak, C. & Krishnan, Y. Recombinant antibody mediated delivery of organelle-specific DNA pH sensors along endocytic pathways. *Nanoscale* 6, 1144-1152 (2014)). However, DAR detection of NO is pH-independent and as expected, the response characteristics of NOckout probes at pH 6 and 7.4 are identical (FIG. 17*d-f*). Thus, the rate of NO production at the Golgi could be directly compared with the in-cell calibration curve in $NOckout^{TGN}$ labeled cells treated with 1 μM thapsigargin. This revealed that NOS3 produces NO with an initial rate of 74±41 nM/sec at the TGN. Interestingly, the rate of NO production at the plasma membrane was ~7-fold faster than at the TGN (FIG. 2*d-e*). Whether the differences in the activities of NOS3 at the plasma membrane and the TGN arose due to the relative abundances of NOS3 at both locations was then investigated. Immunostaining for NOS3 as well as the Golgi marker Giantin revealed counterintuitively, that only ~40% of total cellular NOS3 was localized at the plasma membrane while a major fraction corresponding to ~60% was localized at the Golgi (FIG. 3*a*, FIG. 17*a*). This indicates that NOS3 at at the plasma membrane is actually ~10 fold more active than at the Golgi.

A mechanistic insight into why the population at the plasma membrane showed greater activity was then sought. Akt mediated phosphorylation of Serine 1177 (S1177) on NOS3 is known to enhance its activity, presumably by recruiting Hsp90 and/or stabilizing the NOS3-calmodulin complex (Fulton, D. et al. Regulation of endothelium-derived nitric oxide production by the protein kinase Akt. *Nature* 399, 597-601 (1999); Garcia-Cardeña G. et al. Dynamic activation of endothelial nitric oxide synthase by Hsp90. *Nature* 392, 821-824 (1998)). However, direct evidence of location-specific S1177 phosphorylation in cells has not yet been observed. To investigate whether such a mechanism might account for the activity difference between NOS3 at either location, NOS3 was probed with two different antibodies. One of these selectively binds S1177 phosphorylated NOS3 (P-NOS3) and the other binds NOS3 irrespective of its post-translational modifications (FIG. 3*b*). The normalized ratio of P-NOS3/total NOS3 shows that plasma membrane is ~7 fold higher than at the Golgi (FIG. 3*b*). The preferential phosphorylation of S1177 NOS3 at the plasma membrane could explain its enhanced activity. This is consistent with biochemical studies on over-expressed, synthetic NOS3 variants that suggest NOS3 at the plasma membrane is highly phosphorylated (Zhang, Q. et al. Functional relevance of Golgi- and plasma membrane-localized endothelial NO synthase in reconstituted endothelial cells. *Arterioscler. Thromb. Vasc. Biol.* 26, 1015-1021 (2006)).

Example 5: Confirmation of the Golgi as a Hotspot for S-Nitrosylation

In order to address the significance of the hypoactive population of NOS3 at the TGN, T-47D cells were immunostained using an antibody specific to S-nitrosocysteine. Co-immunostaining with GM130 revealed a significant abundance of S-nitrosylated proteins at the Golgi in T-47D as well as MCF-7 cells (FIG. 4*a*, FIG. 18*b*). However, normal breast epithelial cell lines such as MCF-10A and 184A1, showed negligible 5-nitrosylation at the Golgi (FIG. 19). Given that basal NOS3 activity at the TGN and the plasma membrane in breast cancer cells are comparable at steady state these studies suggest that despite the lower amounts of NO produced at the TGN, S-nitrosylation of proteins at the TGN is far higher than at the plasma membrane. NO depletion by PTIO treatment showed that S-nitrosylation at the Golgi was greatly diminished (FIG. 20). Treating cells with 1400 W, a specific inhibitor of NOS2 led to no change in S-nitrosylation at the Golgi revealing that NOS3 was responsible for S-nitrosylation at the TGN (FIG. 21).

Importantly, prolonged inhibition of NOS3 with L-NAME dramatically reduced 5-nitrosylation at the Golgi. Further, the Golgi underwent fragmentation as revealed by anti-GM130 immunostaining (FIG. 4*b-c*). This fragmented morphology was observed when the cells were treated with chemical scavengers specific for NO such as PTIO, Methylene Blue (MB) and Hemoglobin (HB) (FIG. 4*b-c*, FIG. 22). Similar observations were made in MCF-7 cells upon NO depletion (FIG. 23). These studies reveal that the Golgi is a cellular hot-spot for 5-nitrosylation of proteins by NOS3, where it is essential for the maintenance of Golgi architecture in breast cancer cells. This is consistent with other studies indicating that S-nitrosylation of Golgi-associated oncogenic proteins like H-Ras or N-Ras and GOLPH3 are linked to cancer progression and tumorigenesis (Lim, K.-H., Ancrile, B. B., Kashatus, D. F. & Counter, C. M. Tumour maintenance is mediated by eNOS. *Nature* 452, 646-649 (2008); Farber-Katz, S. E. et al. DNA damage triggers Golgi dispersal via DNA-PK and GOLPH3. *Cell* 156, 413-427 (2014)). In addition to Golgi fragmentation, NO scavenging also hampered cell growth by inducing cell sensescence (FIG. 24).

Small molecule inhibitors were then screened to identify the molecular pathway by which NOS3 inhibition induces Golgi fragmentation. This is based on the rationale that inhibiting a protein on this pathway should also block methylene blue-induced Golgi fragmentation. To rule out any contribution from ROS producing enzymes or from NOS2, the specific ROS scavenger TEMPOL and NOS2 inhibitor 1400 W were used, and none of these treatments fragmented the Golgi (Lee, J. E. et al. Dependence of Golgi apparatus integrity on nitric oxide in vascular cells: implications in pulmonary arterial hypertension. *Am. J. Physiol. Heart Circ. Physiol.* 300, H1141-58 (2011)). Treatment with sildenafil citrate, a cGMP phosphodiester inhibitor, also did not fragment the Golgi ruling out the participation of cGMP synthase activation due to NO (FIG. 4*c*). Treatment with the Rho A kinase inhibitor Y-27632 revealed that MB-induced Golgi fragmentation was not mediated by apoptosis (FIG. 4*c*). A range of small molecule inhibitors against kinases that have previously ascribed roles in Golgi fragmentation were then used. DNA-PK with NU7441 was ruled out (Farber-Katz, S. E. et al. DNA damage triggers Golgi dispersal via DNA-PK and GOLPH3. *Cell* 156, 413-427 (2014)). Compounds containing an indirubin core have broad specificity for Cyclin dependent kinases (CDKs) and Src kinases. It was found that both indirubin-e804 (I-E804) and indirubin-3'-monoxime (1-3'M) completely blocked MB-induced Golgi fragmentation (FIG. 4*c*). CDK1, CDK2 and CDK5 were ruled out, using (R)-Roscovitine (Rosco). Interestingly, the Src kinase inhibitor SU6656, reduced MB-induced Golgi fragmentation by ~50% (Blake, R. A. et al. SU6656, a selective src family kinase inhibitor, used to probe growth factor signaling. *Mol. Cell. Biol.* 20, 9018-9027 (2000)). Importantly, treatment with Latrunculin B (LatB) and inhibitor of actin polymerization completely blocked MB-induced Golgi fragmentation revealing that Golgi fragmentation due to NOS3 inhibition is actin-mediated (FIG. 4*c-d*) (Skupien, A. et al. CD44 regulates dendrite morphogenesis through Src tyrosine kinase-dependent positioning of the Golgi. *J. Cell Sci.* 127, 5038-5051 (2014)).

Example 6: Comparison of NOckout Probes with Conventional NO Probes

Currently the most widely used approach to detect NOS activity relies on NO-sensitive small molecule probes (Kojima, H. et al. Detection and imaging of nitric oxide with novel fluorescent indicators: diaminofluoresceins. *Anal. Chem.* 70, 2446-2453 (1998): Ye, X., Rubakhin, S. S. & Sweedler, J. V. Detection of nitric oxide in single cells. *Analyst* 133, 423-433 (200S); Lim, M. H., Xu, D. & Lippard, S. J. Visualization of nitric oxide in living cells by a copper-based fluorescent probe. *Nat. Chem. Biol.* 2, 375-380 (2006)). However the reacted probe molecules diffuse rapidly, blurring out spatial information (FIG. 26 and Table 6).

TABLE 6

Benchmarking NOckout against commercially available NO probes.

| Parameters | DAF-2DA (Commercial NO detection kits) (FIG. 26) | G-geNOp (protein sensor for NO) | NOckout |
|---|---|---|---|
| Ratiometric | No (FIG. 26a) | No (FIG. 27a) | Yes (FIGS. 1b-d and FIGS. 10a-c) |
| Mode of sensing | Fluorescence turn on (FIGS. 26a and c) | Fluorescence turn off (FIGS. 27a and c) | Fluoresence turn on (FIGS. 10b-c and FIGS. 11a-b) |
| Sensitive towards pH | Yes (FIGS. 26b and d) | Yes (FIGS. 27d-e) | No (FIG. 10d and FIG. 17e) |
| $Fe^{2+}$ supplementation | Not required (FIGS. 26a and c) | Required (FIGS. 27a-c) | Not required (FIGS. 10b-c and FIGS. 11a-b) |

TABLE 6-continued

Benchmarking NOckout against commercially available NO probes.

| Parameters | DAF-2DA (Commercial NO detection kits) (FIG. 26) | G-geNOp (protein sensor for NO) | NOckout |
|---|---|---|---|
| Maximum in-cellulo fold change | 7500% (FIG. 26c) | −15% (FIG. 27c) | 200% (FIG. 1f) |
| Organelle targetability | No (FIG. 26a) | Yes | Yes (FIGS. 11c-d. FIG. 12 and FIG. 13) |
| Reversible | No | Quasi-reversible | No (FIGS. 10b-c and FIGS. 11a-b) |

Recently described protein-based reporters offer the necessary spatial resolution and are quasi-reversible but are pH and ROS sensitive, require millimolar $Fe^{2+}$ supplementation, show limited sensitivity compared to small molecules and are not quantitative (FIG. 27 and Table 6) (Eroglu, E. et al. Development of novel FP-based probes for live-cell imaging of nitric oxide dynamics. *Nat. Commun.* 7, 10623 (2016)). NOckout probes combine the selective and photostable chemistry of small molecules while offering the stable spatial localization that is available to proteins. These probes are ratiometric, modular, sub-cellularly targetable and hence well suited to measure NOS3 activity with sub-cellular resolution.

By simultaneously mapping NOS3 activity at two different locations in the same cell using NOckout probes, it was found that cytosolic $Ca^{2+}$ elevation selectively activated the population of NOS3 at the plasma membrane. This is consistent with studies in endothelial cells expressing synthetic NOS3 variants targeted either to the plasma membrane or the TGN (Sessa, W. C. et al. The Golgi association of endothelial nitric oxide synthase is necessary for the efficient synthesis of nitric oxide. *J. Biol. Chem.* 270, 17641-17644 (1995); Zhang, Q. et al. Functional relevance of Golgi- and plasma membrane-localized endothelial NO synthase in reconstituted endothelial cells. *Arterioscler. Thromb. Vasc. Biol.* 26, 1015-1021 (2006)). Using NOckout to directly compare the activities of both pools without modulating NOS3 abundance at either location, it was found that NOS3 was 10-fold more active at the plasma membrane than at the TGN, suggesting that these two populations might be chemically different. Indeed, it was possible to pinpoint that the plasma membrane population had a specific post-translational modification phosphorylated S1177 unlike the population at the Golgi.

Specifically in cancer, plasma membrane-associated NOS3 has been posited to mediate processes such as angiogenesis, metastasis and epithelial mesenchymal transition through players such as E-cadherin, EGFR and matrix metalloproteinases (Vahora, H., Khan, M. A., Alalami, U. & Hussain, A. The potential role of nitric oxide in halting cancer progression through chemoprevention. *J. Cancer Prev.* 21, 1-12 (2016)). Interestingly, $Ca^{2+}$ elevation in epithelial cancer cells occurs near the plasma membrane, which could potentially selectively activate plasma membrane-associated NOS3 (Ellefsen, K. L. & Parker, I. Dynamic Ca2+ imaging with a simplified lattice light-sheet microscope: A sideways view of subcellular Ca2+ puffs. *Cell Calcium* 71, 34-44 (2018)). NOckout probes provide direct evidence that treatment with $E_2$, a ligand that binds the estrogen receptor in $ER^+$ breast cancers, selectively activates plasma membrane-associated NOS3.

Interestingly, despite the low activity of NOS3 at the TGN, abundant S-nitrosylation at the Golgi in breast cancer cells was observed. This indicates a role for the hypoactive population of NOS3 at the TGN in terms of a slow, yet sustained release of NO. S-nitrosylation at the Golgi in these cells is essential for the maintenance of Golgi architecture through Src kinase mediated mechanism, the disruption of which leads to cell senescence. S-nitrosylation of Golgi associated proteins such as HRas, NRas and GOLPH3 regulate cell cycle progression in cancer (Lim, K.-H., Ancrile, B. B., Kashatus, D. F. & Counter, C. M. Tumour maintenance is mediated by eNOS. *Nature* 452, 646-649 (2008); Farber-Katz, S. E. et al. DNA damage triggers Golgi dispersal via DNA-PK and GOLPH3. *Cell* 156, 413-427 (2014)). In fact, impeding cell cycle progression by disrupting Golgi morphology also promotes cell survival (Farber-Katz, S. E. et al. DNA damage triggers Golgi dispersal via DNA-PK and GOLPH3. *Cell* 156, 413-427 (2014)). Impeding S-nitrosylation could promote such a scenario, suggesting a possible mechanism invoked by the cell to bypass apoptosis until environmental conditions favor cell growth.

Despite the clear significance of both sub-cellular pools of NOS3, it has proved challenging thus far to deconvolute the contribution of either pool to the modulation of cardiac function, wound healing or cancer progression (Xu, W., Liu, L. Z., Loizidou, M., Ahmed, M. & Charles, I. G. The role of nitric oxide in cancer. *Cell Res.* 12,311-320 (2002); Zhang, Q. et al. Functional relevance of Golgi- and plasma membrane-localized endothelial NO synthase in reconstituted endothelial cells. *Arterioscler. Thromb. Vasc. Biol.* 26, 1015-1021 (2006); Lee, P. C. et al. Impaired wound healing and angiogenesis in eNOS-deficient mice. *Am. J. Physiol.* 277, H1600-8 (1999)). NOckout probes can be applied to potentially identify molecular players that selectively modulate the activity of distinct sub-cellular NOS3 pools for basic a.s well as clinical applications. This modular technology can be expanded to quantitatively map NOS activities in endothelial cells, neuronal cells or immune cells by using appropriate targeting modules and tuning the sensing fluorophore (Jani., M. S., Veetil, A. T. & Krishnan, Y. Precision immunomodulation with synthetic nucleic acid technologies. *Nat. Rev. Mater.* (2019). doi:10.1038/s41578-019-0105-4).

Figure 5:
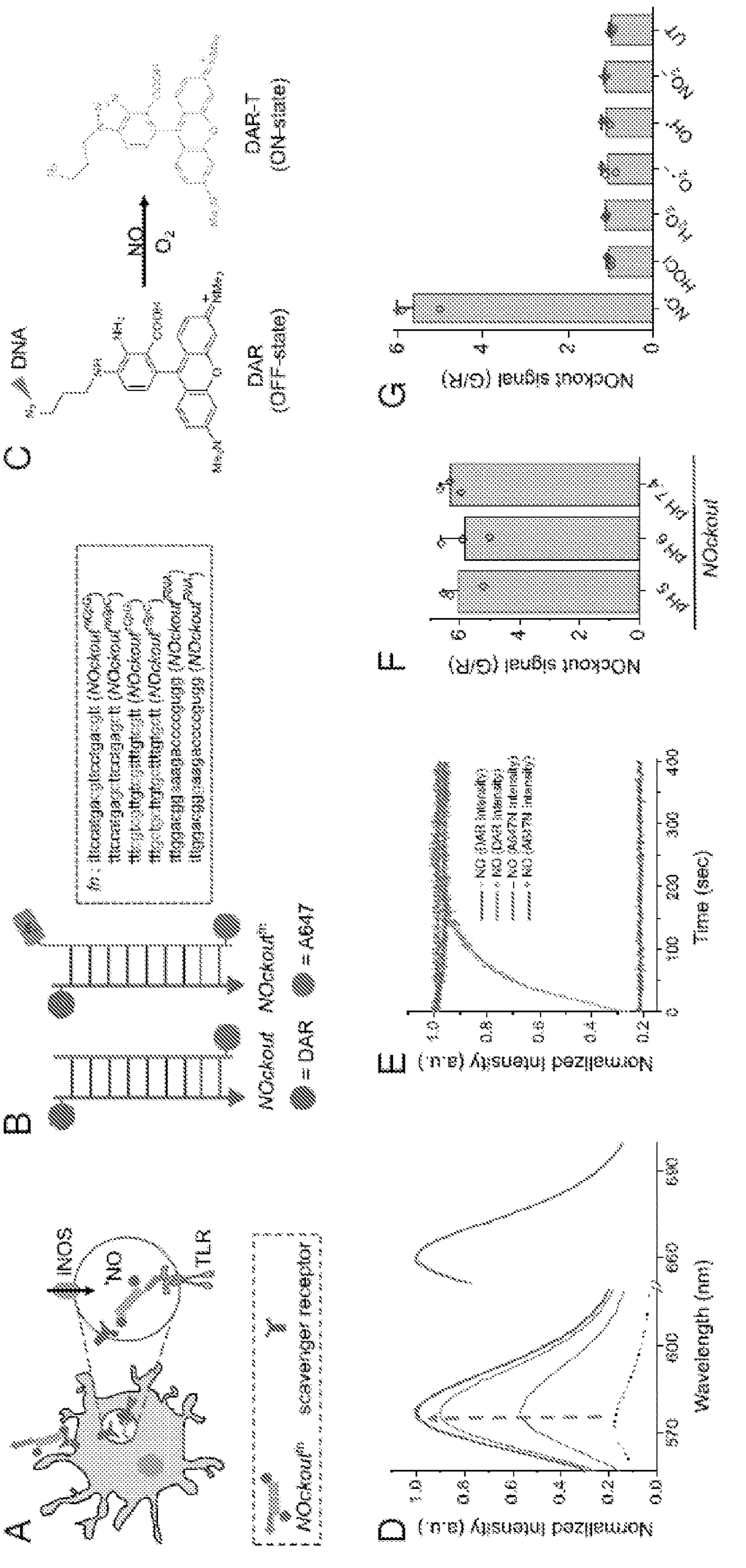
FIG. 5. Design, sensitivity and specificity of NOckout probes: (a) Schematic of TLR-mediated NOS2 activation by $NOckout^{Fn}$. $NOckout^{Fn}$, displaying a functional PAMP (Fn, blue), is phagocytosed and binds its cogitate TLR-receptor (green hook) to activate NOS2 (green circle) and elevate phagosomal NO levels (b) Schematic of the design of NOckout and $NOckout^{Fn}$ probes. NOckout is assembled from a ssDNA (24-mer) carrying an NO sensing fluorophore (DAR, green circle) and a complementary DNA strand displaying a normalizing fluorophore (A647, red circle). $NOckout^{Fn}$ carries a functional (Fn) immunostimulatory CpG DNA or RNA motif as an overhang specific to mouse ($NOckout^{mCpG}$ or $NOckout^{iRNA}$) or zebrafish TLR receptors ($NOckout^{zCpG}$ or $NOckout^{iRNA}$) (from top to bottom SEQ ID NOs:13, 14, 15, 16, 17,and 18). (c) Reaction with NO turns the non-fluorescent DAR probe (off-state) on NOckout into the highly fluorescent DAR-T (on-state). (d) Fluorescence spectra of NOckout (250 nM) in sodium phosphate buffer (pH 6.0, 50 mM) recorded in the DAR channel (green, $\lambda_{ex}$=550 nm, $\lambda_{em}$=575 nm) and in the A647 channel (red, $\lambda_{ex}$=645 nm, $\lambda_{em}$=660 nm) by adding DEA NONOate (50 µM, pH 6.0). Spectra in the DAR-channel (G) were recorded in 30s intervals (green traces). (e) Representative kinetic trace of NOckout in the DAR channel with (red) and without (black) DEA NONOate (50 µM, pH 6.0). Intensity in A647 channel before and after addition of DEA NONOate is shown in blue and green respectively. (f) Fold change of NOckout represented as G/R values in pH 5, pH 6 and pH 7 buffers. (g) In vitro specificity of NOckout against various ROS and RNS. NOckout (250 nm, pH 6.0) was incubated with NO (50 µM of DEA NONOate), HOCl (5 µM). $H_2O_2$ (100□µM), $O_2^-$ (100 µM), OH (100 µM) and $NO_2$ (100 µM) for 6 minutes at room temperature and the intensities were plotted as (G/R) values corresponding to DAR (G) to that of A647 (R). Error bars are standard deviations for n=3 independent trials.

Example 7: Design, Synthesis and Determination of Sensitivity and Specificity of NOckout Probes A series of ratiometric, fluorescent NO sensitive DNA nanodevices denoted $NOckout^{fn}$ were first designed where fn denotes a functional DNA or RNA sequence that can potentially be a PAMP (FIG. 5*b*). The basic NOckout device comprises three modules namely the NO detection chemistry, a normalizing dye for ratiometric quantitation of NO and a duplex DNA motif for internalization by specific cell types and stable compartmental localization thereafter. NOckout variants comprise a 24-base pair DNA duplex composed of two strands S1 and S2 bearing four functionalities (Table 1). The first is an NO sensing dye based on diaminorhodamine (DAR) which is attached via a polyethylene glycol linker to the 5' end of S1 (FIG. 1*a*, FIGS. 34 and 35 and FIG. 33). DAR is quenched due to intramolecular photoinduced electron transfer (PeT) from the aromatic diamino group (OFF state, Φ=0.0005, Φ.ε ~39 $M^{-1}$ $cm^{-1}$, FIG. *b*). Reaction with NO leads to a highly fluorescent triazole (DAR-T) due to relief of PeT (ON state, Φ=0.42, ε=31920 $M^{-1}$ $cm^{-1}$ FIG. 1*b*). DAR-T is highly photostable, bright and its fluorescence is pH invariant.

The second functionality is a normalizing dye ATTO647N (A647) attached to the 5'-end of the S2 strand (FIG. 1*a* and FIG. 33). A647 is the normalizing fluorophore, chosen for its pH insensitivity, molar brightness (Φ=0.65, Φ.ε ~97500 $M^{-1}$ $cm^{-1}$) and chemical inertness towards ROS and reactive nitrogen species (RNS). All NOckout variants were assembled in near quantitative yields by annealing equimolar ratios of S1 and S2 strands and characterized by gel electrophoresis (FIG. 36).

The third functionality in every NOckout variant is a dsDNA module responsible for targeting the nanodevice into phagosomes of microglia in live zebrafish brains. This is essentially the 24 base pair DNA duplex formed by the hybridization of S1 and S2. This DNA duplex also facilitates endocytosis of all NOckout variants by macrophages in culture through the scavenger receptor mediated endocytosis pathway.

The fourth functionality in all NOckout variants is a functional, immunogenic oligodeoxynucleotide (ODN) or oligoribonucleotide (ORN) phosphorothioate sequence denoted fn, and the resultant devices are denoted $NOckout^{fn}$. The ODN or ORN sequence in $NOckout^{fn}$ devices are located at the 3' end of S2 as single stranded overhangs in the basic NOckout device (FIG. 5*a*). The ODN sequences 1826 and 2007 are well-characterized CpG sequences and agonists for specific TLRs in mouse and in zebrafish respectively. They trigger murine TLR-9 and zebrafish TLR-9/21 and for clarity are denoted mCpG and zCpG respectively (FIG. 5*a*). The corresponding $NOckout^{fn}$ devices are denoted NOckout $^{mCpG}$ and $NOckout^{zCpG}$ respectively. Control ODN sequences were also used to create $NOckout^{mGpC}$ and $NOckout^{zGpC}$ devices. The sequences in these controls had the same base composition as mCpG and zCpG, but the CpG motifs were replaced with non-immunostimulatory GpC motifs (FIG. 1*a*). Similarly $NOckout^{iRNA}$ was created, displaying an immunostimulatory RNA (iRNA) sequence of bacterial origin shown to activate the recently characterized mouse TLR-13 receptor. A non-immunostimulatory control, called $NOckout^{RNA}$, incorporated the same sequence with a single G to A point mutation (FIG. 5*a*). An important consideration in the design of $NOckout^{Fn}$ probes is that the lumen of every LE or phagosome of interest encounters the trigger and detector simultaneously. This means that the time between receptor engagement and NO detection is tightly controlled, which allows one to compare NO signals across endosomes or phagosomes at a given time.

As shown in FIG. 10, the bio-conjugation steps employed in the synthesis of NOckout probe are shown.

Step 1. Synthesis of bifunctional PEG conjugate DBCO-PEG-NH-BOC: 10 kDa polyethylene glycol linker (3 mg, 0.0003 mmol) was dissolved in 150 μL freshly dry DMSO. 2 μL of extra dry trimethylamine (TEA) was added to the above solution to maintain a pH ~8.0 and the mixed by constant stirring. To that mixture, DBCO-NHS (20 mM, cat no #761524, Sigma) ester dissolved in dry DMSO (50 μL) was added. The reaction mixture was stirred at room temperature for ~3 hours and subsequently the mixture was diluted by adding of excess of (100×) water to bring down the DMSO content in the mixture less than 1% (w/v). The clear reaction mixture was then loaded to an Amicon ultra centrifugation filter (MWCO ~3 kDa, Merck Millipore) to remove excess of DBCO-NHS ester by spinning at 12000 rpm for 10 min at 4° C. The centrifugation step was repeated using milli-Q water until no trace of DBCO-NHS was detected in the filtrate using UV-Vis spectroscopy ($\lambda_{ab}$=309 nm, ε=12000 $M^{-1}$ $cm^{-1}$). The product was subsequently lyophilized to obtain a white fluffy powder and it was stored at −80° C. for up to 6 months.

Step 2. Deprotection of DBCO-PEG-NH-BOC: Removal of tert-butyloxycarbonyl (t-Boc) group in DBCO-PEG-NH-BOC (2 mg) was achieved by dissolving it an Eppendorf tube (1.5 ml) containing 200 μL mixture of trifluoroacetic acid/dichloromethane (5:95 v/v). The mixture was stirred overnight at room temperature. Subsequently, the solvent mixture was evaporated by using a gentle nitrogen flow. 100 μL milli-Q water was added to the residue and followed by this trimethylamine (TEA) was added till the pH of the solution reached 7.0. The solution was further centrifuged with milli-Q water using a MWCO ~3 kDa filter to remove excess TEA. The product was quantified by UV-Vis spectroscopy using DBCO absorption ($\lambda_{ab}$=309 nm, ε=12000 $M^{-1}$ $cm^{-1}$) and subsequently lyophilized to store at −80° C. for up to 6 months Step 3. DNA-PEG conjugation: A 24-mer ssDNA containing 5'-azido group (Table 1) was dissolved in 50 mM potassium phosphate buffer pH 7.4 to a final concentration of 50 μM. DBCO-PEG-$NH_2$ (60 μM) was added to the ssDNA solution and the reaction mixture was stirred overnight. Completion of the click reaction was monitored by musing a 15% native PAGE gel shift assay (FIG. 35). Purification of the reaction mixture was performed by using a 10 kDa MWCO Amicon ultra centrifugal filter tubes (2 mL, Merck Millipore) using phosphate buffer VI 7.4) as an eluent. The attachment of PEG to the ssDNA was confirmed from the retarded mobility of ssDNA-PEG-NH2 conjugate compared to the ssDNA on the native polyacrylamide gel (15%) (FIG. 36*a*).

Step 3. Synthesis of ssDNA-PEG-DBCO: Capping of the terminal —$NH_2$ group in ssDNA-PEG-$NH_2$ (45 μM, dissolved in phosphate buffer, pH 7.4) with a DBCO group was achieved by reacting it with DBCO-NHS (20 mM, Cat No #761524, Sigma) dissolved in DMSO. The mixture was let to stir for 3 hours at room temperature and excess of DBCO-NHS was subsequently removed by using a 3 kDa Amicon filter as described above. Pure product obtained after centrifugation was quantified by using UV-Vis spectroscopy using DBCO absorbance ($\lambda_{ab}$=309 nm, ε=12000 $M^{-1}$ $cm^{-1}$) and was stored at −80° C. See FIG. 36*a* for gel characterization of the product.

Step 4. Synthesis of ssDNA-PEG-DAR: An aliquot of 3.33 μL (3 mM) of DAR-$N_3$ in DMSO was mixed with 50 μM of ssDNA-PEG-DBCO in 100 μL of phosphate buffer (pH 7.4, 50 mM). The reaction was stirred overnight at room temperature to achieve a 1:1 labeling of ssDNA with the DAR-$N_3$. The crude reaction mixture was centrifuged multiple rounds (12000 rpm for 10 min at 4° C.) to remove unreacted DAR-$N_3$ till no trace of it was detected in the filtrate ($\lambda_{em}$=571 nm, ε=7.8×104 $M^{-1}$ $cm^{-1}$). A ratio of 1:1 labeling of the DAR to the DNA was confirmed by using UV-Vis spectroscopy (FIG. 35). See FIG. 36*a* for gel characterization of the product.

NOckout and NOckout$^{Fn}$ synthesis: NOckout was assembled by annealing 24-mer ssDNA-PEG-DAR (20 μM) with a 24-mer 5'-ATTO647N labeled complementary ssDNA (20 μM) in phosphate buffer (50 mM, pH 7.2). The individual ssDNA samples were mixed together and the mixture was subsequently annealed from 70° C. to room temperature by applying a temperature gradient of 5° C./15 minutes using ThermoMixer C (Eppendorf). The annealed sample was further incubated at 4° C. for 2 hours. The formation of NOckout was verified using native polyacrylamide gel electrophoresis (15%) as shown in FIG. 36. Six functionally different NOckout$^{Fn}$ probes were used in this study (see FIG. 1*a*). All these probes were synthesized by using a similar protocol that was described above for NOckout assembly by using different complementary ssDNA strand carrying A647N fluorophore (e.g. mCpG sequence, Table 1). 24-mer ssDNA-PEG-DAR (20 μM) DNA was annealed with corresponding 24-mer functional A647N strand (20 μM) in pH 7.2 phosphate buffer. Self-assembly and integrity of the probes (FIG. 36*b-e*) were checked using native PAGE as described below.

Gel electrophoresis: Native polyacrylamide gels containing 15% acrylamide [30:1 acrylamide/bisacrylamide] were used for the gel electrophoresis assays. Gels were run in 1× TBE buffer (90 mM Tris.HCl, 90 mM boric acid, and 2 mM EDTA, pH 8.3) at room temperature. Post run, gels were first imaged with ChemiDoc MP imaging system (Bio-rad, USA) to visualize DAR or pHrodo conjugated (605/55 filter, green epi illumination) and ATTO647N conjugated (695/55 filter, red epi illumination) DNA oligonucleotides. Ethidium bromide (1 μg/ml) was used to stain DNA duplex and it was imaged with a GelDoc-It imaging system (UVP, USA, $\lambda_{ex}$=302 nm).

In vitro fluorescence measurements: All fluorescence studies were carried out on a Fluoromax-4 (Horiba Scientific, Japan) spectrophotometer. 10 μM stock of NOckout or NOckout$^{Fn}$ sensors were diluted to a 100 nM final concentration in 50 mM sodium phosphate buffer, pH 5.0, 6.0 or 7.2. The emission spectra of DAR and A647N were acquired by exciting the sample at 550 nm and 650 nm respectively. Fluorescence emission spectra were collected in the range of 560-620 nm (slit width=2 nm) for DAR and 655-700 nm (slit width=2 nm) for A647N. Diethylamine NONOate (DEA NONOate, Cayman Chemicals, United States) was used as fast NO donor. The half-life of DEA NONOate is 2 minutes and 16 minutes at 37° C. and 25° C., respectively, in 100 mM phosphate buffer (pH 7.4). DEA NONOate liberates 1.5 moles of NO per mole of parent compound. Fluorescence signal from NOckout. (100 nm) was recorded sequentially in the DAR (G) and A647N (R) channels before and after the addition of DEANONOate (30 μM) at timed intervals (30 s). Emission intensity maximum of DAR was at 571 nm before $NO^-$ addition and it shifted to 578 mu after $NO^-$ addition. In vitro fold change of all the NOckout sensors were calculated and expressed as the ratio of DAR signal to that of the A647N signal, which is represented as a G/R value.

pH Insensitivity of NOckout probes: pH insensitivity of NOckout probes are critical for error-free reporting of NO from acidic intracellular compartments. All the seven NOckout probes synthesized were validated as pH insensitive in the range of pH 5-pH 7.4 (SI FIG. 4). Briefly, NOckout (500 nM in 100 μL) was reacted with 20 μM DEANONOate in pH 6 phosphate buffer (50 mM) to reach the maximum fluorescence in the DAR channel. NOckout was subsequently purified using a 3 kDa MWCO Amicon filter by using ultra-centrifugation (12000, rpm, 4° C.). NOckout samples (100 nM) were aliquoted to three different 100 μL microfuge tube containing acetate buffer (pH 5.0, 100 mM), phosphate buffer (pH 6.0, 100 mM) and phosphate buffer (pH 7.4, 100 nM) to a final volume of 100 μL. The samples were incubated for 10 minutes at room temperature to equilibrate and subsequently fluorescence spectra were recorded in DAR (G) and A647N (R) channels. The G/R ratio were calculated and it was found to be independent of pH fluctuations (FIG. 37).

Synthesis of pHlickr: pH sensor pHlickr is a 24-mer dsDNA duplex carrying a pH sensing fluorophore pHrodo ($\lambda_{ex}$=540 nm, $\lambda_{em}$=580 nm) at the 5'-end of one of the ssDNA strands and ATTO647N fluorophore on the 5'-end of the complementary ssDNA (see Table 1 for the DNA sequences). pHrodo was attached to the ssDNA using a standard thiol-maleimide conjugation reaction. Briefly, 200 μL of 50 μM ssDNA (in 50 mM phosphate buffer, pH 7.4) carrying a thiol modification at the 5'-terminal was mixed with 200 μM of pHrodo maleimide (2.8 μL from a 14 mM stock in dry DMSO). The reaction mixture was stirred at room temperature for 3 hours and subsequently diluted to final volume of 1 mL using milli-Q water. This solution was then centrifuged using a 3 kDa MWCO ultracentrifugation filter to remove unreacted pHrodo-maleimide. The presence of pHrodo in the filtrate was negated by using UV-Vis spectroscopy ($\lambda_{ab}$=560 nm, ε=65,000). The ratio of ssDNA to the conjugated pHrodo was conformed to be 1:1 before proceeding to the annealing step. Annealing of 20 μM ssDNA-pHrodo (in 50 mM of phosphate buffer, pH 7.2) with 20 μM of ssDNA-ATTO647N strand was carried in a ThermoMixer (Eppendorf) at 70° C. to room temperature by applying a temperature drop of 5° C./15 minutes. The annealed sample was further cooled at room temperature and pHlickr formation was verified using 15% polyacrylamide gel electrophoresis (SI FIG. S6). The yield of pHlickr assembly was found to be quantitative.

pH sensitivity of pHlickr was tested using 200 nM sample in acetate buffer (pH 4.5), phosphate butler (pH 6.0) and phosphate buffer (pH 7.4) as shown in in SI FIG. S6. A 3.5-fold decrease in fluorescence intensity was observed in the pHrodo emission maxima ($\lambda_{em}$=580 nm) corresponding to a pH decrease from 7.4 to 4.5. The fold change of pHlickr was calculated as ratio of fluorescence intensity observed for pHrodo at 580 nm to that of the fluorescence intensity of ATTO647N at 660 inn and is shown in SI FIG. S6.

Example 8: Response Characterization of NOckout Sensors

To check the response characteristics of NOckout variants to NO in vitro, the NO donor DEANONOate (20 μM) was added to 250 nM of NOckout in phosphate buffer, pH 6.0 and monitored DAR-T and A647 fluorescence intensities as a function of time. DAR fluorescence (G) increased rapidly upon NO addition and the time required for 50% reaction ($t_{1/2}$) under these conditions was ~60 s (FIG. 5*c*). The intensity of A647 (R) remained constant and the ratio of DAR/A647 fluorescence intensities, i.e., the G/R ratio, showed a ~6.0 fold change upon complete reaction of the sensor (FIG. 5*c-d*). The NO response characteristics of all the NOckout devices were similar within error and were insensitive to pH from pH 5-7.4 (FIG. 5*d* and FIGS. 37 and 38). They are thus suitable to map NO in acidic organelles. FIG. 5*e* shows the representative response kinetics of NOckout (250 nM) to 30 μM DEANONOate at pH 6.

All NOckout variants proved highly specific to NO over other reactive species both in vitro and in cells. The response of NOckout to various reactive oxygen species (HOCl, $H_2O_2$, $O_2^{*-}$ and OH*) was tested by measuring the in vitro fold change in G/R before and after addition of indicated reactive species. NOckout showed ~5-fold greater specificity to NO over any other ROS in vitro (FIG. 5*f*).

Figure 6:
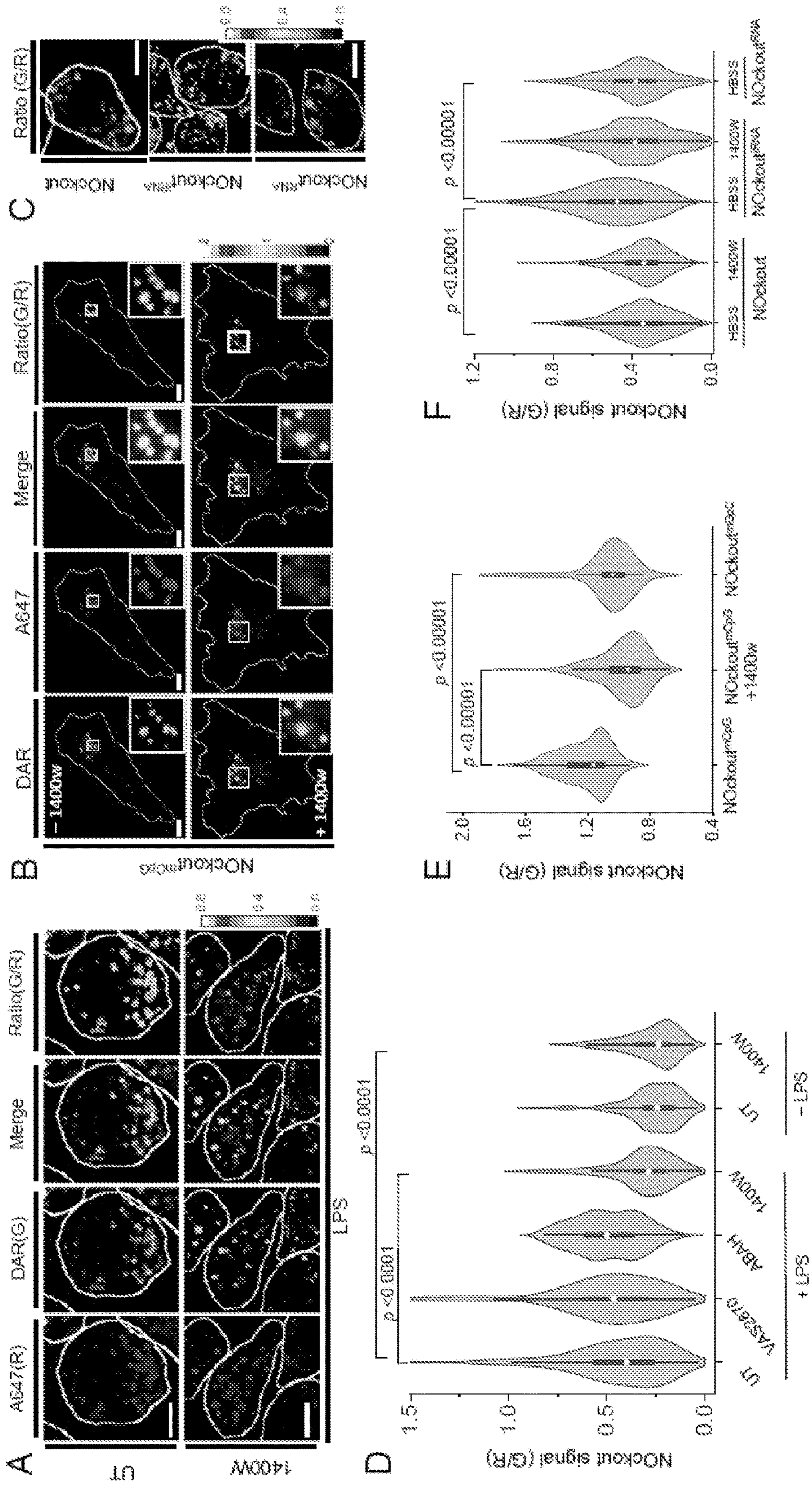
FIG. 6. NOckout$^{Fn}$ detects NO in mouse primary microglia and in alveolar macrophages: (a) Representative confocal images of NOckout from LPS (1 □g/mL) primed J774A.1 macrophages in A647 (R) and DAR (G) channels in the absence (upper panel) or presence (lower panel) of NOS2 inhibitor 1400 W. G/R intensities are represented as heat maps (b) Representative confocal images of NOckout$^{mCpG}$ from mouse primary microglia. Cells were incubated with NOckout$^{mCpG}$ (500 nM) in the absence (upper panel) or presence (lower panel) of 1400 W for 120 min in DMEM, imaged in DAR(G) and A647(R) channels and converted into G/R heat maps. (c) Representative heat map (G/R) images of NOckout, NOckout$^{iRNA}$ NOckout$^{iRNA}$ treated J774A.1 cells. (d) Violin plot of the distribution of G/R values of ~200 individual endosomes (n=30 cells) of J774A.1 cells treated with VAS2870, ABAH and 1400 W in the presence and absence of LPS. (e) Violin plot of the distribution of G/R values of ~100 individual endosomes (n=20 cells) in primary microglia treated with NOckout$^{mCpG}$ and NOckout$^{mGpC}$. (f) Violin plot of the distribution of G/R values of ~200 individual endosomes (n=30 cells) in J774A.1 macrophages treated with NOckout$^{RNA}$ variants in the presence mid absence of 1400 W. All experiments were performed in triplicate. P values are obtained using Kruskal-Wallis statistical test across the dataset.

To check the specificity of NOckout to NO, endosomes of J774A.1 macrophages primed with lipopolysaccharide (LPS) were labeled with NOckout and imaged in the DAR (G) and A647 (R) channels from where the G/R maps were obtained as described (FIG. 6*a*, Methods). Macrophages express scavenger receptors that bind and traffic dsDNA along the endo-lysosomal pathway. They also express ROS and NO producing enzymes, NADPH-oxidase (NOX), myeloperoxidase (MPO) and NOS2 respectively. Priming macrophages either with CpG oligonucleotides or endotoxins such as LPS induces the expression of these enzymes (FIGS. 41 and 42).

The in-cell specificity of NOckout can be evaluated by measuring the contribution of the reactive species produced by NOX, MPO and NOS2 to the observed fold change in G/R ratio upon LPS stimulation. It was found that if NOckout displayed no functional immunogenic sequence it showed negligible NOS2 activation. Therefore, in order to trigger NO2 activity for these experiments, the cells had to be explicitly activated by LPS treatment. J774A.1 cells primed with LPS was incubated, labelled with NOckout in the presence and absence of VAS2870. ABAH or 1400 W that pharmacologically NOX, MPO and NOS2 respectively (FIG. 43). FIG. 6*a* shows representative images of NOckout labeled J774A.1 cells in G and R channels in the presence and absence of 1400 W. Inhibiting NOX or MPO did not affect NOckout response, ruling out any contribution of ROS to the observed signal (FIGS. 6*b-c* & FIG. 44). However, inhibiting NOS2 with 1400 W reduced the signal by ~50%, indicating that NOckout was highly specific to NOS2 (FIG. 6*c*). FIG. 6*b* shows the distribution of G/R values of ~200 endosomes for each experiment. As NOS2 activity is not pan-endosomal, specificity is given by quantifying the percentage of endosomes that show G/R values higher than the mean G/R value in endosomes of unstimulated, NOS2 inhibited cells, as the latter corresponds to basal endosomal NO levels (FIG. 6*c*). Importantly, it was observed NOS2 activation by NOckout alone was insignificant. In fact, NOS2 activity had to be explicitly triggered by treating cells with LPS (FIGS. 6*b-c*).

Example 9: NOckout$^{fn}$ Devices Trigger NOS2 Activity in Microglia

Given that NOckout did not trigger NOS2 activity, it was modified to display DNA and RNA sequences that function as pathogen associated molecular patterns (PAMPs) in order to engage the endosomal Toll-like receptors (TLRs) of the host cell and thereby activate NOS2 (FIG. 5*g*). Nucleic acid-based PAMPs are recognized by the innate immune system through specific pattern recognition receptors (PRRs), namely TLRs. Specific TLRs recognize structurally distinct nucleic acid PAMPs present in "non-self-DNA" or "non-self RNA". Non-self-DNA is endocytosed by innate immune cells through scavenger receptors and is recognized by endosome-resident TLR-9, while non-self RNA is recognized by TLR-7/8 or TLR-3, both of which subsequently activate NOS2 and NOX (Dalpke, A. H. et al. Immunostimulatory CpG-DNA activates murine microglia. *J. Immunol.* 168, 4854-4863 (2002); Iliev, A. I., Stringaris, A. K., Nau, R. & Neumann, H. Neuronal injury mediated via stimulation of microglial toll-like receptor-9 (TLR9). *FASEB J.* 18, 412-414 (2004); To. E. E. et al. Endosomal NOX2 oxidase exacerbates virus pathogenicity and is a target for antiviral therapy. Nat Commun 8, 69 (2017)).

mCpG, a ligand for marine TLR-9, was displayed on NOckout to give NOckout$^{mCpG}$. NOckout$^{mCpG}$ is internalized by macrophages from the extracellular milieu by scavenger receptor mediated endocytosis. Based on the mechanism of action of mCpG, endosomal NOckout$^{mCpG}$ is expected to engage TLR-9, activate NOS2 and generate NO (FIG. 5*g*). Therefore, NOckout$^{mCpG}$ is expected to trigger and detect NO in selected endosomes in the first two hours of TLR-9 activation. NOckout$^{mCpG}$ (500 nM) was incubated with primary mouse microglia for 90 min in the presence and absence of 1400 W and the G/R ratio of ~100 individual endosomes from ~50 cells was computed (FIG. 6*d*). This revealed much higher overall levels of NO in endosomes comparable to what was observed for LPS activation. NO-rich endosomes in NOckout$^{mCpG}$ treated cells showed G/R values >1.0, that was reduced by ~60% upon inhibiting NOS2 (FIG. 6*e* & FIG. 48). Substituting, the CpG motif in NOckout$^{mGpC}$ with the non-immunostimulatory GpC motif to give NOckout$^{mGpC}$ led to a 40% reduction of NO-rich endosomes. (FIG. 6*e*, n=100 endosomes). Cumulatively this indicates that NOckout$^{mGpC}$ detects NO produced by NOS2 that has been activated due to the mCpG moiety engaging TLR-9. Next, colocalization studies were conducted to verify the identify of the compartments in J774A.1 cells containing NOckout. The time at which the steady-state NO measurements were performed was 90 min postpulsing. At 90 min, NOckout showed >60% colocalization with the late endosomal marker fluorescein isothiocyanate-labeled ovalbumin (FIG. 48A). Immunofluoresence with anti-LAMP-1 showed that no lysosomes were labeled (FIG. 48B). Thus, NOckout probes predominately measure NO in LEs of J774A.1 cells.

Next, the immunogenicity of the various PAMPS was quantified alone and when they were displayed on NOckout$^{fn}$ probes by detecting TNF-α levels arising from TLR stimulation. We treated J774A.1 cells with each PAMP motif, for example mCpG, zCpG, RNA, or iRNA and their corresponding NOckout display vairent and quantified TNFα in the extracellular milieu by enzyme-linked immunisorbent assay (ELISA) (FIG. 47). Plain NOckout, devoid of any PAMP, did not generate TNF-α beyond basal levels in cell culture. This correlates well with our finding that NOckout alone does not activate NOS2. NOckout$^{mCpG}$ and NOckout$^{iRNA}$ treatment led to high TNF-α production. Importantly, these constructs were as immunogenic as the corresponding PAMP alone, indicating that PAMP display on the NOckout scaffold does not appreciably alter the immunogenicity of the PAMP. One base swap of CpG to GpC or single A to G mutation, that each converts the PAMPs to nonimmunogenic motifs in either NOckout$^{mGpC}$ or NOckout$^{RNA}$, led to a dramatic reduction in TNF-α levels when the eels were treated with these probes. These supported the findings that the nonimmunogenic mGpC and RNA motifs alone were incompetent at TNF-α production (FIG. 47). Importantly, NOckout probes do not stimulate their cognate TLR indefinitely. This is because, beyond 2 h in cell culture, the probe is degraded in lysosomes, likely by DNase II, NOckout probes therefore can reliably report on endosomal NO levels only up to 2 h postinternalization (FIG. 45).

To study whether the NOckout scaffold could be more generally programmed to display specific PAMPs that could trigger their cognate PRRs, NOckout was designed to display an immunostimulatory RNA sequence that is a ligand for the murine TLR-13 receptor (Oldenburg, M. et al. TLR13 recognizes bacterial 23S rRNA devoid of erythromycin resistance-forming modification. *Science* (80-) 337, 1111-1115 (2012)). TLR-13 was recently identified as the cognate receptor for a 13-base long immunogenic RNA, denoted iRNA (FIG. 5*a*). iRNA is derived from the domain V of the ribosomal RNA (rRNA) that is conserved across several pathogenic Gram negative bacteria, and effectively triggers NO production in innate immune cells.

As described earlier, $NOckout^{iRNA}$ was made which displayed iRNA that is expected to trigger NOS2 activity by engaging TLR-13 (FIG. 5*a*). $NOckout^{iRNA}$ (500 mM) was incubated with J774A.1 cells for 90 min in the presence and absence of 1400 W. The G/R ratios of ~200 endosomes from ~50 cells was compared with the G/R ratios obtained for the plain NOckout device (FIGS. 6*f*-*g*). $NOckout^{iRNA}$ showed ~40% more NO-rich endosomes compared to basal levels (G/R≥0.5, FIG. 5*g*). This was reduced to near basal levels either upon inhibiting NOS2 or upon using $NOckout^{RNA}$, where the PAMP sequence corresponds to iRNA having a single G to A mutation that abolishes binding to TLR-13 (FIG. 5*g* & FIG. 48). This reveals that $NOckout^{iRNA}$ engages TLR-13 and detects NO produced due to NOS2 activity. Thus, NOckout is an effective ratiometric NO detection platform to image NOS2 activity arising from PAMP-TLR engagement.

Example 10: Phagosomal Localization of NOckout Probes in Zebrafish Microglia

Since NOckout sensors can be rationally designed to predictably trigger NOS2 activity through precise pathways in cultured cells, it was applied to study TLR signaling in vivo. Zebrafish is a powerful genetic model to dissect host-pathogen interactions, as one can image innate immune cells in live vertebrates with sub-cellular resolution. Further, the innate immune signaling component can be specifically isolated in the larval stage due to the late onset of adaptive immunity in zebrafish. Here, NOS2 activation in microglia of zebrafish was studied by microinjecting PAMP-programmed NOckout probes into the optic tectum of larvae 3-4 days post fertilization (dpf) (FIG. 7*a*).

First, the sub-cellular localization of extraneously introduced NOckout probes in the zebrafish brain was established. In the mammalian brain, fragmented DNA is internalized by scavenger receptors present on microglia which results in their intracellular localization in these cells. Since this information is missing in zebrafish, a 24 bp duplex DNA labeled with A647N ($dsDNA^{A647}$) was injected in the optic tectum of Tg(apoe:eGFP) larvae 3 dpf where microglia are marked with GFP (FIG. 7*b*). It was found that 30 min post injection, $dsDNA^{A647}$ was internalized specifically by microglia, and not by neurons (SI FIG. 17). The subcellular localization of the injected dsDNA probe in the optic tectum of Tg(mpeg:eGFP) fish where all macrophages are marked with GFP was then verified. Live imaging over longer time-scales revealed that several actively moving microglia rapidly phagocytosed particles of $dsDNA^{A647}$, with many microglia performing multiple phagocytic events (FIG. 7*c*). The sizes of the intracellular compartments containing internalized $dsDNA^{A647}$ cargo even by live imaging were ~2-4 μm, again consistent with phagosomes rather than endosomes. Co-injection of $dsDNA^{TMR}$ with apoptotic marker AnnexinV-Cy5 revealed substantial colocalization of $dsDNA^{TMR}$ with apoptotic bodies prior to their uptake by microglia (FIG. 6*d* & FIG. 49). This revealed that the uptake mechanism of DNA probes by microglia is via phagocytosis. Post uptake, $dsDNA^{TMR}$ and annexin V-Cy5 extensively colocalized in phagosomes of microglia seen as large, discrete puncta 1-3 μm in diameter (FIG. 6*d*). This is consistent with other observations where extracellular DNA or extracellular RNA form condensed, apoptotic bodies to expedite their clearance by macrophages through phagocytosis.

Since phagosomes of all macrophages are known to have an acidic milieu, the lumenal acidity of these compartments were checked using a GFP-compatible. DNA-based pH sensor denoted as pHlickr (FIG. 39). pHlickr comprises the pH sensitive dye, pHrodo, attached to the 5' end of the unlabeled strand in $dsDNA^{A647}$. It ratiometrically reports pH, as protonation of pHrodo results in high fluorescence (G) while the fluorescence of the A647 moiety is unchanged. The ratio of pHrodo to A647 (G/R) as a function of increasing acidity revealed increasing G/R values (FIG. 39). Injection of pHlickr in Tg(mpeg:eGFP) larvae, revealed that the G/R ratio inside microglia was 1.6-fold higher than the G/R ratio of extracellular puncta (FIGS. 7*e*-*f*). This reveals that the large compartments containing pHlickr are acidic reaffirming that these compartments are indeed phagosomes (FIG. 7*e*). Taken together, this indicates that extraneously introducing dsDNA molecules in the optic tectum of zebrafish results in its incorporation into apoptotic bodies that are rapidly phagocytosed by microglia.

Example 11: Single Stranded RNA can Act as a PAMP in Zebrafish

Whether NOckout probes could map phagosomal NO generated by activating NOS2 through the engagement of TLR receptors in live brains was then tested. To achieve this, the well-characterized CpG ODN, zCpG, was displayed on NOckout to give $NOckout^{zCpG}$ (FIG. 5*a*). zCpG synergistically binds both TLR-9 and TLR-21 through a GTCGTT motif and triggers a strong immune response in zebrafish, producing IL-1, IFN-γ and TNF-γ, although NOS2 activation has not yet been explicitly demonstrated in this system. When $NOckout^{zCpG}$ was injected into the optic tectum of 3 dpf old fish, it was internalized into phagosomes of microglia, and then imaged as described earlier (FIG. 8*a*). Puncta of $NOckout^{zCpG}$ that were not internalized by microglia showed a low G/R ratio consistent with negligible NO levels, while $NOckout^{zCpG}$ localized in phagosomes showed a high G/R ratio, consistent with high phagosomal NO levels (FIG. 8*b*).

Figure 8:
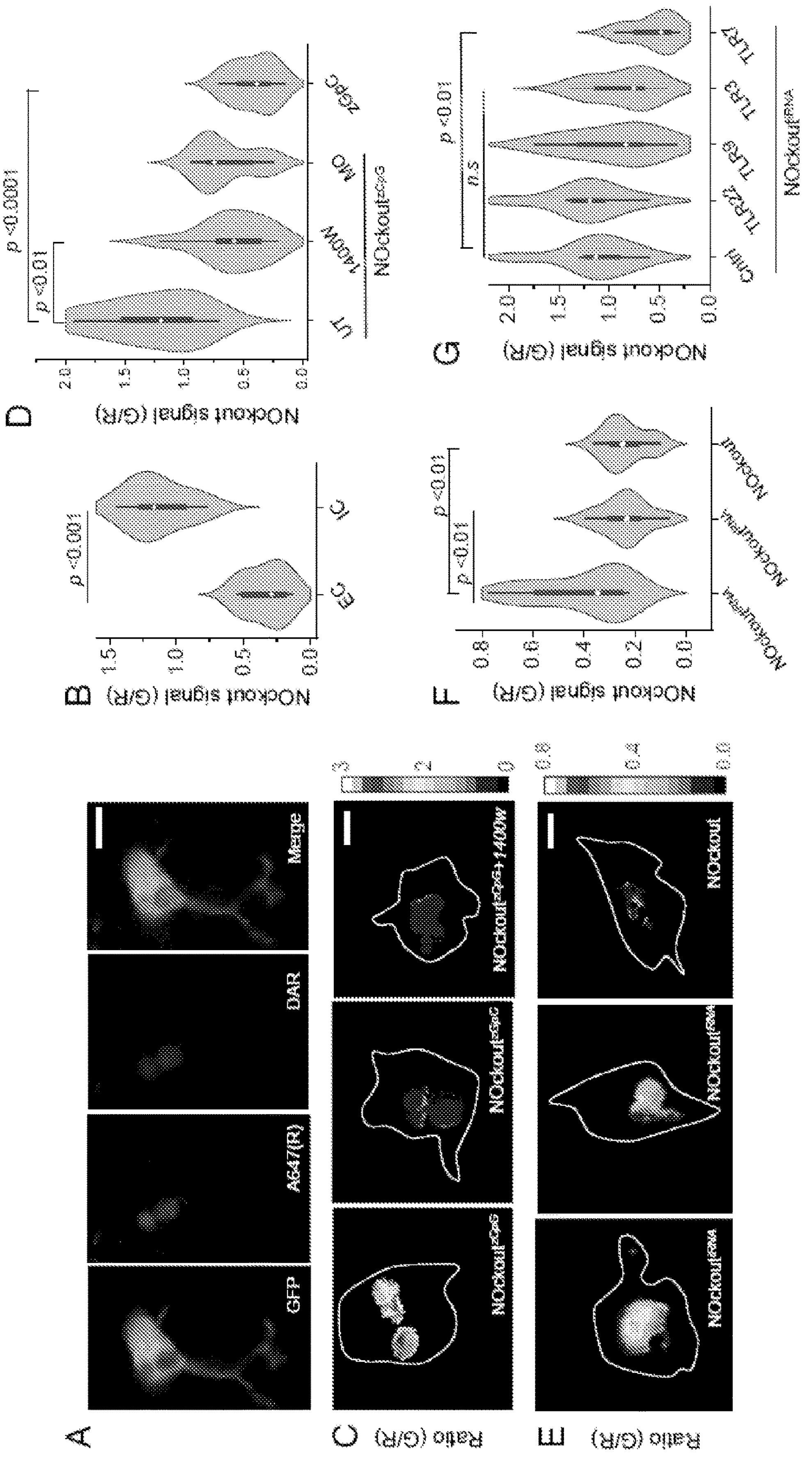
FIG. 8. NOckout$^{zCpG}$ and NOckout$^{iRNA}$ elevate phagosomal NO in zebrafish microglia: (a) Representative three-color image showing phagosomal localization of NOckout$^{zCpG}$ in microglia of 3 dpf Tg(mpeg1:eGFP) fish. A647 (R) is the reference fluorophore and DAR signal (G) is shown in blue. (b) NOckout$^{zCpG}$ signal from the extracellular milieu (EC) and intracellular (IC) phagosomes are plotted as the ratio of DAR (G) to A647 channel intensities (n=10 phagosomes from n=5 fish). (c) Representative G/R heatmaps of phagosomes in fish injected with NOckout$^{zCpG}$, NOckout$^{zGpC}$ and NOckout$^{zCpG}$+1400 W samples (0.2 pmoles in HBSS). (d) Violin plot of G/R distribution in ~10 individual phagosomes injected with NOckout$^{zCpG}$ in different conditions (n=5 fish). (e) Representative G/R heatmaps of phagosomes labeled with NOckout$^{iRNA}$, NOckout$^{RNA}$ or NOckout (20-40 nL) (f) Violin plot of G/R distributions of ~10 individual phagosomes (n=5 fish). (g) G/R values of ~10 phagosomes in morpholino knockdowns of the indicated TLR receptors (n=5 fish per trial). All experiments were performed in triplicate. Scale bar: 5 µm. P values obtained using Kruskal-Wallis statistical test across data set.

The G/R ratios of ~20 such phagosomes were significantly higher than those obtained with plain NOckout, indicating high levels of phagosomal NO and consistent with effective NOS2 activation (FIG. 8*c* & FIG. 51*a*). This was reduced by ~50% when NOS2a, the NOS2 ortholog of zebrafish, was pharmacologically inhibited with 1400 W or if the CpG motif in $NOckout^{zCpG}$ was substituted with a non-immunostimulatory GpC motif as seen in $NOckout^{zGpC}$ (FIG. 8*d*) Morpholino knockdown of NOS2a also reduced the signal by ~40% (FIG. 8*d* & FIG. 51*a*). This indicates that immunostimulatory sequences displayed on NOckout devices engage their cognate TLRs in the zebrafish brain and trigger NOS2 activity resulting in high phagosomal NO.

Using NOckout technology, it was discovered that pathogenic RNA of bacterial origin can act as PAMPs in zebrafish, and its cognate Toll-like receptor was identified. Bacterial pathogens such as *M. marinum* and *M. leprae* in macrophages of zebrafish are effectively neutralized in the phagosome by NOS2 activation due to TLR engagement. Ten out of the twenty putative TLR receptors in zebrafish have human orthologs, and the cognate ligands for only a few have been pinpointed (Table 7).

TABLE 7

| Zebrafish TLRs | Zebrafish PAMPs | Mammalian TLRs | Mammalian PAMPs |
|---|---|---|---|
| TLR1 | | TLR1 | lipopeptides and peptidoglycan |
| TLR2 | lipopeptides; Pam3CSk4 | TLR2 | lipoproteins, lipoteichoic acid |
| TLR3 | dsRNA; Poly I:C | TLR3 | dsRNA |
| TLR4a/b | | TLR4 | LPS or Mannan |
| TLR5a/b | flagellin | TLR5 | flagellin |
| TLR7 | | TLR6 | lipopeptide |
| TLR8a/b | | TLR7 | ssRNA |
| TLR9 | CpG-ODNs | TLR8 | ssRNA |
| TLR14 | | TLR9 | CpG-ODNs |
| TLR18 | | TLR10 | |
| TLR19 | | TLR13 | rRNA |

TABLE 7-continued

| Zebrafish TLRs | Zebrafish PAMPs | Mammalian TLRs | Mammalian PAMPs |
|---|---|---|---|
| TLR20a | | | |
| TLR21 | CpG-ODNs | | |
| TLR22 | dsRNA; Poly I:C | | |

For example, TLR-3 and TLR-22 of zebrafish sense dsRNA and poly (LC) while TLR-9 and TLR-21 sense CpG-ODNs. However, it is not yet frown whether ssRNA can trigger an immunogenic response, or even function as a PAMP, in zebrafish. In contrast, the highly conserved iRNA sequence, derived from the ribosomal RNA of pathogens such as *S. aureas* and *E. coli* engages murine TLR-13, eliciting NO production and is now recognized as a PAMP in mice. Interestingly, this RNA sequence is also conserved in many natural aquatic pathogens that infect zebrafish such as *Edwardsiella tarda, Aeromonas hydraphila* and *Francisella philomiragia* (FIG. 52 & Table 8). A further in was made to determine whether iRNA could act as a PAMP in zebrafish, and if so, whether using NOckout technology could help identify its cognate TLR.

TABLE 8

| Species | 23s rRNA sequence | Comments |
|---|---|---|
| *S. Typhimurium* | 2095 ACGGAAAGACCCC 2107 (SEQ ID NO: 46) | Used to study innate immunity in zebrafish |
| *M. Marinum* | 2260 AAAGACCCC 2268 (SEQ ID NO: 47) | Widely used as a model for studying innate immunity in zebrafish |
| *M. Tuberculosis* | 2255 AAAGACCCC 2263 (SEQ ID NO: 48) | *Tuberculosis* model in zebrafish |
| *M. Leprae* | 2277 AAAGACCCC 2285 (SEQ ID NO: 49) | Used to study innate immunity in zebrafish |
| *Aeromonas hydrophila* | 2045 ACGGAAAGACCCC 2057 (SEQ ID NO: 50) | Aquatic bacterium that cause high mortality in zebrafish, NO/ROS production observed during infection |
| *Edwardsiella tarda* | 2048 ACGGAAAGACCCC 2060 (SEQ ID NO: 51) | Natural pathogen of zebrafish. Induces robust NO production within 2 h in Japanese flounder. |
| *E. coli* | 2054 ACGGAAAGACCCC 2066 (SEQ ID NO: 52) | |
| *Francisella philomiragia* | 2047 ACGGAAAGACCCC 2059 (SEQ ID NO: 53) | NOS2 upregulation reported in zebrafish |

Table 8 shows bacterial species hosting the immunogenic 13nt rRNA sequence in their 23s rRNA. Aquatic pathogens such as *Aeromonas hydrophila* and *Edwardsiella tarda* (in bold) has 100% sequence conservation. *Mycobacterium* has partial sequence identity.

As before, the iRNA sequence was displayed on NOckout to give NOckout$^{iRNA}$ and tested its capacity to generate phagosomal NO (FIG. 5*a*). Post injection of NOckout$^{iRNA}$ in the brain, it was efficiently phagocytosed by microglia. The G/R ratios of ~20 phagosomes revealed appreciable levels of NO compared to phagosomes labeled with unfunctionalized NOckout (FIGS. 8*e-f*). Further, a single A to G mutation in the iRNA sequence that renders it non-immunostimulatory in mice was used to create NOckout$^{RNA}$. Analogous experiments with NOckout$^{RNA}$ revealed a ~3.5-fold decrease in phagosomal NO levels (FIG. 8*e-f* & FIG. 51*b*).

Since ssRNA also acts as a PAMP in zebrafish, this suggests an evolutionarily conserved mechanism to detect ssRNAs. It was therefore reasoned that the PRR responsible was also likely to be a TLR. To identify the TLR responsible, phagosomal NO in zebrafish where specific endosomal TLRs were knocked down was then imaged. Specifically, when TLR7 was knocked down, the G/R, ratio of ~10 NOckout$^{RNA}$-labeled phagosomes showed ~40% signal reduction (FIG. 4*g*, FIG. 52*b*). This indicates that iRNA engages zebrafish TLR7 to activate NOS2 and induce phagosomal NO production in microglia. The G/R signal was unaffected when TLRs such as TLR3, TLR9 or TLR22 were knocked down (FIG. 8*g*).

In mammals, TLR-7 is an endosomal or phagosomal PRR that is known to engage ssRNA of viral or bacterial origin and shows ~56% sequence identity with zebrafish TLR7 (zTLR7). An homology model of the predicted structure of zTLR7 with the crystal structure of macaque TLR7 complexed with ssRNA. reveals marked structural similarity (FIG. 54). Importantly, zTLR7 showed conserved amino acid residues within its predicted ssRNA binding pocket (FIG. 55). Further, zTLR7 is highly expressed in 3 dpf larval zebrafish (FIG. 53). This reaffirms that ssRNA acts a PAMP by engaging zebrafish TLR7 in microglia, activating NOS2a Which produces phagosomal NO.

In summary, small molecules reporters for NO are bright, photostable, specific and pH-insensitive, yet post-reaction, the probe molecules diffuse rapidly, obscuring spatial information. Protein based NO sensors offer spatial resolution, but have comparatively poor sensing characteristics, cannot be targeted to phagosomes and are pH-sensitive. NOckout probes leverage the 1:1 stoichiometry of DNA hybridization to display an NO sensitive fluorophore, an internal reference dye and a dsDNA domain to target the phagosome. Microinjecting NOckout nanodevices in live brains resulted in them being packaged into apoptotic bodies and being exclusively targeted to phagosomes in microglia. Since NOckout nanodevices are pH-insensitive they are well-suited to map NO in the acidic phagosomal milieu.

Importantly, NOckout nanodevices can be programmed to display a specific nucleic acid PAMP with precise and uniform stoichiometries to give NOckout$^{fn}$ devices that engage their cognate TLR receptor to thereby activate NOS2. This leads to phagosomal NO production that is detected by the NOckout probe. This modular, “trigger and detect” design enabled us to make six different NOckout variants with identical reporting capabilities that each engage a distinct TLR receptor depending on the PAMP displayed. By displaying well characterized immunogenic sequences such as mCpG or zCpG, murine TLR-9 and zebrafish TLR-9/TLR-21 could be activated respectively. It was found that while the basic NOckout scaffold was non-immunogenic, NOckout$^{fn}$ devices could activate NOS2 by engaging a specific TLR in primary microglia either in culture or in live zebrafish brains. While NOS2 activation due to PAMP recognition by the cognate TLR receptor is well established in cultured murine and human cells, using NOckout, it is possible to now directly map NOS2 activity in live cells and in live brains which has not been previously possible.

NOckout can be used to map NO arising from NOS2 activation in the first few hours following PAMP-PRR association in vivo. It can be used to assay PAMP-TLR recognition, identify or validate ligands for PRRs with undetermined specificities, and potentially estimate their relative procilivities to activate NOS2. The DNA scaffold can be modified to display more than one PAMP in precise stoichiometies using three-way or four-way junctions, and the resultant combination NOckout devices can be applied to identify TLRs that could act synergistically or antagonistically. One can also envisage substituting, NO detection chemistries for various ROS detection chemistries to map the in vivo activity of phagosomal ROS-producing enzymes arising from TLR activation. A technology that can map the dynamics of NO within phagosomes of innate immune cells in vivo could thereby offer new insights into the dynamics of host-pathogen interactions. Since resistant microbes use several mechanisms to bypass phagosomal degradation, NO mapping could help identify how resistant pathogens survive the phagosome.

NOckout reporters are applicable without further modification to transparent model organisms such as *Caenorhabditis elegans* and *Drosophila melanogaster*. One can also envisage NOckout being deployed in certain regions of mouse brain, for example, cerebral cortex. One caveat of Nockout technology is that, currently, it can be used to detect NO produced due to preexisting and actively translated NOS2 and is not suitable for sustained detection NO over transcriptional time scales. This limitation can be overcome by replacing dsDNA backbone by a peptide nucleic acid or L-DNA backbone to improve its cellular stability. This highly modular imaging platform can be applied to study the early stages of the innate immune response at very high chemical resolution.

The ability of NOckout technology to deliver new biological insight is demonstrated by the identification of a new class of PAMPs zebrafish, namely ssRNA. Mammals have achieved the sophistication to discriminate between ssRNA PAMPs of different origin: ssRNA from microbes are sensed by TLR-7 or TLR-8, while rRNA from bacteria is sensed by TLR-13. Yet, similar information on ssRNA sensing was previously unknown in zebrafish. Using NOckout$^{iRNA}$ it was determined that ssRNAs can indeed act as PAMPs and triggers NOS2 activity in zebrafish. Using morpholino knockdowns, it is possible to identify the cognate TLR responsible for this signaling mechanism.

NOckout nanodevices combine the attractive reporter characteristics of small molecule NO sensitive dyes with the stable localization provided by DNA. They can thereby map NO in vivo arising from NOS2 activation in the first few hours following PAMP-PRR association. NOckout technology can be applied to study PAMP-TLR recognition, identify ligands for PRRs with undetermined specificities, and estimate their relative proclivities to activate NOS2. The DNA scaffold also enables the stoichiometric display of more than one PAMP through the use of 3-way or 4-way junctions, and the resultant combination NOckout devices can be applied to identify those TLRs that act synergistically or antagonistically. One can also envisage substituting NO detection chemistries for various ROS detection chemistries to map the in vivo activity of phagosomal ROS producing enzymes arising from TLR activation. A technology that can map the dynamics of NO within phagosomes of innate immune cells in vivo will therefore offer new insights into the dynamics of host-pathogen interactions. Since resistant microbes use several mechanisms to by-pass phagosomal degradation, NO mapping could help identify how resistant pathogens survive the phagosome. This highly modular imaging platform can be applied to study the early stages of the innate immune response at very high chemical resolution.

BIBLIOGRAPHY

Part 1: DNA-Based Fluorescent Probe Maps NOS3 Activity

1. Hess, D. T., Matsumoto, A., Kim. S.-O., Marshall, H. E. &. Stamler, J. S. Protein S-nitrosylation: purview and parameters. Nat. Rev. Mol. Cell Biol. 6, 150-166 (2005).
2. Bredt D. S. & Snyder, S. H. Nitric oxide: a physiologic messenger molecule. Annu. Rev. Biochem. 63,175-195 (1994).
3. Lim, K.-H., Ancrile, B. B., Kashatus, D. F. & Counter, C. M. Tumour maintenance is mediated by eNOS. Nature 452, 646-649 (2008).
4. Xu, W., Liu. L. Z., Loizidou M., Ahmed. M. & Charles, I. G. The role of nitric oxide in cancer. Cell Res. 12, 311-320 (2002).
5. Fukumura, D., Kashiwagi, S. & Jain, R. K. The role of nitric oxide in tumour progression. Nat. Rev. Cancer 6, 521-534 (2006).
6. Lahdenranta, J. et al. Endothelial nitric oxide synthase mediates lymphangiogenesis and lymphatic metastasis. Cancer Res. 69, 2801-2808 (2009).
7. Ying, L. & Hofseth, L. J. An emerging role for endothelial nitric oxide synthase in chronic inflammation and cancer. Cancer Res. 67, 1407-1410 (2007).
8. Thomsen, L. L. et al. Nitric oxide synthase activity in human breast cancer. Br. J. Cancer 72, 41-44 (1995).
9. Tschugguel, W. et al. Expression of inducible nitric oxide synthase in human breast cancer depends on tumor grade. Breast Cancer Res. Treat. 56, 145-151 (1999).
10. Martin, J. H., Begum S., Alalami, O., Harrison, A. & Scott, K. W. Endothelial nitric oxide synthase: correlation with histologic grade, lymph node status and estrogen receptor expression in human breast cancer. Tumour Biol. 21, 90-97 (2000).
11. Choudhari, S. K., Chaudhary, M., Bagde, S., Gadbail, A. R. & Joshi, V. Nitric oxide and cancer: a review. World J Sing Oncol, 11, 118 (2013).
12. Sowa, G. et al. Trafficking of endothelial nitric-oxide synthase in living cells. Quantitative evidence supporting the role of palmitoylation as a kinetic trapping mechanism limiting membrane diffusion. J. Biol. Chem. 274, 22524-22531 (1999).
13. Sessa, W. C. et al. The Golgi association of endothelial nitric oxide synthase is necessary for the efficient synthesis of nitric oxide. J. Biol. Chem. 270, 17641-17644 (1995).
14. Zhang, Q. et al. Functional relevance of Golgi- and plasma membrane-localized endothelial NO synthase in reconstituted endothelial cells. Arterioscler. Thromb. Vasc. Biol. 26, 1015-1021 (2006).
15. Jin Z.-G. Where is endothelial nitric oxide synthase more critical: plasma membrane or Golgi? Arterioscler. Thromb. Vasc. Biol. 26, 959-961 (2006).
16. Modi, S. et al. A DNA nanomachine that maps spatial and temporal pH changes inside living cells. Nat. Nanotechnol. 4, 325-330 (2009).
17. Surana, S., Bhat, J. M., Koushika, S. P. & Krishnan, Y. An autonomous DNA nanomachine maps spatiotemporal pH changes in a multicellular living organism. Nat. Commun. 2, 340 (2011).
18. Chakraborty, K., Leung, K. & Krishnan, Y. High lumenal chloride in the lysosome is critical for lysosome function. Elife 6, e28862 (2017).
19. Narayanaswamy, N. et al. A pH-correctable, DNA-based fluorescent reporter for organellar calcium. Nat. Methods 16, 95-102 (2019).
20. Leung, K., Chakraborty, K., Saminathan, A. & Krishnan, Y. A DNA nanomachine chemically resolves lysosomes in live cells. Nat. Nanotechnol. 14, 176-183 (2019).
21. Thekkan, S. et al. A DNA-based fluorescent reporter maps HOCl production in the maturing phagosome. Nat. Chem. Biol. 15, 1165-1172 (2019).
22. Kojima, H. et al. Bioimaging of nitric oxide with fluorescent indicators based on the rhodamine chromophore. Anal. Chem. 73, 1967-1973 (2001).
23. Kojima, H. et al. Detection and imaging of nitric oxide with novel fluorescent indicators: diaminofluoresceins. Anal. Chem. 70, 2446-2453 (1998).
24. You, M. et al. DNA probes for monitoring dynamic and transient molecular encounters on live cell membranes. Nat. Nanotechnol. 12, 453-459 (2017).
25. Ferreira, C. S. M., Cheung, M. C., Missailidis, S., Bisland, S. & Gariépy, J. Phototoxic aptamers selectively enter and kill epithelial cancer cells. Nucleic Acids Res. 37, 866-876 (2009).
26. Yang, Y.-M., Huang, A., Kaley, G. & Sun, D. eNOS uncoupling and endothelial dysfunction in aged vessels. Am. J. Physiol. Heart Circ. Physiol. 297, H1829-36 (2009).
27. Lundberg, J. O., Weitzberg, E. & Gladwin, M. T. The nitrate-nitrite-nitric oxide pathway in physiology and therapeutics. Nat. Rev. Drug Discov. 7, 156-167 (2008).
28. Fulton, D., Gratton, J. P. & Sessa, W. C. Post-translational control of endothelial nitric oxide synthase: why isn't calcium/calmodulin enough? J. Pharmacol. Exp. Ther. 299, 818-824 (2001).
29. Fulton, D. et al. Localization of endothelial nitric-oxide synthase phosphorylated on serine 1179 and nitric oxide in Golgi and plasma membrane defines the existence of two pools of active enzyme. J. Biol. Chem. 277, 4277-4284 (2002).
30. Goldstein, S., Russo, A. & Samuni, A. Reactions of PTIO and carboxy-PTIO with *NO, *NO2, and O2-*. J. Biol. Chem. 278, 50949-50955 (2003).
31. Fulton, D. et al. Regulation of endothelium-derived nitric oxide production by the protein kinase Akt. Nature 399, 597-601 (1999).
32. Veetil, A. T., Jani, M. S. &. Krishnan, Y. Chemical control over membrane-initiated steroid signaling with a DNA nanocapsule. Proc. Natl. Acad. Sci. USA 115, 9432-9437 (2018).
33. Fulton, D. et al. Targeting of endothelial nitric-oxide synthase to the cytoplasmic face of the Golgi complex or plasma membrane regulates Akt- versus calcium-dependent mechanisms for nitric oxide release. J. Biol. Chem. 279, 30349-30357 (2004).
34. Lytton, J., Westlin, M. & Hanley, M. R. Thapsigargin inhibits the sarcoplasmic or endoplasmic reticulum Ca-ATPase family of calcium pumps. J. Biol. Chem. 266, 17067-17071 (1991).

35. Namin, S. M., Nofallah, S., Joshi, M. S., Kavallieratos, K. & Tsoukias, N. M. Kinetic analysis of DAF-FM activation by NO: toward calibration of a NO-sensitive fluorescent dye. Nitric Oxide 28, 39-46 (2013).
36. Jiang, S. et al. Real-time electrical detection of nitric oxide in biological systems with sub-nanomolar sensitivity. Nat. Commun. 4, 2225 (2013).
37. Ramamurthi, A. & Lewis, R. S. Measurement and modeling of nitric oxide release rates for nitric oxide donors. Chem. Res. Toxicol. 10, 408-413 (1997).
38. Modi, S., Halder, S., Nizak, C. & Krishnan, Y. Recombinant antibody mediated delivery of organelle-specific DNA pH sensors along endocytic pathways. Nanoscale 6, 1144-1152 (2014).
39. Garcia-Cardeña, G. et al. Dynamic activation of endothelial nitric oxide synthase by Hsp90. Nature 392, 821-824 (1998).
40. Farber-Katz, S. E. et al. DNA damage triggers Golgi dispersal via DNA-PK and GOLPH3. Cell 156, 413-427 (2014).
41. Lee, J. E. et al. Dependence of Golgi apparatus integrity on nitric oxide in vascular cells: implications in pulmonary arterial hypertension. Am. J. Physiol. Heart Circ. Physiol. 300. H1141-58 (2011).
42. Blake, R. A. et al. SU6656, a selective src family kinase inhibitor, used to probe growth factor signaling. Mol. Cell. Biol. 20, 9018-9027 (2000).
43. Skupien, A. et al. CD44 regulates dendrite morphogenesis through Src tyrosine kinase-dependent positioning of the Golgi. J. Cell Sci. 127, 5038-5051 (2014).
44. Ye, X., Rubakhin, S. S. & Sweedler, J. V. Detection of nitric oxide in single cells. Analyst 133, 423-433 (2008).
45. Lim, M. H., Xu, D. & Lippard, S. J. Visualization of nitric oxide in living cells by a copper-based fluorescent probe. Nat. Chem. Biol. 2, 375-380 (2006).
46. Eroglu, E. et al. Development of novel FP-based probes for live-cell imaging of nitric oxide dynamics. Nat. Commun 7, 10623 (2016).
47. Vahora, H., Khan, M. A., Alalami, U. & Hussain, A. The potential role of nitric oxide in halting cancer progression through chemoprevention. J. Cancer Prev. 21, 1-12 (2016).
48. Ellefsen K. L. & Parker, I. Dynamic Ca2+ imaging with a simplified lattice light-sheet microscope: A sideways view of subcellular Ca2+ puffs. Cell Calcium 71, 34-44 (2018).
49. Lee, P. C. et al. Impaired wound healing and angiogenesis eNOS-deficient mice. Am. J. Physiol. 277, H1600-8 (1999).
50. Jane, M. S, Veetil, A. T. & Krishnan, Y. Precision immunomodulation with synthetic nucleic acid technologies. Nat. Rev. Mater. (2019). doi:10.1038/s41578-019-0105-4.
51. Yao, L., Smith, B. T. & Aubé, J. Base-promoted reactions of bridged ketones and 1,3- and 1,4-haloalkyl azides: competitive alkylation vs azidation reactions of ketone enolates. J. Org. Chem. 69, 1720-1722 (2004).
52. Schindelin, J. et al. Fiji: an open-source platform for biological-image analysis. Nat. Methods 9, 676-682 (2012).
53. Awad, H. H. & Stanbury D. M. Autoxidation of NO in aqueous solution. Int. J. Chem. Kinet. 25, 375-381 (1993).
54. Lewis, R. S. & Deen, W. M. Kinetics of the reaction of nitric oxide with oxygen in aqueous solutions. Chem. Res. Toxicol. 7, 568-574 (1994).
55. Brandes R. P. & Janiszewski, M. Direct detection of reactive oxygen species ex vivo. Kidney Int. 67, 1662-1664 (2005).
56. Duarte, A. J. & da Silva, J. C. G. E. Reduced fluoresceinamine as a fluorescent sensor for nitric oxide. Sensors (Basel) 10, 1661-1669 (2010).
57. Debacq-Chainiaux, F., Erusalimsky, J. D., Campisi, J. & Toussaint, O. Protocols to detect senescence-associated beta-galactosidase (SA-betagal) activity, a biomarker of senescent cells in culture and in vivo. Nat. Protoc. 4, 1798-1806 (2009).

Part 2: DNA Nanodevices for Mapping Nitric Oxide in Living Brain

58. Stuart, L. M. & Ezekowitz, R. A. B. Phagocytosis: elegant complexity. Immunity 22, 539-550 (2005).
59. Underhill, D. M. & Ozinsky, A. Phagocytosis of microbes: complexity in action. Annu. Rev. Immunol. 20, 825-852 (2002).
60. Dupré-Crochet, S., Erard, M. & Nüße, O. ROS production in phagocytes: why, when, and where? J. Leukoc. Biol. 94, 657-670 (2013).
61. Wink, D. A. et al. Nitric oxide and redox mechanisms in the immune response. J. Leukoc. Biol. 89, 873-891 (2011).
62. Takeuchi, O. & Akira, S. Pattern recognition receptors and inflammation. Cell 140, 805-820 (2010).
63. Mogensen, T. H. Pathogen recognition and inflammatory signaling in innate immune defenses. Clin. Microbiol. Rev. 22, 240-73, Table of Contents (2009).
64. West, A. P., Koblansky, A. A. & Ghosh, S. Recognition and signaling by toll-like receptors. Annu. Rev. Cell Dev. Biol. 22, 409-437 (2006).
65. Li, Y., Li. Y., Cao, X., Jin, X. & Jin, T. Pattern recognition receptors in zebrafish provide functional and evolutionary insight into innate immune signaling pathways. Cell Mol Immunol 14, 80-89 (2017).
66. Ciao, J. J. et al. Cutting edge: bacterial DNA and LPS act in synergy in inducing nitric oxide production in RAW 264.7 macrophages. J. Immunol. 163, 4095-4099 (1999).
67. Utaisincharoen, P. Anuntagool, N., Chaisuriya, P., Pichyangkul, S. & Sirisinha, S. CpG ODN activates NO and NOS2 production in mouse macrophage cell line (RAW 264.7). Clin. Exp. Immunol. 128, 467-473 (2002).
68. Pacelli, R. et al. Nitric oxide potentiates hydrogen peroxide-induced killing of *Escherichia coli*. J. Exp. Med. 182, 1469-1479 (1995).
69. Kaplan, S. S., Lancaster, J. R., Basford, R. E. &. Simmons, R. L. Effect of nitric oxide on staphylococcal killing and interactive effect with superoxide. Infect. Immun. 64, 69-76 (1996).
70. Gregory, S. H., Wing, E. J., Hoffman, R. A. & Simmons, R. L. Reactive nitrogen intermediates suppress the primary immunologic response to Listeria. J. Immunol. 150, 2901-2909 (1993).
71. Miller, B. H. et al. Mycobacteria inhibit nitric oxide synthase recruitment to phagosomes during Macrophage infection. Infect. Immun. 72, 2872-2878 (2004).
72. L. Davis, A. S. et al. Mechanism of inducible nitric oxide synthase exclusion from mycobacterial phagosomes. PLoS Pathog. 3, e 186 (2007).
73. Cambier, C. J. et al. Mycobacteria manipulate macrophage recruitment through coordinated use of membrane lipids. Nature 505, 218-222 (2014).
74. Giustarini, D., Rossi, R., Milzani, A. & Dalle-Donne, I. in Nitric Oxide, Part F 440, 361-380 (Elsevier, 2008).

75. Kojima, H. et al. Detection and imaging of nitric oxide with novel fluorescent indicators: diaminofluoresceins. Anal. Chem 70, 2446-2453 (1998).
76. McQuade, L. E. & Lippard, S. J. Fluorescent probes to investigate nitric oxide and other reactive nitrogen species in biology (truncated form: fluorescent probes of reactive nitrogen species). Curr. Opin. Chem. Biol. 14, 43-49 (2010).
77. Yu, H., Xiao, Y. & Jin, L. A lysosome-targetable and two-photon fluorescent probe for monitoring endogenous and exogenous nitric oxide in living cells. J. Am. Chem. Soc. 134, 17486-17489 (2012).
78. Pisano, J. M. & Firestone R. A. Lysosomotropic Agents III1. Synthesis of N-Retinyl Morpholine. Synth Commun 11, 375-378 (1981).
79. Eroglu, E. et al. Development of novel FP-based probes for live-cell imaging of nitric oxide dynamics. Nat Commun 7, 10623 (2016).
80. Kojima, H. et al. Bioimaging of Nitric Oxide with Fluorescent Indicators Based on the Rhodamine Chromophore. Anal. Chem. 73, 1967-1973 (2001).
81. Veetil, A. T. et al. Cell-targetable DNA nanocapsules for spatiotemporal release of caged bioactive small molecules. Nat. Nanotechnol. 12, 1183-1189 (2017).
82. Chakraborty, K., Veetil, A. T., Jaffrey, S. R. & Krishnan, Y. Nucleic Acid-Based Nanodevices in Biological Imaging. Annu. Rev. Biochem. 85, 349-373 (2016).
83. Yeh, D.-W. et al. Toll-like receptor 9 and 21 have different ligand recognition profiles and cooperatively mediate activity of CpG-oligodeoxynucleotides in zebrafish. Proc. Natl. Acad. Sci. USA 110, 20711-20716 (2013).
84. Oldenburg, M. et al. TLR13 recognizes bacterial 23S rRNA devoid of erythromycin resistance-forming modification. Science (80-.). 337, 1111-1115 (2012).
85. Li, X.-D. & Chen, Z. J. Sequence specific detection of bacterial 23S ribosomal RNA by TLR13. Elife 1, e00102 (2012).
86. Anrather, J., Racchumi, G. & Iadecola, C. NF-kappaB regulates phagocytic NADPH oxidase by inducing the expression of gp91phox. J. Biol. Chem. 281, 5657-5667 (2006).
87. Berlato, C. et al. Involvement of suppressor of cytokine signaling-3 as a mediator of the inhibitory effects of IL-10 on lipopolysaccharide-induced macrophage activation. J. Immunol. 168, 6404-6411 (2002).
88. Wind, S. et al. Comparative pharmacology of chemically distinct NADPH oxidase inhibitors. Br. J. Pharmacol. 161, 885-898 (2010).
89. Kettle, A. J., Gedye, C. A. & Winterbourn, C. C. Mechanism of inactivation of myeloperoxidase by 4-aminobenzoic acid hydrazide. Biochem. J. 321 (Pt 2), 503-508 (1997).
90. Garvey, E. P. et al. 1400 W is a slow, tight binding, and highly selective inhibitor of inducible nitric-oxide synthase in vitro and in vivo. J. Biol. Chem. 272, 4959-4963 (1997).
91. Lee, B. L. & Barton, G. M. Trafficking of endosomal Toll-like receptors. Trends Cell Biol. 24, 360-369 (2014).
92. Dalpke, A. H. et al. Immunostimulatory $C_pG$-DNA activates murine microglia. J. Immunol. 168, 4854-4863 (2002).
93. Iliev, A. I., Stringaris, A. K., Nau, R. & Neumann, H. Neuronal injury mediated via stimulation of microglial toll-like receptor-9 (TLR9). FASEB J. 18, 412-414 (2004).
94. To, E. E. et al. Endosomal NOX2 oxidase exacerbates virus pathogenicity and is a target for antiviral therapy. Nat Commun 8, 69 (2017).
95. Meijer, A. H. & Spaink, H. P. Host-pathogen interactions made transparent with the zebrafish model. Curr Drug Targets 12, 1000-1017 (2011).
96. Peri, F. & Nüsslein-Volhard, C. Live imaging of neuronal degradation by microglia reveals a role for v0-ATPase a1 in phagosomal fusion in vivo. Cell 133, 916-927 (2008).
97. Renshaw, S. A. & Trede. N. S. A model 450 million years in the making: zebrafish and vertebrate immunity. Dis. Model. Mech. 5, 38-47 (2012).
98. Egensperger, R., Maslim, J., Bisti, S., Holländer, H. & Stone, J. Fate of DNA from retinal cells dying during development: uptake b microglia and macroglia (Müller cells). Brain Res. Dev. Brain Res. 97, 1-8 (1996).
99. Li Y. et al. Microglial activation by uptake of fDNA via a scavenger receptor. J. Neuroimmunol. 147, 50-55 (2004).
100. Sierra, A. et al. Microglia shape adult hippocampal neurogenesis through apoptosis-coupled phagocytosis. Cell Stem Cell 7, 483-495 (2010).
101. Mazaheri F. et al. Distinct roles for BAI1 and TIM-4 in the engulfment of dying neurons by microglia. Nat Commun 5, 4046 (2014).
102. Madigan, C. A. et al. A Macrophage Response to *Mycobacterium leprae* Phenolic Glycolipid Initiates Nerve Damage in Leprosy. Cell 170, 973-985.e10 (2017).
103. Matsuo, A. et al. Teleost TLR22 recognizes RNA duplex to induce IFN and protect cells from birnaviruses. J. Immunol. 181, 3474-3485 (2008).
104. Ishibe, K. et al. Comparative analysis of the production of nitric oxide (NO) and tumor necrosis factor-alpha (TNF-alpha) from macrophages exposed to high virulent and low virulent strains of *Edwardsiella tarda*. Fish Shellfish Immunol. 27, 386-389 (2009).
105. Rodríguez, I., Novoa, B. & Figueras, A. Immune response of zebrafish (*Danio rerio*) against a newly isolated bacterial pathogen *Aeromonas hydrophila*. Fish Shellfish Immunol. 25, 239-249 (2008).
106. Brudal E. et al. Establishment of three *Francisella* infections in zebrafish embryos at different temperatures. Infect. Immun. 82, 2180-2194 (2014).
107. Jensen, S. & Thomsen, A. R. Sensing of RNA viruses: a review of innate immune receptors involved in recognizing RNA virus invasion. J. Virol. 86, 2900-2910 (7017).
108. Diebold, S. S., Kaisho, T., Hemmi, H., Akira, S. & Reis e Sousa, C. Innate antiviral responses by means of TLR7-mediated recognition of single-stranded RNA. Science (80-.). 303, 1529-1531 (2004).
109. Mancuso, G. et al. Bacterial recognition by TLR7 in the lysosomes of conventional dendritic cells. Nat. Immunol. 10, 587-594 (2009).
110. Nishiya T., Kajita, E., Miwa, S. & Defranco, A. L. TLR3 and TLR7 are targeted to the same intracellular compartments by distinct regulatory elements. J. Biol. Chem 280, 37107-37117 (2005).
111. Zhang, Z. et al. Structural Analysis Reveals that Toll-like Receptor 7 Is a Dual Receptor for Guanosine and Single-Stranded RNA. Immunity 45, 737-748 (2016).

The invention claimed is:

1. A nucleic acid complex comprising:

a first single-stranded nucleic acid molecule comprising a fluorophore crosslinked to the first single-stranded nucleic acid molecule, wherein the fluorophore comprises diaminorhodamine-4-methylamine (DAR-4M) conjugated to a dibenzocyclooctyne-polyethylene glycol (DBCO-$PEG_n$) linker, wherein n equals 4-12; and a second single-stranded nucleic acid molecule that is partially or fully complementary to the first single-stranded molecule, wherein the nucleic acid complex further comprises a first label and a targeting moiety conjugated to the first single-stranded nucleic acid molecule or the second single-stranded nucleic acid molecule, wherein the first label is capable of producing a signal, and wherein the intensity of the signal is at least dependent on concentration of the nucleic acid complex in the sample.

2. The nucleic acid complex of claim 1, wherein n=10.

3. The nucleic acid complex of claim 1, wherein the first label is a fluorophore.

4. The nucleic acid complex of claim 1, wherein the first label is Alexa488 or Alexa647.

5. The nucleic acid complex of claim 1, wherein the first label is crosslinked to the second single-stranded nucleic acid molecule.

6. The nucleic acid complex of claim 1, wherein the targeting moiety is crosslinked to the second single-stranded nucleic acid molecule.

7. The nucleic acid complex of claim 1, wherein the targeting moiety comprises a cholesterol moiety, a DNA aptamer, oligodeoxynucleotide phosphorothioate (ODP), or oligoribonucleotide phosphorothioate (ORP).

8. The nucleic acid complex of claim 1, wherein the first label and the targeting moiety are crosslinked to the second single-stranded nucleic acid molecule.

9. The nucleic acid complex of claim 1, wherein the first label is Alexa488 and the targeting moietylabel is a cholesterol moiety.

10. The nucleic acid complex of claim 1, wherein the first label is Alexa647 and the targeting moiety is a DNA aptamer.

11. The nucleic acid complex of claim 1, wherein the first single-stranded nucleic acid molecule has the following sequence:

```
                                    (SEQ ID NO: 01)
5'-/5AzideN/ATC AAC ACT GCA CAC CAG ACA GCA-3'.
```

12. The nucleic acid complex of claim 1, wherein the second single-stranded nucleic acid molecule has the following sequence:

```
                                    (SEQ ID NO: 02)
5'-/Alexa488N/TGC TGT CTG GTG TGC AGT GTT GAT/

3-CholTEG/-3'
or

                                    (SEQ ID NO: 03)
5'-GGC TAT AGC ACA TGG GTA AAA CGA CTT TGC T/

Alexa647N/G TCT GGT GTG CAG TGT TGA T-3'.
```

13. The nucleic acid complex of claim 1, wherein the first label is ATTO647N and the targeting moiety is oligodeoxynucleotide phosphorothioate (ODP), or oligoribonucleotide phosphorothioate (ORP).

14. The nucleic acid complex of claim 13, wherein the first single-stranded nucleic acid molecule has the following sequence:

```
                                    (SEQ ID NO: 04)
5'-/DAR-PEG10/ATC AAC ACT GCA CAC CAG ACA GCA-3'.
```

15. The nucleic acid complex of claim 14, wherein the second single-stranded nucleic acid molecule has the following sequence:

```
(S2-strand)
                                    (SEQ ID NO: 05)
5'-/ATTO647N/TGC TGT CTG GTG TGC AGT GTT GAT-3';

(NOckout1826CpG)
                                    (SEQ ID NO: 06)
5'-/ATTO647N/TGC TGT CTG GTG TGC AGT GTT GAT

tttccatgacgttcctgacgtt-3';

(NOckout1826GC)
                                    (SEQ ID NO: 07)
5'-/ATTO647N/TGC TGT CTG GTG TGC AGT GTT GAT

tttccatgagcttcctgacctt-3';

(NOckout2007CpG)
                                    (SEQ ID NO: 08)
5'-/ATTO647N/TGC TGT CTG GTG TGC AGT GTT GAT

tttcgtcgttgtcgttttgtcgtt-3';

(NOckout2007GC)
                                    (SEQ ID NO: 09)
5'-/ATTO647N/TGC TGT CTG GTG TGC AGT GTT GAT

tttgctgctgtgcttttgtgctt-3';

(NOckoutRNA);
                                    (SEQ ID NO: 10)
5'-/ATTO647N/TGC TGT CTG GTG TGC AGT GTT GAT

tttggacggaaaagaccccgugg-3'

(NOckoutRNA)
                                    (SEQ ID NO: 11)
5'-/ATTO647N/TGC TGT CTG GTG TGC AGT GTT GAT

tttggacgggaagaccccgugg-3';
or

(pHlicker-SH)
                                    (SEQ ID NO: 12)
5'-HS-ATC AAC ACT GCA CAC CAG ACA GCA-3'.
```

16. A method for determining nitric oxide concentration in a sample comprising:

a) contacting the sample with the nucleic acid complex according to claim 13;

b) measuring the intensity of the signal; and c) determining the nitric oxide concentration from the measured signal.

17. The method of claim 16, wherein determining nitric oxide concentration is in plasma membrane, trans Golgi network, phagosome, macrophage, or microglia.

* * * * *